(12) United States Patent
Sleeman et al.

(10) Patent No.: US 7,083,791 B2
(45) Date of Patent: Aug. 1, 2006

(54) METHODS FOR ENHANCING IMMUNE RESPONSES BY FIBROBLAST GROWTH FACTOR RECEPTOR 5 POLYPEPTIDES

(75) Inventors: Matthew Sleeman, GT Bradley (GB); J. Greg Murison, Auckland (NZ)

(73) Assignee: Genesis Research & Development Corporation Limited, Auckland (NZ)

( * ) Notice: Subject to any disclaimer, the term of this patent is extended or adjusted under 35 U.S.C. 154(b) by 158 days.

(21) Appl. No.: 10/613,413

(22) Filed: Jul. 3, 2003

(65) Prior Publication Data

US 2004/0058849 A1 Mar. 25, 2004

Related U.S. Application Data

(63) Continuation-in-part of application No. PCT/NZ03/00105, filed on May 27, 2003, which is a continuation-in-part of application No. 10/157,444, filed on May 28, 2002, now abandoned, which is a continuation-in-part of application No. 09/823,038, filed on Mar. 28, 2001, now Pat. No. 6,797,271, and a continuation-in-part of application No. 09/383,586, filed on Aug. 26, 1999, now Pat. No. 6,242,419, which is a continuation-in-part of application No. 09/276,268, filed on Mar. 25, 1999, now abandoned.

(60) Provisional application No. 60/221,216, filed on Jul. 25, 2000.

(51) Int. Cl.
*A61K 38/00* (2006.01)
*A61K 38/16* (2006.01)
*C07K 14/00* (2006.01)

(52) U.S. Cl. .............................. 424/185.1; 424/198.1; 514/12; 530/350

(58) Field of Classification Search .................. 514/12; 424/185.1
See application file for complete search history.

(56) References Cited

U.S. PATENT DOCUMENTS

| | | | |
|---|---|---|---|
| 2001/0016335 A1 | 8/2001 | Young et al. | |
| 2002/0009776 A1 | 1/2002 | Saris et al. | |
| 2002/0037557 A1 | 3/2002 | Jing et al. | |
| 2002/0103125 A1 | 8/2002 | Ashkenazi | |

FOREIGN PATENT DOCUMENTS

| WO | WO 98/49302 | 11/1998 |
|---|---|---|
| WO | WO 99/10364 | 5/1999 |
| WO | WO 99/21859 | 5/1999 |
| WO | WO 99/6308 A | 12/1999 |
| WO | WO 00/24756 | 5/2000 |
| WO | WO 00/73454 A | 12/2000 |
| WO | WO 01/00673 A | 1/2001 |
| WO | WO 01/09327 A | 2/2001 |
| WO | WO 01/49715 A2 | 7/2001 |
| WO | WO 01/53312 | 7/2001 |
| WO | WO 01/53455 A | 7/2001 |
| WO | WO 01/60991 A | 8/2001 |
| WO | WO 01/70977 A2 | 9/2001 |

OTHER PUBLICATIONS

Maher, Pamela, "p38 Mitogen-activated Protein Kinase Activation is Required for Fibroblast Growth Factor-2-stimulated Cell Proliferation but not Differentiation", The Journal of Biological Chemistry, Jun. 18, 1999, pp. 17491-17498, vol. 274, No. 25.

Bouju, Sophie, et al., "Molecular cloning and functional expression of a novel human gene encoding two 41-43 kDa skeletal muscle internal membrane proteins", BiochemJ., 1998, pp. 594-556, vol. 335, Great Britain.

Gruss, Hans-Jürgen, and Dower, Stephen, K., "Tumor Necrosis Factor Ligand Superfamily: Involvement in the Pathology of Malignant Lymphomas", Blood, the Journal of the American Society of Hematology, Jun. 15, 1998, pp. 3378-3404, vol. 85, No. 12.

Pietu, Genevieve, et al., "Novel Gene Transcropts Preferentially Expressed in Human Muscles Revealed by Quantitative Hybridization of a High Density cDNA Array", Genome Research, 1996, 492-503, vol. 6.

Banner, David, W., et al. "Crystal Structure of the Soluble Human 55 kd TNF Receptor—Human TNF β Complex: Implications for TNF Receptor Activation", Cell, May 7, 1993, pp. 431-445, vol. 73.

(Continued)

*Primary Examiner*—Ruixiang Li
(74) *Attorney, Agent, or Firm*—Speckman Law Group PLLC; Janet Sleath; Ann W. Speckman

(57) ABSTRACT

Isolated fibroblast growth factor receptor (FGFR5) polypeptides and polynucleotides encoding such polypeptides are provided. Also provided are modulators of FGFR5 gene expression and binding molecules that specifically bind to and agonize or antagonize FGFR5 polypeptide function. Specific binding molecules include antibodies, functional fragments thereof, as well as scFv and Camelidae heavy chain IgG that specifically bind to FGFR5 thereby modulating the activity of FGFR5 and, thus, are effective agents suitable for the treatment of diseases such as osteopontin-mediated autoimmune disease, such as systemic lupus erythematosus, bone disorders including osteoporosis and osteopetrosis, and cancers, including cellular carcinomas such as hepatocellular carcinomas.

5 Claims, 28 Drawing Sheets

OTHER PUBLICATIONS

Yaspo, Marie-Laure, et al., "Cloning of a Novel Human Putative Type Ia Integral Membrane Protein Mapping to 21q22.3", Genomics, Apr. 1, 1998, pp. 133-136, vol. 49.
Hattori, M., et al., GenPept Accession No. CAB90552, submitted May 5, 2000.
Pietu, G., et al., GenPept Accession No. AAC78827, submitted 1996.
Hayette, S., et al., GenPept Accession No. AAC64321, submitted 1998.
Bauer, H., et al., GenPept Accession No. AAD09175, submitted 1994.
Hemmati-Brivanlou, A., et al., GenPept Accession No. AAB30638, submitted Nov. 3, 1994.
Givol, D., GenPept Accession No. CAA41209, submitted Feb. 20, 1991.
Shi, D.L., et al., GenPept Accession No. CAA53271, submitted 1993.
Katoh, O., et al., GenPept Accession No. AAB25535, submitted 1993.
Bachner, D., et al., GenPept Accession No. CAB65272, submitted 1999.
Xu, J., et al., GenPept Accession No. AAF03400, submitted 1999.
Cabibbo, A., et al., GenPept Accession No. AAF20364, submitted 2000.
Isogai, T., et al., GenPept Accession No. BAA91786, submitted Feb. 16, 2000.
Wilson, R., et al., GenPept Accession No. AAB42225, submitted 1994.
Riboldo Tunnicliffe, G.R., et al., GenPept Accession No. AAC15584, submitted Sep. 1997.
Bouchon, A., et., GenPept Accession No. AAF69825, submitted 2000.
Shibata, T., GenPept Accession No. BAA18909, submitted Apr. 8, 1994.
Jang, w., et al., GenPept Accession No. AAC83205, submitted 1999.
Poustka, A., et al., GenPept Accession No. CAB55955, submitted Sep. 1999.
Dear, T. N., et al., Swiss-Prot Accession No. P14730, submitted 1988.
Coglievina, M., et a., Swiss-Prot Accession No. P53104, submitted 1997.
Weterman, M.A.J., et al., Swiss-Prot Accession No. Q14956, submitted 1995.
Naghpal, S., et al., Swiss-Prot Accession No. Q99969, submitted Oct. 1997.
Poustka. A., et al., PIR Accession No. T17265, submitted Oct. 15, 1999.
Shi, D.L., et al., PIR Accession No. S38579, submitted Nov. 1993.
Marra, M., et al., The WashU-HHMI Mouse EST Project, Accession No. AA184346, Feb. 17, 1997.
Marra, M., et al., The WashU-HHMI Mouse EST Project, Accession No. AI119658, Sep. 2, 1998.
Marra, M., et al., The WashU-HHMI Mouse EST Project, Accession No. AA231415, Feb. 26, 1997.
Marra, M., et al., The WashU-HHMI Mouse EST Project, Accession No. AA498840, Jul. 1, 1997.
Marra, M., et al., The WashU-HHMI Mouse EST Project, Accession No. AA636311, 1996.
Marra, M., et al., The WashU-HHMI Mouse EST Project, Accession No. AI050489, Jul. 9, 1998.
Marra, M., et al., The WashU-HHMI Mouse EST Project, Accession No. AA921460, Apr. 20, 1998.
Marra, M., et al., The WashU-HHMI Mouse EST Project, Accession No.AI466595, Mar. 9, 1999.
Marra, M., et al., The WashU-HHMI Mouse EST Project, Accession No. AI287088, Nov. 24, 1998.
Marra, M., et al., The WashU-HHMI Mouse EST Project, Accession No. W77540, Jun. 20, 1996.
Marra, M., et al., The WashU-HHMI Mouse EST Project, Accession No. AA646983, Oct. 28, 1997.
Marra, M., et al., The WashU-HHMI Mouse EST Project, Accession No.AI116725, Feb. 13, 1997.
Marra, M., et al., The WashU-HHMI Mouse EST Project, Accession No.AA475668, Jun. 18, 1997.
Ko, M.S.H., et al., Systematic analyses of genes expressed in fertilized mouse eggs (The ERATO/Doi Project at Wayne State University). Accession No. C86502, Mar. 11, 1998.
Sleeman, M., et al., "*Identification of a new 1-15, fibroblast growth factor receptor, FGFR5*" 18-20 Gene, Elsevier Biomedical Press., Amsterdam NL, Jun. 2001, vol. 271, No. 2, 27.

Figure 1

| | |
|---|---|
| MTRSPALLLLLLGALPSAEAARGPPRMADKVVPRQVARLGRTVRLQCPVEGDPPPLTMWT | 60 |
| KDGRTIHSGWSRFRVLPQGLKVKEVEAEDAGVYVCKATNGFGSLSVNYTLIIMDDISPGK | 120 |
| ESPGPGGSSGGQEDPASQQWARPRFTQPSKMRRRVIARPVGSSVRLKCVASGHPRPDIMW | 180 |
| MKDDQTLTHLEASEHRKKKWTLSLKNLKPEDSGKYTCRVSNKAGAINATYKVDVIQRTRS | 240 |
| KPVLTGTHPVNTTVDFGGTTSFQCKVRSDVKPVIQWLKRVEYGSEGRHNSTIDVGGQKFV | 300 |
| VLPTGDVWSRPDGSYLNKLLISRARQDDAGMYICLGANTMGYSFRSAFLTVLPDPKPPGP | 360 |
| PMASSSSSTSLPWPVVIGIPAGAVFILGTVLLWLCQTKKKPCAPASTLPVPGHRPPGTSR | 420 |
| ERSGDKDLPSLAVGICEEHGSAMAPQHILASGSTAGPKLYPKLYTDVHTHTHTHTCTHTL | 480 |
| SCGGQGSSTPACPLSVLNTANLQALCPEVGIWGPRQQVGRIENNGGRVS | 529 |

Figure 9
A     FGFR5β-treated PBMC
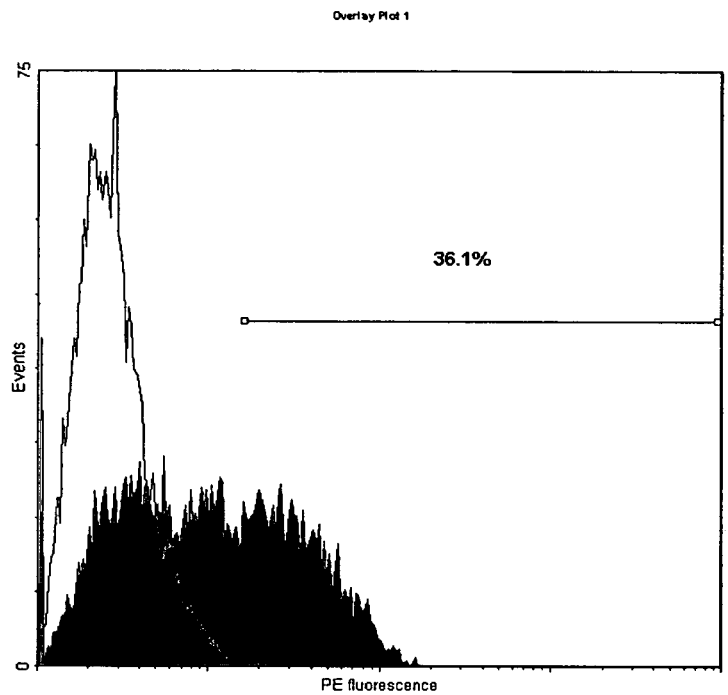
B     FGFR5γ-treated PBMC
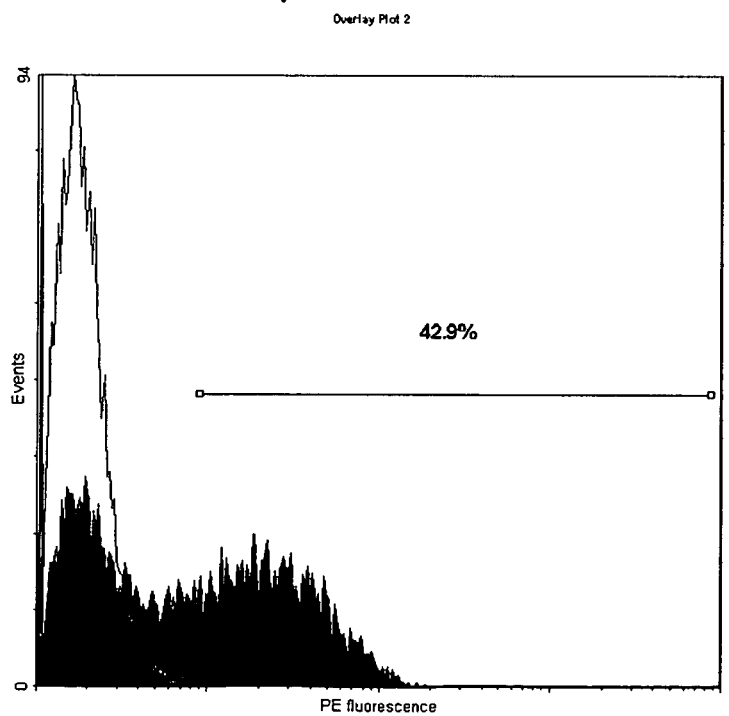

Figure 10

```
MTPSPLLLLLLPPLLLGAFPPAAAARGPPKMADKVVPRQVARLGRTVRLQCPVEGDPPPL      60
TMWTKDGRTIHSGWSRFRVLPQGLKVKQVEREDAGVYVCKATNGFGSLSVNYTLVVLDDI     120
SPGKESLGPDSSSGGQEDPASQQWARPRFTQPSKMRRRVIARPVGSSVRLKCVASGHPRP     180
DITWMKDDQALTRPEAAEPRKKKWTLSLKNLRPEDSGKYTCRVSNRAGAINATYKVDVIQ     240
RTRSKPVLTGTHPVNTTVDFGGTTSFQCKVRSDVKPVIQWLKRVEYGAEGRHNSTIDVGG     300
QKFVVLPTGDVWSRPDGSYLNKPL                                        324
```

Figure 11
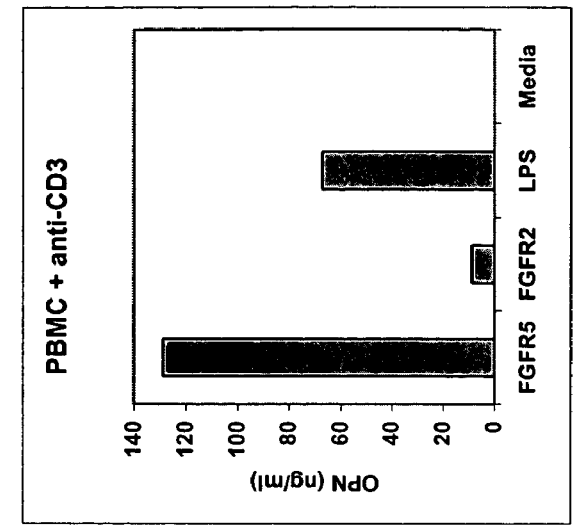
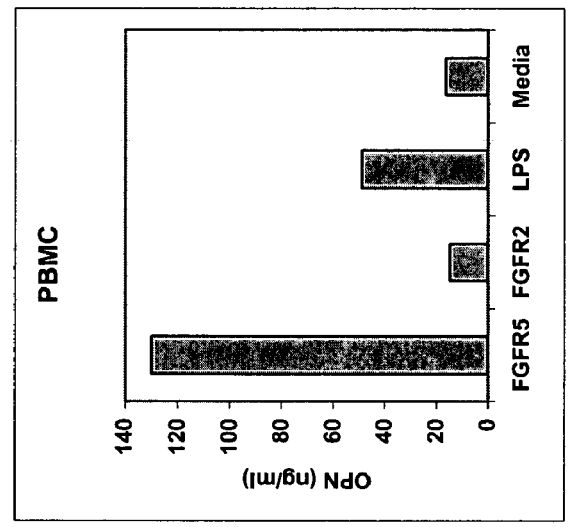
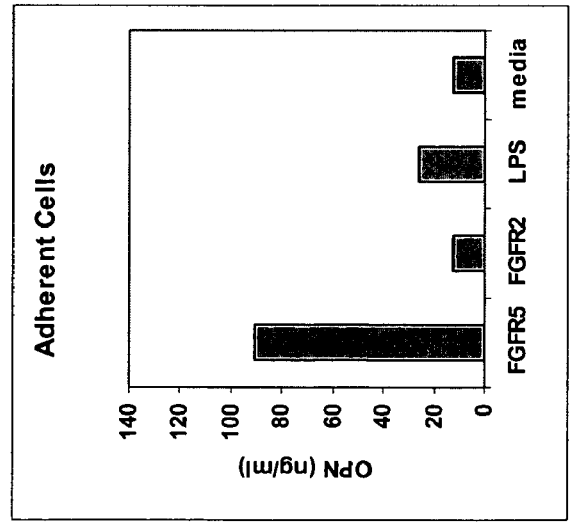

Figure 12
A
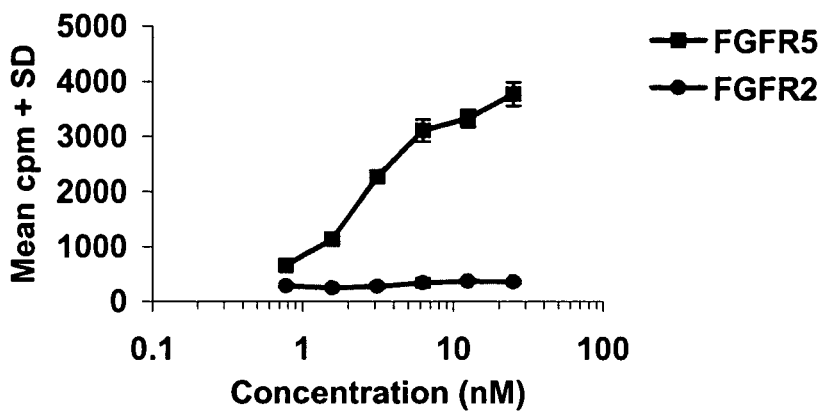
FGFR5 Induces the Proliferation of BMC
B
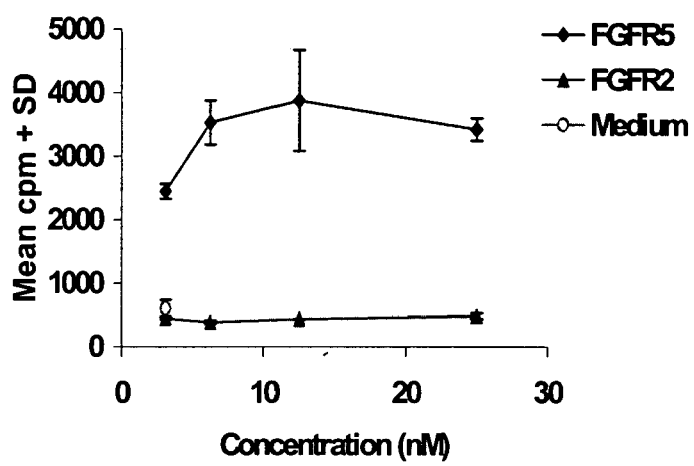
FGFR5 Induced Proliferation of non-adherent BMCs
C
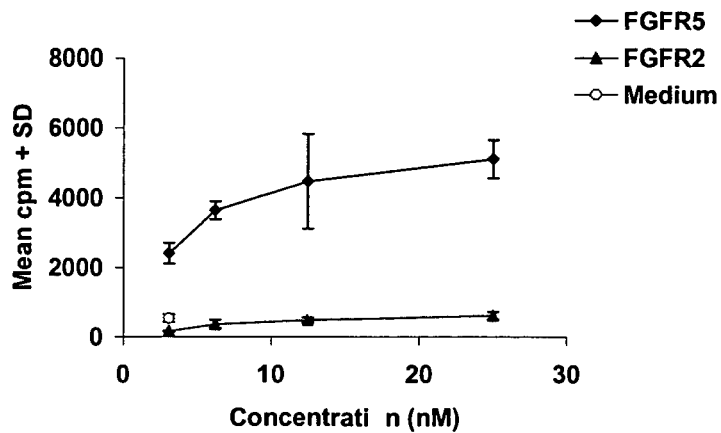
FGFR5 Induced Proliferation of adherent BMCs Effect of FGFR5 on 6AVS cell proliferation

Figure 15
A
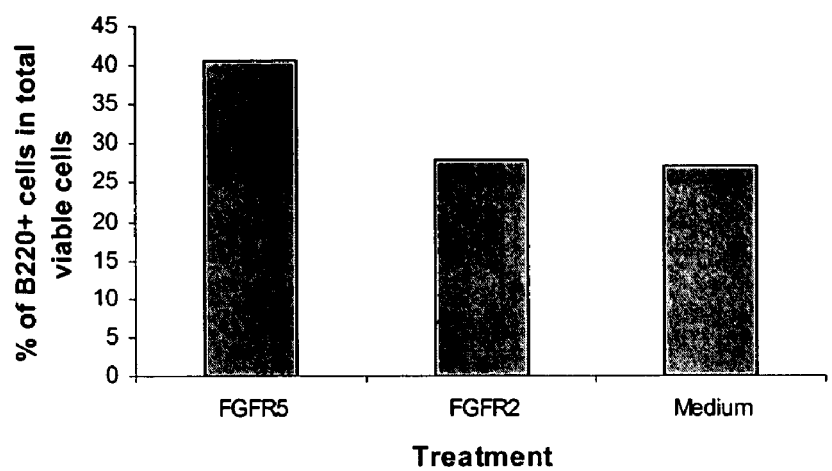
B
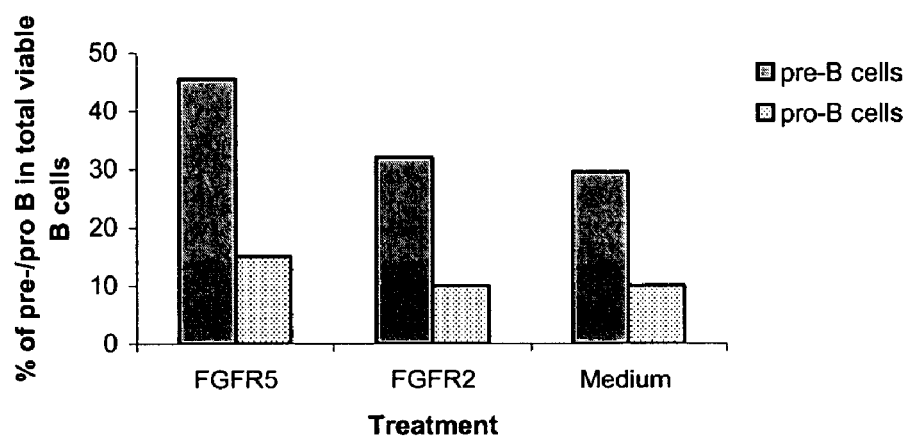

Effect of FGFR5 on CFU-pre-B formation from BMCs

METHODS FOR ENHANCING IMMUNE RESPONSES BY FIBROBLAST GROWTH FACTOR RECEPTOR 5 POLYPEPTIDES

CROSS-REFERENCE TO RELATED APPLICATIONS

This application claims priority as a continuation-in-part of International Patent Application No. PCT/NZ03/00105, filed May 27, 2003 and is a continuation-in-part of U.S. patent application Ser. No. 10/157,444, filed May 28, 2002, now abandoned which is a continuation-in-part of U.S. patent application Ser. No. 09/823,038, filed Mar. 28, 2001, now U.S. Pat. No. 6,797,271 which claims priority to International Patent Application No. PCT/NZ00/00015, filed Feb. 18, 2000; and to U.S. Provisional Patent Application No. 60/221,216, filed Jul. 25, 2000, and is a continuation-in-part of U.S. patent application Ser. No. 09/383,586, filed Aug. 26, 1999, now U.S. Pat. No. 6,242,419; which is a continuation-in-part of U.S. patent application Ser. No. 09/276,268, filed Mar. 25, 1999, now abandoned.

TECHNICAL FIELD OF THE INVENTION

This invention relates to polynucleotides and polypeptides derived from lymph node stromal cells from flaky skin (fsn –/–) mice, human homologues of such polynucleotides, polypeptides, antibodies and other molecules that specifically bind to the inventive polypeptides, and the use of such polynucleotides, polypeptides, and binding molecules in therapeutic and diagnostic methods. The present invention also relates to polynucleotides encoding FGFR5 and homologues thereof as well as to splice variants of FGFR5 that are uniquely expressed in various cell types and associated with diseases such as autoimmune diseases and cancers. Specific binding molecules include antibodies, functional fragments thereof, as well as scFv and Camelidae heavy chain IgG that specifically bind to FGFR5 thereby modulating the activity of FGFR5. Thus, specific binding molecules encompass agonists and/or antagonists of FGFR5 activity that are effective agents suitable for the treatment of diseases such as osteopontin-mediated autoimmune disease, such as systemic lupus erythematosus, bone disorders including osteoporosis and osteopetrosis, and cancers, including cellular carcinomas such as hepatocellular carcinomas.

BACKGROUND OF THE INVENTION

Lymph vessels and nodes are important components of the body's immune system. Lymph nodes are small lymphatic organs that are located in the path of lymph vessels. Large molecules and cells, including foreign substances, enter into the lymphatic vessels and, in circulating through these vessels, pass through the lymph nodes. Here, any foreign substances are concentrated and exposed to lymphocytes. This triggers a cascade of events that constitute an immune response, protecting the body from infection and from cancer.

Lymph nodes are surrounded by a dense connective tissue network that forms a supporting capsule. This network extends into the body of the lymph node, forming an additional framework of support. Throughout the remainder of the organ, a fine meshwork can be identified that comprises reticular fibres and the reticular cells that produce and surround the fibres. These features provide a support for the main functional cells of the lymphatic system, which are T- and B-lymphocytes. Additional cell types found in lymph nodes include macrophages, follicular dendritic cells, and endothelial cells that line the blood vessels servicing the node.

The cells within lymph nodes communicate with each other in order to defend the body against foreign substances. When a foreign substance, or antigen, is present, it is detected by macrophages and follicular dendritic cells that take up and process the antigen, and display parts of it on their cell surface. These cell surface antigens are then presented to T- and B-lymphocytes, causing them to proliferate and differentiate into activated T-lymphocytes and plasma cells, respectively. These cells are released into the circulation in order to seek out and destroy antigen. Some T- and B-lymphocytes will also differentiate into memory cells. Should these cells come across the same antigen at a later date, the immune response will be more rapid.

Once activated T- and B-lymphocytes are released into the circulation, they can perform a variety of functions that lead to the eventual destruction of antigen. Activated T-lymphocytes can differentiate into cytotoxic lymphocytes (also known as killer T-cells) which recognise other cells that have foreign antigens on their surface and kill the cell by causing them to lyse. Activated T-lymphocytes can also differentiate into helper T-cells which will then secrete proteins in order to stimulate B-lymphocytes, and other T-lymphocytes, to respond to antigens. In addition, activated T-lymphocytes can differentiate into suppressor T-cells which secrete factors that suppress the activity of B-lymphocytes. Activated B-lymphocytes differentiate into plasma cells, which synthesise and secrete antibodies that bind to foreign antigens. The antibody-antigen complex is then detected and destroyed by macrophages, or by a group of blood constituents known as complement.

Lymph nodes can be dissociated and the resulting cells grown in culture. Cells that adhere to the tissue culture dishes can be maintained for some length of time and are known as stromal cells. The cultured cells are a heterogeneous population and can be made up of most cells residing within lymph nodes, such as reticular cells, follicular dendritic cells, macrophages and endothelial cells. It is well known that bone marrow stromal cells play a critical role in homing, growth and differentiation of hematopoietic progenitor cells. Proteins produced by stromal cells are necessary for the maintenance of plasma cells in vitro. Furthermore, stromal cells are known to secrete factors and present membrane-bound receptors that are necessary for the survival of lymphoma cells.

An autosomal recessive mutation, designated flaky skin (fsn –/–), has been described in the inbred A/J mouse strain (The Jackson Laboratory, Bar Harbour, Me.). The mice have a skin disorder similar to psoriasis in humans. Psoriasis is a common disease affecting 2% of the population, which is characterised by a chronic inflammation associated with thickening and scaling of the skin. Histology of skin lesions shows increased proliferation of the cells in the epidermis, the uppermost layer of skin, together with the abnormal presence of inflammatory cells, including lymphocytes, in the dermis, the layer of skin below the epidermis. While the cause of the disease is unclear, psoriasis is associated with a disturbance of the immune system involving T lymphocytes. The disease occurs more frequently in family members, indicating the involvement of a genetic factor as well. Mice with the fsn gene mutation have not only a psoriatic-like skin disease but also other abnormalities involving cells of the immune and hematopoietic system. These mice have markedly increased numbers of lymphocytes associated with enlarged lymphoid organs, including the spleen and lymph nodes. In addition, their livers are enlarged, and the mice are anaemic. Genes and proteins expressed in abnormal lymph nodes of fsn−/− mice may thus influence the development or function of cells of the immune and hematopoietic system, the response of these cells in inflammatory disorders, and the responses of skin and other connective tissue cells to inflammatory signals.

There is a need in the art to identify genes encoding proteins that function to modulate all cells of the immune system. These proteins from normal or abnormal lymph nodes may be useful in modifying the immune responses to tumour cells or infectious agents such as bacteria, viruses, protozoa and worms. Such proteins may also be useful in the treatment of disorders where the immune system initiates unfavourable reactions to the body, including Type I hypersensitivity reactions (such as hay fever, eczema, allergic rhinitis and asthma), and Type II hypersensitivity reactions (such as transfusion reactions and haemolytic disease of newborns). Other unfavourable reactions are initiated during Type III reactions, which are due to immune complexes forming in infected organs during persistent infection or in the lungs following repeated inhalation of materials from moulds, plants or animals, and in Type IV reactions in diseases such as leprosy, schistosomiasis and dermatitis.

Novel proteins of the immune system may also be useful in treating autoimmune diseases where the body recognises itself as foreign. Examples of such diseases include rheumatoid arthritis, Addison's disease, ulcerative colitis, dermatomyositis and lupus. Such proteins may also be useful during tissue transplantation, where the body will often recognise the transplanted tissue as foreign and attempt to kill it, and also in bone marrow transplantation when there is a high risk of graft-versus-host disease where the transplanted cells attack their host cells, often causing death.

There thus remains a need in the art for the identification and isolation of genes encoding proteins expressed in cells of the immune system for use in the development of therapeutic agents for the treatment of disorders including those associated with the immune system.

SUMMARY OF THE INVENTION

The present invention is based upon the identification and isolation of FGFR5 polypeptides and functional portions of polypeptides expressed in lymph node stromal cells of fsn −/− mice and human homologues of such polypeptides, together with polynucleotides encoding such polypeptides and expression vectors and host cells comprising such polynucleotides. Within certain embodiments, the present invention provides compositions comprising such polynucleotides, and methods for their use. More specifically, the present invention provides polynucleotides encoding various FGFR5 homologues and splice variants, polypeptides encoded by the inventive polynucleotides, and antibodies and other FGFR5 binding molecules that are useful in therapeutic and diagnostic methods disclosed herein.

In specific embodiments, isolated polypeptides are provided that comprise an amino acid sequence selected from the group consisting of sequences provided in SEQ ID NO: 5–8, 13–15, and variants of such sequences, as defined herein. Isolated polypeptides that comprise at least a functional portion of a polypeptide comprising an amino acid sequence selected from the group consisting of: (a) sequences provided in SEQ ID NO: 5–8, and 13–15; and (b) variants of a sequence of SEQ ID NO: 5–8, and 13–15, as defined herein, are also provided.

In other embodiments, the present invention provides isolated polynucleotides comprising a nucleotide sequence selected from the group consisting of: (a) sequences provided in SEQ ID NO: 1–4 and 9; (b) complements of sequences provided in SEQ ID NO: 1–4 and 9; (c) reverse complements of sequences provided in SEQ ID NO: 1–4 and 9; (d) reverse sequences of sequences provided in SEQ ID NO: 1–4 and 9; and (e) variants of the sequences of (a)–(d), as defined herein.

Still further embodiments of the present invention provide splice variants of the FGFR5 polynucleotide presented in SEQ ID NOs: 1–4 and 9. Exemplary splice variants include the polynucleotides presented herein as SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142.

Other embodiments provide polynucleotides comprising a nucleotide sequence selected from the group consisting of: (a) sequences provided in SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; (b) complements of sequences provided in SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; (c) reverse complements of sequences provided in SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; (d) reverse sequences of sequences provided in SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142; and (e) variants of the sequences of (a)–(d), as defined herein.

The present invention also provides polypeptides encoded by the splice variant polynucleotides of SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142. Exemplary polypeptides encoded by these splice variants include the polypeptides presented herein as SEQ ID NOs: 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143.

In certain embodiments, isolated polypeptides are provided that comprise an amino acid sequence selected from the group consisting of sequences provided in SEQ ID NOs: 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143, and variants of such sequences, as defined herein. Isolated polypeptides which comprise at least a functional portion of a polypeptide comprising an amino acid sequence selected from the group consisting of: (a) sequences provided in SEQ ID NOs: 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143; and (b) variants of a sequence of SEQ ID NOs: 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143, as defined herein, are also provided.

In related embodiments, the present invention provides expression vectors comprising the above polynucleotides, together with host cells transformed with such vectors.

In another aspect, the present invention provides fusion proteins comprising at least one polypeptide of the present invention.

Still further aspects of the present invention provide antibodies and/or other binding molecules that bind to one or more antigenic epitopes present on one or more of the polypeptides presented herein. Within certain embodiments, antibodies are antagonists of FGFR5 activity while other embodiments provide agonists of FGFR5 activity. As discussed in further detail herein, antibodies may be selected from the group consisting of polyclonal antibodies and monoclonal antibodies and may comprise one or more fragments of a monoclonal antibody such as, for example, a Fab fragment or an scFv. Binding molecules include, for example, small molecules that bind to and either antagonize or agonize the activity of FGFR5.

As detailed below, the isolated polynucleotides, polypeptides and antibodies of the present invention may be usefully employed in the preparation of therapeutic agents for the treatment of autoimmune diseases and other immunological disorders. In related embodiments, methods for modulating the growth of blood vessels, and for the treatment of disorders such as inflammatory disorders, disorders of the immune system, cancer, sarcoidal and granulomatous disorders, fibroblast growth factor-mediated disorders and viral disorders are provided. Examples of such disorders include HIV-infection; epithelial, lymphoid, myeloid, stromal and neuronal cancers; arthritis; inflammatory bowel disease; and cardiac failure.

The present invention further encompasses methods for modulating an immune response, for down-regulating the expression of osteopontin, and/or for treating disorders characterized by an elevated level of osteopontin, such as systemic lupus erythematosus, by reducing the effective amount, inactivating, and/or inhibiting the activity of an inventive polypeptide comprising a sequence of SEQ ID NO: 5–8, and 13–15 (known as FGFR5) or a variant thereof, or a polynucleotide that encodes such a polypeptide. Alternatively or additionally, such methods may reduce the effective amount of, inactivate, and/or inhibit the activity of a polypeptide encoded by one of the FGFR5 splice variants indicated above including, but not limited to, the polypeptides provided within of SEQ ID NOs: 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143.

Such methods include administering a component selected from the group consisting of: antibodies, or antigen-binding fragments thereof, that specifically bind to FGFR5; soluble FGFR5 ligands; small molecule inhibitors of FGFR5; anti-sense oligonucleotides to FGFR5; FGFR5-specific small interfering RNA molecules (siRNA or RNAi); monomeric soluble FGFR5; and engineered soluble FGFR5 molecules that bind FGFR5 ligand but do not stimulate signaling. As used herein, the term "elevated level" refers to a level that is higher than the average normal level for a specific patient population. The inventive methods may thus be employed in the treatment of disorders characterized by an abnormal or excessive level of OPN compared to levels seen in a normal healthy population.

Thus, the present invention provides compositions comprising modulators of FGFR5 gene expression. Such modulators include, but are not limited to (a) small molecule inhibitors of gene expression, (b) anti-sense oligonucleotides, and (c) small interfering RNA molecules (siRNA or RNAi). Anti-sense oligonucleotides include (a) anti-sense expression vectors; (b) anti-sense oligodeoxyribonucleotides, (c) anti-sense phosphorothioate oligodeoxyribonucleotides, (d) anti-sense oligoribonucleotides, and (e) anti-sense phosphorothioate oligoribonucleotides.

Within certain embodiments, modulators of FGFR5 gene expression specifically bind to polynucleotides including: (a) polynucleotides comprising a sequence selected from the group consisting of SEQ ID NO: 1–4 and 9; (b) complements of a polynucleotide comprising a sequence selected from the group consisting of SEQ ID NO: 1–4 and 9; (c) reverse sequences of a polynucleotide comprising a sequence selected from the group consisting of SEQ ID NO: 1–4 and 9; (d) polynucleotides that encode a polypeptide comprising a sequence selected from the group consisting of: SEQ ID NO: 5–8 and 13–15; (e) complements of polynucleotides that encode a polypeptide comprising a sequence selected from the group consisting of: SEQ ID NO: 5–8 and 13–15; and (f) reverse sequences of polynucleotides that encodes a polypeptide comprising a sequence selected from the group consisting of: SEQ ID NO: 5–8 and 13–15. Alternatively or additionally, modulators of the present invention specifically bind to one or more polynucleotide selected from the group consisting of SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142.

Within certain aspects of the present invention, the modulators of FGFR5 gene expression are effective in decreasing FGFR5 gene expression when contacted with a population of cells expressing FGFR5. Within other aspects, the modulators of FGFR5 gene expression are effective in decreasing osteopontin gene expression when contacted with a population of cells expressing FGFR5.

Other embodiments of the present invention provide compositions comprising binding agents wherein the binding agents are modulators of FGFR5 polypeptide function and wherein the binding agents include (a) small molecules; (b) antibodies or antigen-binding fragments thereof; (c) small chain antibody fragments (scFv); (d) camelid heavy chain antibodies (HCAb) or heavy chain variable domains thereof ($V_{HH}$); and (e) FGFR5 ligands or antigen-binding fragments thereof.

Within certain aspects of these embodiments, the binding agents specifically bind to polypeptides including (a) polypeptides encoded by a polynucleotide comprising a sequence selected from the group consisting of SEQ ID NO: 1–4 and 9 or a complement thereof; and (b) polypeptides comprising a sequence selected from the group consisting of: SEQ ID NO: 5–8 and 13–15. Within additional or alternative aspects, the binding agents specifically bind to a polypeptide including (a) polypeptides encoded by a polynucleotide selected from the group consisting of SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142 or (b) polypeptides comprising a sequence selected from the group consisting of SEQ ID NOs: 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143.

Depending upon the precise application contemplated, binding agents may be agonists of FGFR5 polypeptide function that are, for example, effective in increasing osteopontin gene expression in a population of cells expressing FGFR5 polypeptide when the agonist is contacted with the population of cells. Alternatively, binding agents may be antagonists of FGFR5 polypeptide function that are, for example, effective in decreasing osteopontin gene expression in a population of cells expressing FGFR5 polypeptide when the antagonist is contacted with the population of cells.

Still further embodiments of the present invention provide methods for modulating osteopontin expression in a population of cells. Within certain aspects, these methods comprise the step of contacting the population of cells with one of the compositions recited herein above. Thus, within certain methods, the modulator of FGFR5 gene expression specifically binds to a polynucleotide including: (a) polynucleotides comprising a sequence selected from the group consisting of SEQ ID NO: 1–4 and 9; (b) complements of polynucleotides comprising a sequence selected from the group consisting of SEQ ID NO: 1–4 and 9; (c) reverse sequences of polynucleotides comprising a sequence selected from the group consisting of SEQ ID NO: 1–4 and 9; (d) polynucleotides that encode polypeptides comprising a sequence selected from the group consisting of: SEQ ID NO: 5–8 and 13–15; (e) complements of polynucleotides that encode polypeptides comprising sequences selected from the group consisting of: SEQ ID NO: 5–8 and 13–15; and (f) reverse sequences of polynucleotides that encode polypeptides comprising sequences selected from the group consisting of: SEQ ID NO: 5–8 and 13–15.

Within these methods, the modulator of FGFR5 gene expression is effective in decreasing FGFR5 gene expression when contacted with a population of cells expressing FGFR5 and/or decreasing osteopontin gene expression when contacted with a population of cells expressing FGFR5. Suitable such modulators of FGFR5 gene expression include anti-sense oligonucleotides such as: (a) anti-sense expression vectors; (b) anti-sense oligodeoxyribonucleotides, (c) anti-sense phosphorothioate oligodeoxyribonucleotides, (d) anti-sense oligoribonucleotides, and (e) anti-sense phosphorothioate oligoribonucleotides.

Within other aspects, the present invention provides methods for modulating osteopontin expression in a population of cells the method comprising the step of contacting the population of cells with the composition comprising a binding agent as recited herein above. For example, such methods employ binding agents that specifically bind to polypeptides such as (a) polypeptides encoded by a polynucleotide comprising a sequence selected from the group consisting of SEQ ID NO: 1–4 and 9 or a complement thereof; and (b) polypeptides comprising a sequence selected from the group consisting of: SEQ ID NO: 5–8 and 13–15. Binding agents include agonists of FGFR5 polypeptide function wherein binding of the agonists to the population of cells results in an increase in osteopontin expression when the agonist is contacted with the population of cells. Alternatively, binding agents include antagonists of FGFR5 polypeptide function wherein binding of the antagonist to the population of cells results in a decrease in osteopontin expression when the antagonist is contacted with the population of cells.

Still further embodiments of the present invention provide modulators of FGFR5 gene expression in a medicament for the treatment of a disease associated with elevated osteopontin expression. Within certain aspects, the modulator includes: (a) small molecule inhibitors of gene expression, (b) anti-sense oligonucleotides, and (c) small interfering RNA molecules (siRNA or RNAi).

Modulators of FGFR5 gene expression specifically bind to polynucleotides including: (a) polynucleotides comprising sequences selected from the group consisting of SEQ ID NO: 1–4 and 9; (b) complements of polynucleotides comprising sequences selected from the group consisting of SEQ ID NO: 1–4 and 9; (c) reverse sequences of polynucleotides comprising a sequence selected from the group consisting of SEQ ID NO: 1–4 and 9; (d) polynucleotides that encodes a polypeptide comprising a sequence selected from the group consisting of: SEQ ID NO: 5–8 and 13–15; (e) complements of polynucleotides that encodes a polypeptide comprising a sequence selected from the group consisting of: SEQ ID NO: 5–8 and 13–15; and (f) reverse sequences of polynucleotides that encode a polypeptide comprising a sequence selected from the group consisting of: SEQ ID NO: 5–8 and 13–15.

Exemplary diseases associated with elevated osteopontin gene expression that are suitably treated with inventive modulators of FGFR5 gene include cancers, multiple sclerosis (MS), systemic lupus erythematosus (SLE), diabetes, rheumatoid arthritis (RA), sarcoidosis, tuberculosis, kidney stones, atherosclerosis, vasculitis, nephritis, arthritis, and osteoporosis.

Within other related aspects of the present invention are provided uses of binding agents in medicaments for the treatment of diseases associated with elevated osteopontin expression wherein the binding agents are antagonists of FGFR5 polypeptide function and wherein the binding agents include: (a) small molecules; (b) antibodies or antigen-binding fragments thereof; (c) small chain antibody fragments (scFv); and (d) a camelid heavy chain antibodies (HCAb) or heavy chain variable domains ($V_{HH}$) thereof.

Exemplary binding agents presented herein specifically bind to polypeptides including: (a) polypeptides encoded by a polynucleotide comprising a sequence selected from the group consisting of SEQ ID NO: 1–4 and 9 or a complement thereof; and (b) polypeptides comprising a sequence selected from the group consisting of: SEQ ID NO: 5–8 and 13–15.

Binding agents such as those recited herein may be suitably employed in the treatment of diseases associated with elevated osteopontin expression including cancers, multiple sclerosis (MS), systemic lupus erythematosus (SLE), diabetes, rheumatoid arthritis (RA), sarcoidosis, tuberculosis, kidney stones, atherosclerosis, vasculitis, nephritis, arthritis, and osteoporosis.

Other embodiments of the present invention provide uses of binding agents in medicaments for the treatment of a diseases associated with reduced osteopontin expression wherein the binding agent is an agonist of FGFR5 polypeptide function and wherein the binding agent includes: (a) small molecules; (b) antibodies or antigen-binding fragments thereof; (c) small chain antibody fragments (scFv); (d) camelid heavy chain antibodies (HCAb) or heavy chain variable domains ($V_{HH}$) thereof; and (e) FGFR5 ligands or FGFR5-binding fragments thereof.

Binding agents suitable for uses in diseases associated with reduced osteopontin expression specifically bind to polypeptides including: (a) polypeptides encoded by polynucleotides comprising a sequence selected from the group consisting of SEQ ID NO: 1–4 and 9 or a complement thereof; and (b) polypeptides comprising a sequence selected from the group consisting of: SEQ ID NO: 5–8 and 13–15. An exemplary disease associated with reduced osteopontin expression is osteopetrosis.

Other embodiments of the present invention provide methods for the treatment of a disease associated with elevated osteopontin expression that comprise the step of administering to a patient one of the compositions recited herein above. Related aspects of the present invention provide methods for the treatment of cancers, including breast cancer, hepatocellular carcinoma, and colon cancer; methods for the treatment of bone disorders, including osteoporosis and osteopetrosis; and methods for the treatment of FGFR5-associated disorders in a patient. Each of these methods comprise the administration of one or more of the compositions presented herein.

Still further embodiments of the present invention provide methods for inhibiting the expression of osteopontin in populations of cells that comprise reducing the amount of a polypeptide in the cells, wherein the polypeptide comprises an amino acid sequence including: (a) a sequence provided in SEQ ID NO: 5–8 and 13–15; (b) sequences having at least 75% identity to a sequence provided in SEQ ID NO: 5–8 and 13–15; (c) sequences having at least 90% identity to a sequence provided in SEQ ID NO: 5–8 and 13–15; and (d) sequences having at least 95% identity to a sequence provided in SEQ ID NO: 5–8 and 13–15.

Related methods for inhibiting the expression of osteopontin in a population of cells, comprise the step of inhibiting the activity of a polypeptide in the population of cells by administering a composition presented herein wherein said polypeptide comprising an amino acid sequence such as: (a) a sequence provided in SEQ ID NO: 5–8 and 13–15; (b) sequences having at least 75% identity to a sequence provided in SEQ ID NO: 5–8 and 13–15; (c) sequences having at least 90% identity to a sequence provided in SEQ ID NO: 5–8 and 13–15; and (d) sequences having at least 95% identity to a sequence provided in SEQ ID NO: 5–8 and 13–15.

Other methods are provided herein for treating disorders characterized by an elevated level of osteopontin that comprise the step of administering a composition that comprises a binding agent that specifically binds to a polypeptide comprising an amino acid sequence selected from the group consisting of: (a) sequences provided in SEQ ID NO: 5–8 and 13–15; (b) sequences having at least 75% identity to a sequence provided in SEQ ID NO: 5–8 and 13–15; (c) sequences having at least 90% identity to a sequence provided in SEQ ID NO: 5–8 and 13–15; and (d) sequences having at least 95% identity to a sequence provided in SEQ ID NO: 5–8 and 13–15.

Still further methods are provided herein for treating a disorder characterized by an elevated level of osteopontin, comprising administering a composition presented herein wherein the composition comprises a modulator of FGFR5 gene expression that binds specifically to a polynucleotide comprising a sequence selected from the group consisting of: (a) sequences provided in SEQ ID NO: 1–4 and 9; (b) sequences having at least 75% identity to a sequence provided in SEQ ID NO: 1–4 and 9; (c) sequences having at least 90% identity to a sequence provided in SEQ ID NO: 1–4 and 9; and (d) sequences having at least 95% identity to a sequence provided in SEQ ID NO: 1–4 and 9.

The above-mentioned and additional features of the present invention, together with the manner of obtaining them, will be best understood by reference to the following more detailed description. All references disclosed herein are hereby incorporated by reference in their entirety as if each was incorporated individually.

BRIEF DESCRIPTION OF THE DRAWINGS

FIG. 1 is the amino acid sequence of the murine FGF receptor muFGFR5β (SEQ ID NO: 6). Several conserved domains were identified that are involved in the dimerization, ligand binding and activity of the receptor. The signal peptide and transmembrane domain are underlined, and the six cysteines conserved among the FGFR family members are in bold and underlined. Four glycosylation sites are double underlined. Three immunoglobulin domains (Ig loops) were identified (Ig loop 1: residues 40–102; Ig loop 2: residues 161–224; Ig loop 3: residues 257–341), as well as two tyrosine kinase phosphorylation sites (residues 198–201, 325–332), a cAMP- and cGMP-dependent protein kinase phosphorylation site (residues 208–215) and four prenyl group binding sites (CAAX boxes). The phosphorylation sites and CAAX boxes are boxed. A heparin binding domain was identified (residues 150–167; boxed and in bold) and this partially overlaps the CAM binding domain (residues 141–160; italics and underlined).

FIG. 9 illustrates the stimulation of NK cell adherence by FGFR5β and FGFR5γ as measured by the presence of anti-CD56 antibodies, markers of NK cells. The filled histograms represent the adherent PBMC stained with the NK cell marker CD56 and the open histograms represent the same cells stained with the isotype-matched control antibody.

FIG. 10 shows the amino acid sequence of human FGFR5 (SEQ ID NO: 8). Several conserved domains were identified that are involved in the dimerization, ligand binding and activity of the receptor. The signal peptide is underlined, and five of the six cysteines conserved among the FGFR family members are in bold and underlined. Three immunoglobulin domains (Ig loops) were identified (Ig loop 1: residues 44–106; Ig loop 2: residues 165–228; Ig loop 3 (partial): residues 261–324), as well as a tyrosine kinase phosphorylation sites (residues 212–219), a cAMP- and cGMP-dependent protein kinase phosphorylation site (residues 202–205) and four prenyl group binding sites (CAAX boxes). The phosphorylation sites and CAAX boxes are boxed. A heparin-binding domain was identified (residues 154–171; boxed and in bold) and this partially overlaps the CAM binding domain (residues 145–164; italics and underlined).

FIGS. 11A–C are bar graphs depicting upregulation of OPN (FIG. 11A), PBMC (FIG. 11B), and adherent PBMC (predominantly monocytes; FIG. 11C) following stimulation with FGFR2, FGFR5, LPS or media alone for 24 hours. Supernatants were collected for cytokine analysis.

FIGS. 12A–C are graphs depicting the effect of FGFR5 on the proliferation of murine bone marrow cells (BMC; FIG. 12A), non-adherent BMC (FIG. 12B) and adherent BMC (FIG. 12C).

FIG. 15 is a bar graph depicting the preferential expansion of pre-B cells where FIG. 15A depicts the percentage of B220+ cells in total viable cells and FIG. 15B depicts the percentage of pre/pro-B cells in total viable B cells.

DETAILED DESCRIPTION OF THE INVENTION

Figure 2:
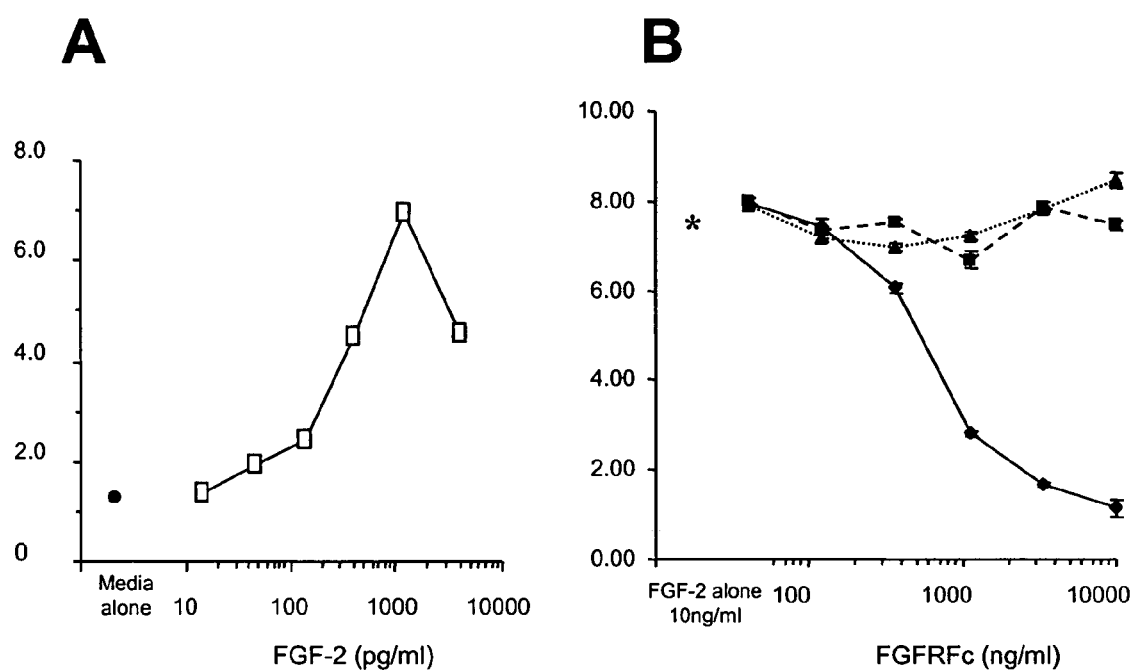
FIG. 2A shows the induction of genes under the control of the SRE. NIH-3T3 SRE cells were stimulated with a titration of FGF-2 in the presence of 10 μg/ml of heparin for 6 hours. Closed circles represent media alone, open squares represent titration of FGF-2.
FIG. 2B shows the competition analysis of NIH-3T3 SRE cells treated with a standard dose of FGF-2 plus heparin in the presence of increasing concentrations of FGFR2Fc (closed diamonds), FGFR5βFc (closed squares), FGFR5γFc (closed triangles) and FGF-2 alone (asterisk). The mean and SD were calculated for both experiments from three separate wells and are represented as fold-induction of the reporter gene relative to control.

In one aspect, the present invention provides polynucleotides isolated from lymph node stromal cells of fsn −/− mice and isolated polypeptides encoded by such polynucleotides, together with human homologues of such polynucleotides and polypeptides.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al., *Methods in Enzymol.* 254: 363–375, 1995 and Kawasaki et al., *Artific. Organs* 20: 836–848, 1996.

In specific embodiments, the isolated polynucleotides of the present invention comprise a polynucleotide sequence selected from the group consisting of sequences provided in SEQ ID NO: 1–4 and 9. Within alternative embodiments are provided splice variants of any one or more of SEQ ID NO: 1–4 and 9. Exemplary splice variants are presented herein as SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142.

Complements of such isolated polynucleotides, reverse complements of such isolated polynucleotides and reverse sequences of such isolated polynucleotides are also provided, together with polynucleotides comprising at least a specified number of contiguous residues (x-mers) of any of the above-mentioned polynucleotides, extended sequences corresponding to any of the above polynucleotides, anti-sense sequences corresponding to any of the above polynucleotides, and variants of any of the above polynucleotides, as that term is described in this specification.

The definitions of the terms "complement", "reverse complement" and "reverse sequence", as used herein, are best illustrated by the following example. For the sequence 5' AGGACC 3', the complement, reverse complement and reverse sequence are as follows:

```
complement              3'TCCTGG 5' reverse complement      3'GGTCCT 5' reverse sequence        5'CCAGGA 3'.
```

Preferably, sequences that are complements of a specifically recited polynucleotide sequence are complementary over the entire length of the specific polynucleotide sequence.

Some of the polynucleotides of the present invention are "partial" sequences, in that they do not represent a full length gene encoding a full length polypeptide. Such partial sequences may be extended by analyzing and sequencing various DNA libraries using primers and/or probes and well known hybridization and/or PCR techniques. Partial sequences may be extended until an open reading frame encoding a polypeptide, a full length polynucleotide and/or gene capable of expressing a polypeptide, or another useful portion of the genome is identified. Such extended sequences, including full length polynucleotides and genes, are described as "corresponding to" a sequence identified as one of the sequences of SEQ ID NO: 1–4 and 9, or a variant thereof, or a portion of one of the sequences of SEQ ID NO: 1–4 and 9, or a variant thereof, when the extended polynucleotide comprises an identified sequence or its variant, or an identified contiguous portion (x-mer) of one of the sequences of SEQ ID NO: 1–4 and 9, or a variant thereof. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Similarly, RNA sequences, reverse sequences, complementary sequences, antisense sequences, and the like, corresponding to the polynucleotides of the present invention, may be routinely ascertained and obtained using the cDNA sequences identified as SEQ ID NO: 1–4 and 9 and/or the splice variant sequences of SEQ ID NOs: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142.

The polynucleotides identified as SEQ ID NO: 1–4 and 9 contain open reading frames ("ORFs") or partial open reading frames encoding polypeptides or functional portions of polypeptides. Open reading frames may be identified using techniques that are well known in the art. These techniques include, for example, analysis for the location of known start and stop codons, most likely reading frame identification based on codon frequencies, etc. Open reading frames and portions of open reading frames may be identified in the polynucleotides of the present invention. Suitable tools and software for ORF analysis are well known in the art and include, for example, GeneWise, available from The Sanger Center, Wellcome Trust Genome Campus, Hinxton, Cambridge, CB10 1SA, United Kingdom; Diogenes, available from Computational Biology Centers, University of Minnesota, Academic Health Center, UMHG Box 43 Minneapolis Minn. 55455; and GRAIL, available from the Informatics Group, Oak Ridge National Laboratories, Oak Ridge, Tenn. Tenn. Once a partial open reading frame is identified, the polynucleotide may be extended in the area of the partial open reading frame using techniques that are well known in the art until the polynucleotide for the full open reading frame is identified. Thus, open reading frames encoding polypeptides and/or functional portions of polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

In another aspect, the present invention provides isolated polypeptides encoded, or partially encoded, by the above polynucleotides. The term "polypeptide", as used herein, encompasses amino acid chains of any length including full length proteins, wherein amino acid residues are linked by covalent peptide bonds. Polypeptides of the present invention may be naturally purified products, or may be produced partially or wholly using recombinant techniques. Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

The term "polypeptide encoded by a polynucleotide" as used herein, includes polypeptides encoded by a nucleotide sequence which includes the partial isolated DNA sequences of the present invention. In specific embodiments, the inventive polypeptides comprise an amino acid sequence selected from the group consisting of sequences provided in SEQ ID NO: 5–8, 13–15, and variants of such sequences. Other embodiments provide polypeptide that comprise an amino acid sequence encoded by a splice variant of one of the FGFR5 polynucleotides presented herein. For example, the present invention provides the amino acid sequences of the following FGFR5 splice variant encoded polypeptides: SEQ ID NOs: 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

All of the polynucleotides and polypeptides described herein are isolated and purified, as those terms are commonly used in the art. Preferably, the polypeptides and polynucleotides are at least about 80% pure, more preferably at least about 90% pure, and most preferably at least about 99% pure.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 75%, more preferably at least 80%, more preferably yet at least 90%, and most preferably, at least 95% or 98% identity to a sequence of the present invention. The percentage identity may be determined using well known techniques. In one embodiment, the percentage identity is determined by aligning the two sequences to be compared as described below, determining the number of identical residues in the aligned portion, dividing that number by the total number of residues in the inventive (queried) sequence, and multiplying the result by 100.

Polynucleotides and polypeptides have a specified percentage identity to a polynucleotide or polypeptide identified in one of SEQ ID NO: 1–9, 13–15; to a splice variant polynucleotide of SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and/or 142; as well as to a polypeptide encoded by one of these splice variant polynucleotides as presented in SEQ ID NOs: 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143, and thus share a high degree of similarity in their primary structure.

In addition to a specified percentage identity to a polynucleotide of the present invention, variant polynucleotides and polypeptides preferably have additional structural and/or functional features in common with a polynucleotide of the present invention. Polynucleotides having a specified degree of identity to, or capable of hybridizing to, a polynucleotide of the present invention preferably additionally have at least one of the following features: (1) they contain an open reading frame, or partial open reading frame, encoding a polypeptide, or a functional portion of a polypeptide, having substantially the same functional properties as the polypeptide, or functional portion thereof, encoded by a polynucleotide in a recited SEQ ID NO; or (2) they contain identifiable domains in common.

Polynucleotide or polypeptide sequences may be aligned, and percentages of identical nucleotides or amino acids in a specified region may be determined against another polynucleotide or polypeptide, using computer algorithms that are publicly available. The BLASTN and FASTA algorithms, set to the default parameters described in the documentation and distributed with the algorithm, may be used for aligning and identifying the similarity of polynucleotide sequences. The alignment and similarity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, *Proc. Natl. Acad. Sci. USA* 85:2444–2448, 1988; and in Pearson, *Methods in Enzymol.* 183:63–98, 1990. The FASTA software package is available from the University of Virginia by contacting the Assistant Provost for Research, University of Virginia, PO Box 9025, Charlottesville, Va. 22906-9025. The BLASTN software is available from the National Center for Biotechnology Information (NCBI), National Library of Medicine, Building 38A, Room 8N805, Bethesda, Md. 20894. The BLASTN algorithm Version 2.0.11 [Jan. 20, 2000] set to the default parameters described in the documentation and distributed with the algorithm, is preferred for use in the determination of polynucleotide variants according to the present invention. The use of the BLAST family of algorithms, including BLASTN, BLASTP and BLASTX, is described in the publication of Altschul et al., "Gapped BLAST and PSI-BLAST: a new generation of protein database search programs," *Nucleic Acids Res.* 25:3389–3402, 1997.

The following running parameters are preferred for determination of alignments and similarities using BLASTN that contribute to the E values and percentage identity for polynucleotides: Unix running command with the following default parameters: blastall -p blastn -d embldb -e 10 -G 0 -E 0 -r 1 -v 30 -b 30 -i queryseq -o results; and parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In]; -o BLAST report Output File [File Out] Optional.

The following running parameters are preferred for determination of alignments and similarities using BLASTP that contribute to the E values and percentage identity of polypeptide sequences: blastall -p blastp -d swissprotdb -e 10 -G 0 -E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

As noted above, the percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity. By way of example, a queried polynucleotide having 220 nucleic acids has a hit to a polynucleotide sequence in the EMBL database having 520 nucleic acids over a stretch of 23 nucleotides in the alignment produced by the BLASTN algorithm using the default parameters. The 23nucleotide hit includes 21 identical nucleotides, one gap and one different nucleotide. The percentage identity of the queried polynucleotide to the hit in the EMBL database is thus 21/220 times 100, or 9.5%.

The percentage identity of polypeptide sequences may be determined in a similar fashion.

The BLASTN and BLASTX algorithms also produce "Expect" values for polynucleotide and polypeptide alignments. The Expect value (E) indicates the number of hits one can "expect" to see over a certain number of contiguous sequences by chance when searching a database of a certain size. The Expect value is used as a significance threshold for determining whether the hit to a database indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being related. For sequences having an E value of 0.01 or less over aligned and matched portions, the probability of finding a match by chance in the EMBL database is 1% or less using the BLASTN algorithm. E values for polypeptide sequences may be determined in a similar fashion using various polypeptide databases, such as the SwissProt database.

According to one embodiment, "variant" polynucleotides and polypeptides, with reference to each of the polynucleotides and polypeptides of the present invention, preferably comprise sequences having the same number or fewer nucleotides or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being related to the polynucleotide or polypeptide of the present invention, measured as having an E value of 0.01 or less using the BLASTN or BLASTX algorithms set at the default parameters. According to a preferred embodiment, a variant polynucleotide is a sequence having the same number or fewer nucleic acids than a polynucleotide of the present invention that has at least a 99% probability of being related to the polynucleotide of the present invention, measured as having an E value of 0.01 or less using the BLASTN algorithm set at the default parameters. Similarly, according to a preferred embodiment, a variant polypeptide is a sequence having the same number or fewer amino acids than a polypeptide of the present invention that has at least a 99% probability of being related as the polypeptide of the present invention, measured as having an E value of 0.01 or less using the BLASTP algorithm set at the default parameters.

In an alternative embodiment, variant polynucleotides are sequences that hybridize to a polynucleotide of the present invention under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents, and extent of base mismatching, the combination of parameters is more important than the absolute measure of any one alone. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity to a polypeptide encoded by a polynucleotide of the present invention. Thus, polynucleotides comprising sequences that differ from the polynucleotide sequences recited in SEQ ID NO: 1–4, 9, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and/or 142, or complements, reverse sequences, or reverse complements of those sequences, as a result of conservative substitutions are contemplated by and encompassed within the present invention.

Additionally, polynucleotides comprising sequences that differ from the polynucleotide sequences recited in SEQ ID NO: 1–4, 9, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and/or 142 or complements, reverse complements or reverse sequences thereof, as a result of deletions and/or insertions totaling less than 10% of the total sequence length are also contemplated by and encompassed within the present invention.

Similarly, polypeptides comprising sequences that differ from the polypeptide sequences recited in SEQ ID NO: 5–8, 13–15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143 as a result of amino acid substitutions, insertions, and/or deletions totaling less than 10% of the total sequence length are contemplated by and encompassed within the present invention, provided the variant polypeptide has functional properties which are substantially the same as, or substantially similar to those of a polypeptide comprising a sequence of SEQ ID NO: 5–8, 13–15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, and 143.

Polynucleotides of the present invention also comprehend polynucleotides comprising at least a specified number of contiguous residues (x-mers) of any of the polynucleotides identified as SEQ ID NO: 1–4 and 9, complements, reverse sequences, and reverse complements of such sequences, and their variants. Similarly, polypeptides of the present invention comprehend polypeptides comprising at least a specified number of contiguous residues (x-mers) of any of the polypeptides identified as SEQ ID NO: 5–8, 13–15, and their variants. As used herein, the term "x-mer," with reference to a specific value of "x," refers to a sequence comprising at least a specified number ("x") of contiguous residues of any of the polynucleotides identified as SEQ ID NO: 1–4 and 9, or the polypeptides identified as SEQ ID NO: 5–8 and 13–15. According to preferred embodiments, the value of x is preferably at least 20, more preferably at least 40, more preferably yet at least 60, and most preferably at least 80. Thus, polynucleotides and polypeptides of the present invention comprise a 20-mer, a 40-mer, a 60-mer, an 80-mer, a 100-mer, a 120-mer, a 150-mer, a 180-mer, a 220-mer, a 250-mer, a 300-mer, 400-mer, 500-mer or 600-mer of a polynucleotide or polypeptide identified as SEQ ID NO: 1–9, 13–15, and variants thereof.

The inventive polynucleotides may be isolated by high throughput sequencing of cDNA libraries prepared from lymph node stromal cells of fsn −/− mice as described below in Example 1. Alternatively, oligonucleotide probes based on the sequences provided in SEQ ID NO: 1–4 and 9 can be synthesized and used to identify positive clones in either cDNA or genomic DNA libraries from lymph node stromal cells of fsn −/− mice by means of hybridization or polymerase chain reaction (PCR) techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art (see, for example, Mullis et al., *Cold Spring Harbor Symp. Quant. Biol.,* 51:263, 1987; Erlich ed., *PCR Technology*, Stockton Press, NY, 1989; Sambrook et al., *Molecular cloning—a laboratory manual*, Cold Spring Harbor Laboratory Press, Cold Spring Harbor, N.Y., 1989). Positive clones may be analyzed by restriction enzyme digestion, DNA sequencing or the like.

The polynucleotides of the present invention may alternatively be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

Polypeptides of the present invention may be produced recombinantly by inserting a DNA sequence that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, insect, yeast or a mammalian cell line such as COS or CHO. The DNA sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence selected from the group consisting of sequences provided in SEQ ID NO: 5–8, 13–15, and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity. Such functional portions generally comprise at least about 5 amino acid residues, more preferably at least about 10, and most preferably at least about 20 amino acid residues. Functional portions of the inventive polypeptides may be identified by first preparing fragments of the polypeptide, by either chemical or enzymatic digestion of the polypeptide or mutation analysis of the polynucleotide that encodes for the polypeptide, and subsequently expressing the resultant mutant polypeptides. The polypeptide fragments or mutant polypeptides are then tested to determine which portions retain the biological activity of the full-length polypeptide.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (Merrifield, *J. Am. Chem. Soc.* 85:2149–2154, 1963). Equipment for automated synthesis of polypeptides is available from suppliers such as Perkin Elmer/Applied BioSystems, Inc. (Foster City, Calif.), and may be operated according to the manufacturer's instructions. Variants of a native polypeptide may be prepared using standard mutagenesis techniques, such as oligonucleotide-directed site-specific mutagenesis (see, for example, Kunkel, *Proc. Natl. Acad. Sci. USA* 82:488–492, 1985). Sections of DNA sequence may also be removed using standard techniques to permit preparation of truncated polypeptides.

The present invention also provides fusion proteins comprising a first and a second inventive polypeptide or, alternatively, a polypeptide of the present invention and a known polypeptide, together with variants of such fusion proteins. The fusion proteins of the present invention may include a linker peptide between the first and second polypeptides.

A polynucleotide encoding a fusion protein of the present invention is constructed using known recombinant DNA techniques to assemble separate polynucleotides encoding the first and second polypeptides into an appropriate expression vector. The 3' end of a polynucleotide encoding the first polypeptide is ligated, with or without a peptide linker, to the 5' end of a DNA sequence polynucleotide encoding the second polypeptide so that the reading frames of the sequences are in phase to permit mRNA translation of the two polynucleotides into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric interference.

The ligated polynucleotides encoding the fusion proteins are cloned into suitable expression systems using techniques known to those of ordinary skill in the art.

The polynucleotide sequences of the present invention encode polypeptides that have important role(s) in growth and development of the immune system, and in responses of the immune system to tissue injury and inflammation as well as other disease states. Some of the polynucleotides contain sequences that code for signal sequences, or transmembrane domains, which identify the protein products as secreted molecules or receptors. The polypeptides of SEQ ID NO: 5–8 have more than 25% identity to members of the fibroblast growth factor (FGF) receptor family of proteins. The inventive polypeptides have important roles in processes such as: modulation of immune responses; differentiation of precursor immune cells into specialized cell types; cell migration; cell proliferation and cell-cell interaction. The polypeptides are important in the defence of the body against infectious agents, and thus important in maintaining a disease-free environment. These polypeptides act as modulators of skin cells, especially since immune cells infiltrate skin during tissue insult, causing growth and differentiation of skin cells. In addition, these polypeptides are immunologically active, making them important therapeutic targets in a large range of disease states.

In one aspect, the present invention provides methods for using one or more of the inventive polypeptides or polynucleotides to treat a disorder in a patient. As used herein, a "patient" refers to any warm-blooded animal, preferably a human.

In this aspect, the polypeptide or polynucleotide is generally present within a composition, such as a pharmaceutical or immunogenic composition. Pharmaceutical compositions may comprise one or more polypeptides, each of which may contain one or more of the above sequences (or variants thereof), and a physiologically acceptable carrier. Immunogenic compositions may comprise one or more of the above polypeptides and an immunostimulant, such as an adjuvant or a liposome, into which the polypeptide is incorporated.

Alternatively, a composition of the present invention may contain DNA encoding one or more polypeptides described above, such that the polypeptide is generated in situ. In such compositions, the DNA may be present within any of a variety of delivery systems known to those of ordinary skill in the art, including nucleic acid expression systems, and bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, vary from individual to individual. In general, the inventive compositions may be administered by injection (e.g., intradermal, intramuscular, intravenous or subcutaneous), intranasally (e.g., by aspiration) or orally. In general, the amount of polypeptide present in a dose (or produced in situ by the DNA in a dose) ranges from about 1 pg to about 100 mg per kg of host, typically from about 10 pg to about 1 mg per kg of host, and preferably from about 100 pg to about 1 µg per kg of host. Suitable dose sizes will vary with the size of the patient, but will typically range from about 0.1 ml to about 2 ml.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the immunogenic compositions of the present invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis* or *M. tuberculosis*. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

The polynucleotides of the present invention may also be used as markers for tissue, as chromosome markers or tags, in the identification of genetic disorders, and for the design of oligonucleotides for examination of expression patterns using techniques well known in the art, such as the microarray technology available from Affymetrix (Santa Clara, Calif.). Partial polynucleotide sequences disclosed herein may be employed to obtain full length genes by, for example, screening of DNA expression libraries, and to isolate homologous DNA sequences from other species using hybridization probes or PCR primers based on the inventive sequences.

The isolated polynucleotides of the present invention also have utility in genome mapping, in physical mapping, and in positional cloning of genes. As detailed below, the polynucleotide sequences identified as SEQ ID NO: 1–4, 9 and their variants, may be used to design oligonucleotide probes and primers. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Affymetrix (Santa Clara, Calif.).

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction. An oligonucleotide probe or primer is described as "corresponding to" a polynucleotide of the present invention, including one of the sequences set out as SEQ ID NO: 1–4, 9, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142 or a variant thereof, if the oligonucleotide probe or primer, or its complement, is contained within one of the sequences set out as SEQ ID NO: 1–4, 9, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142 or a variant of one of the specified sequences. Oligonucleotide probes and primers of the present invention are substantially complementary to a polynucleotide disclosed herein.

Two single stranded sequences are said to be substantially complementary when the nucleotides of one strand, optimally aligned and compared, with the appropriate nucleotide insertions and/or deletions, pair with at least 80%, preferably at least 90% to 95% and more preferably at least 98% to 100% of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA—DNA hybridization stringencies, annealing and melting temperatures, and potential for formation of loops and other factors, which are well known in the art. Tools, and software suitable for designing probes and PCR primers are well known in the art and include the software program available from Premier Biosoft International, 3786 Corina Way, Palo Alto, Calif. 94303–4504. Preferred techniques for designing PCR primers are also disclosed in Dieffenbach, C W and Dyksler, G S. *PCR Primer: a laboratory manual*, CSHL Press: Cold Spring Harbor, N.Y., 1995.

A plurality of oligonucleotide probes or primers corresponding to a polynucleotide of the present invention may be provided in a kit form. Such kits generally comprise multiple DNA or oligonucleotide probes or primers, each probe or primer being specific for a polynucleotide sequence. Kits of the present invention may comprise one or more probes or primers corresponding to a polynucleotide of the present invention, including a polynucleotide sequence identified in SEQ ID NO: 1–4, 9, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, and 142.

In one embodiment useful for high-throughput assays, the oligonucleotide probe kits of the present invention comprise multiple probes in an array format, wherein each probe is immobilized at a predefined, spatially addressable, location on the surface of a solid substrate. Array formats which may be usefully employed in the present invention are disclosed, for example, in U.S. Pat. Nos. 5,412,087 and 5,545,451, and PCT Publication No. WO 95/00450, the disclosures of which are hereby incorporated by reference.

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The polypeptides provided by the present invention may additionally be used in assays to determine biological activity, to raise antibodies, to isolate corresponding ligands or receptors, in assays to quantify levels of protein or cognate corresponding ligand or receptor, as anti-inflammatory agents, and in compositions for the treatment of diseases of the immune system.

The present invention further provides methods and compositions for modulating the levels and/or inhibiting the activity of an inventive polypeptide or polynucleotide. As used herein, the term "modulate" or "modulating" is meant to include an increase or a decrease in polynucleotide expression and/or an increase or a decrease in polypeptide function. Thus, as the term "modulate" is used within the context of polypeptide function, a "modulator" broadly encompasses both "agonists" of protein function and "antagonists" of protein function wherein the term "agonists" refers to, for example, modulator molecules, compounds, and/or compositions that increase polypeptide function whereas the term "antagonist" refers to modulators that decrease polypeptide function.

Methods employing modulators of the present invention include administering a molecule, compound and/or composition selected from the group consisting of: antibodies, antigen-binding fragments thereof, small chain antibody variable domain fragments (scFv), and/or camelid heavy chain antibody (HCAb) or heavy chain variable domain thereof ($V_{HH}$) that specifically bind to a polypeptide of the present invention; soluble ligands that bind to an inventive polypeptide; small molecule inhibitors of the inventive polypeptides and/or polynucleotides; anti-sense oligonucleotides to the inventive polynucleotides; small interfering RNA molecules (siRNA or RNAi) that are specific for a polynucleotide or polypeptide of the present invention; and engineered soluble polypeptide molecules that bind a ligand of an inventive polypeptide but do not stimulate signaling.

The present invention further provides methods and compositions for reducing the levels and/or inhibiting the activity of an inventive polypeptide or polynucleotide. Such methods include administering a component selected from the group consisting of: antibodies, or antigen-binding fragments thereof, that specifically bind to a polypeptide of the present invention; soluble ligands that bind to an inventive polypeptide; small molecule inhibitors of the inventive polypeptides and/or polynucleotides; anti-sense oligonucleotides to the inventive polynucleotides; small interfering RNA molecules (siRNA or RNAi) that are specific for a polynucleotide or polypeptide of the present invention; and engineered soluble polypeptide molecules that bind a ligand of an inventive polypeptide but do not stimulate signaling.

Modulating the activity of a polypeptide described herein may be accomplished by reducing or inhibiting expression of the polypeptides, which can be achieved by interfering with transcription and/or translation of the corresponding polynucleotide. Polypeptide expression may be inhibited, for example, by introducing anti-sense expression vectors; by introducing anti-sense oligodeoxyribonucleotides, anti-sense phosphorothioate oligodeoxyribonucleotides, anti-sense oligoribonucleotides or antisense phosphorothioate oligoribonucleotides; or by other means well known in the art. All such anti-sense polynucleotides are referred to collectively herein as "anti-sense oligonucleotides".

The anti-sense oligonucleotides disclosed herein are sufficiently complementary to the polynucleotide encoding the inventive polypeptide to bind specifically to the polynucleotide. The sequence of an anti-sense oligonucleotide need not be 100% complementary to that of the polynucleotide in order for the anti-sense oligonucleotide to be effective in the inventive methods. Rather an anti-sense oligonucleotide is sufficiently complementary when binding of the anti-sense oligonucleotide to the polynucleotide interferes with the normal function of the polynucleotide to cause a loss of utility, and when non-specific binding of the oligonucleotide to other, non-target, sequences is avoided. The present invention thus encompasses polynucleotides in an anti-sense orientation that inhibit translation of the inventive polypeptides. The design of appropriate anti-sense oligonucleotides is well known in the art. Oligonucleotides that are complementary to the 5' end of the message, for example the 5' untranslated sequence up to and including the AUG initiation codon, should work most efficiently at inhibiting translation. However, oligonucleotides complementary to either the 5'- or 3'-nontranslated, non-coding, regions of the targeted polynucleotide can be used.

Cell permeation and activity of anti-sense oligonucleotides can be enhanced by appropriate chemical modifications, such as the use of phenoxazine-substituted C-5 propynyl uracil oligonucleotides (Flanagan et al., *Nat. Biotechnol.* 17:48–52 (1999)) or 2'-O-(2-methoxy) ethyl (2'-MOE)-oligonucleotides (Zhang et al., *Nat. Biotechnol.* 18:862–867 (2000)). The use of techniques involving anti-sense oligonucleotides is well known in the art and is described, for example, in Robinson-Benion et al., *Methods in Enzymol.* 254:363–375 (1995) and Kawasaki et al., *Artific. Organs* 20:836–848 (1996).

Expression of a polypeptide of the present invention may also be specifically suppressed by methods such as RNA interference (RNAi). A review of this technique is found in *Science*, 288:1370–1372, 2000. Briefly, traditional methods of gene suppression, employing anti-sense RNA or DNA, operate by binding to the reverse sequence of a gene of interest such that binding interferes with subsequent cellular processes and therefore blocks synthesis of the corresponding protein. RNAi also operates on a post-translational level and is sequence specific, but suppresses gene expression far more efficiently. Exemplary methods for controlling or modifying gene expression are provided in WO 99/49029, WO 99/53050 and WO01/75164, the disclosures of which are hereby incorporated by reference. In these methods, post-transcriptional gene silencing is brought about by a sequence-specific RNA degradation process which results in the rapid degradation of transcripts of sequence-related genes. Studies have shown that double-stranded RNA may act as a mediator of sequence-specific gene silencing (see, for example, Montgomery and Fire, *Trends in Genetics*, 14:255–258, 1998). Gene constructs that produce transcripts with self-complementary regions are particularly efficient at gene silencing.

It has been demonstrated that one or more ribonucleases specifically bind to and cleave double-stranded RNA into short fragments. The ribonuclease(s) remains associated with these fragments, which in turn specifically bind to complementary mRNA, i.e. specifically bind to the transcribed mRNA strand for the gene of interest. The mRNA for the gene is also degraded by the ribonuclease(s) into short fragments, thereby obviating translation and expression of the gene. Additionally, an RNA-polymerase may act to facilitate the synthesis of numerous copies of the short fragments, which exponentially increases the efficiency of the system. A unique feature of RNAi is that silencing is not limited to the cells where it is initiated. The gene-silencing effects may be disseminated to other parts of an organism.

The polynucleotides of the present invention may thus be employed to generate gene silencing constructs and/or gene-specific self-complementary, double-stranded RNA sequences that can be delivered by conventional art-known methods. A gene construct may be employed to express the self-complementary RNA sequences. Alternatively, cells are contacted with gene-specific double-stranded RNA molecules, such that the RNA molecules are internalized into the cell cytoplasm to exert a gene silencing effect. The double-stranded RNA must have sufficient homology to the targeted gene to mediate RNAi without affecting expression of non-target genes. The double-stranded DNA is at least 20 nucleotides in length, and is preferably 21–23 nucleotides in length. Preferably, the double-stranded RNA corresponds specifically to a polynucleotide of the present invention. The use of small interfering RNA (siRNA) molecules of 21–23 nucleotides in length to suppress gene expression in mammalian cells is described in WO 01/75164. Tools for designing optimal inhibitory siRNAs include that available from DNAengine Inc. (Seattle, Wash.).

One RNAi technique employs genetic constructs within which sense and antisense sequences are placed in regions flanking an intron sequence in proper splicing orientation with donor and acceptor splicing sites. Alternatively, spacer sequences of various lengths may be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes.

As used herein, the phrase "contacting a population of cells with a genetic construct, anti-sense oligonucleotide or RNA molecule" includes any means of introducing a nucleic acid molecule into any portion of one or more cells by any method compatible with cell viability and known to those of ordinary skill in the art. The cell or cells may be contacted in vivo, ex vivo, in vitro, or any combination thereof.

For in vivo uses, a genetic construct, anti-sense oligonucleotide or RNA molecule may be administered by various art-recognized procedures. See, e.g., Rolland, *Crit. Rev. Therap. Drug Carrier Systems* 15:143–198 (1998), and cited references. Both viral and non-viral delivery methods have been used for gene therapy. Useful viral vectors include, for example, adenovirus, adeno-associated virus (AAV), retrovirus, vaccinia virus and avian poxvirus. Improvements have been made in the efficiency of targeting genes to tumor cells with adenoviral vectors, for example, by coupling adenovirus to DNA-polylysine complexes and by strategies that exploit receptor-mediated endocytosis for selective targeting. See, e.g., Curiel et al., *Hum. Gene Ther.*, 3:147–154 (1992); and Cristiano and Curiel, *Cancer Gene Ther.* 3:49–57 (1996). Non-viral methods for delivering polynucleotides are reviewed in Chang & Seymour, (Eds) *Curr. Opin. Mol. Ther.*, vol. 2 (2000). These methods include contacting cells with naked DNA, cationic liposomes, or polyplexes of polynucleotides with cationic polymers and dendrimers for systemic administration (Chang & Seymour, Ibid.). Liposomes can be modified by incorporation of ligands that recognize cell-surface receptors and allow targeting to specific receptors for uptake by receptor-mediated endocytosis. See, for example, Xu et al., *Mol. Genet. Metab.*, 64:193–197 (1998); and Xu et al., *Hum. Gene Ther.*, 10:2941–2952 (1999).

Tumor-targeting bacteria, such as Salmonella, are potentially useful for delivering genes to tumors following systemic administration (Low et al., *Nat. Biotechnol.* 17:37–41 (1999)). Bacteria can be engineered ex vivo to penetrate and to deliver DNA with high efficiency into mammalian epithelial cells in vivo and in vitro. See, e.g., Grillot-Courvalin et al., *Nat. Biotechnol.* 16:862–866 (1998). Degradation-stabilized oligonucleotides may be encapsulated into liposomes and delivered to patients by injection either intravenously or directly into a target site. Alternatively, retroviral or adenoviral vectors, or naked DNA expressing anti-sense RNA for the inventive polypeptides, may be delivered into patient's cells in vitro or directly into patients in vivo by appropriate routes. Suitable techniques for use in such methods are well known in the art.

The present invention further provides binding agents, such as antibodies and antigen-binding fragments thereof, small chain antibody variable domain fragments (scFv), and/or camelid heavy chain antibody (HCAb) or heavy chain variable domain thereof ($V_{HH}$) which specifically bind to a polypeptide disclosed herein, or to a portion or variant thereof. A binding agent is said to "specifically bind" to an inventive polypeptide if it reacts at a detectable level with the polypeptide, and does not react detectably with unrelated polypeptides under similar conditions. Any agent that satisfies this requirement may be a binding agent. For example, a binding agent may be a ribosome, with or without a peptide component, an RNA molecule, or a polypeptide. In a preferred embodiment, a binding agent is an antibody, or an antigen-binding fragment thereof, small chain antibody variable domain fragments (scFv), and/or camelid heavy chain antibody (HCAb) or heavy chain variable domain thereof ($V_{HH}$). The ability of a binding agent to specifically bind to a polypeptide can be determined, for example, in an ELISA assay using techniques well known in the art.

The present invention further provides binding agents, such as antibodies and antigen-binding fragments thereof, which specifically bind to a polypeptide disclosed herein, or to a portion or variant thereof. A binding agent is said to "specifically bind" to an inventive polypeptide if it reacts at a detectable level with the polypeptide, and does not react detectably with unrelated polypeptides under similar conditions. Any agent that satisfies this requirement may be a binding agent. For example, a binding agent may be a ribosome, with or without a peptide component, an RNA molecule, or a polypeptide. In a preferred embodiment, a binding agent is an antibody or an antigen-binding fragment thereof. The ability of an antibody, or antigen-binding fragment thereof, to specifically bind to a polypeptide can be determined, for example, in an ELISA assay using techniques well known in the art.

An "antigen-binding site," or "antigen-binding fragment" of an antibody refers to the part of the antibody that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the inventive polypeptide is initially injected into any of a wide variety of mammals (e.g., mice, rats, rabbits, sheep or goats). The polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the inventive polypeptide may then be purified from such antisera by, for example, affinity chromatography using the polypeptide coupled to a suitable solid support.

Monoclonal antibodies specific for an inventive polypeptide may be prepared using the technique of Kohler and Milstein, *Eur. J. Immunol.* 6:511–519, 1976, and improvements thereto. These methods involve the preparation of immortal cell lines capable of producing antibodies having the desired specificity. Such cell lines may be produced from spleen cells obtained from an animal immunized as described above. The spleen cells are then immortalized by, for example, fusion with a myeloma cell fusion partner, preferably one that is syngeneic with the immunized animal. A variety of fusion techniques well known in the art may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may then be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of molecules are known in the art that comprise antigen-binding sites capable of exhibiting the binding properties of an antibody molecule. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment, which comprises both antigen-binding sites. An "Fv" fragment can be produced by preferential proteolytic cleavage of an IgM, IgG or IgA immunoglobulin molecule, but are more commonly derived using recombinant techniques known in the art. The Fv fragment includes a non-covalent $V_H$::$V_L$ heterodimer including an antigen-binding site which retains much of the antigen recognition and binding capabilities of the native antibody molecule (Inbar et al. *Proc. Nat. Acad. Sci. USA* 69:2659–2662 (1972); Hochman et al. *Biochem* 15:2706–2710 (1976); and Ehrlich et al. *Biochem* 19:4091–4096 (1980)).

The present invention further encompasses humanized antibodies that specifically bind to an inventive polypeptide. A number of humanized antibody molecules comprising an antigen-binding site derived from a non-human immunoglobulin have been described, including chimeric antibodies having rodent V regions and their associated CDRs fused to human constant domains (Winter et al. *Nature* 349:293–299 (1991); Lobuglio et al. *Proc. Nat. Acad. Sci. USA* 86:4220–4224 (1989); Shaw et al. *J Immunol.* 138:4534–4538 (1987); and Brown et al. *Cancer Res.* 47:3577–3583 (1987)); rodent CDRs grafted into a human supporting FR prior to fusion with an appropriate human antibody constant domain (Riechmann et al. *Nature* 332: 323–327 (1988); Verhoeyen et al. *Science* 239:1534–1536 (1988); and Jones et al. *Nature* 321:522–525 (1986)); and rodent CDRs supported by recombinantly veneered rodent FRs (European Patent Publication No. 519,596, published Dec. 23, 1992). These "humanized" molecules are designed to minimize unwanted immunological responses towards rodent antihuman antibody molecules which limit the duration and effectiveness of therapeutic applications of those moieties in human recipients.

Equally suited to the practice of the present invention are single-chain antibodies fragments, including scFv and Camelidae heavy chain antibodies (HCAb) that specifically bind to one of the FGFR5 polypeptides presented as SEQ ID NOs: 5–8, 13–15 and/or to one of the splice variant polynucleotide encoded polypeptides presented as SEQ ID NOs: 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101,.103, 105, 107, 109, 111,113, 115, 117, 119, 121, 123, 125, 127, 129, 131, 133, 135, 137, 139, 141, and 143 as well as variants of any of these polypeptides.

ScFv presented herein comprise an antibody heavy chain variable region ($V_H$) operably linked to an antibody light chain variable region ($V_L$) wherein the heavy chain variable region and the light chain variable region together or individually form a binding site for specifically binding an FGFR5 polypeptide presented herein. ScFv may comprise a $V_H$ region at the amino-terminal end and a $V_L$ region at the carboxy-terminal end. Equally suitable are scFv that comprise a $V_L$ region at the amino-terminal end and a $V_H$ region at the carboxy-terminal end. ScFv disclosed herein may, optionally, further comprise a polypeptide linker operably linked between the heavy chain variable region and the light chain variable region. Polypeptide linkers of the present invention generally comprise between 1 and 50 amino acids. More preferred are polypeptide linkers of at least 2 amino acids. Within other embodiments, however, polypeptide linkers are preferably between 3 and 12 amino acids. An exemplary linker peptide for incorporating between scFv heavy and light chains comprises the 5 amino acid sequence Gly-Gly-Gly-Gly-Ser. Alternative exemplary linker peptides comprise one or more tandem repeats of the sequence Gly-Gly-Gly-Gly-Ser to create linkers comprising, for example, the sequences Gly-Gly-Gly-Gly-Ser-Gly-Gly-Gly-Gly-Ser, Gly-Gly-Gly-Gly-Ser-Gly-Gly-Gly-Gly-Ser-Gly-Gly-Gly-Gly-Ser, and Gly-Gly-Gly-Gly-Ser-Gly-Gly-Gly-Gly-Ser-Gly-Gly-Gly-Gly-Ser-Gly-Gly-Gly-Gly-Ser.

Other embodiments of the present invention provide Camelidae heavy chain antibodies (HCAb) that specifically bind to polypeptides presented as SEQ ID NOs: 5–8, 13–15 and variants thereof. These heavy chain antibodies are a class of IgG that are devoid of light chains that are produced by animals of the genus Camelidae (including camels, dromedaries, and llamas). Hamers-Casterman et al., *Nature* 363:446–448 (1993). HCAbs have a molecular weight of ~95 kDa instead of the ~160 kDa for conventional IgG antibodies. Their binding domains consist only of the heavy-chain variable domains, referred to as $V_{HH}$s to distinguish them from conventional $V_H$s. Muyldermans et al., *J. Mol. Recognit.* 12:131–140 (1999). Since the first constant domain ($C_H1$) is absent (spliced out during mRNA processing due to loss of a splice consensus signal), the variable domain ($V_{HH}$) is immediately followed by the hinge region, the $C_H2$ and the $C_H3$ domains. Nguyen et al., *Mol. Immunol.* 36:515–524 (1999); Woolven et al., *Immunogenetics* 50:98–101 (1999). Although the HCAbs are devoid of light chains, they have an authentic antigen-binding repertoire. The current knowledge about the genetic generation mechanism of HCAbs is reviewed by Nguyen et al. *Adv. Immunol* 79:261–296 (2001) and Nguyen et al., *Immunogenetics* 54:39–47 (2002). Similarly, sharks, including the nurse shark, display antigen receptor-containing single monomeric V-domains. Irving et al., *J. Immunol. Methods* 248:31–45 (2001); Roux et al., *Proc. Natl. Acad. Sci. USA* 95:11804 (1998).

$V_{HH}$s comprise the smallest available intact antigen-binding fragment (~15 kDa, 118–136 residues). The affinities of $V_{HH}$s are typically in the nanomolar range and comparable with those of Fab and scFv fragments. In addition, $V_{HH}$s are highly soluble and more stable than the corresponding derivatives of scFv and Fab fragments. $V_{HH}$s carry amino acid substitutions that make them more hydrophilic and prevent the prolonged interaction with BiP (Immunoglobulin heavy-chain binding protein), which normally binds to the H-chain in the Endoplasmic Reticulum (ER) during folding and assembly, until it is displaced by the L-chain. Because of the $V_{HH}$s's increased hydrophilicity, secretion from the ER is improved.

Within certain embodiments, functional $V_{HH}$s may be obtained from proteolysed HCAb of an immunized camelid, by direct cloning of $V_{HH}$ genes from B-cells of an immunized camelid resulting in recombinant $V_{HH}$s, or from naive or synthetic libraries. $V_{HH}$s with desired antigen specificity may also be obtained through phage display methodology. Using $V_{HH}$s in phage display is much simpler and more efficient as compared with Fabs or scFvs, since only one domain needs to be cloned and expressed to obtain a functional antigen-binding fragment. Muyldermans, *Biotechnol.* 74:277–302 (2001); Ghahroudi et al., *FEBS Lett.* 414:521–526 (1997); and van der Linden et al., *J. Biotechnol.* 80:261–270 (2000).

Alternatively, ribosome display methodology may be suitably employed for the identification and isolation of scFv and/or $V_{HH}$ molecules having the desired binding activity and affinity. Irving et al., *J. Immunol. Methods* 248:31–45 (2001). Ribosome display and selection has the potential to generate and display large libraries representative of the theoretical optima for naive repertoires ($10^{14}$).

Other embodiments provide $V_{HH}$-like molecules generated, through the process of camelisation, by modifying non-Camelidae $V_H$s, such as human $V_H$s, to improve their solubility and prevent non-specific binding, by replacing residues on the $V_L$ side of $V_H$s with $V_{HH}$-like residues, thereby mimicking the more soluble $V_{HH}$ fragments. Camelised $V_H$ fragments, particularly those based on the human framework, are expected to exhibit a greatly reduced immune response when administered in vivo to a patient and, accordingly, are expected to have significant advantages for therapeutic purposes. Davies et al., *FEBS Lett.* 339:285–290 (1994); Davies et al., *Protein Eng.* 9:531–537 (1996); Tanha et al., *J. Biol. Chem.* 276:24774–24780 (2001); and Riechmann et al., *Immunol. Methods* 231:25–38 (1999).

A wide variety of expression systems are available in the art for the production of anti-FGFR5 antibody fragments including Fab fragments, scFv, and $V_{HH}$s. For example, suitable to the large-scale production of antibody fragments and antibody fusion proteins are expression systems of both prokaryotic and eukaryotic origin. Particularly advantageous are expression systems that permit the secretion of large amounts of antibody fragments into the culture medium.

Eukaryotic expression systems for large-scale production of antibody fragments and antibody fusion proteins have been described that are based on mammalian cells, insect cells, plants, transgenic animals, and lower eukaryotes. For example, the cost-effective, large-scale production of antibody fragments can be achieved in yeast fermentation systems. Large-scale fermentation of these organisms is well known in the art and is currently used for bulk production of several recombinant proteins. Yeasts and filamentous fungi are accessible for genetic modifications and the protein of interest may be secreted into the culture medium. In addition, some of the products comply with the GRAS (Generally Regarded as Safe) status-they do not harbor pyrogens, toxins, or viral inclusions.

The methylotrophic and other yeasts like *Candida boidinii, Hansenula polymorpha, Pichia methanolica*, and *Pichia pastoris* are well know systems for the production of heterologous proteins. High levels of proteins in milligram to gram quantities can be obtained and scaling up to fermentation for industrial applications is possible.

The *P. pastoris* system is used in several industrial-scale production processes. For example, the use of Pichia for the expression of scFv fragments as well as recombinant antibodies and fragments thereof have been described. Ridder et al., *Biotechnology* 13:255–260 (1995); Anadrade et al., *J. Biochem (Tokyo)* 128:891–895 (2000); Pennell et al., *Res. Immunol.* 149:599–603 (1998). In shake-flask cultures, levels of 250 mg/L to over 1 g/L of scFv or $V_{HH}$ can be achieved. Eldin et al., *J. Immunol. Methods* 201:67–75 (1997); Freyre et al., *J. Biotechnol.* 76:157–163 (2000).

Similar expression systems for scFv have been described for *Saccharomyces cerevisiae, Schizosaccharomyces pombe, Yarrowia lipolytica*, and *Kluyveromyces lactis*. Horwitz et al., *Proc. Natl. Acad. Sci. USA* 85:8678–8682 (1988); Davis et al., *Biotechnology* 9:165–169 (1991); and Swennen et al., *Microbiology* 148:41–50 (2002). Filamentous fungi, such as Trichoderma and Aspergillus, have the capacity to secrete large amounts of proteins. This property may be exploited for the expression of scFv and $V_{HH}$s. Radzio et al., *Process-biochem.* 32:529–539 (1997); Punt et al., *Trends Biotechnol.* 20:200–206 (2002); Verdoes et al., *Appl. Microbiol. Biotechnol.* 43:195–205 (1995); Gouka et al., *Appl. Microbiol. Biotechnol.* 47:1–11 (1997); Ward et al., *Biotechnology* 8:435–440 (1990); Archer et al., *Antonie Van Leeuvenhoek* 65:245–250 (1994); Durand et al., *Enzyme Microb. Technol.* 6:341–346 (1988); Keranen et al., *Curr. Opin. Biotechnol.* 6:534–537 (1995); Nevalainen et al., *J. Biotechnol.* 37:193–200 (1994); Nyyssonen et al., *Biotechnology* 11:591–595 (1993); and Nyyssonen et al., PCT WO 92/01797 (1992).

The following examples are offered by way of illustration, not limitation.

EXAMPLE 1

Isolation of cDNA Sequences From Murine Lymph Node Stromal Cell Expression Libraries The cDNA sequences of the present invention were obtained by high-throughput sequencing of cDNA expression libraries constructed from murine fsn −/− lymph node stromal cells as described below.

cDNA Libraries from Lymph Node Stromal Cells (MLSA and MLSE)

Lymph nodes were removed from flaky skin fsn −/− mice, the cells dissociated and the resulting single cell suspension placed in culture. After four passages, the cells were harvested. Total RNA, isolated using TRIzol Reagent (BRL Life Technologies, Gaithersburg, Md.), was used to obtain mRNA using a Poly(A) Quik mRNA isolation kit (Stratagene, La Jolla, Calif.), according to the manufacturer's specifications. A cDNA expression library (referred to as the MLSA library) was then prepared from the mRNA by Reverse Transcriptase synthesis using a Lambda ZAP Express cDNA library synthesis kit (Stratagene, La Jolla, Calif.). A second cDNA expression library, referred to as the MLSE library, was prepared exactly as above except that the cDNA was inserted into the mammalian expression vector pcDNA3 (Invitrogen, Carlsbad Calif.).

The nucleotide sequence of a cDNA clone isolated from the MLSA library is given in SEQ ID NO: 1, with the corresponding amino acid sequence being provided in SEQ ID NO: 5.

EXAMPLE 2

Characterization of Isolated cDNA Sequences

The isolated cDNA sequences were compared to sequences in the EMBL DNA database using the computer algorithm BLASTN, and the corresponding polypeptide sequences (DNA translated to protein in each of 6 reading frames) were compared to sequences in the SwissProt database using the computer algorithm BLASTP. Specifically, comparisons of DNA sequences provided in SEQ ID NO: 1–4 to sequences in the EMBL (Release 60, September 1999) DNA database, and amino acid sequences provided in SEQ ID NO: 5–8 to sequences in the SwissProt and TrEMBL (up to Oct. 20, 1999) databases were made as of Dec. 31, 1999. The cDNA sequences of SEQ ID NO: 1–4, and their corresponding polypeptide sequences (SEQ ID NO: 5–8, respectively) were determined to have less than 75% identity (determined as described above) to sequences in the EMBL and SwissProt databases using the computer algorithms BLASTN and BLASTP, respectively.

Using automated search programs to screen against sequences coding for known molecules reported to be of therapeutic and/or diagnostic use, the isolated polynucleotides of SEQ ID NO: 1–4 were determined to encode polypeptide sequences that are members of the fibroblast growth factor (FGF) receptor family (SEQ ID NO: 5–8). A family member is herein defined to have at least 20% identical amino acid residues in the translated polypeptide to a known protein or member of a protein family.

Fibroblast growth factor receptors belong to a family of four single membrane-spanning tyrosine kinases (FGFR1 to 4). These receptors serve as high-affinity receptors for 23 growth factors (FGF1 to 23). FGF receptors have important roles in multiple biological processes, including mesoderm induction and patterning, cell growth and migration, organ formation and bone growth (Xu, *Cell Tissue Res.* 296:33–43, 1999). Further analysis of the sequence revealed the presence of a putative transmembrane domain and intracellular domain, similar to other FGF receptors.

EXAMPLE 3

Isolation of Full Length cDNA Sequence of a Murine Fibroblast Growth Factor Receptor Homolog The full-length cDNA sequence of a murine fibroblast growth factor receptor homolog was isolated as follows.

The MLSA cell cDNA library (described in Example 1) was screened with an [$\alpha^{32}$P]-dCTP labeled cDNA probe corresponding to nucleotides 1 to 451 of the coding region within SEQ ID NO: 1. Plaque lifts, hybridization and screening were performed using standard molecular biology techniques. The determined polynucleotide sequence of the full-length murine FGFR gene (referred to as muFGFR5β) is provided in SEQ ID NO: 2, with the corresponding polypeptide sequence being provided in SEQ ID NO: 6.

Analysis of the polynucleotide sequence of SEQ ID NO: 2 revealed the presence of a putative transmembrane domain encoded by nucleotides 1311 to 1370. The polypeptide sequence (SEQ ID NO: 6; FIG. 1) has regions similar to the extracellular domain of the fibroblast growth factor receptor family. The amino acid sequence of the extracellular domain of muFGFR5β is provided in SEQ ID NO: 13, while the amino acid sequence of the intracellular domain is provided in SEQ ID NO: 14.

A splice variant of SEQ ID NO: 2 was also isolated from the MLSA cDNA library as described in Example 1. The determined polynucleotide sequence of the splice variant (referred to as FGFR5γ) is provided in SEQ ID NO: 3 and the corresponding polypeptide sequence is provided in SEQ ID NO: 7. The splice regions are in an equivalent position to splice sites for previously described FGF receptors (Ornitz, *J. Biol. Chem.* 296:15292–15297 (1996); Wilkie, *Current Biology* 5:500–507 (1995); Miki, *Proc. Natl. Acad. Sci. USA* 89:246–250 (1992), thus establishing that this molecule (referred to herein as FGFR5) is a FGF receptor homolog. The main difference between the two FGFR5 splice variants is that muFGFR5β contains three extracellular Ig-domains, while FGFR5γ contains only two such domains.

To examine the structural similarities between FGFR5γ and FGFR5β and the other members of the FGF receptor family, 3D Swiss modeller (Petisch, *Bio/Technology* 13:658–660 (1995); Peitsch, *Biochem Soc Trans.* 24:274–279 (1996); and Guex and Peitsch, *Electrophoresis* 18:2714–2723 (1997)) was employed to produce a predicted crystal structure of the extracellular domain of FGFR5γ. These studies showed that the crystal structure of FGFR5 deviates from that of the known FGFR1 structure between residues 188 and 219 of SEQ ID NO: 7 (SEQ ID NO: 15). These residues correlate with an area of low homology between FGFR5 and other members of the FGF receptor family that may have a critical role in defining ligand specificity.

The critical residues for ligand binding have previously been identified in co-crystallization studies of FGFR1 binding FGF-2 (Plotnikov et al., *Cell* 98:641–650 (1999)). Alignment of FGFR5γ with FGFR1 showed that many of these residues are conserved or are a conservative substitution. Conserved ligand binding residues between the two receptors are found at residues 66, 68, 146, 178, 181, 183 and 216 of SEQ ID NO: 7, while conservative substitutions of potential ligand binding residues are found at residues 64, 180 and 226 of SEQ ID NO: 7. When visualized on the predicted crystal structure of FGFR5γ, these residues line the groove of the ligand binding domain. Thus, while the overall degree of similarity between FGFR5 and other FGF receptors (i.e. FGFR 1–4) is relatively low, the extracellular domains of the FGFR5 splice variants have all the conserved residues important for ligand binding.

The main difference between the FGFR5 receptor and other family members is the lack of an intracellular tyrosine kinase domain. With the four previously identified FGF receptors (FGFR1–4), signal transduction is mediated by ligand binding and receptor dimerization, resulting in autophosphorylation of the tyrosine residues within the intracellular RTK domain and phosphorylation of a number of intracellular substrates, initiating several signal transduction cascades. The FGFR5β and FGFR5γ splice variants described herein both contain tyrosine residues in the intracellular domain demonstrating similarity to a SHP binding motif (residues 458–463 of SEQ ID NO: 6 and 367–377 of SEQ ID NO: 7). SHPs are protein tyrosine phosphatases that participate in cellular signalling and that have previously been identified in the cytoplasmic domains of many receptors eliciting a broad range of activities. The presence of such motifs in the cytoplasmic domain of FGFR5 is thus indicative of signalling, and modification of these motifs may be employed to modulate signal transduction initiated by binding of a ligand to FGFR5. These motifs are conserved between the mouse FGFR5s and the human homologs described below (Example 4). Removal or modification of these signaling motifs and/or the cytoplasmic domain of FGFR5 may be employed to engineer a soluble FGFR5-like molecule that binds to the FGFR5 ligand without stimulating signaling. Such a molecule may be usefully employed to modulate the binding, and therefore activity, of FGFR5.

EXAMPLE 4

Isolation of a Human FGF Receptor Homolog

The cDNA encoding the partial murine FGF receptor (SEQ ID NO: 1) was used to search the EMBL database (Release 58, March 1999) to identify human EST homologs. The identified EST (Accession Number AI245701) was obtained from Research Genetics, Inc (Huntsville Ala.) as I.M.A.G.E. Consortium clone ID 1870593. Sequence determination of the complete insert of clone 1870593 resulted in the identification of 520 additional nucleotides. The insert of this clone did not represent the full-length gene. The determined nucleotide sequence of the complete insert of clone 1870593, which represents the extracellular domain of the human FGF receptor homolog, is given in SEQ ID NO: 4 and the polypeptide sequence of the extracellular domain in SEQ ID NO: 8. Several conserved domains were identified in SEQ ID NO: 8 that are involved in the dimerization, ligand binding and activity of the receptor. These are shown in FIG. 10.

Both murine and human FGFR5 are structurally similar to FGFR1–4, the other members of the FGFR family. In the extracellular domain, three immunoglobulin-like motifs are present that are flanked by conserved cysteine residues. The Ig-1 loop is the least conserved of the three Ig loops and is not required for ligand binding, but regulates binding affinity (Shi et al., *Mol. Cell. Biol.* 13:3907–3918 (1993)). The Ig-3 loop is involved in ligand selectivity (Ornitz et al., *Science* 268:432–436 (1996)).

An acidic box is characteristic in FGFR1–4 and is involved in binding divalent cations, including copper and calcium. Acidic boxes are important for interaction with cell adhesion molecules, extracellular matrix and heparin (Patstone and Maher, *J. Biol. Chem.* 271:3343–3346 (1996)). The acidic box in FGFR5 is smaller than in the other four receptors or absent.

The cell adhesion molecule (CAM) homology and heparin-binding domain is also characteristic of the extracellular domain (Szebenyi and Fallon, *Int. Rev. Cytol.* 185:45–106 (1999)). The CAM homology region is a binding site for L1, N-CAM and N-cadherin (Doherty et al., *Perspect Dev Neurobiol.* 4(2–3): 157–68 (1996)).

The FGFR5 heparin-binding domain is typical of other FGFR heparin-binding domains and consists of a cluster of basic and hydrophobic residues flanked by Lys residues (Kan et al., *Science* 259:1918–1921 (1993)). Heparin or heparan sulfate proteoglycans are essential co-factors for the interaction of FGFs with FGFRs and it has been shown that heparin is a growth-factor independent ligand for FGFR4 (Gao and Goldfarb, *EMBO J.* 14:2183–2190 (1995)).

EXAMPLE 5

Characterization of the Murine FGF Receptor Homolog

Soluble forms of the murine FGF receptor homolog muFGFR5β and splice variant FGFR5γ (SEQ ID NOs: 2 and 3, respectively) were expressed in mammalian cells and the purified proteins used to determine the ligand binding specificity of the receptor molecules as follows.

The extracellular domains of muFGFR5β and FGFR5γ were amplified by PCR using primers MS158 and MS159 (SEQ ID NOs: 10 and 11, respectively) and cloned into the expression vector pcDNA3 containing the Fc fragment from human IgG1. These soluble recombinant proteins, referred to as FGFR5βFc and FGFR5γFc, were expressed in HEK293 cells (ATCC No. CRL-1573, American Type Culture Collection, Manassas, Va.) and purified using an Affiprep protein A column (Biorad, Hercules Calif.).

FGF-2 (basic fibroblast growth factor) has previously been demonstrated to bind all FGF receptors but with a range of affinities. Binding of muFGFR5β to FGF-2 was demonstrated by co-incubating the purified protein and FGF-2 in the presence of protein G Sepharose (Amersham Pharmacia, Uppsala, Sweden) and resolving complexes formed on denaturing polyacrylamide gels. FGF-2 (2 µg) was incubated with 5 µg FGFR5βFc, FGF Receptor 2 (FGFR2Fc) or unrelated protein (MLSA8790Fc) in 5 µl protein G Fast Flow beads (Pharmacia, Uppsala, Sweden), PBS and 0.1% Triton X-100 for 60 min at 4° C. The beads were washed three times in 0.1% Triton X-100/PBS and resuspended in 20 µl loading buffer (0.1 M DTT, 10% sucrose, 60 mM Tris.HCl pH 6.8, 5% SDS and 0.01% bromophenol blue). The samples were analysed on a 12% polyacrylamide gel. FGF-2, FGFR2Fc, FGFR5βFc and MLSA8790Fc (1 µg of each) were loaded on the gel for comparison. After staining of the gel with Coomassie blue, a doublet of bands were visible in the lane containing FGFR5βFc, indicating that a complex formed between the FGF-2 and the murine FGF receptor homolog FGFR5βFc, and that FGF-2 is a ligand for the novel FGF receptor homolog. A doublet was also observed in the lane containing the FGFR2Fc, which was the positive control. No doublet was observed in the negative control lane containing the MLSA8790Fc protein.

The binding specificity of the murine FGF receptor homolog FGFR5βFc was further examined by repeating the experiment described above, replacing the FGF-2 with another known growth factor, epidermal growth factor (EGF). In this experiment, EGF did not bind to FGFR2Fc, FGFR5βFc or MLSA8790Fc, indicating that binding of FGF-2 to the murine FGF receptor homolog FGFR5βFc was specific. Similarly, in subsequent experiments employing FGF-7, no binding of FGFR2Fc, FGFR5βFc or MLSA8790Fc was observed.

To determine the difference in binding affinity between FGFR5 and FGFR2, the ability of FGFR5βFc and FGFR5γFc to inhibit FGF signalling in FGF-responsive NIH-3T3 SRE reporter cells was examined. Fibroblast growth factors typically signal via phosphorylation of the receptor tyrosine kinase domain stimulating the MAP kinase pathway. This eventually leads to activation of genes under the control of the serum response element (SRE). Reporter constructs containing concatamerized SRE sequences upstream of a luciferase reporter gene were stably transfected into NIH-3T3 cells. Reporter activity was measured by measuring luciferase levels. As shown in FIG. 2A, a dose dependent response of NIH-3T3 SRE cells to FGF-2 was seen in the presence of heparin. Using a standard dose of FGF-2 in the presence of heparin, an increasing concentration of FGFR2Fc, FGFR5βFc or FGFR5γFc was titrated onto the NIH-3T3 SRE cells and luciferase activity was measured. Increasing concentrations of FGFR2Fc, the positive control, reduced the luciferase signal in FGF-2 stimulated cells (FIG. 2B). However, titrating FGFR5βFc and FGFR5γFc did not inhibit FGF-mediated luciferase signal from the NIH-3T3 SRE cells. These results show that FGF-2 has lower affinity for either FGFR5β or FGFR5γ than for FGFR2, and indicate that the ligand specificity of FGFR5 is different to those of the other members of the FGF receptor family.

EXAMPLE 6

Sequence Determination of a Polynucleotide Fragment Containing Genomic Murine FGFR5β

As noted above, the two splice variants muFGFR5β and muFGFR5γ do not contain the classical receptor tyrosine kinase domain present in other known FGF receptors. In order to investigate the existence of a splice variant of FGFR5 containing a classical receptor tyrosine kinase (RTK) domain, the genomic DNA of FGFR5 was cloned and sequenced as follows.

Mouse genomic DNA was isolated from L929 cells using standard techniques. A genomic polynucleotide fragment containing murine FGFR5β was PCR amplified using primers MS157 and MS166 (SEQ ID NOs: 11 and 12, respectively). The 1.4 kb polynucleotide fragment was cloned into a T-tailed pBluescript SK$^{2+}$ vector. The sequence of the insert of this plasmid was determined using standard primer walking sequencing techniques. The sequence of the genomic fragment containing murine FGFR5β is given in SEQ ID NO: 9. This sequence extends from the 3' untranslated region to the sequence encoding the 5' end of the mature FGFR5 receptor minus the signal sequence. No alternative exons expressing an RTK domain were identified.

EXAMPLE 7

Stimulation of Cell Growth By Murine FGFR5β and FGFR5γ

RAW264.10 cells are derived from a murine macrophage cell line generated from BALB/c mice, and are macrophage and osteoblast precursors. Stimulation of RAW264.10 cells (Hamilton et al., *J. Exp. Med.* 148:811–816 (1978)) and peripheral blood mononuclear cells (PBMC) in the presence of the murine FGFR5β and FGFR5γ (also referred to herein as FGFRβ and FGFRγ, respectively) was demonstrated as follows.

The murine FGF receptor homolog, muFGFR5β, and splice variant FGFR5γ (SEQ ID NOs: 2 and 3, respectively) were expressed in mammalian cells and purified as murine FGFR5β-Fc and FGFR5γ-Fc fusion proteins as described above. The FGFR5β- and FGFR5γ-Fc fusion proteins were titrated from 10 nM in 0.05 ml media (DMEM supplemented with 5% FBS, 2mM L-glutamine (Sigma, St Louis Mo.), 1 mM sodium pyruvate (Life Technologies, Gibco BRL, Gaithersburg Md.), 0.77 mM L-asparagine (Sigma), 0.2 mM arginine (Sigma), 160 mM penicillin G (Sigma), 70 mM dihydrostreptomycin sulfate (Boehringer Mannheim, Roche Molecular Biochemicals, Basel, Switzerland) in a 96-well flat-bottomed microtitre plate. Purified human FGFR2-Fc fusion protein was used as control and titrated from 10 nM.

Figure 3:
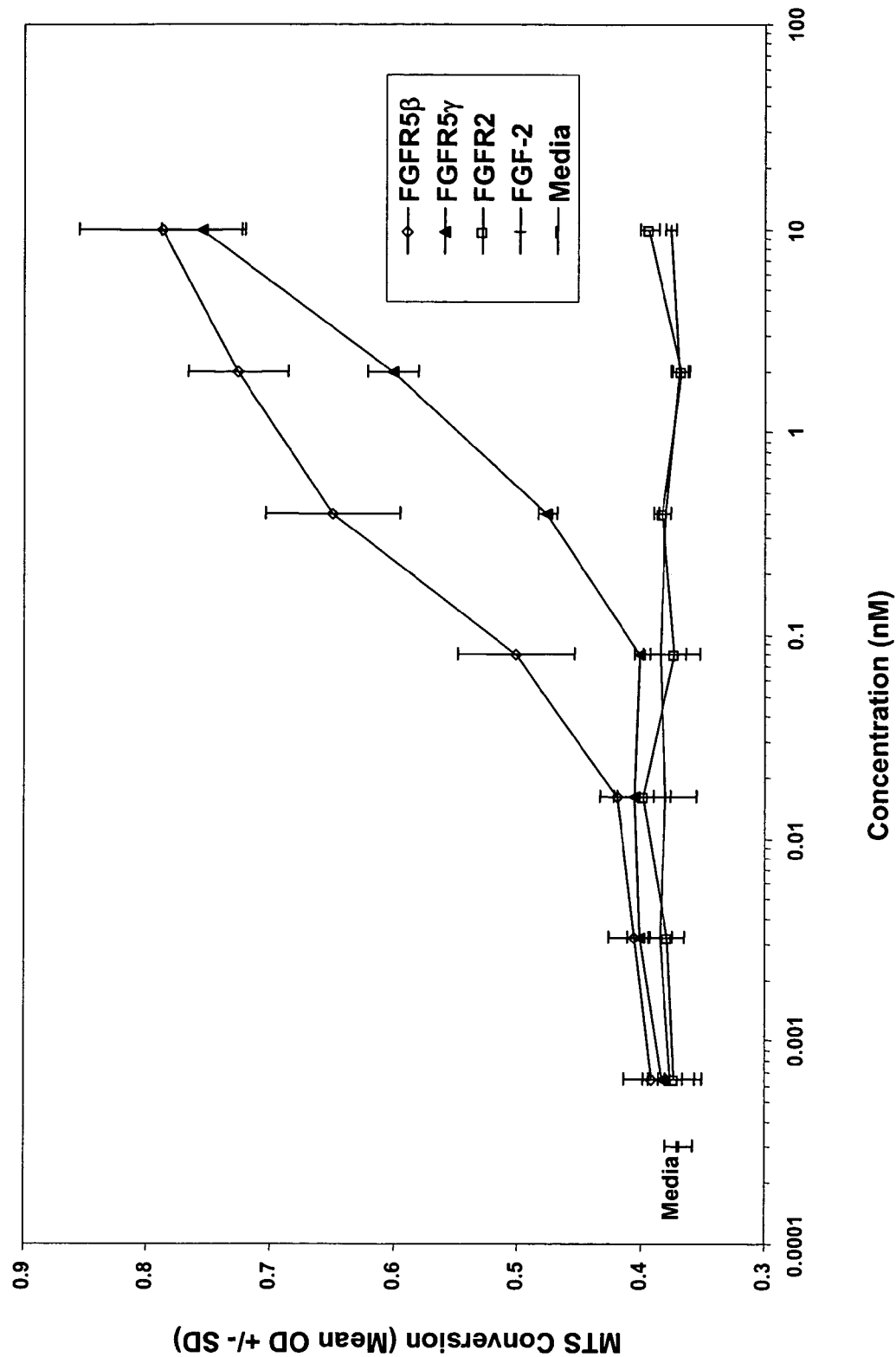
FIG. 3 illustrates the stimulation of growth of RAW264.10 cells by FGFR5β and FGFR5γ. This stimulation was not observed when FGF-2 and FGFR2 were used as controls. This stimulation was also not induced by the growth medium.

RAW264.10 cells were added to each well in 0.05 ml media at a concentration of 2×10$^4$ cells/ml. The plate was incubated at 37° C. in a humidified atmosphere containing 10% $CO_2$ for 4 days. Cell growth was determined by MTS dye conversion and quantified using an ELISA reader. As shown in FIG. 3, both murine FGFR5β-Fc and FGFR5γ-Fc fusion proteins stimulated the growth of RAW264.10 cells at concentrations of 100 pM and greater of Fc fusion protein.

These results demonstrated that FGFR5β and FGFR5γ are immunostimulatory molecules that directly activate a macrophage cell line. The macrophage cell line used in these assays (RAW264.10) has previously been shown to differentiate into osteoblasts when stimulated with a variety of known bone morphogenic agents. The effects of FGFR5β and FGFR5γ on these cells suggest that these molecules may also stimulate the differentiation and activation of osteoblasts. Weidemann and Trueb (*Genomics* 69:275–279 (2000)), have shown that FGFR5 is expressed in cartilaginous tissues. When viewed in the context of the data provided above, this suggests that FGFR5 may play a role in bone formation and may therefore have applications in fracture repair and bone diseases, such as osteoporosis and osteopetrosis.

EXAMPLE 8

Stimulation of Proliferation and Adherent Peripheral Blood Mononuclear Cells (PBMC) By Murine FGFR5β and FGFR5γ

Stimulation of PBMC to adhere to plastic by murine FGFR5β and FGFR5γ Fc fusion proteins was demonstrated as follows.

Figure 4:
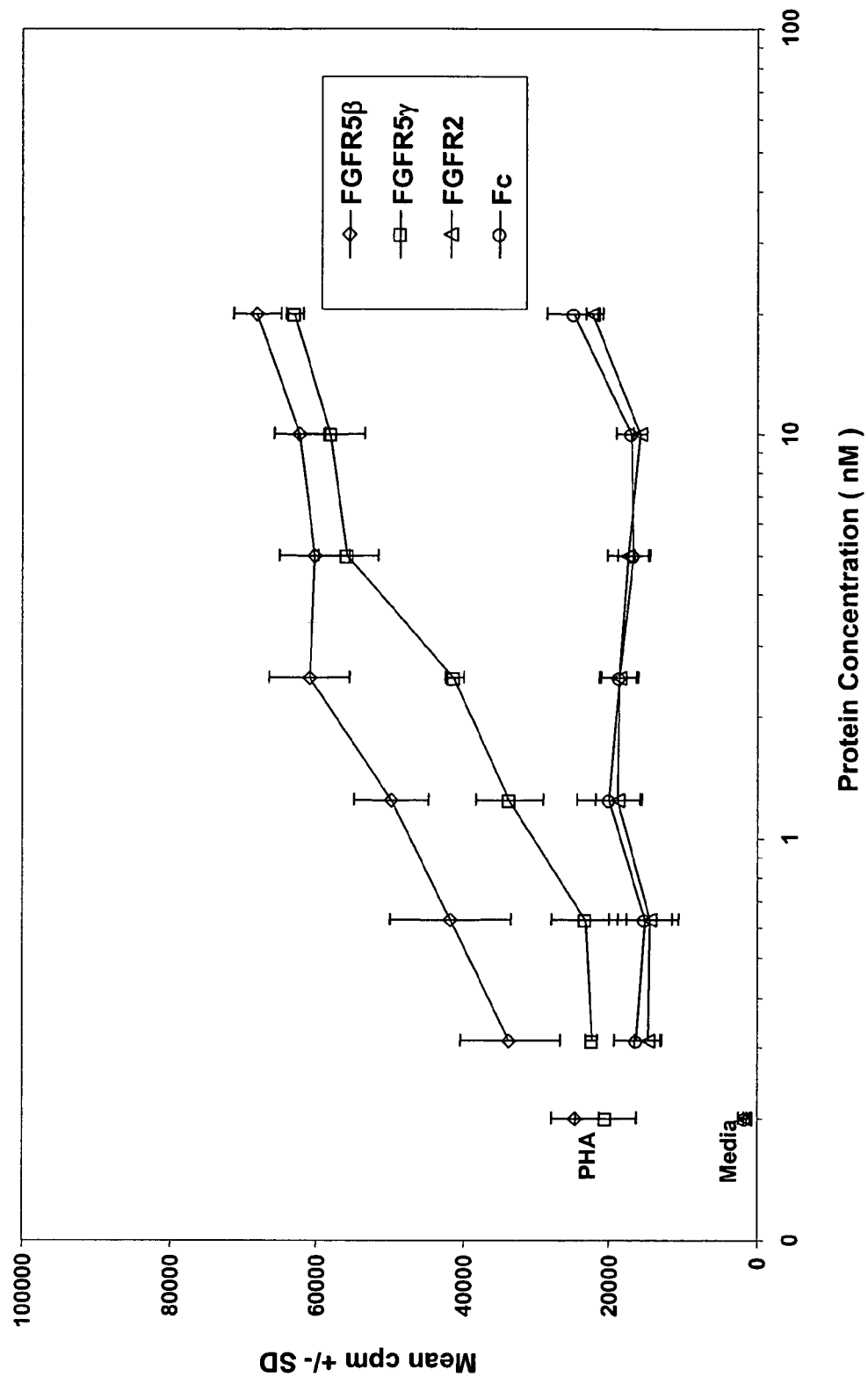
FIG. 4 illustrates the enhancing proliferative effect of FGFR5β and FGFR5γ on PHA-induced PBMC. The enhanced proliferation was not observed when FGFR2 or purified IgG Fc was used.
Figure 5:
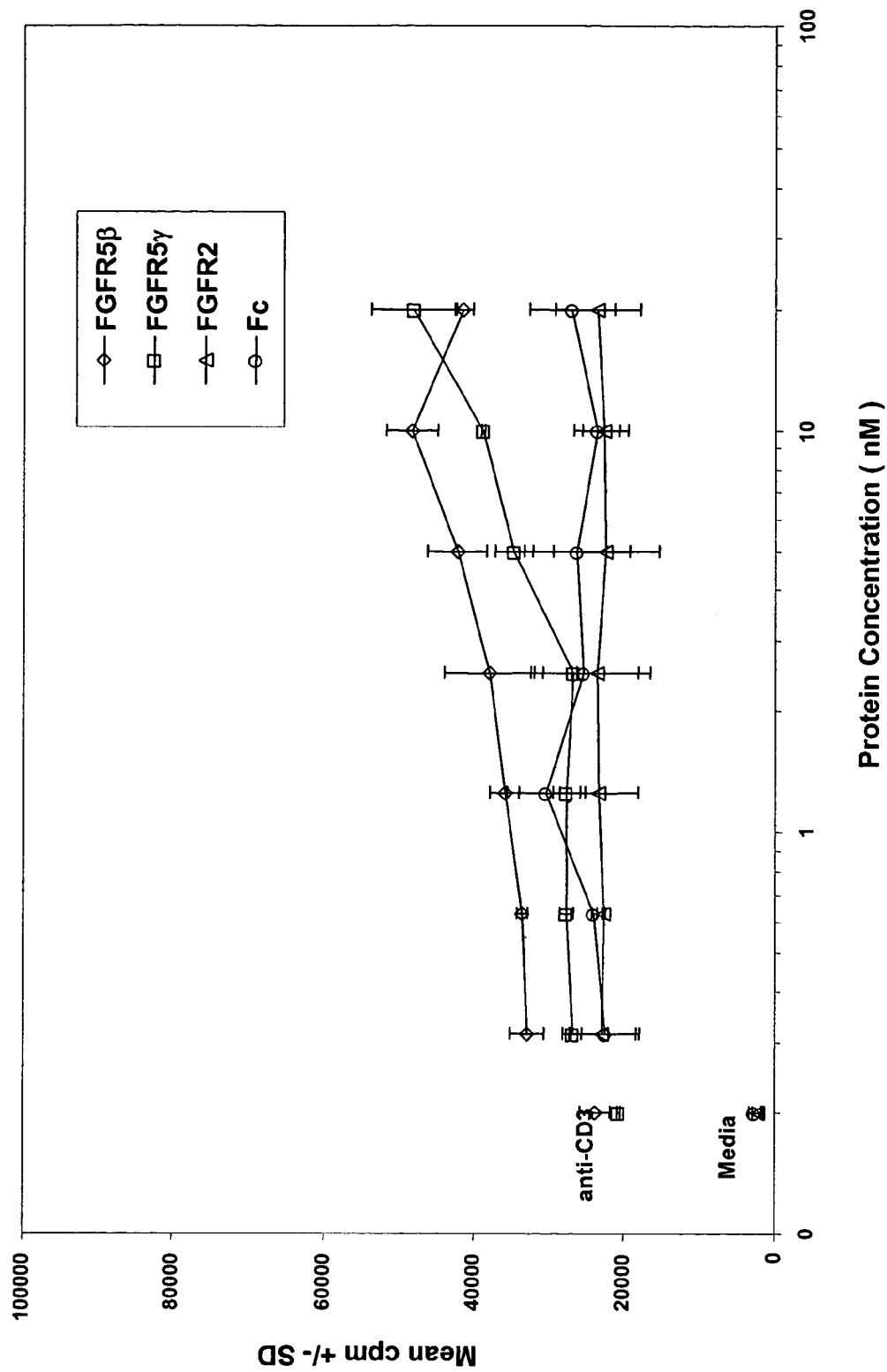
FIG. 5 shows the enhanced proliferation of anti-CD3 stimulated PBMC by FGFR5β and FGFR5γ. The enhanced proliferation was not observed when FGFR2 or purified FC was used as stimulants.
Figure 6:
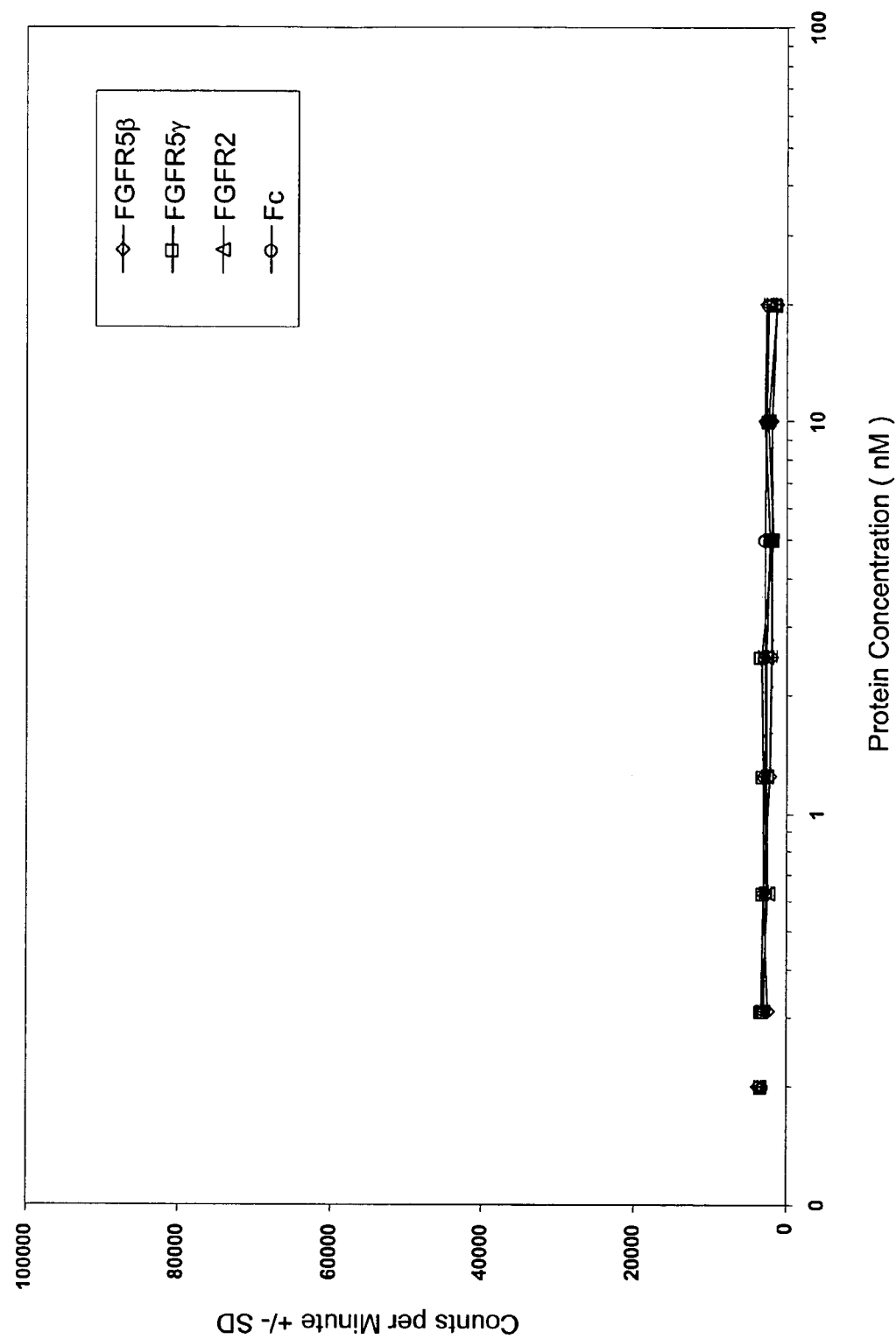
FIG. 6 demonstrates that FGFR5β and FGFR5γ, or the controls FGFR2 or IgG Fc did not stimulate proliferation of PBMC in the absence of PHA.

Purified FGFR5β-Fc and FGFR5γ-Fc fusion proteins were titrated from 20 nM into 0.1 ml media per well of 96 well microtiter plates. Purified human FGFR2-Fc fusion protein and human IgG Fc were used as controls. PBMC were harvested from blood by density gradient centrifugation and resuspended in media to a concentration of 2×10$^6$ cells/ml. Phytohaemagglutinin (PHA), Pokeweed mitogen (PWM), anti-CD3 antibody or media was added to the PBMC and 0.1 ml of cells dispensed to each well. The plates were incubated for 3 days at 37° C. in a humidified atmosphere containing 5% $CO_2$ in air. Cell proliferation was quantified by pulsing the plates with tritiated ($^3$H)-thymidine for the final 16 hours of culture. The cells were then harvested and $^3$H-thymidine incorporation quantified by standard liquid scintillation counting. FIGS. 4–6 show that murine FGFR5β and FGFR5γ fusion proteins enhanced proliferation of PBMCs activated with either PHA or anti-CD3 but did not induce the proliferation of PBMC on their own. Proliferation was not stimulated with human FGFR2-Fc fusion protein or human IgG Fc.

Figure 7:
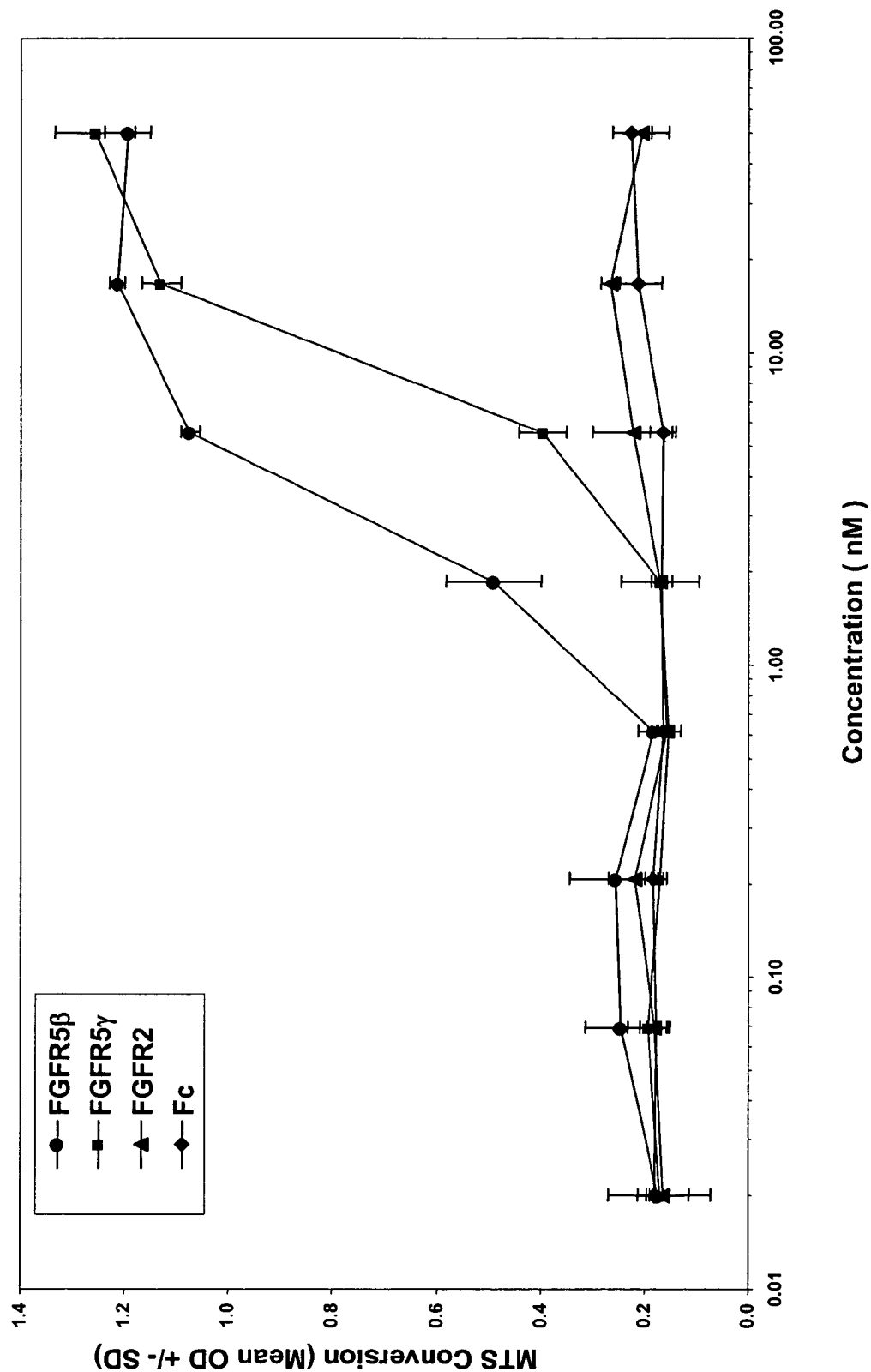
FIG. 7 illustrates the stimulation of PBMC adherence by FGFR5β and FGFR5γ but not by FGFR2 or purified IgG Fc.
Figure 8:
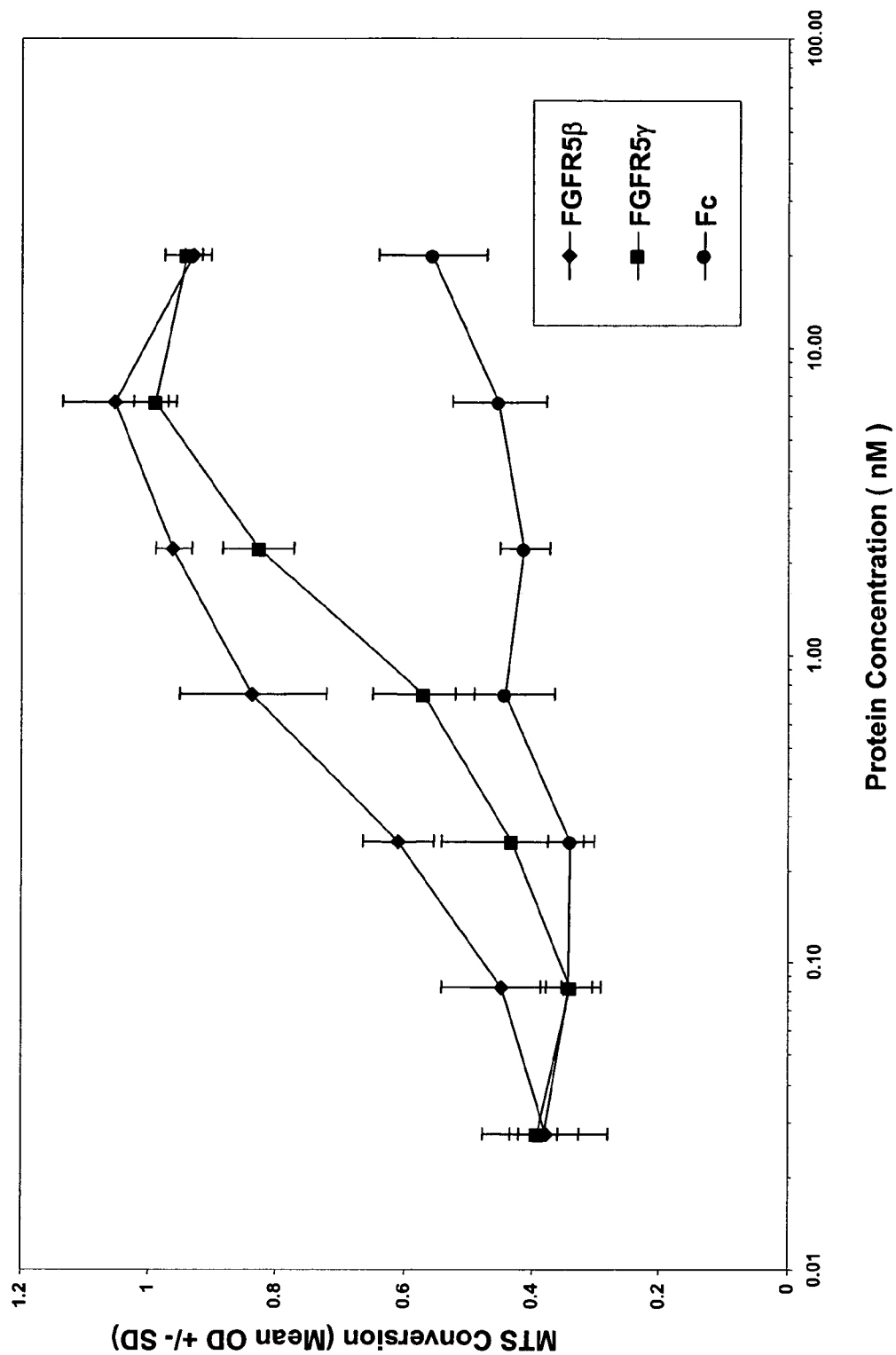
FIG. 8 shows the stimulation of adherent PHA-stimulated PBMC by FGFR5β and FGFR5γ but not by purified IgG Fc.

MuFGFR5β and muFGFR5γ (SEQ ID NO: 2 and 3, respectively) were expressed in mammalian cells and purified as Fc fusion proteins as described above. The muFGFR5β-Fc and muFGFR5γ-Fc fusion proteins were titrated from 10 nM into 0.1 ml media per well of 96 well microtitre plates. Peripheral blood mononuclear cells (PBMC) were harvested from blood by density gradient centrifugation and resuspended in media to a concentration of $2\times10^6$ cells/ml. PHA or media (RPMI 1640 supplemented with 5% FBS, 2 mM L-glutamine (Sigma), 160 mM penicillin G (Sigma), and 70mM dihydrostreptomycin sulfate (Boehringer Mannheim) was added to the PBMC and 0.1 ml of cells dispensed to each well. The plates were incubated for 3 days at 37° C. in a humidified atmosphere containing 5% $CO_2$ in air. The non-adherent cells were removed with three media washes. Media (0.05 ml) containing MTS/PES solution (CellTiter96 Aqueous One Solution Cell Proliferation Assay, Promega, Madison, Wis.) was dispensed to each well and the plate incubated for 4 hrs before the degree of dye conversion was quantified using a 96-well ELISA plate reader. FIGS. 7 and 8 show that muFGFR5β and muFGFR5γ Fc fusion proteins stimulated, in a dose dependent manner, the adherence of PBMC as well as the proliferation of the adherent PBMC. Furthermore, PHA stimulation augmented this effect. These results demonstrate that FGFR5β and FGFR5γ are capable of enhancing the proliferative effects of known immunostimulatory molecules on a mixed population of human haemopoietic cells, namely PBMC.

EXAMPLE 9

Activation of Natural Killer Cells By Murine FGFR5β and FGFR5γ

This Example discloses the activation of Natural Killer (NK) cells by muFGFR5β-Fc and muFGFR5γ-Fc fusion proteins.

Peripheral blood mononuclear cells (PBMC) were harvested from blood by density gradient centrifugation and resuspended in media (RPMI 1640 supplemented with 5% FBS, 2 mM L-glutamine (Sigma), 160 mM penicillin G (Sigma), 70 mM dihydrostreptomycin sulfate (Boehringer Mannheim)) to a concentration of $2\times10^6$ cells/ml. Purified muFGFR5β-Fc and muFGFR5γ-Fc fusion proteins were added to the cells at a concentration of 10 nM and the cells were cultured in 6 well plates (3 ml/well) for 3 days at 37° C. in a humidified atmosphere containing 5% $CO_2$ in air. Purified human FGFR2-Fc fusion protein was used as control. The non-adherent cells were removed with three media washes. The adherent cells were collected by light trypsinization and scraping. The cells were washed into staining buffer and their phenotype determined by standard flow cytometric techniques using the NK cell marker CD56 and a control isotype antibody.

As shown in FIG. 9, muFGFR5β-Fc and muFGFR5γ-Fc fusion proteins stimulated the adherence and/or growth of adherent cells from human PBMC, with approximately 50% of these cells being NK cells. The filled histograms represent the adherent PBMC stained with the NK cell marker CD56 and the open histograms represent the same cells stained with the isotype-matched control antibody. FGFR2 did not stimulate the adherence of PBMC and therefore there were no cells to analyze from these cultures. These results demonstrate that FGFR5β and FGFR5γ are immunostimulatory molecules that directly activate NK cells. These results, plus those provided in Example 8, above, demonstrated that FGFR5 can enhance immune responses, and may therefore be usefully employed to enhance vaccine responses and anti-cancer therapies.

EXAMPLE 10

Stimulation of Gene Expression in Human Monocytes By Murine FGFR5β-Fc Fusion Protein This Example discloses genes that were overexpressed in human monocytes stimulated with the murine FGFR5β-Fc fusion protein.

Monocytes were purified from human peripheral blood mononuclear cells (PBMC) by adherence for 2 hours at 37° C. Cells were stimulated with 100 nM of soluble FGFR5β human IgG Fc fusion protein or soluble FGFR2 human IgG Fc fusion protein. After 0 and 12 hours the adherent monocytes were collected and total RNA extracted from the cells using Trizol reagent (Invitrogen Corp., Carlsbad Calif.) following the manufacturer's instructions. The RNA was amplified and aminoallyl UTP incorporated using the Ambion MessageAmp aRNA kit (Ambion Inc, Austin Tex.) following the manufacturer's instructions.

The extracted amplified RNA from the FGFR5β and FGFR2-treated cells was labelled with either Cy3 or Cy5 dye (Amersham Pharmacia Biotech, Buckinghamshire UK), respectively, by indirect aminoallyl dUTP labeling and hybridized to 2 Clontech Atlas Glass 3.8 gene microarrays (BD Biosciences Clontech, Palo Alto, Calif.). The slides were washed, scanned and analyzed using Axon GenePix scanner and software (Axon Instruments Inc., Union City, Calif.). Where indicated, quantitative PCR was used to validate the microarray data and quantify the mRNA for genes not present on the array. Primers and probe sets were purchased from Perkin Elmer/Applied Biosystems (Foster City, Calif.) and MWB Biotech (Ebersberg, Germany) and all PCR reactions were run on a Perkin Elmer/Applied Biosystems 7700 following the manufacturer's instructions.

Treatment of monocytes with FGFR5β-Fc up-regulated expression of the 26 genes listed in Table 1 below. The up-regulation of three of the genes was confirmed by quantitative PCR. In addition, the expression of eight human cytokines was analyzed by quantitative PCR and the results of this analysis are shown in Table 1.

FGFR5-Fc stimulated a dramatic up-regulation in the levels of osteopontin (OPN) and TGFβ but had only modest effects on the other cytokines. This profile of gene expression was very unlike that described for other stimulators of monocytes such as LPS, *Mycobacterium tuberculosis*, GM-CSF and M-CSF, which stimulate modest OPN expression but pronounced expression of pro-inflammatory cytokines such as IL-1β, IL-6, IL-8 IL-10, IL-12 and TNFα (Rosenberger et al., *J. Immunol.* 164:5894–904 (2000); Suzuki et al., *Blood* 96:2584–2591 (2000); Hashimoto et al., *Blood* 94:837–844 (1999); Hashimoto et al., *Blood* 94:845–852 (1999); Boldrick et al., *Proc. Natl. Acad. Sci. USA* 99:972–977 (2002); Ragno et al., *Immunol.* 104:99–108 (2001)).

TABLE 1

Genes up-regulated in monocytes following treatment with FGFR5

|  | GENBANK | Microarray Fold up-regulation | Quantitative PCR Fold up-regulation |
|---|---|---|---|
| Secreted Molecules |  |  |  |
| Osteopontin | NM_000582 | 4.95 | 48.4 |
| Interferon, alpha 8 | NM_002170 | 2.27 | ND |
| EXODUS | NM_004591 | 2.27 | 6.3 |
| IL-1β | XO2532 | Not Determined (ND) | 3.4 |
| IL8 | NM_000584 | ND | 5.5 |
| IL-10 | NM_000572 | ND | undetectable |
| IL-12 p35 | NM_000882 | ND | undetectable |
| IL-12 p40 | NM_002187 | ND | undetectable |
| IL-20 | NM_018724 | ND | undetectable |
| TGFβ | NM_000660 | ND | 27.3 |
| TNFα | XO1394 | ND | 4.0 |
| Channels and Receptors |  |  |  |
| MICA | NM_000247 | 2.08 | 4.7 |
| TIE1 | NM_005424 | 3.30 | ND |
| Calcium channel, voltage-dependent, beta 4 subunit | NM_000726 | 2.44 | ND |
| LDL receptor-related protein 8 | NM_004631 | 2.20 | ND |
| Cytoskeletal Molecules |  |  |  |
| Myosin VI | NM_004999 | 1.89 | ND |
| Myosin, heavy polypeptide 1 | NM_005963 | 2.12 | ND |
| Troponin C, slow | NM_003280 | 1.88 | ND |
| Kinectin 1 kinesin receptor | NM_004986 | 1.73 | ND |
| Signalling Molecules |  |  |  |
| Protein kinase C, iota | NM_002740 | 2.26 | ND |
| Protein tyrosine phosphatase, non-receptor type 9 MEG-2 | NM_002833 | 1.85 | ND |
| Importin alpha 6 | NM_002269 | 2.17 | ND |
| Protein kinase, X-linked | NM_005044 | 1.92 | ND |
| Suppression of tumorigenicity 5 | NM_005418 | 3.16 | ND |
| RAR-related orphan receptor B | NM_006914 | 2.08 | ND |
| Zinc finger protein 124 HZF-16 | NM_003431 | 2.94 | ND |
| Metabolism |  |  |  |
| Ubiquitin-conjugating enzyme | NM_003341 | 2.41 | ND |
| Transplantation antigen P35B | NM_003313 | 2.48 | ND |
| UDP glycosyltransferase 2 | NM_001075 | 2.35 | ND |
| Alcohol dehydrogenase 2 | NM_000668 | 2.41 | ND |
| Solute carrier family 18 vesicular monoamine, member 1 | NM_003053 | 2.07 | ND |
| Seryl-tRNA synthetase | NM_006513 | 1.88 | ND |
| Other |  |  |  |
| H1 histone family, member 1 | NM_005325 | 1.99 | ND |
| Chr. 8 open reading frame 1 | NM_004337 | 2.08 | ND |

In addition to demonstrable upregulation of OPN mRNA, PBMC and adherent PBMC (predominantly monocytes) were stimulated with FGFR2, FGFR5, LPS or media alone for 24 hours and the supernatants collected for cytokine analysis. LPS induced the production of the expected pro-inflammatory cytokines such as IL-1, IL-6, and TNFα whereas FGFR5 did not. In contrast, FGFR5 stimulated both PBMC and adherent PBMC to produce 90 and 130 ng/ml of osteopontin, respectively. LPS stimulated 20 and 50 ng/ml of osteopontin and FGFR2 and the media control cultures contained less than 20 ng/ml of OPN. See, FIGS. 11A–C. These results are consistent with the microarray and real time PCR results presented in Table 1, above, and demonstrate that FGFR5 selectively stimulated osteopontin production by PBMC.

A second microarray analysis of genes up-regulated by FGFR5 was performed using the Affymetrix, Inc. (Santa Clara, Calif.) Gene Chip microarray technology. Adherent human PBMC were stimulated with media, FGFR2-Fc or FGFR5-Fc for 12 hours and the RNA was collected, amplified, and labelled with a fluorescent dye. The labelled RNA was hybridized to Gene Chips printed with oligonucleotides that represent all of the genes in the human transcriptome. Fluorescently labelled cRNA were generated using the protocols provided by Affymetrix and the labelled RNA was hybridized to the chips.

150 genes up-regulated in monocyte-derived macrophages (MDMs) stimulated with FGFR5-Fc were identified that were not up-regulated in MDM treated with media alone or with FGFR2-Fc. An analysis of the genes up-regulated in MDM by FGFR5 reveals a pattern of gene expression which is similar to that described for IL-4 and IL-13 activated macrophage. See Table 2. The M2 macrophages, like those stimulated by FGFR5, do not express pro-inflammatory cytokines but express inhibitors of inflammation such as IL-1 receptor antagonist and the Decoy IL-1 receptor. These cells are known as alternatively activated or M2 macrophage and are thought to have different functions to LPS or IFNγ activated macrophage (M1 macrophage). M2 macrophages are found in tumours, allergic individuals and are thought to play a role in tissue repair whereas the M1 macrophages are the classically activated macrophage that engulf and kill bacteria (reviewed in Nature Reviews in Immunology (2003) Vol 3, 23–35). It is possible that the selective stimulation of M2 macrophage by FGFR5 administration may be beneficial in some therapeutic settings such as wound healing. This microarray experiment also confirmed our previous observations that osteopontin and TGFβ1 were overexpressed and that CD14 was down-regulated following FGFR5 stimulation of MDM cells and that many adhesion-associated genes were up-regulated—an observation that is consistent with the growth and adhesion promoting activity of FGFR5 on monocyte-derived macrophage (MDM) cells.

The Affymetrix microarray experiments identified the overexpression of the TNF superfamily member, LIGHT (aka TNFSF14), a known growth factor for activated T-cells that acts as a co-stimulant for these cells. Quantitative PCR was employed to confirm that LIGHT expression was upregulated in FGFR5-stimulated MDM cells. Without wishing to be limited to a specific mode of action, it is believed that the FGFR5-dependent over-expression of LIGHT in MDM cells may explain how FGFR5 augments the proliferation of anti-CD3 driven T-cell proliferation.

TABLE 2

Genes differentially expressed in M1 or M2 macrophage

| M1 Macrophage | M2 Macrophage |
|---|---|
| TLR2 and 4 | Scavenger receptor A and B |
| TNFα, IL-1, IL-6, IL-12 | CD163 |
| IL-1R Type I | Mannose Receptor |
| CXCL8, CXCL9, CXCL10, CXCL11 | CD23 |
| CCL2, *CCL3*, CCL4, CCL5 | IL-1 receptor antagonist |
|  | Decoy IL-1 R type II |
|  | CCL17, CCL22, *CCL24* |
|  | (*Eotaxin 2*) Arginase |

(Genes indicated by italics are upregulated in FGFR5 stimulated MDM)

In total, the results presented herein demonstrate that FGFR5 is a potent stimulator of osteopontin expression. Osteopontin (OPN) is a multifunction protein secreted by activated macrophages that shares most of the functions described herein for FGFR5. More specifically, OPN is a potent immunostimulatory molecule (O'Regan et al., *Immunol. Today* 21:475–478 (2000)) that stimulates macrophage adherence, activation, cytokine secretion and growth. It has been shown that OPN is a regulator of T-cell responses in that it augments CD3-induced proliferation, IFNγ production, and CD40 ligand expression. OPN also enhances Th1 and inhibits Th2 cytokine expression. It directly induces macrophages to produce IL-12 and inhibits IL-10 expression by LPS stimulated macrophages (Ashkar et al., *Science* 287:860–864 (2000)). OPN has also been shown to induce B cell proliferation and auto-reactive antibody production and it appears that OPN may preferentially activate a CD5+ subset of B-cells and induce the production of auto-antibodies.

Osteopontin has been linked with a number of pathophysiological states including a variety of tumors; autoimmune diseases such as multiple sclerosis (MS), systemic lupus erythematosus (SLE), diabetes and rheumatoid arthritis; granulomatous inflammation such as sarcoidosis and tuberculosis; and pathological calcifications such as kidney stones and atherosclerosis (Giachelli and Steitz, *Matrix Biol.* 19:615–622 (2000)). Elevated levels of OPN are found in the sera of SLE patients and the autoimmune-prone MRL mice. Recently two groups described a central role for OPN in multiple sclerosis (Chabas et al., *Science* 294:1731–1735 (2001) and Jansson, *J. Immunol.* 168:2096–2099 (2002)). OPN is prevalent in the plaques of MS patients and, due to its immunostimulatory properties, it has been proposed that OPN plays a role in the progression of MS. This effect was demonstrated in experimental allergic encephalopathy (EAE), the murine model for MS. Mice that lacked the OPN gene were resistant to progressive EAE and had frequent remissions when compared to wild-type mice expressing OPN.

SLE is an autoimmune disorder that affects 24 out of 100,000 individuals in the USA. Afflicted individuals usually develop nephritis, arthritis and dermatitis. Auto-antibody production, complement activation, immune complex deposition, Fc receptor ligation and leukocyte infiltration of the target organs are among the immunopathogenic events.

The chromosomal location of FGFR5 is 4p16. Genetic screens on large numbers of SLE patients show that a mutation at this location is associated with disease. FGFR5 sequence analysis may thus be used to identify individuals at risk of developing SLE by determining whether a mutation exists.

OPN has also been shown to function in bone remodelling by inhibiting calcification. Inhibition of OPN expression, by reducing the level or binding of FGFR5, may thus be useful in the treatment of osteoporosis.

Many of the effects described for FGFR5 may be mediated by its ability to induce high levels of osteopontin expression. Osteopontin is clearly a key molecule in the progression of a number of disease processes and therefore regulators of osteopontin expression, such as FGFR5, are targets for therapeutics for osteopontin-mediated diseases, including SLE, vasculitis, atherosclerosis, nephritis and arthritis.

EXAMPLE 11

Analysis of FGFR5 Expression Using Real Time PCR

This example discloses that FGFR5 is abundantly expressed in polymorphonuclear leucocytes (PMN) and PBMC.

Primers and a probe were designed to Exons 1 and 2 of human FGFR5 and used in real time quantitative PCR studies to determine the relative abundance of FGFR5 mRNA in a variety of cell lines and tissues. The primer sequences were; GGCTTCGGCAGCCTTA and CATTAGCCCAGGGAAGGAGAG. The sequence of the probe used was CAACTACACCCTCGTCGTGCTGGATGA. These experiments revealed that FGFR5 is expressed at very low levels by most cell types but is more abundantly expressed by polymorphonuclear leucocytes (PMN) and PBMC.

EXAMPLE 12

Analysis of FGFR5 Expression Using FGFR5-Specific Polyclonal Antibodies

This example discloses the preparation of a rabbit anti-FGFR5 polyclonal antisera and its utility in detecting the expression of FGFR5 protein in a variety of normal and disease tissues from humans.

Polyclonal antibodies were generated to the extracellular domain of FGFR5β by immunizing rabbits with murine FGFR5β extracellular domain fused to human IgG1 Fc fragment emulsified in complete Freund's adjuvant. The FGFR5-specific immune response was boosted by three subcutaneous injections at weekly intervals with the same protein and then twice with pure murine FGFR5β extracellular domain protein. Antisera were collected from the rabbits and the IgG purified by Protein A affinity chromatography.

Antibodies raised to the human IgG Fc portion of the immunogen were removed by absorption to Sephadex beads coated with human IgG. The resultant polyclonal antibody specifically reacted with human and mouse FGFR5 but did not recognize human FGFR1, 2, 3, or 4 Fc fusion proteins (purchased from R&D Systems, Minneapolis Minn.) in ELISA or by Western blotting.

Immunohistochemical analysis of human normal and diseased tissue arrays (SuperBioChips Laboratories, Seoul, Korea) revealed that FGFR5 was expressed in a minor population of granulocytes in the red pulp region of the spleen. FGFR5expressing granulocytes were also found in a number of tissues including the stomach, lung and small intestine. FGFR5 expression was also detected in skeletal muscle, skin and kidney. In addition, expression of FGFR5 was found in tissue biopsies from a hepatocellular carcinoma and a squamous cell carcinoma.

Diabetes

FGFR5 was detected in cells within the islets of Langerhans of the pancreas and may therefore play a role in diabetes (see, Kim et al. *Biochim. Biophys. Acta* 1518: 152–156 (2001)), especially given the immunostimulatory properties of this molecule.

Rheumatoid Arthritis

Patients with rheumatoid arthritis often form inflammatory, granulomatous lesions under the skin that are referred to as rheumatoid nodules. Sections from rheumatoid nodules were stained and confirmed to express FGFR5.

Sarcoidosis

Sarcoidosis is thought to be an autoimmune disease that is characterized by the formation of non-caseating sterile granulomas. Granulomas are nodular lesions that form due to chronic localized stimulation of macrophages that differentiate into large epithelioid cells, histiocytes, and giant cells.

Two human sarcoidosis patient biopsy samples were cut and stained for FGFR5 expression. The first biopsy sample was a lymph node that was filled with numerous small granulomas surrounded by lymphoid tissue. The granulomas expressed FGFR5 to varying degrees ranging from moderate to no expression. Some of the giant cells, present in the more mature granulomas, stained quite strongly for FGFR5 whereas the histiocytes of others stained only weakly. Scattered in amongst the granulomas were remnants of lymphoid follicles and granulocytes. The granulocytes stained intensely with the antibody whereas pockets of lymphoid cells expressed lower levels of FGFR5.

The second biopsy was taken from the liver and contained many small inflammatory foci that exhibited a different structure to the archetypal granuloma observed in the first biopsy sample. The liver cells in the second biopsy sample expressed FGFR5 protein. In contrast to the lymph node sample, fewer of the leukocytes expressed high levels of FGFR5 while all of the leukocytes present in a small, presumably emerging, lesion expressed very high levels of FGFR5. These experiments demonstrated that FGFR5 is expressed in granulomas and granulocytes and may be expressed by some lymphocytes.

In total the results obtained with these two biopsy samples demonstrate the expression of FGFR5 in sarcoid lesions and suggest that FGFR5 may participate in fuelling the disease process.

Murine Bone

A humerus was collected from an adult mouse, fixed in buffered formalin, embedded in wax, sectioned, and stained for FGFR5 expression. Some, but not all, cells stained for FGFR5. Megakaryocytes, chondrocytes, osteocytes, and stomal cells/osteoblasts all expressed FGFR5 whereas 95% of the small haemopoietic cells did not. It was impossible to identify the 5% of haemopoietic cells expressing FGFR5 based on their morphological characteristics alone.

EXAMPLE 13

Generation of Monoclonal Antibodies Directed Against Murine FGFR5

This Example discloses the preparation of murine monoclonal antibodies specific for an epitope on the murine FGFR5 extracellular domain.

Four mice were immunized with murine FGFR5 extracellular domain (ECD) fused to the murine IgG3 Fc. Serum samples collected from the mice were tested for antibodies reactive to murine FGFR5. Two of the four mice were confirmed to produce anti-FGFR5 antibodies. A single mouse having the highest titer of FGFR5 antibodies was reimmunized with the FGFR5-Fc fusion protein. Splenocytes were isolated from this mouse and standard methods were employed to fuse the splenocytes to myeloma cells to generate hybridomas. After the fusion, the cells were dispensed into eighteen 96-well plates and cultured in media to select for hybridomas.

700 independent hybridoma lines were screened for FGFR5-reactive antibodies using the murine FGFR5β ECD fused to human IgG Fc in an ELISA assay. Three independent, positive hybidomas were identified and further screened for FGFR5-specific antibodies using murine FGFR1–4 human IgG Fc fusion proteins (commercial). The hybridomas specific for FGFR5 were subcloned and supernatants generated and tested in the following immunohistochemical and ELISA assays.

The three monoclonal antibodies were used to validate the FGFR5 expression profile revealed by the rabbit polyclonal antisera described herein. A series of assays revealed that all three antibodies recognized a similar epitope and competed for binding to the recombinant FGFR5 protein. One of these three monoclonal antibodies, clone 15G6, was used in the following assays.

A series of immunohistochemistry experiments was performed using the monoclonal antibody on human peripheral blood leucocytes fixed to slides by cytocentrifugation. These experiments revealed that FGFR5 is expressed in the granules of polymorphonuclear (PMN) leucocytes and monocytes, however, not all PMN expressed FGFR5 with ~10% expressing little or no FGFR5, ~20% expressing moderate levels of FGFR5 and the remainder expressing high levels of the protein. This staining pattern suggests that FGFR5 may be regulated during PMN activation of maturation.

EXAMPLE 14

Identification of FGFR5 Transcripts cDNA encoding FGFR5 was PCR amplified from 6AVS cells, a bone marrow stromal cell line, and subjected to sequence analysis to confirm that these cells express splice variants of FGFR5. The 6AVS cells express a membrane tethered form of FGFR5 (i.e. it contains a transmembrane domain) but the extracellular domain of the protein was approximately 200 bp shorter than the predicted full-length sequence. This form of FGFR5 is referred to herein as FGFR5δ. The 200 bp fragment encodes ~70 amino acids that form part of the distal region of the second Ig domain, the acid box, CAM (cell adhesion molecule)-binding and heparin binding domains. The resulting receptor encoded by the splice variant created a receptor with an extracellular domain made up of 2 Ig domains linked together with a novel region unlike any other known FGF receptor. The expression of FGFR5δ by bone marrow cells suggests that this transcript plays a role in haemopoiesis. The polynucleotide and amino acid sequences of FGFR5δ are presented herein as SEQ ID NOs: 144 and 145, respectively.

EXAMPLE 15

Effects of FGFR5 Administration In Vivo

This Example discloses the effects of in vivo administration of FGFR5β protein to mice.

Experiment 1 used BALB/cByJ mice and experiment 2 used C3H/HeJ mice. Both sets of mice were injected subcutaneously with 5 μg (55 nM in 0.1 ml PBS) of murine FGFR5β extracellular domain (ECD)-murine IgG3 Fc fusion protein in the morning and the same dose in the evening (i.e. each mouse received 10 μg per day) for five days. Control mice received PBS alone. On the sixth day, the mice were sacrificed and the draining lymph nodes (axillary and lateral axillary) were removed. A single cell suspension was generated from the lymph nodes of each mouse and the number of cells collected from each mouse was determine by trypan blue viability counting using a haemocytometer. The lymph node cells collected from the FGFR5-treated mice were then pooled. The lymph node cells collected from the PBS-treated mice were amalgamated into a separate pool of cells. The cells from both the FGFR5 and PBS-treated mice were then stained for the cell surface antigens listed in Table 3, below, and analysed by flow cytometry.

In a third experiment, C3H/HeJ mice were injected subcutaneously with 10 μg (110 nM in 0.1 ml PBS) of murine FGFR5β ECD-human IgG1 Fc fusion protein in one injection per day for 5 days. While the treatment regime differed from that used in Experiments 1 and 2 above, the total dose of protein administered to the mice was not altered. Control mice were administered human IgG1 Fc fragments alone. On the sixth day, the mice were sacrificed and the draining lymph nodes (axillary and lateral axillary) removed. The number of cells collected from each mouse and the presence of cell surface antigens was determined as described above.

As shown in Table 3, in vivo administration of FGFR5 was found to stimulate lymphadenopathy, or enlargement of the lymph nodes. When compared to mice treated with Fc protein, the frequency of B cells doubled in the draining lymph nodes of FGFR5treated mice. An analysis of the cell cycle state of the B cells by flow cytometry indicated that they were not expanding but were either selectively migrating or being retained in the lymph nodes. This is consistent with the data provided above showing that FGFR5 causes the growth of macrophages but not T or B cells in culture. The cells were, however, activated as there was an increase in the number of cells expressing the very early activation antigen, CD69.

TABLE 3

Comparison of three in vivo experiments testing the effects of soluble FGFR5 in mice

| Markers | Cell type recognized | Experiment 1 Balb/c | | Experiment 2 C3H/HeJ | | Experiment 3 C3H/HeJ | |
|---|---|---|---|---|---|---|---|
| | | Murine Fc FGFR5 | PBS | Murine Fc FGFR5 | PBS | Human Fc FGFR5 | Human Fc |
| CD3 | T cell | 63 | 81 | 59 | 82 | 32 | 67 |
| CD19 | B cell | 35 | 21 | 39 | 16 | 61 | 26 |
| Class II | B cell and macrophage | 41 | 20 | ND* | ND | ND | ND |
| CD45R | B cell | ND | ND | ND | ND | 72 | 31 |
| CD69 | Activated cells | 23 | 14 | 18 | 10 | 21 | 10 |

*ND = Not determined

Axillary lymph node cells from treated mice were placed in culture and incubated with $^3$H-thymidine for 18 hours then harvested and analyzed. The cells from the FGFR5treated mice incorporated more thymidine than the control mice indicating that they were dividing. These studies suggested that FGFR5-induced localized B-cell-dominated lymphadenopathy is caused by localized cellular proliferation.

In order to more accurately target the draining lymph nodes and to monitor the effects of the control and test protein in the same mouse, a footpad injection protocol was utilized. According to this model, the test stimulant was injected under the right hind footpad and the control protein under the left hind footpad. The lymphatic drainage of this site routes to the popliteal lymph nodes. 24 hours after injection, the lymph nodes were collected and the cells counted and stained with antibodies to determine whether the T- or B-cells were activated.

EXAMPLE 16

Effect of FGFR5 on Bone Marrow Growth and Differentiation

This Example discloses the effects of FGFR5 on haemopoiesis through stimulation of murine bone marrow cells (BMC).

The effect of FGFR5-Fc on bone marrow growth was assessed in a standard tritiated thymidine proliferation assay. Briefly, murine bone marrow cells were collected from the humerus and resuspended in DMEM supplemented with 5% FBS, 2 mM L-glutamine (Sigma, St Louis Mo.), 1 mM sodium pyruvate (Life Technologies, Gibco BRL, Gaithersburg Md.), 0.77 mM L-asparagine (Sigma), 0.2 mM arginine (Sigma), 160 mM penicillin G (Sigma), 70 mM dihydrostreptomycin sulfate (Boehringer Mannheim, Roche Molecular Biochemicals, Basel, Switzerland) at $2 \times 10^6$ cells/ml. The cells were seeded into 96 well round bottom plates in 0.1 ml of media and various concentrations of FGFR5-Fc, FGFR2-Fc, IL-7 or media added to the plates in 0.1 ml media. The cultures were then incubated at 37° C. in a humidified atmosphere containing 10% $CO_2$ in air for 3 days. Tritiated thymidine was added to the cultures for the final 16 hrs and cells harvested onto glass fibre filters and thymidine incorporation quantified by standard liquid scintillation counting. FIG. 12A shows that FGFR5 induces a dose dependent proliferation of murine bone marrow cells. Bone marrow contains numerous haemopoietic cell types at various stages of differentiation and therefore FGFR5 may stimulate the growth of one or many of these cell types. The following experiments were performed to determine which cells grew in response to FGFR5-Fc stimulation.

The effect of FGFR5 on the proliferation of non-adherent and adherent BMCs is presented in FIGS. 12B (non-adherent BMCs) and 12C (adherent BMCs). Murine bone marrow cells were isolated from 6–8 week old female Balb/c mice. Adherent BMCs were prepared by inoculating cells into 96-well plates at $1\times10^6$ cells/well, incubating at 37° C. for 3 hours and then removing non-adherent cell. The non-adherent BMCs were harvested after incubating BMCs in culture dishes at 37° C. for 3 hours to remove adherent cells and then seeded into a 96-well plate at $2\times10^6$ cells/well. The mean cell proliferation in the presence of varying concentrations of FGFR5, FGFR2 or Medium control was measured from the incorporation of tritiated thymidine. Data represent mean cpm±SD.

Figure 13:
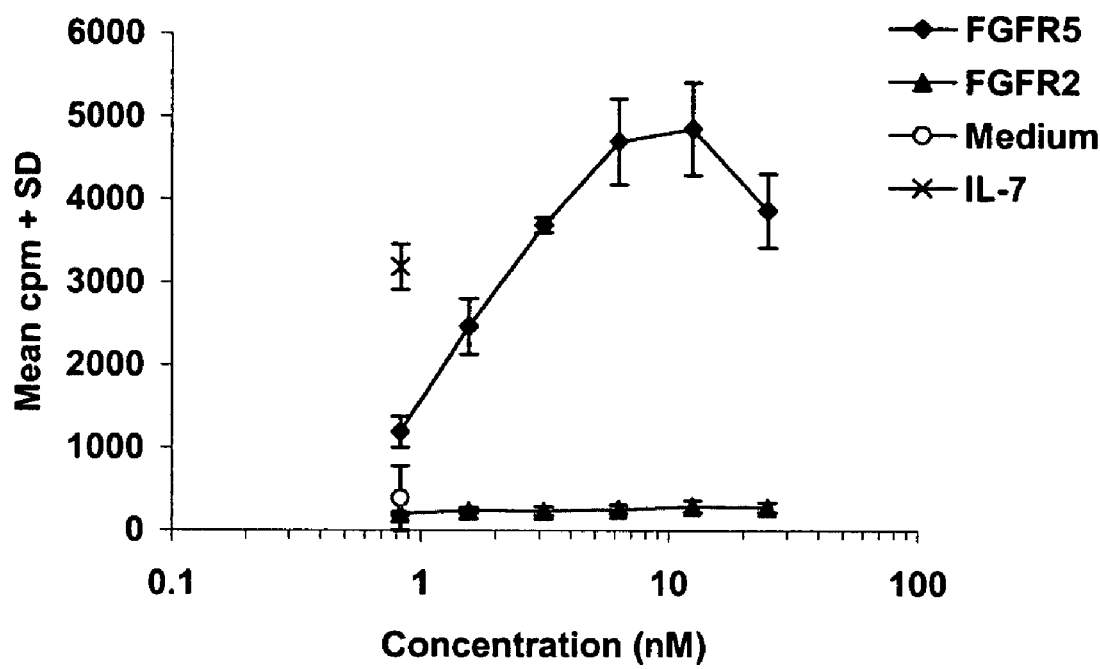
FIG. 13 is a graph depicting the effect of FGFR5 on the proliferation of bone marrow stromal cells.

The effect of FGFR5 on the proliferation of aggregated (stromal cell enriched) BMCs is presented in FIG. 13. Aggregated BMCs were prepared as described previously (Parkin et al., *J. Immunol.* 169:2292–2302 (2002) and distributed into 96-well plates at $5.5\times10^4$ cells/well. The mean cell proliferation in the presence of varying concentrations of FGFR5, FGFR2 or medium control and IL-7 (10 ng/ml) was measured from the incorporation of tritiated thymidine. Data represent mean cpm±SD.

Figure 14:
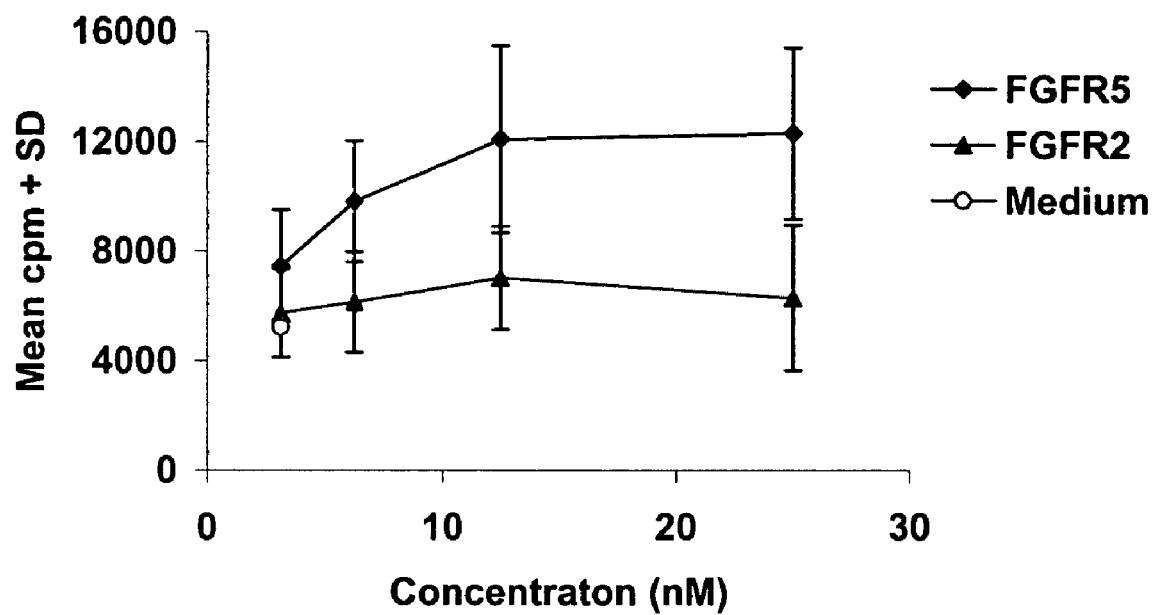
FIG. 14 is a graph depicting the effect of FGFR5 on 6AVS cell proliferation.

The effect of FGFR5 on proliferation of the murine bone marrow cell line 6AVS is presented in FIG. 14. 6AVS cells ($2\times10^3$ cells/well) were seeded into 96-well plates, in DMEM supplemented with 0.05% FBS and incubated with varying concentrations of FGFR5 or FGFR2 in a humidified incubator at 37° C. and 5% $CO_2$ in air. [$^3$H]-thymidine incorporation levels were assessed at day 3, after a 16 hour pulse. The data are presented as mean cpm±SD of triplicate wells.

The non-adherent bone marrow cells proliferating in response to FGFR5 stimulation were identified by flow cytometry. Bone marrow cells were distributed into 6-well plates ($2\times10^6$/ml, 3 ml/well) with or without FGFR5 (25 nM) or FGFR2 (25 nM). After incubating at 37° C., 5% $CO_2$, for 3 days, the surface phenotype of the cells was determined with immunofluorescence labeling. FGFR5 stimulates the preferential expansion of pre-B cells in culture as illustrated in FIGS. 15A (% of B220+ cells in total viable cells) and 15B (% of pre/pro-B in total viable B cells).

Figure 16:
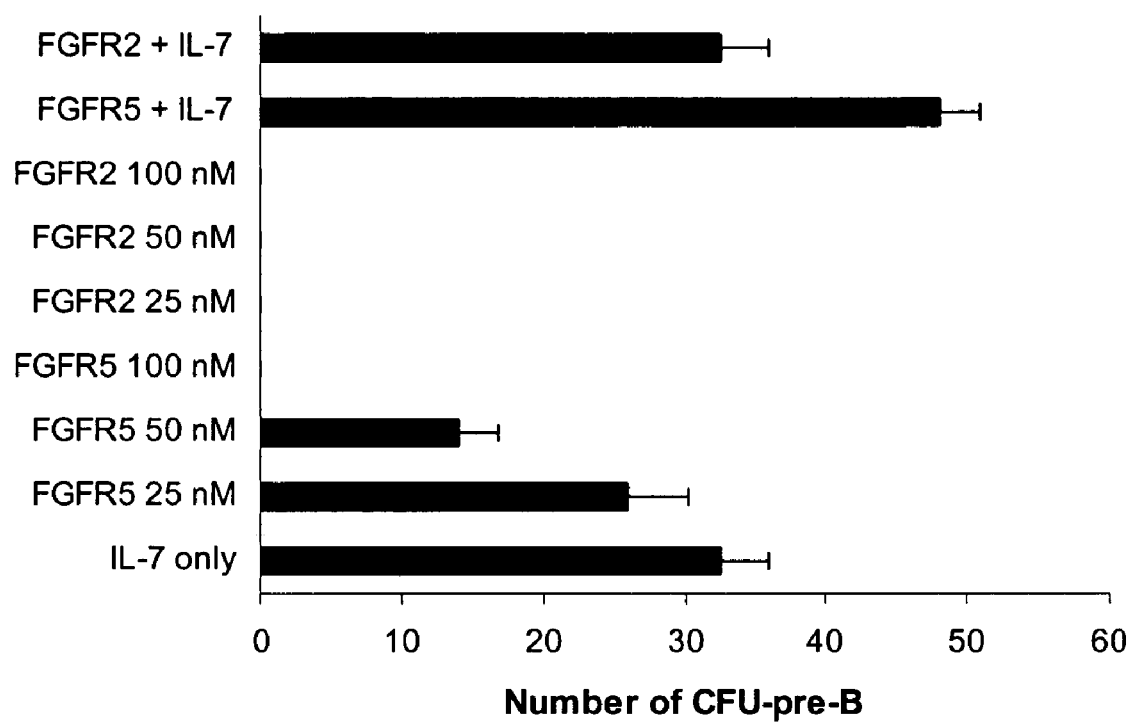
FIG. 16 is a bar graph depicting the effect of FGFR5 on CFU pre-B formation from BMC.

B-cell colony formation assays were utilized to determine whether FGFR5 had a direct effect on B-cell development. The effect of FGFR5 on CFU-pre-B formation from BMC is presented in FIG. 16. Bone marrow cells ($5\times10^4$) in 1 ml of complete IMDM media containing 10 ng/ml IL-7, or the indicated amount of FGFR5/FGFR2, or the combination of 25 nM FGFR5/FGFR2 and 10 ng/ml IL-7 were plated in 35-mm culture dishes and incubated at 37° C., 5% $CO_2$. Complete media consisted of IMDM, 1% methylcellulose, 30% FBS, $10^{-4}$ M 2-mercaptoethanol, 2 mM L-glutamine, 100 U/ml penicillin and 100 µg/ml streptomycin. Colonies comprising >30 cells were quantified after 7 days. Data represent mean cpm±SD from duplicate cultures.

After 10 days of culture, the colonies were counted. There were no colonies detected in either the media or FGFR2 stimulated cultures whereas FGFR5 and IL-7 stimulated growth of equivalent numbers of colonies. The results demonstrated that FGFR5 and IL-7 had an additive effect suggesting that FGFR5 and IL-7 triggered complimentary but distinct growth and development signals.

Colonies formed following FGFR5 stimulation had a similar appearance to the pre-B cells colonies induced by IL-7. These data suggested that each colony arose from one responsive precursor cell and that IL-7 and FGFR5 had a direct effect on the cells—not via any accessory cells that are spatially separated from the responders in the gelatinous media. These data also demonstrated that FGFR5 stimulated the formation of pre-B cells from BMC cultures.

Treatment with either FGFR5 or IL-7 induced growth of B cells as all expressed CD45R (B220), however, FGFR5 stimulated the growth of cells with a more mature B-cell phenotype. The FGFR5 stimulated cells contained 33% IgM+B-cells whereas only 10% of the cells generated in the IL-7 cultures were of this phenotype. In accordance with this observation, the FGFR5 colonies appeared to be smaller on average than the IL-7 colonies suggesting that FGFR5 stimulated cells of a more mature phenotype. The effects of FGFR5 appeared to mimic those of TSLP which stimulates B-cell colony formation in these assays and preferentially induced growth of B220+IgM+B-cells.

EXAMPLE 17

Secretion of Native FGFR5 By PMN and Detection Using an FGFR5-Specific ELISA

Figure 17:
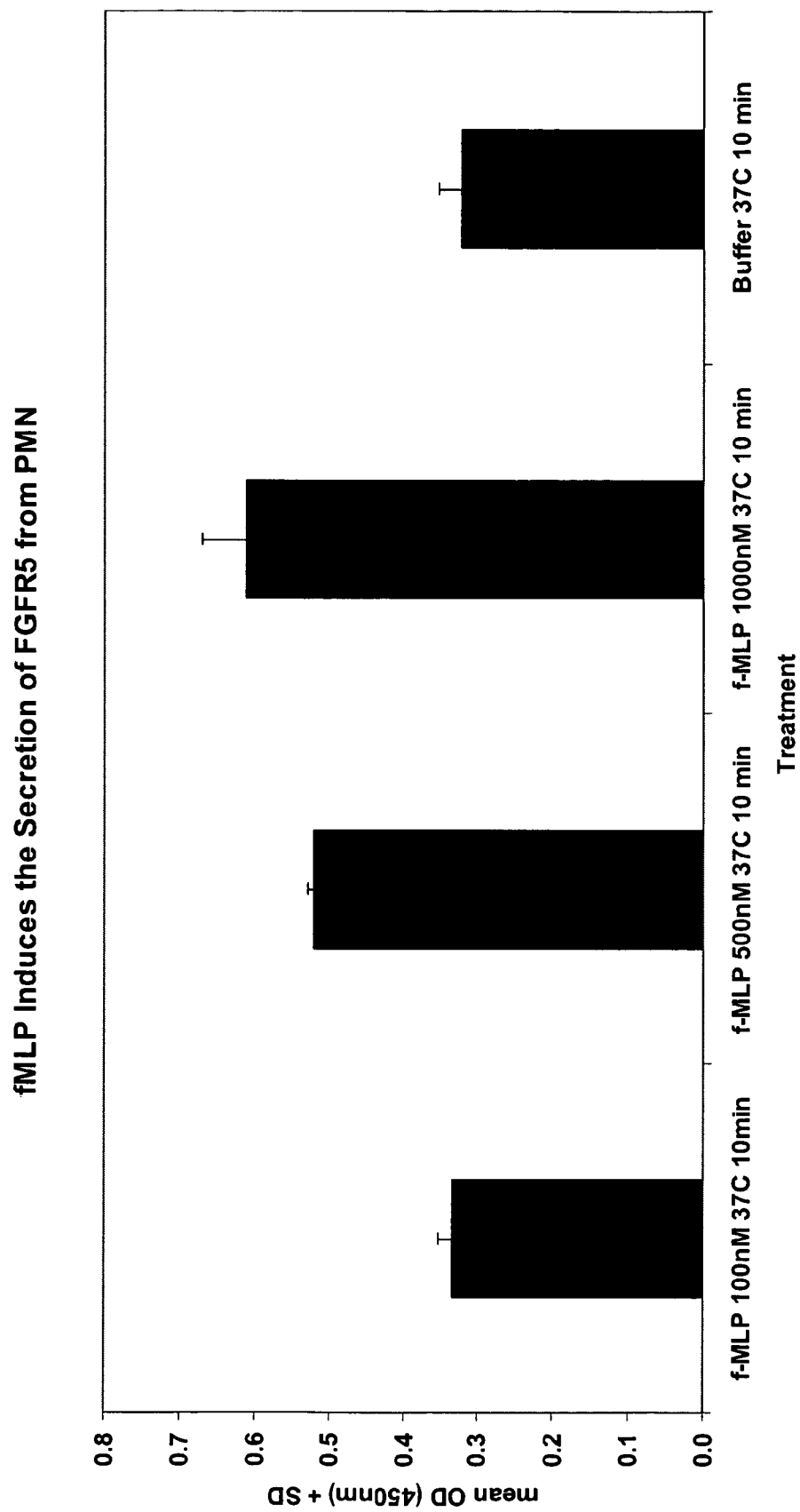
FIG. 17 is a bar graph depicting the effect of fMLP on inducing the secretion of FGFR5 from polymorphonuclear leukocytes (PMN).
Figure 18:
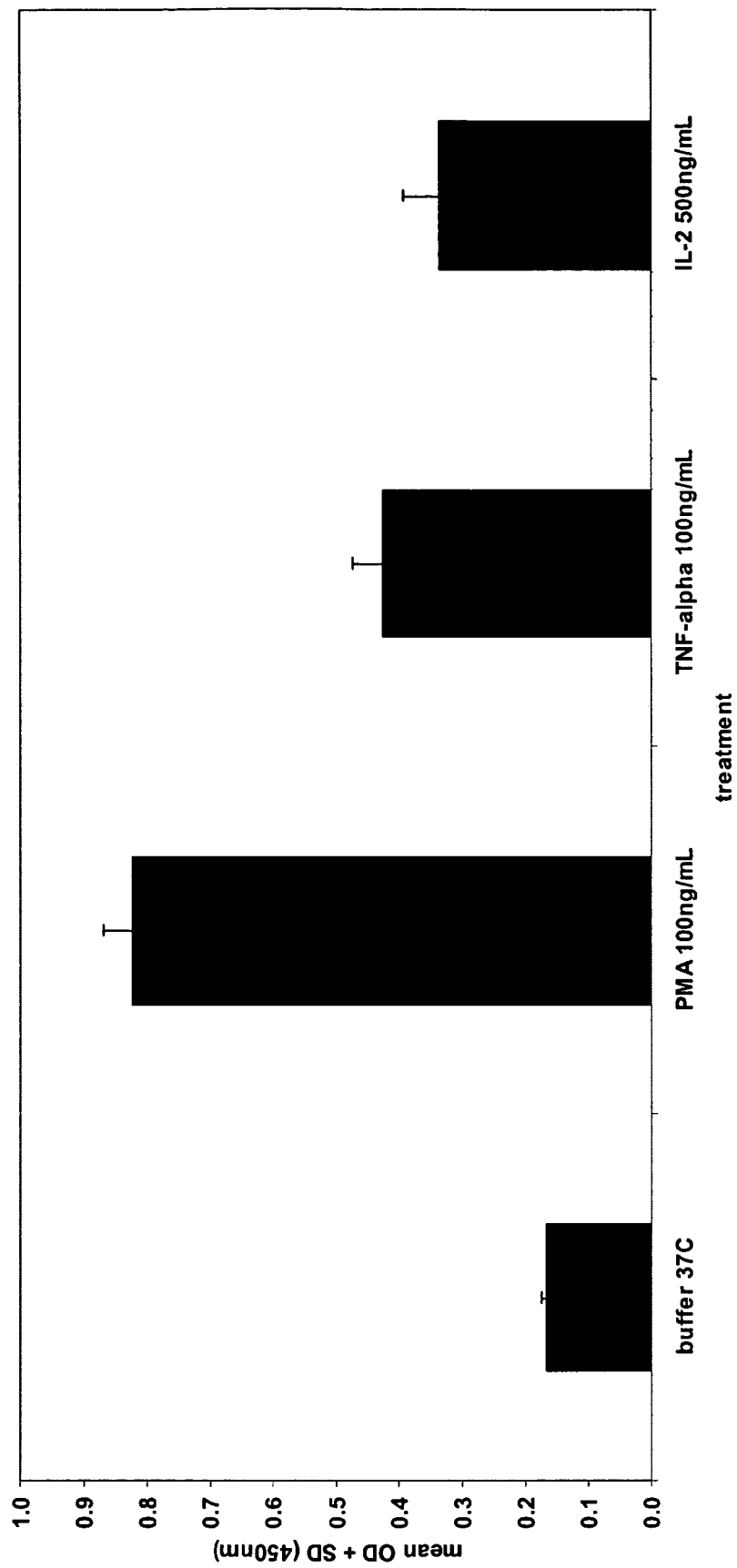
FIG. 18 is a bar graph depicting the effect of PMA, TNFα, and IL-2 on the induction of FGFR5 secretion by PMN.

FGFR5 is expressed in the granules of PMN and is released during the process of degranulation induced by a variety of agents including PMA, fMLP, TNFα, and IL-2. PMN were purified from human blood by a combination of dextran sedimentation and separation on a 1.077 g/ml density gradient. PMN were resuspended in Hanks Balanced Salt Solution (HBSS) at a density of $5\times10^6$/ml and stimulated with various stimulants for 10 minutes. The supernatant was collected from the cells and the presence of soluble FGFR5 determined using an FGFR5-specific ELISA. The results of these assays are shown in FIGS. 17 and 18.

Figure 19:
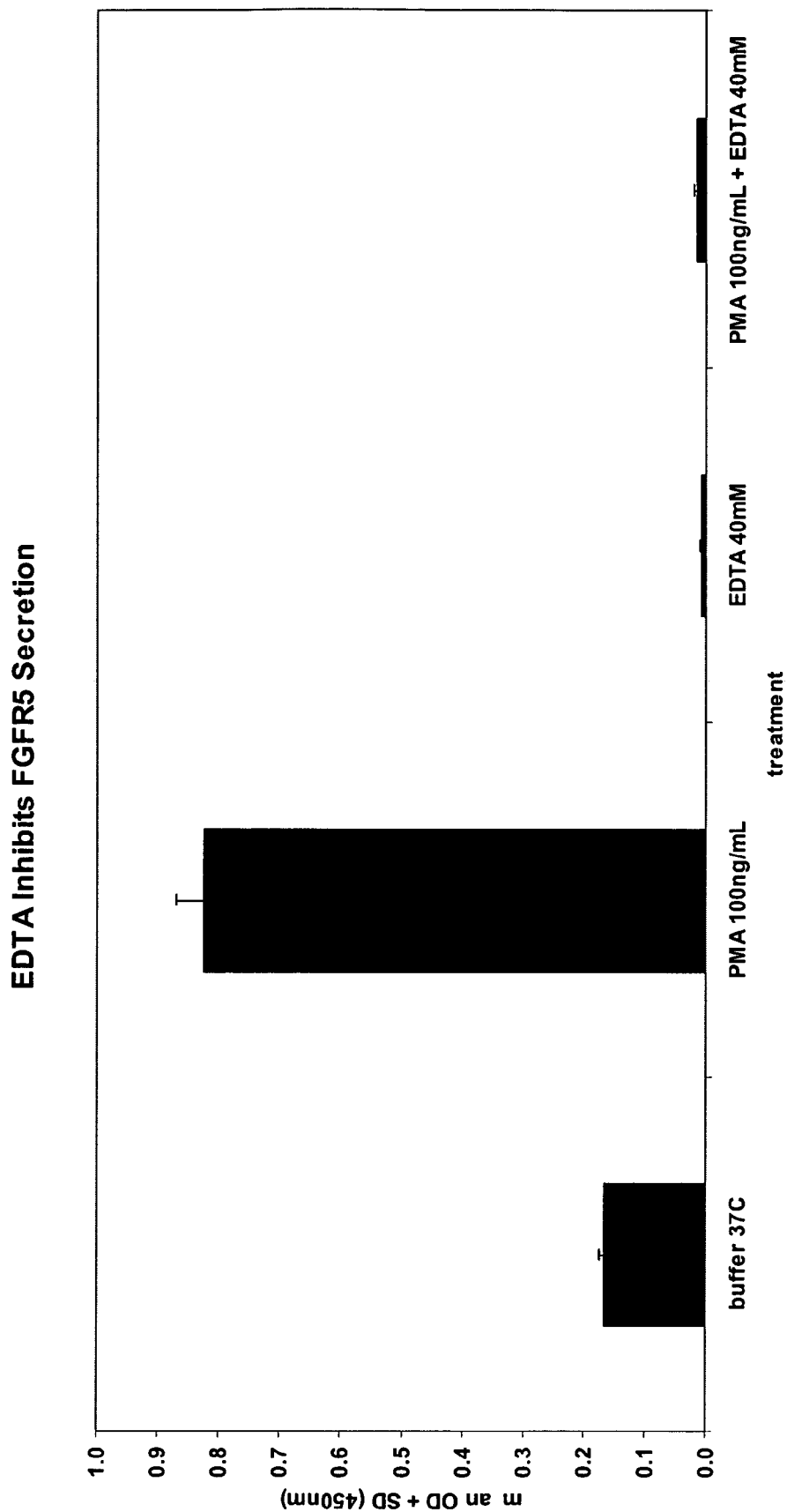
FIG. 19 is a bar graph depicting the effect of EDTA on inhibition of FGFR5 secretion.

As shown in FIG. 19 the release of FGFR5 from the cells was inhibited by the addition of 40 nM EDTA which is known to inhibit PMN deganulation. The ELISA was developed using FGFR5-specific polyclonal and monoclonal antibodies. The monoclonal antibody was used as a capture reagent and the polyclonal antibody to detect the captured FGFR5. The assay can detect 20 ng/ml of recombinant murine monomeric FGFR5β. The ELISA was specific in that it did not detect FGFR2. The secretion of FGFR5 from PMNs, post stimulation, with physiologically relevant stimuli such as TNFα indicate that it is likely to be released at sites of inflammation. This combined with its ability to augment immune reactions both in vitro and in vivo indicate that it is likely to be a natural pro-inflammatory agent.

EXAMPLE 18

Effect of Monomeric, Dimeric, and Tetrameric FGFR5 on Adherent Peripheral Blood Mononuclear Cell (PBMC) and Anti-CD3 Induced PBMC Growth This Example discloses that the murine anti-FGFR5 monoclonal antibody 15G6 described in Example 11 enhanced the activity of the FGFR5 by crosslinking either the dimeric FGFR5-Fc fusion protein or monomeric FGFR5.

Figure 20:
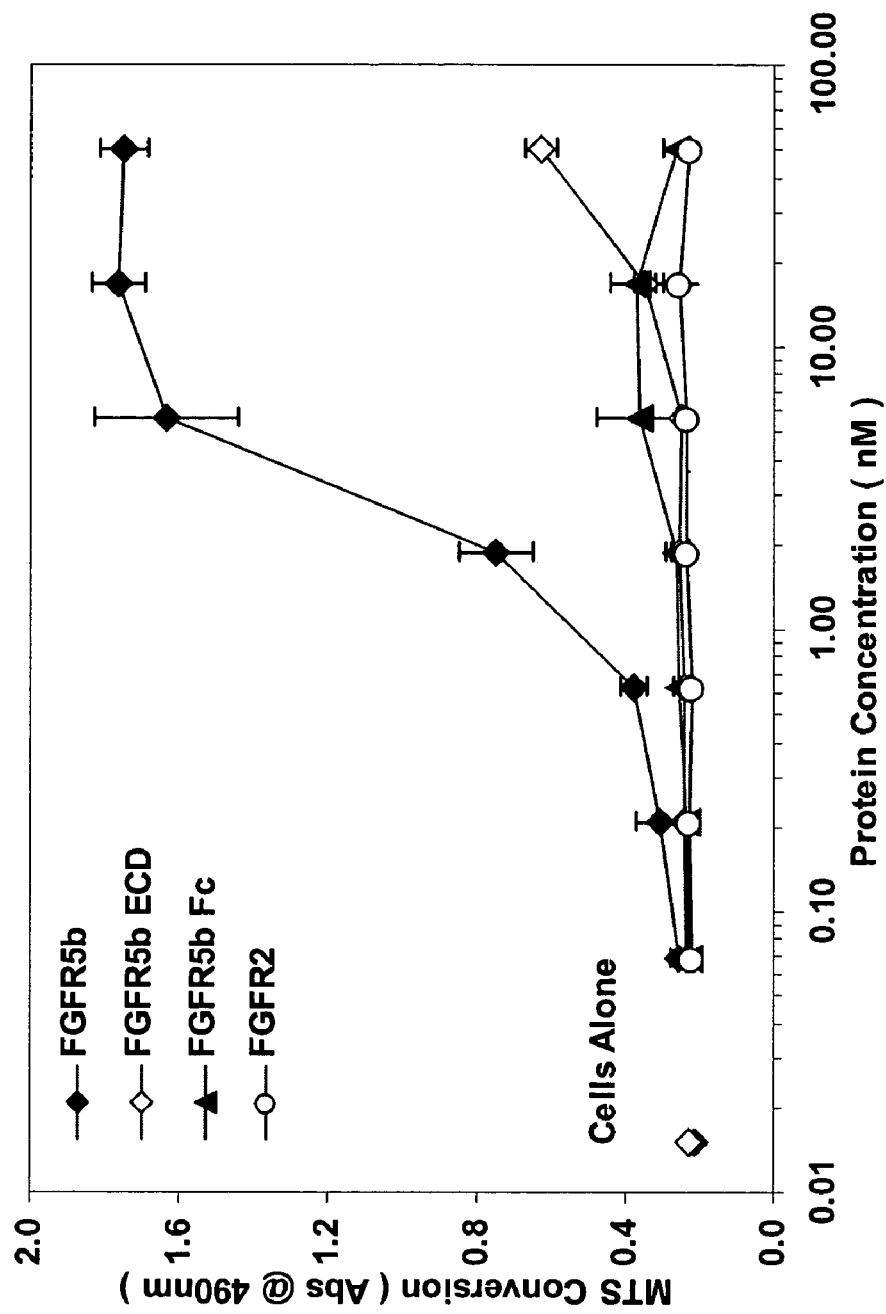
FIGS. 20 and 21 are graphs showing that monomeric FGFR5 does not augment anti-CD3 stimulated proliferation of PBMC.
Figure 21:
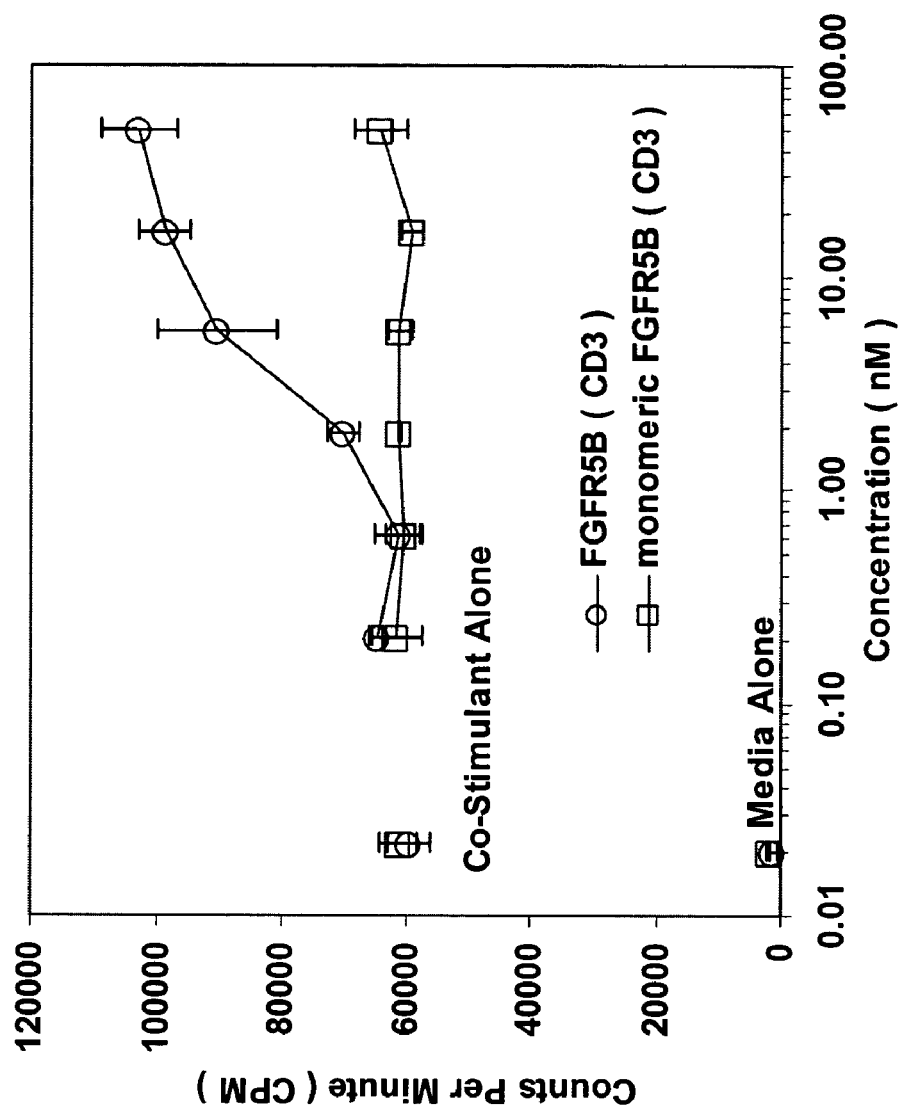
Figure 22:
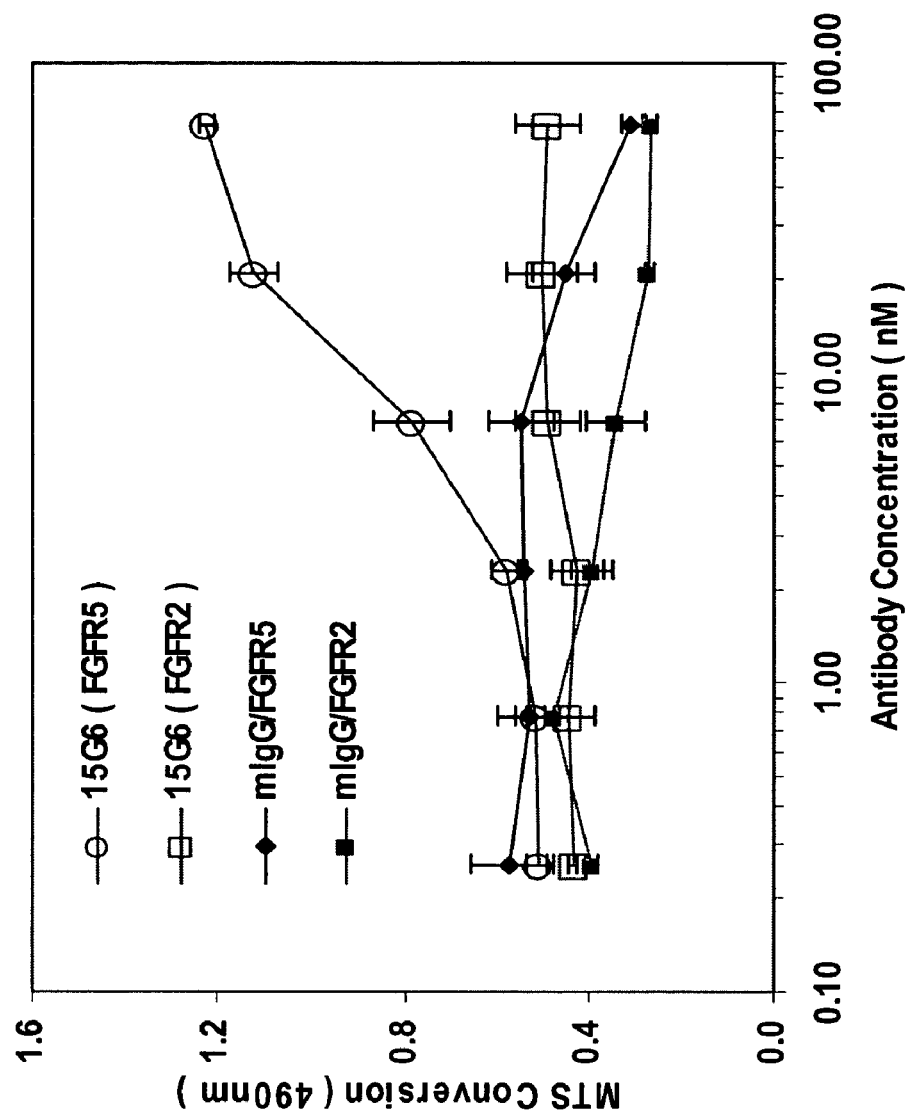
FIG. 22 is a graph showing that dimerization of FGFR5-Fc to form tetramers augments the ability of FGFR5-Fc to stimulate growth of adherent PBMC.

Monomeric FGFR5 was generated by cleaving the Fc region from the FGFR5-Fc fusion protein such that a 55 kDa FGFR5 extracellular domain was released. The protein was tested in assays and showed 100-fold less activity in either of the standard human PBMC assays routinely used to test the biological effects of FGFR5. FIGS. 20 and 21. Dimerization of FGFR5-Fc to form tetramers augmented the ability of FGFR5-Fc to stimulate the growth of adherent PBMC. FIG. 22.

Figure 23:
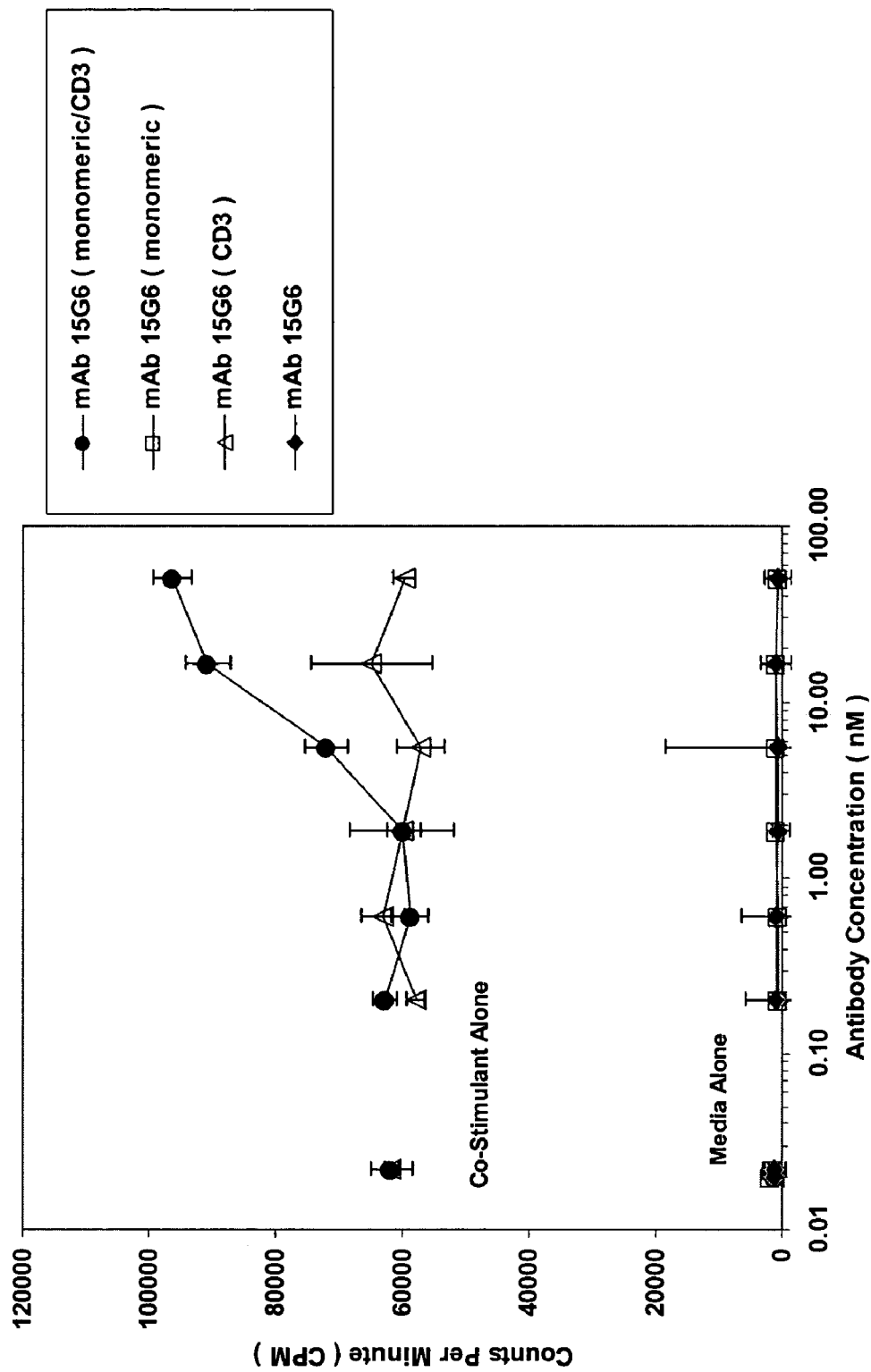
FIG. 23 is a graph showing that dimerized monomeric FGFR5 augments the growth of anti-CD3 induced PBMC proliferation in a similar manner as the dimeric FGFR5-Fc fusion protein.
Figure 24:
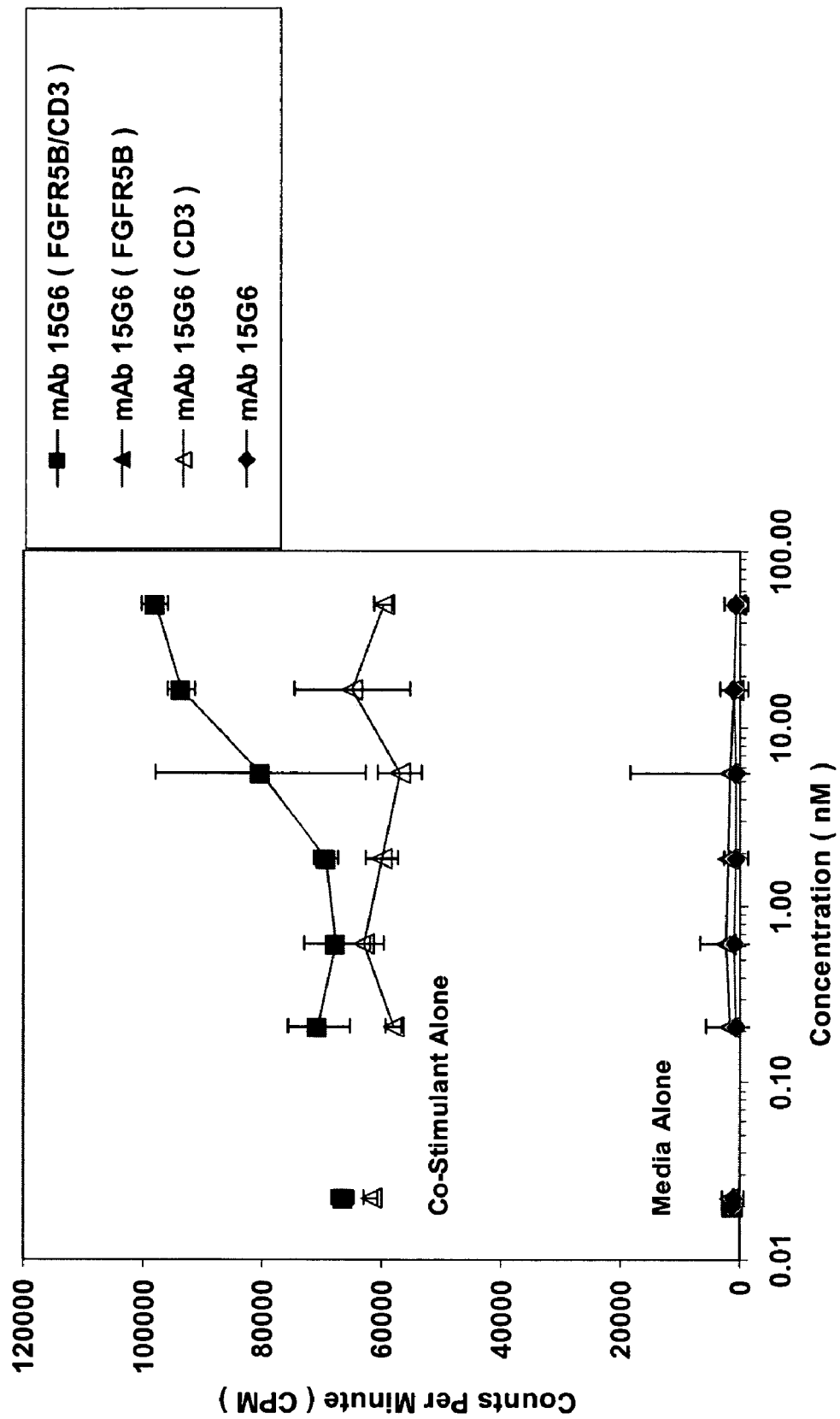
FIG. 24 is a graph showing that dimerized FGFR5-Fc (i.e. tetrameric FGFR5-Fc) augments the anti-CD3 induced growth of human PBMC.
Figure 25:
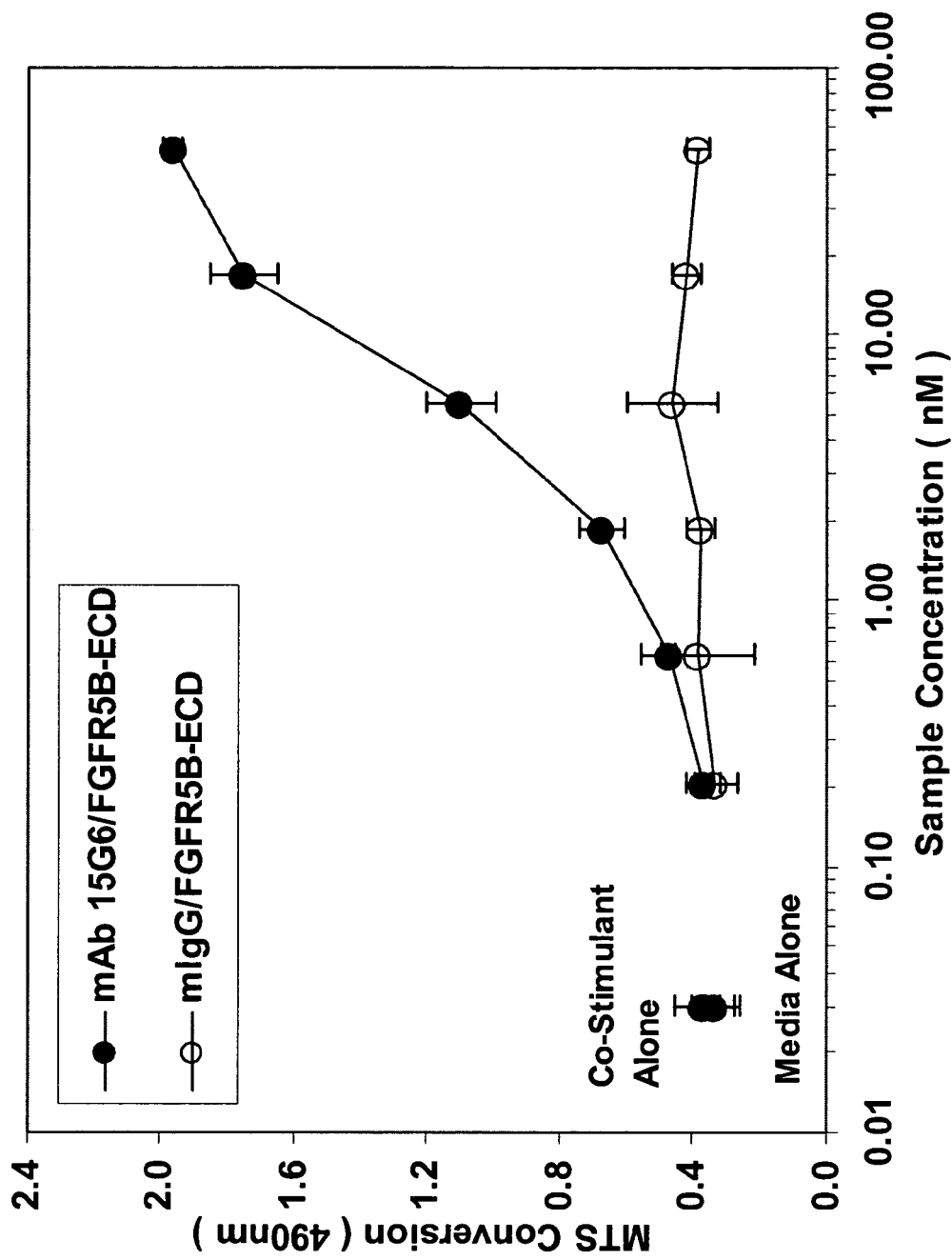
FIGS. 25 and 26 are graphs showing that the FGFR5-specific monoclonal antibody enhances the activity of the monomeric FGFR5 and dimeric FGFR5-Fc fusion protein in the PBMC adherence assay.
Figure 26:
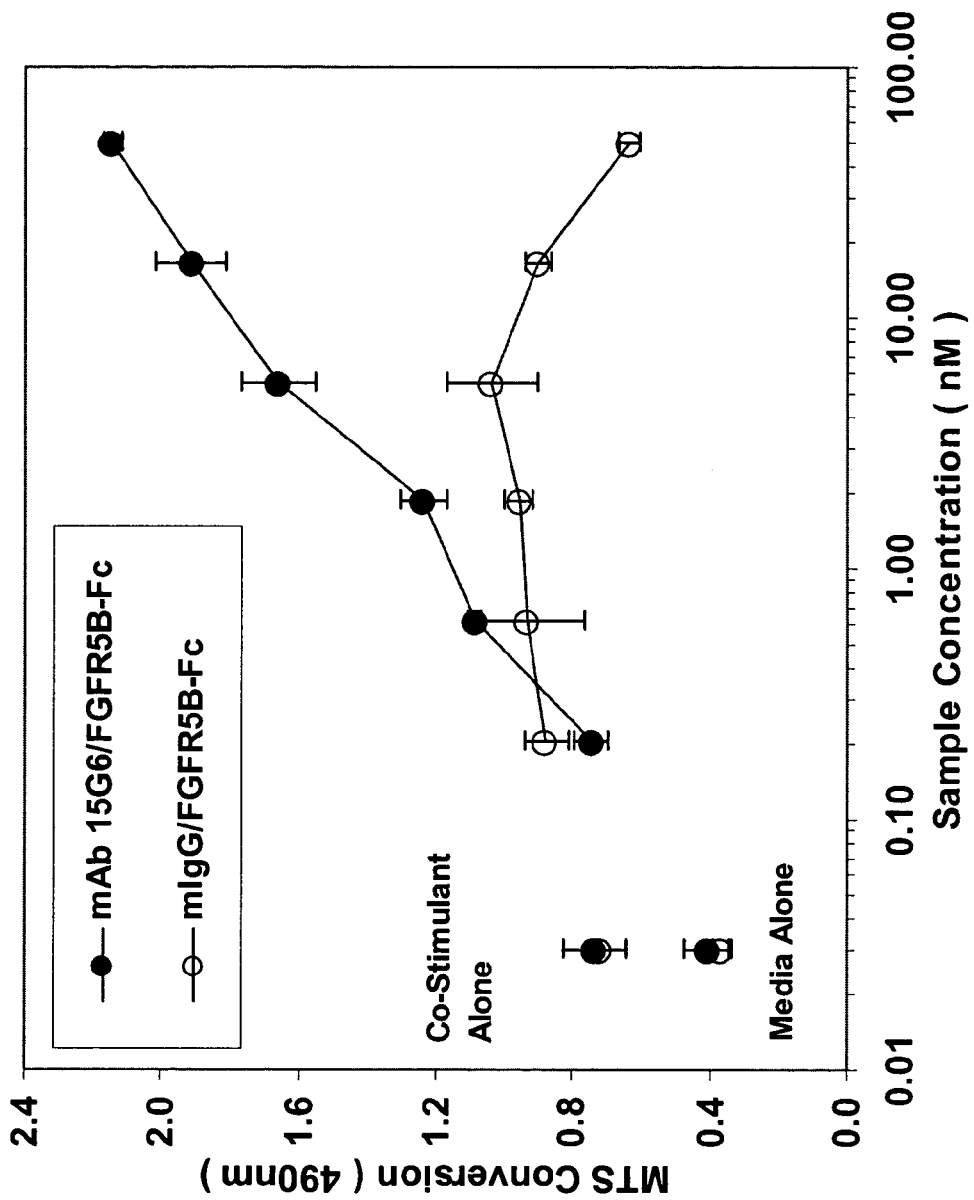

The monoclonal antibody to FGFR5 was capable of dimerizing the monomer thereby recovering its activity. While monomeric FGFR5 was incapable of augmenting anti-CD3 stimulated PBMC proliferation, FIG. 21, the dimerized monomeric FGFR5 augmented the growth of anti-CD3 induced PBMC proliferation in a similar manner as the dimeric FGFR5-Fc fusion protein. FIG. 23. Furthermore, dimerized FGFR5-Fc (i.e. tetrameric FGFR5-Fc) augmented the anti-CD3 induced growth of human PBMC. FIG. 24. In a similar fashion the FGFR5-specific monoclonal antibody enhanced the activity of the monomeric FGFR5 and dimeric FGFR5-Fc fusion protein in the PBMC adherence assay. FIGS. 25 and 26.

In total, these data demonstrate that multimerisation of FGFR5 enhanced its activity. Without wishing to be limited to any specific mechanism of action, these data suggest that a cell-associated form of FGFR5 may be more potent than a naturally occurring soluble version of the protein unless the soluble FGFR5 is first polymerized by, for example, attachment to a scaffolds such as one or more extracellular matrix proteins.

EXAMPLE 19

Heparin is an FGFR5-Binding Molecule and Inhibitor of FGFR5 Function

Many studies have shown that fibroblast growth factors bind to their receptors in the context of heparin-like glycosaminoglycans (HLGAG). Both FGFs and their receptors are heparin-binding proteins and the 3 components, FGF, FGFR and HLGAG, form a complex and induce signalling. A series of experiments were performed to determine whether FGFR5 is a heparin-binding protein and whether heparin alters the effects of FGFR5 on the immune system. The heparin-binding abilities of FGFR5 were tested chromatographically. FGFR5 was run onto a heparin Hi-Trap affinity column (Amersham Pharmacia Biotech) and the bound protein eluted with a salt gradient.

Figure 27:
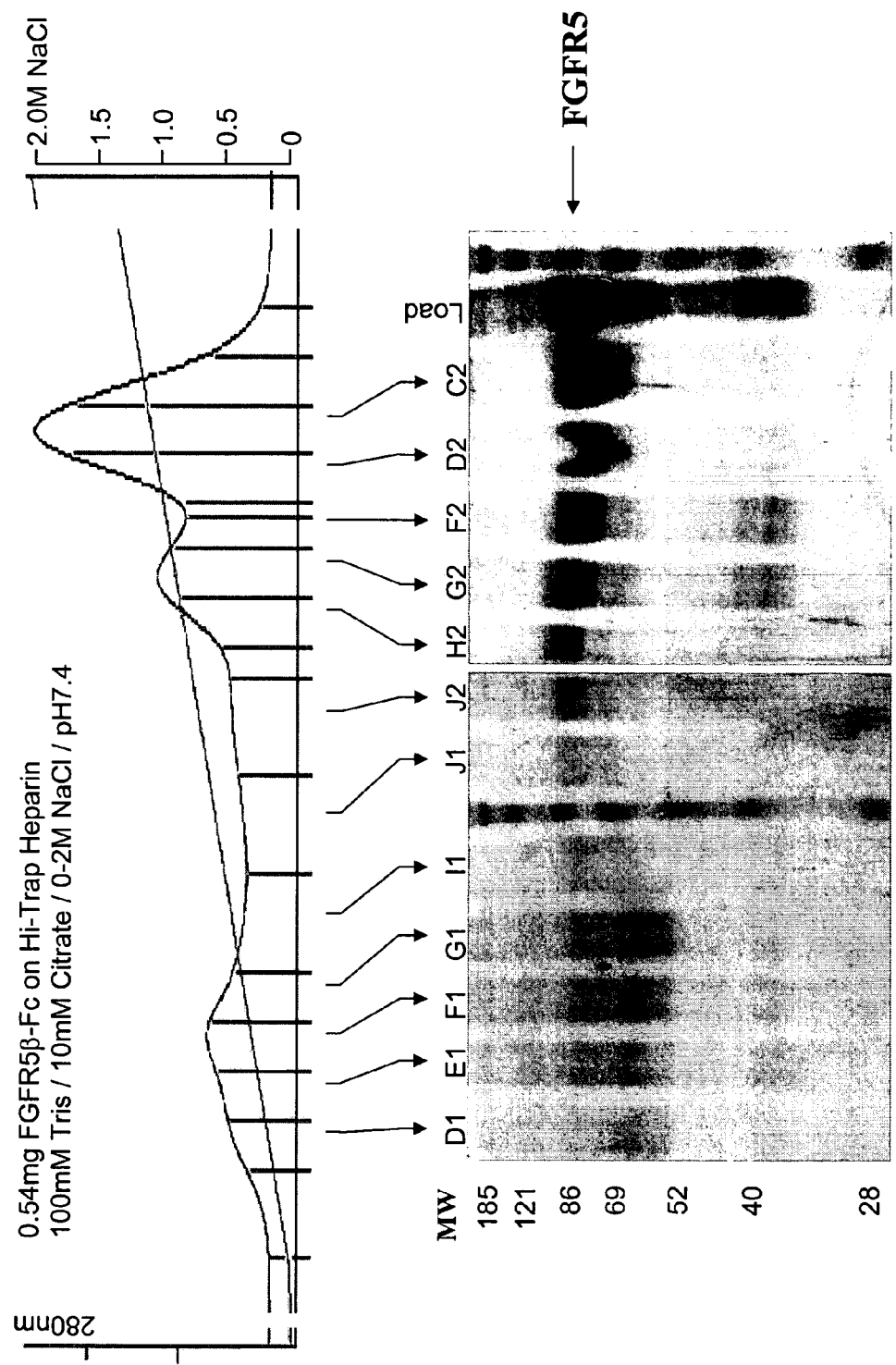
FIG. 27 is a graph showing that FGFR5 binds to a heparin Hi-Trap affinity column (Amersham Pharmacia Biotech; Piscataway, N.J.) and is eluted with a salt gradient with a peak at ~1 M NaCl.

FIG. 27 shows that FGFR5 bound to heparin and that the majority of the protein was eluted with ~1 M NaCl. Analysis of the proteins eluted from the column on SDS-PAGE gels confirmed that FGFR5 eluted from the column at this salt concentration.

Figure 28:
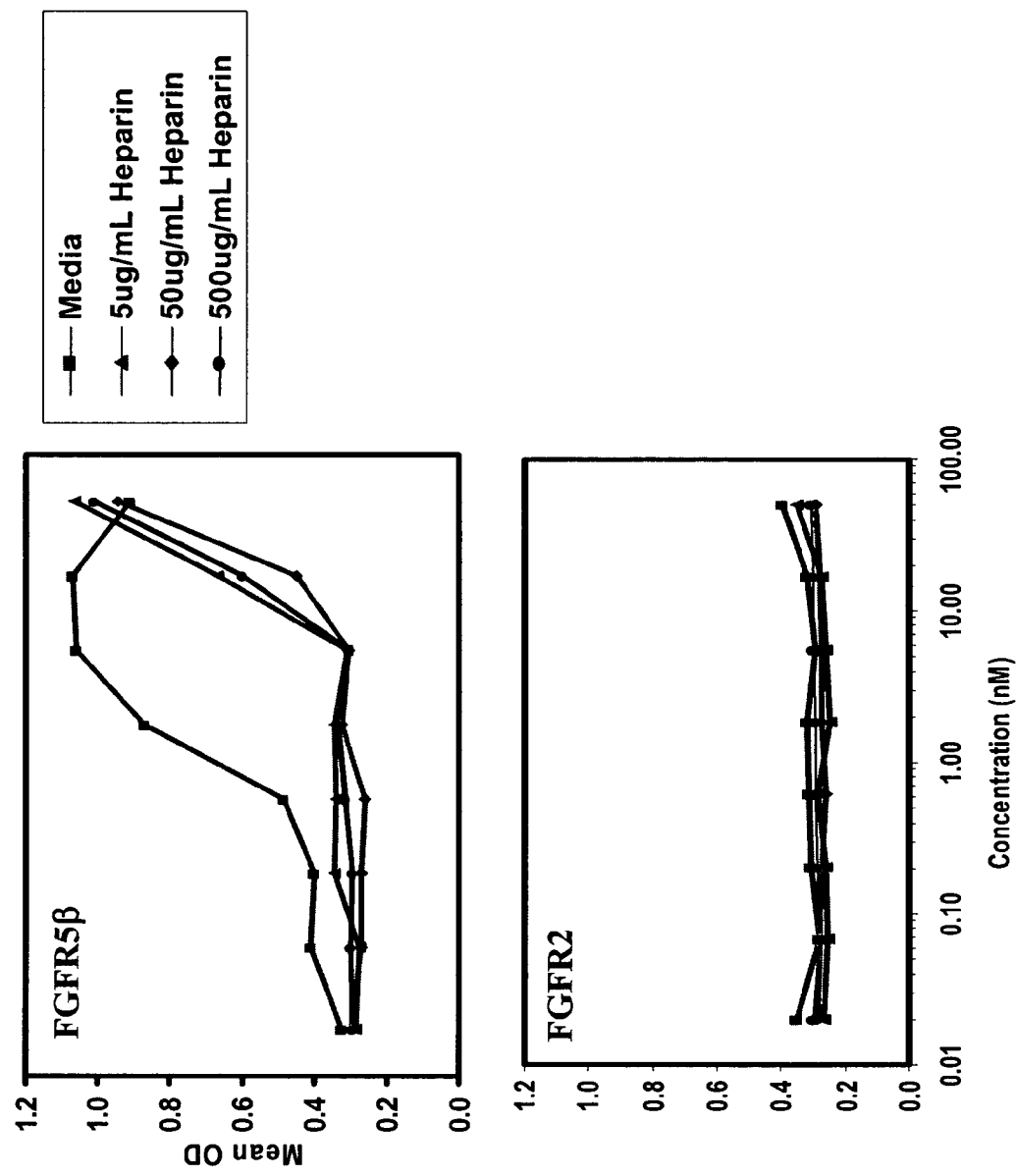
FIG. 28 is a graph showing that heparin inhibits the function of FGFR5 at a concentration of 5 μg/ml thereby blocking the ligand binding portion of FGFR5.

Heparin was added to the macrophage adherence assay to determine whether it would influence the ability of FGFR5 to stimulate the growth of adherent PBMC. As shown in FIG. 28 heparin inhibited the function of FGFR5 at a concentration of 5 ug/ml. These results suggested that heparin blocks the ligand binding portion of FGFR5, that the heparin-binding domain of FGFR5 is involved in the binding of the cognate ligand responsible for the functions of FGFR5, that the ligand may be a HLGAG, and that heparin or heparin-like molecules could serve as inhibitors of FGFR5 function.

SEQ ID NOS: 1–145 are set out in the attached Sequence Listing. The codes for polynucleotide and polypeptide sequences used in the attached Sequence Listing conform to WIPO Standard ST.25 (1988), Appendix 2.

Although the present invention has been described in terms of specific embodiments, changes and modifications can be carried out without departing from the scope of the invention which is intended to be limited only by the scope of the appended claims. All references cited herein, including patent references and non-patent references, are hereby incorporated by reference in their entireties.

We claim:

1. A method for enhancing an immune response in a patient, comprising administering to the patient a composition comprising an isolated polypeptide, wherein the polypeptide comprises SEQ ID NO: 8, and wherein said composition enhances an immune response in the patient.

2. The method of claim 1, wherein the composition further comprises at least one component selected from the group consisting of: physiologically acceptable carriers; and non-specific immune response enhancers.

3. The method of claim 2, wherein the physiologically acceptable carrier is selected from the group consisting of: water, saline, alcohol, lipids, waxes, buffers, mannitol, lactose, starch, magnesium stearate, sodium saccharine, talcum, cellulose, glucose, sucrose, magnesium carbonate and biodegradable microspheres.

4. The method of claim 2, wherein the non-specific immune response enhancer is an adjuvant.

5. The method of claim 1, wherein the composition is administered by injection.

* * * * *

UNITED STATES PATENT AND TRADEMARK OFFICE
CERTIFICATE OF CORRECTION

PATENT NO. : 7,083,791 B2
APPLICATION NO. : 10/613413
DATED : August 1, 2006
INVENTOR(S) : Matthew Sleeman and J. Greg Murison It is certified that error appears in the above-identified patent and that said Letters Patent is hereby corrected as shown below:

| Col. No. | Line(s) | Edits |
|---|---|---|
| 55 | (-) | Within SEQ ID NO. 4, After "Organism:," please change "Mouse" to "Human" |
| 63 | (-) | Within SEQ ID NO. 8, After "Organism:," please change "Mouse" to "Human" |

Signed and Sealed this

Fifth Day of December, 2006

JON W. DUDAS
*Director of the United States Patent and Trademark Office*

SEQUENCE LISTING

```
<160> NUMBER OF SEQ ID NOS: 145

<210> SEQ ID NO 1
<211> LENGTH: 384
<212> TYPE: DNA
<213> ORGANISM: Mouse
<220> FEATURE:
<221> NAME/KEY: misc_feature
<222> LOCATION: (1)...(384)
<223> OTHER INFORMATION: n = A,T,C or G

<400> SEQUENCE: 1
ggtggacttc ggtgggacaa cgtccttcca gtgcaaggtg cgcagtgacg tgaagcctgt      60
gatccagtgg ctgaagcggg tggagtacgg ctccgaggga cgccacaact ccaccattga     120
tgtgggtggc cagaagtttg tggtgttgcc cacgggtgat gtgtggtcac ggcctgatgg     180
ctcctacctc aacaagctgc tcatctctcg ggcccgccag gatgatgctg gcatgtacat     240
ctgcctaggt gcaaatacca tgggctacag tttccgtagc gccttcctca ctgtattacc     300
agaccccaaa cctccagggc ctcctatggc ttcttcatcg tcatccacaa gcctgccatg     360
```

-continued gcctgtggng atcggcatcc cagc          384

<210> SEQ ID NO 2
<211> LENGTH: 1967
<212> TYPE: DNA
<213> ORGANISM: Mouse

<400> SEQUENCE: 2

| | | | | |
|---|---|---|---|---|
| gctgcgcgcc | cccgcgctga | tccctgtcga | gcgtctacgc | gcctcgcttc ctttgcctgg | 60 |
| agctcggcgc | cgaggggggc | cggaccctgg | ctctgcggcc | gcgacctggg tcttgcgggc | 120 |
| ctgagccctg | agtggcgtcc | agtccagctc | ccagtgaccg | cgcccctgct tcaggtccga | 180 |
| ccggcgagat | gacgcggagc | cccgcgctgc | tgctgctgct | attgggggcc ctcccgtcgg | 240 |
| ctgaggcggc | gcgaggaccc | ccaagaatgg | cagacaaagt | ggtcccacgg caggtggccc | 300 |
| gcctgggccg | cactgtgcgg | ctacagtgcc | cagtggaggg | ggacccacca ccgttgacca | 360 |
| tgtggaccaa | agatggccgc | acaatccaca | gtggctggag | ccgcttccgt gtgctgcccc | 420 |
| agggtctgaa | ggtgaaggag | gtggaggccg | aggatgccgg | tgtttatgtg tgcaaggcca | 480 |
| ccaatggctt | tggcagcctc | agcgtcaact | acactctcat | catcatggat gatattagtc | 540 |
| cagggaagga | gagccctggg | ccaggtggtt | cttcgggggg | ccaggaggac ccagccagcc | 600 |
| agcagtgggc | acgcctcgc | ttcacacagc | cctccaagat | gaggcgccga gtgattgcac | 660 |
| ggcctgtggg | tagctctgtg | cggctcaagt | gtgtggccag | tgggcaccca cggccagaca | 720 |
| tcatgtggat | gaaggatgac | cagaccttga | cgcatctaga | ggctagtgaa cacagaaaga | 780 |
| agaagtggac | actgagcttg | aagaacctga | agcctgaaga | cagtggcaag tacacgtgcc | 840 |
| gtgtatctaa | caaggccggt | gccatcaacg | ccacctacaa | agtggatgta atccagcgga | 900 |
| ctcgttccaa | gcctgtgctc | acagggacac | accctgtgaa | cacaacggtg gacttcggtg | 960 |
| ggacaacgtc | cttccagtgc | aaggtgcgca | gtgacgtgaa | gcctgtgatc cagtggctga | 1020 |
| agcgggtgga | gtacggctcc | gagggacgcc | acaactccac | cattgatgtg ggtggccaga | 1080 |
| agtttgtggt | gttgcccacg | ggtgatgtgt | ggtcacggcc | tgatggctcc tacctcaaca | 1140 |
| agctgctcat | ctctcgggcc | cgccaggatg | atgctggcat | gtacatctgc ctaggtgcaa | 1200 |
| ataccatggg | ctacagtttc | cgtagcgcct | tcctcactgt | attaccagac cccaaacctc | 1260 |
| cagggcctcc | tatggcttct | tcatcgtcat | ccacaagcct | gccatggcct gtggtgatcg | 1320 |
| gcatcccagc | tggtgctgtc | ttcatcctag | gcactgtgct | gctctggctt tgccagacca | 1380 |
| agaagaagcc | atgtgcccca | gcatctacac | ttcctgtgcc | tgggcatcgt cccccaggga | 1440 |
| catcccgaga | acgcagtggt | gacaaggacc | tgccctcatt | ggctgtgggc atatgtgagg | 1500 |
| agcatggatc | cgccatggcc | ccccagcaca | tcctggcctc | tggctcaact gctgccccca | 1560 |
| agctgtaccc | caagctatac | acagatgtgc | acacacacac | acatacacac acctgcactc | 1620 |
| acacgctctc | atgtggaggg | caaggttcat | caacaccagc | atgtccacta tcagtgctaa | 1680 |
| atacagcgaa | tctccaagca | ctgtgtcctg | aggtaggcat | atgggggcca aggcaacagg | 1740 |
| ttgggagaat | tgagaacaat | ggaggaagag | tatcttaggg | tgccttatgg tggacactca | 1800 |
| caaacttggc | catatagatg | tatgtactac | cagatgaaca | gccagccaga ttcacacacg | 1860 |
| cacatgttta | aacgtgtaaa | cgtgtgcaca | actgcacaca | caacctgaga aaccttcagg | 1920 |
| aggatttggg | gtgtgacttt | gcagtgacat | gtagcgatgg | ctagttg | 1967 |

<210> SEQ ID NO 3
<211> LENGTH: 1742

<212> TYPE: DNA
<213> ORGANISM: Mouse

<400> SEQUENCE: 3

```
gcgcggcgcc ccgggcccct cgcccgccg cccctcttcc ccgccctcgc caagcctcgc      60
cgtttatccg cgcggacagc gcgccccgcg ccccagcccg ccctagccg ccagcgccca     120
ggtagcgccg ccccgcccag gccgggcccg ggggcgcggg gggcgggatg cggcgcccgg    180
ggcagcgatg accgcgtcgc gctgctcagg ggcccggctc tgaccccgtt gcctgctgcg    240
cgccccgcg ctgatccctg tcgagcgtct acgcgcctcg cttcctttgc ctggagctcg     300
gcgccgaggg gggccggacc ctggctctgc ggccgcgacc tgggtcttgc gggcctgagc    360
cctgagtggc gtccagtcca gctcccagtg accgcgcccc tgcttcaggt ccgaccggcg    420
agatgacgcg gagccccgcg ctgctgctgc tgctattggg ggccctcccg tcggctgagg    480
cggcgcgaga tgatattagt ccagggaagg agagccctgg gccaggtggt tcttcggggg    540
gccaggagga cccagccagc cagcagtggg cacggcctcg cttcacacag ccctccaaga    600
tgaggcgccg agtgattgca cggcctgtgg gtagctctgt gcggctcaag tgtgtggcca    660
gtgggcaccc acggccagac atcatgtgga tgaaggatga ccagaccttg acgcatctag    720
aggctagtga acacagaaag aagaagtgga cactgagctt gaagaacctg aagcctgaag    780
acagtggcaa gtacacgtgc cgtgtatcta caaggccgg tgccatcaac gccacctaca    840
aagtggatgt aatccagcgg actcgttcca agcctgtgct cacagggaca caccctgtga    900
acacaacggt ggacttcggt gggacaacgt ccttccagtg caaggtgcgc agtgacgtga    960
agcctgtgat ccagtggctg aagcgggtgg agtacggctc cgagggacgc acaactcca   1020
ccattgatgt gggtggccag aagtttgtgg tgttgcccac gggtgatgtg tggtcacggc   1080
ctgatggctc ctacctcaac aagctgctca tctctcgggc ccgccaggat gatgctggca   1140
tgtacatctg cctaggtgca ataccatgg gctacagttt ccgtagcgcc ttcctcactg    1200
tattaccaga ccccaaaacct cctccagggc ctcctatggc ttcttcatcg tcatccacaa   1260
gcctgccatg gcctgtggtg atcggcatcc agctggtgg tgtcttcatc ctaggcactg    1320
tgctgctctg gctttgccag accaagaaga agccatgtgc cccagcatct acacttcctg   1380
tgcctgggca tcgtccccca gggacatccc gagaacgcag tggtgacaag gacctgccct   1440
cattggctgt gggcatatgt gaggagcatg gatccgccat ggccccccag cacatcctgg   1500
cctctggctc aactgctggc cccaagctgt accccaagct atacacagat gtgcacacac   1560
acacacatac acacacctgc actcacacgc tctcatgtgg agggcaaggt tcatcaacac   1620
cagcatgtcc actatcagtg ctaaatacag cgaatctcca agcactgtgt cctgaggtag   1680
gcatatgggg gccaaggcaa caggttggga gaattgagaa caatggagga agagtatctt   1740
ag                                                                 1742
```

<210> SEQ ID NO 4
<211> LENGTH: 1004
<212> TYPE: DNA
<213> ORGANISM: Mouse

<400> SEQUENCE: 4

```
gcggccgcga ccccaggtcc ggacaggccg agatgacgcc gagccccctg ttgctgctcc      60
tgctgccgcc gctgctgctg ggggccttcc caccggccgc cgcgcccga ggccccccaa     120
agatggcgga caaggtggtc ccacggcagg tggccggctg ggccgcactg tgcggctgca    180
```

-continued

```
gtgccagtgg aggggaccc gccgccgctg accatgtgga ccaaggatgg ccgcaccatc      240
cacagcggct ggagccgctt ccgcgtgctg ccgcaggggc tgaaggtgaa gcaggtggag      300
cgggaggatg ccggcgtgta cgtgtgcaag gccaccaacg gcttcggcag ccttagcgtc      360
aactacaccc tcgtcgtgct ggatgacatt agcccaggga aggagagcct ggggcccgac      420
agctcctctg ggggtcaaga ggaccccgcc agccagcagt gggcacgacc gcgcttcaca      480
cagccctcca agatgaggcg ccgggtgatc gcacggcccg tgggtagctc cgtgcggctc      540
aagtgcgtgg ccagcgggca ccctcggccc gacatcacgt ggatgaagga cgaccaggcc      600
ttgacgcgcc agaggccgc tgagcccagg aagaagaagt ggacactgag cctgaagaac      660
ctgcggccgg aggacagcgg caaatacacc tgccgcgtgt cgaaccgcgc gggcgccatc      720
aacgccacct acaaggtgga tgtgatccag cggacccgtt ccaagcccgt gctcacaggc      780
acgcaccccg tgaacacgac ggtggacttc gggggggacca cgtccttcca gtgcaaggtg      840
cgcagcgacg tgaagccggt gatccagtgg ctgaagcgcg tggagtacgg cgccgagggc      900
cgccacaact ccaccatcga tgtgggcggc cagaagtttg tggtgctgcc cacgggtgac      960
gtgtggtcgc ggcccgacgg ctcctacctc aataagccgc tccc                     1004
```

<210> SEQ ID NO 5
<211> LENGTH: 126
<212> TYPE: PRT
<213> ORGANISM: Mouse
<220> FEATURE:
<221> NAME/KEY: VARIANT
<222> LOCATION: (1)...(126)
<223> OTHER INFORMATION: Xaa = Any Amino Acid

<400> SEQUENCE: 5

```
Val Asp Phe Gly Gly Thr Thr Ser Phe Gln Cys Lys Val Arg Ser Asp
 1               5                  10                  15

Val Lys Pro Val Ile Gln Trp Leu Lys Arg Val Glu Tyr Gly Ser Glu
            20                  25                  30

Gly Arg His Asn Ser Thr Ile Asp Val Gly Gly Gln Lys Phe Val Val
        35                  40                  45

Leu Pro Thr Gly Asp Val Trp Ser Arg Pro Asp Gly Ser Tyr Leu Asn
    50                  55                  60

Lys Leu Leu Ile Ser Arg Ala Arg Gln Asp Asp Ala Gly Met Tyr Ile
65                  70                  75                  80

Cys Leu Gly Ala Asn Thr Met Gly Tyr Ser Phe Arg Ser Ala Phe Leu
                85                  90                  95

Thr Val Leu Pro Asp Pro Lys Pro Pro Gly Pro Pro Met Ala Ser Ser
            100                 105                 110

Ser Ser Ser Thr Ser Leu Pro Trp Pro Val Xaa Gly Ile Pro
        115                 120                 125
```

<210> SEQ ID NO 6
<211> LENGTH: 529
<212> TYPE: PRT
<213> ORGANISM: Mouse

<400> SEQUENCE: 6

```
Met Thr Arg Ser Pro Ala Leu Leu Leu Leu Leu Gly Ala Leu Pro
 1               5                  10                  15

Ser Ala Glu Ala Ala Arg Gly Pro Pro Arg Met Ala Asp Lys Val Val
            20                  25                  30

Pro Arg Gln Val Ala Arg Leu Gly Arg Thr Val Arg Leu Gln Cys Pro
```

```
                    35                  40                  45
Val Glu Gly Asp Pro Pro Leu Thr Met Trp Thr Lys Asp Gly Arg
 50                  55                  60
Thr Ile His Ser Gly Trp Ser Arg Phe Arg Val Leu Pro Gln Gly Leu
 65                  70                  75                  80
Lys Val Lys Glu Val Glu Ala Glu Asp Ala Gly Val Tyr Val Cys Lys
                     85                  90                  95
Ala Thr Asn Gly Phe Gly Ser Leu Ser Val Asn Tyr Thr Leu Ile Ile
                100                 105                 110
Met Asp Asp Ile Ser Pro Gly Lys Glu Ser Pro Gly Pro Gly Gly Ser
                115                 120                 125
Ser Gly Gly Gln Glu Asp Pro Ala Ser Gln Gln Trp Ala Arg Pro Arg
130                 135                 140
Phe Thr Gln Pro Ser Lys Met Arg Arg Arg Val Ile Ala Arg Pro Val
145                 150                 155                 160
Gly Ser Ser Val Arg Leu Lys Cys Val Ala Ser Gly His Pro Arg Pro
                165                 170                 175
Asp Ile Met Trp Met Lys Asp Asp Gln Thr Leu Thr His Leu Glu Ala
                180                 185                 190
Ser Glu His Arg Lys Lys Lys Trp Thr Leu Ser Leu Lys Asn Leu Lys
                195                 200                 205
Pro Glu Asp Ser Gly Lys Tyr Thr Cys Arg Val Ser Asn Lys Ala Gly
                210                 215                 220
Ala Ile Asn Ala Thr Tyr Lys Val Asp Val Ile Gln Arg Thr Arg Ser
225                 230                 235                 240
Lys Pro Val Leu Thr Gly Thr His Pro Val Asn Thr Thr Val Asp Phe
                245                 250                 255
Gly Gly Thr Thr Ser Phe Gln Cys Lys Val Arg Ser Asp Val Lys Pro
                260                 265                 270
Val Ile Gln Trp Leu Lys Arg Val Glu Tyr Gly Ser Glu Gly Arg His
                275                 280                 285
Asn Ser Thr Ile Asp Val Gly Gly Gln Lys Phe Val Val Leu Pro Thr
                290                 295                 300
Gly Asp Val Trp Ser Arg Pro Asp Gly Ser Tyr Leu Asn Lys Leu Leu
305                 310                 315                 320
Ile Ser Arg Ala Arg Gln Asp Asp Ala Gly Met Tyr Ile Cys Leu Gly
                325                 330                 335
Ala Asn Thr Met Gly Tyr Ser Phe Arg Ser Ala Phe Leu Thr Val Leu
                340                 345                 350
Pro Asp Pro Lys Pro Pro Gly Pro Pro Met Ala Ser Ser Ser Ser Ser
                355                 360                 365
Thr Ser Leu Pro Trp Pro Val Val Ile Gly Ile Pro Ala Gly Ala Val
                370                 375                 380
Phe Ile Leu Gly Thr Val Leu Leu Trp Leu Cys Gln Thr Lys Lys Lys
385                 390                 395                 400
Pro Cys Ala Pro Ala Ser Thr Leu Pro Val Pro Gly His Arg Pro Pro
                405                 410                 415
Gly Thr Ser Arg Glu Arg Ser Gly Asp Lys Asp Leu Pro Ser Leu Ala
                420                 425                 430
Val Gly Ile Cys Glu Glu His Gly Ser Ala Met Ala Pro Gln His Ile
                435                 440                 445
Leu Ala Ser Gly Ser Thr Ala Gly Pro Lys Leu Tyr Pro Lys Leu Tyr
                450                 455                 460
```

```
Thr Asp Val His Thr His Thr His Thr Cys Thr His Thr Leu
465                 470                 475                 480

Ser Cys Gly Gly Gln Gly Ser Ser Thr Pro Ala Cys Pro Leu Ser Val
            485                 490                 495

Leu Asn Thr Ala Asn Leu Gln Ala Leu Cys Pro Glu Val Gly Ile Trp
            500                 505                 510

Gly Pro Arg Gln Gln Val Gly Arg Ile Glu Asn Asn Gly Gly Arg Val
            515                 520                 525

Ser

<210> SEQ ID NO 7
<211> LENGTH: 439
<212> TYPE: PRT
<213> ORGANISM: Mouse

<400> SEQUENCE: 7

Met Thr Arg Ser Pro Ala Leu Leu Leu Leu Leu Gly Ala Leu Pro
  1               5                  10                  15

Ser Ala Glu Ala Ala Arg Asp Asp Ile Ser Pro Gly Lys Glu Ser Pro
                 20                  25                  30

Gly Pro Gly Gly Ser Ser Gly Gly Gln Glu Asp Pro Ala Ser Gln Gln
             35                  40                  45

Trp Ala Arg Pro Arg Phe Thr Gln Pro Ser Lys Met Arg Arg Arg Val
         50                  55                  60

Ile Ala Arg Pro Val Gly Ser Ser Val Arg Leu Lys Cys Val Ala Ser
 65                  70                  75                  80

Gly His Pro Arg Pro Asp Ile Met Trp Met Lys Asp Asp Gln Thr Leu
                 85                  90                  95

Thr His Leu Glu Ala Ser Glu His Arg Lys Lys Lys Trp Thr Leu Ser
            100                 105                 110

Leu Lys Asn Leu Lys Pro Glu Asp Ser Gly Lys Tyr Thr Cys Arg Val
        115                 120                 125

Ser Asn Lys Ala Gly Ala Ile Asn Ala Thr Tyr Lys Val Asp Val Ile
    130                 135                 140

Gln Arg Thr Arg Ser Lys Pro Val Leu Thr Gly Thr His Pro Val Asn
145                 150                 155                 160

Thr Thr Val Asp Phe Gly Gly Thr Thr Ser Phe Gln Cys Lys Val Arg
                165                 170                 175

Ser Asp Val Lys Pro Val Ile Gln Trp Leu Lys Arg Val Glu Tyr Gly
            180                 185                 190

Ser Glu Gly Arg His Asn Ser Thr Ile Asp Val Gly Gly Gln Lys Phe
        195                 200                 205

Val Val Leu Pro Thr Gly Asp Val Trp Ser Arg Pro Asp Gly Ser Tyr
    210                 215                 220

Leu Asn Lys Leu Leu Ile Ser Arg Ala Arg Gln Asp Asp Ala Gly Met
225                 230                 235                 240

Tyr Ile Cys Leu Gly Ala Asn Thr Met Gly Tyr Ser Phe Arg Ser Ala
                245                 250                 255

Phe Leu Thr Val Leu Pro Asp Pro Lys Pro Pro Gly Pro Pro Met
            260                 265                 270

Ala Ser Ser Ser Ser Thr Ser Leu Pro Trp Pro Val Val Ile Gly
        275                 280                 285

Ile Pro Ala Gly Ala Val Phe Ile Leu Gly Thr Val Leu Leu Trp Leu
    290                 295                 300
```

```
Cys Gln Thr Lys Lys Lys Pro Cys Ala Pro Ser Thr Leu Pro Val
305                 310                 315                 320

Pro Gly His Arg Pro Gly Thr Ser Arg Glu Arg Ser Gly Asp Lys
                325                 330                 335

Asp Leu Pro Ser Leu Ala Val Gly Ile Cys Glu His Gly Ser Ala
            340                 345                 350

Met Ala Pro Gln His Ile Leu Ala Ser Gly Ser Thr Ala Gly Pro Lys
        355                 360                 365

Leu Tyr Pro Lys Leu Tyr Thr Asp Val His Thr His Thr His
    370                 375                 380

Thr Cys Thr His Thr Leu Ser Cys Gly Gly Gln Gly Ser Ser Thr Pro
385                 390                 395                 400

Ala Cys Pro Leu Ser Val Leu Asn Thr Ala Asn Leu Gln Ala Leu Cys
                405                 410                 415

Pro Glu Val Gly Ile Trp Gly Pro Arg Gln Gln Val Gly Arg Ile Glu
            420                 425                 430

Asn Asn Gly Gly Arg Val Ser
            435

<210> SEQ ID NO 8
<211> LENGTH: 322
<212> TYPE: PRT
<213> ORGANISM: Mouse

<400> SEQUENCE: 8

Arg Arg Ala Pro Cys Cys Ser Cys Cys Arg Arg Cys Cys Trp Gly
1               5                   10                  15

Pro Ser His Arg Pro Pro Pro Glu Ala Pro Gln Arg Trp Arg Thr
                20                  25                  30

Arg Trp Ser His Gly Arg Trp Pro Ala Gly Pro His Cys Ala Ala Ala
            35                  40                  45

Val Pro Val Glu Gly Asp Pro Pro Leu Thr Met Trp Thr Lys Asp
    50                  55                  60

Gly Arg Thr Ile His Ser Gly Trp Ser Arg Phe Arg Val Leu Pro Gln
65                  70                  75                  80

Gly Leu Lys Val Lys Gln Val Glu Arg Glu Asp Ala Gly Val Tyr Val
                85                  90                  95

Cys Lys Ala Thr Asn Gly Phe Gly Ser Leu Ser Val Asn Tyr Thr Leu
            100                 105                 110

Val Val Leu Asp Asp Ile Ser Pro Gly Lys Glu Ser Leu Gly Pro Asp
        115                 120                 125

Ser Ser Ser Gly Gly Gln Glu Asp Pro Ala Ser Gln Gln Trp Ala Arg
    130                 135                 140

Pro Arg Phe Thr Gln Pro Ser Lys Met Arg Arg Val Ile Ala Arg
145                 150                 155                 160

Pro Val Gly Ser Ser Val Arg Leu Lys Cys Val Ala Ser Gly His Pro
                165                 170                 175

Arg Pro Asp Ile Thr Trp Met Lys Asp Gln Ala Leu Thr Arg Pro
            180                 185                 190

Glu Ala Ala Glu Pro Arg Lys Lys Lys Trp Thr Leu Ser Leu Lys Asn
        195                 200                 205

Leu Arg Pro Glu Asp Ser Gly Lys Tyr Thr Cys Arg Val Ser Asn Arg
    210                 215                 220

Ala Gly Ala Ile Asn Ala Thr Tyr Lys Val Asp Val Ile Gln Arg Thr
```

-continued

```
               225                 230                 235                 240
Arg Ser Lys Pro Val Leu Thr Gly Thr His Pro Val Asn Thr Thr Val
                245                 250                 255
Asp Phe Gly Gly Thr Thr Ser Phe Gln Cys Lys Val Arg Ser Asp Val
            260                 265                 270
Lys Pro Val Ile Gln Trp Leu Lys Arg Val Glu Tyr Gly Ala Glu Gly
        275                 280                 285
Arg His Asn Ser Thr Ile Asp Val Gly Gly Gln Lys Phe Val Val Leu
    290                 295                 300
Pro Thr Gly Asp Val Trp Ser Arg Pro Asp Gly Ser Tyr Leu Asn Lys
305                 310                 315                 320
Pro Leu
```

<210> SEQ ID NO 9
<211> LENGTH: 1423
<212> TYPE: DNA
<213> ORGANISM: Mouse

<400> SEQUENCE: 9

```
tctgtgcggc tcaagtgtgt ggccagtggg cacccacggc cagacatcat gtggatgaag      60
gatgaccaga ccttgacgca tctagaggct agtgaacaca gaaagaagaa gtggacactg     120
agcttgaaga acctgaagcc tgaagacagt ggcaagtaca cgtgccgtgt atctaacaag     180
gccggtgcca tcaacgccac ctacaaagtg gatgtaatcc gtgagtggtg ggtctgtggt     240
aggacagggg cccgtggtgc ctaaaactgt gctgacatgt ttgttttttcc ttggcttaga     300
gcggactcgt tccaagcctg tgctcacagg gacacaccct gtgaacacaa cggtggactt     360
cggtgggaca acgtccttcc agtgcaaggt gcgcagtgac gtgaagcctg tgatccagtg     420
gctgaagcgg gtggagtacg gctccgaggg acgccacaac tccaccattg atgtgggtgg     480
ccagaagttt gtggtgttgc ccacgggtga tgtgtggtca cggcctgatg gctcctacct     540
caacaagctg ctcatctctc gggcccgcca ggatgatgct ggcatgtaca tctgcctagg     600
tgcaaatacc atgggctaca gtttccgtag cgccttcctc actgtattac caggtgtgtg     660
tgtgggctgc ccaccccatg tttactctca gtctctacca ttggtctggg ctgtcctggg     720
gttccccaat gtccacttag caagtggggc ctccctatcc ttttcccttc gttgtgggtt     780
atccttgcct catagggagt tcaggggtgc tgcccatata gttcacattt ggctggttg      840
ccccattaat atagggacat tctgtcccct actcttcttc ttaatctctc ttgcagaccc     900
caaacctcca gggcctccta tggcttcttc atcgtcatcc acaagcctgc catggcctgt     960
ggtgatcggc atcccagctg gtgctgtctt catcctaggc actgtgctgc tctggctttg    1020
ccagaccaag aagaagccat gtgccccagc atctacactt cctgtgcctg gcatcgtcc     1080
cccagggaca tcccgagaac gcagtggtga caaggacctg ccctcattgg ctgtgggcat    1140
atgtgaggag catggatccg ccatggcccc ccagcacatc ctggcctctg gctcaactgc    1200
tggccccaag ctgtaccccca agctatacac agatgtgcac acacacacac atacacacac    1260
ctgcactcac acgctctcat gtggagggca aggttcatca acaccagcat gtccactatc    1320
agtgctaaat acagcgaatc tccaagcact gtgtcctgag gtaggcatat gggggccaag    1380
gcaacaggtt gggagaattg agaacaatgg aggaagagta tct                       1423
```

<210> SEQ ID NO 10
<211> LENGTH: 35
<212> TYPE: DNA

<210> SEQ ID NO 11
<211> LENGTH: 37
<212> TYPE: DNA
<213> ORGANISM: Mouse

<400> SEQUENCE: 10
cgggatccag gccatggcag gcttgtggat gacga        35

<210> SEQ ID NO 11
<211> LENGTH: 37
<212> TYPE: DNA
<213> ORGANISM: Mouse

<400> SEQUENCE: 11
ccgctcgagt agatactctt cctccattgt tctcatt      37

<210> SEQ ID NO 12
<211> LENGTH: 18
<212> TYPE: DNA
<213> ORGANISM: Mouse

<400> SEQUENCE: 12
ctgtgcggct caagtgtg                           18

<210> SEQ ID NO 13
<211> LENGTH: 373
<212> TYPE: PRT
<213> ORGANISM: Mouse

<400> SEQUENCE: 13

Met Thr Arg Ser Pro Ala Leu Leu Leu Leu Leu Gly Ala Leu Pro
 1               5                  10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
                35                  40                  45

Val Glu Gly Asp Pro Pro Pro Leu Thr Met Trp Thr Lys Asp Gly Arg
 50                  55                  60

Thr Ile His Ser Gly Trp Ser Arg Phe Arg Val Leu Pro Gln Gly Leu
65                   70                  75                  80

Lys Val Lys Glu Val Glu Ala Glu Asp Ala Gly Val Tyr Val Cys Lys
                 85                  90                  95

Ala Thr Asn Gly Phe Gly Ser Leu Ser Val Asn Tyr Thr Leu Ile Ile
                100                 105                 110

Met Asp Asp Ile Ser Pro Gly Lys Glu Ser Pro Gly Pro Gly Gly Ser
            115                 120                 125

Ser Gly Gly Gln Glu Asp Pro Ala Ser Gln Gln Trp Ala Arg Pro Arg
        130                 135                 140

Phe Thr Gln Pro Ser Lys Met Arg Arg Arg Val Ile Ala Arg Pro Val
145                 150                 155                 160

Gly Ser Ser Val Arg Leu Lys Cys Val Ala Ser Gly His Pro Arg Pro
                165                 170                 175

Asp Ile Met Trp Met Lys Asp Asp Gln Thr Leu Thr His Leu Glu Ala
            180                 185                 190

Ser Glu His Arg Lys Lys Lys Trp Thr Leu Ser Leu Lys Asn Leu Lys
        195                 200                 205

Pro Glu Asp Ser Gly Lys Tyr Thr Cys Arg Val Ser Asn Lys Ala Gly
    210                 215                 220

Ala Ile Asn Ala Thr Tyr Lys Val Asp Val Ile Gln Arg Thr Arg Ser
225                 230                 235                 240

```
Lys Pro Val Leu Thr Gly Thr His Pro Val Asn Thr Thr Val Asp Phe
            245                 250                 255

Gly Gly Thr Thr Ser Phe Gln Cys Lys Val Arg Ser Asp Val Lys Pro
            260                 265                 270

Val Ile Gln Trp Leu Lys Arg Val Glu Tyr Gly Ser Glu Gly Arg His
            275                 280                 285

Asn Ser Thr Ile Asp Val Gly Gly Gln Lys Phe Val Val Leu Pro Thr
            290                 295                 300

Gly Asp Val Trp Ser Arg Pro Asp Gly Ser Tyr Leu Asn Lys Leu Leu
305                 310                 315                 320

Ile Ser Arg Ala Arg Gln Asp Asp Ala Gly Met Tyr Ile Cys Leu Gly
                325                 330                 335

Ala Asn Thr Met Gly Tyr Ser Phe Arg Ser Ala Phe Leu Thr Val Leu
            340                 345                 350

Pro Asp Pro Lys Pro Pro Gly Pro Pro Met Ala Ser Ser Ser Ser Ser
            355                 360                 365

Thr Ser Leu Pro Trp
        370

<210> SEQ ID NO 14
<211> LENGTH: 135
<212> TYPE: PRT
<213> ORGANISM: Mouse

<400> SEQUENCE: 14

Cys Gln Thr Lys Lys Pro Cys Ala Pro Ala Ser Thr Leu Pro Val
1               5                   10                  15

Pro Gly His Arg Pro Pro Gly Thr Ser Arg Glu Arg Ser Gly Asp Lys
            20                  25                  30

Asp Leu Pro Ser Leu Ala Val Gly Ile Cys Glu Glu His Gly Ser Ala
        35                  40                  45

Met Ala Pro Gln His Ile Leu Ala Ser Gly Ser Thr Ala Gly Pro Lys
    50                  55                  60

Leu Tyr Pro Lys Leu Tyr Thr Asp Val His Thr His Thr His Thr His
65                  70                  75                  80

Thr Cys Thr His Thr Leu Ser Cys Gly Gly Gln Gly Ser Ser Thr Pro
                85                  90                  95

Ala Cys Pro Leu Ser Val Leu Asn Thr Ala Asn Leu Gln Ala Leu Cys
            100                 105                 110

Pro Glu Val Gly Ile Trp Gly Pro Arg Gln Gln Val Gly Arg Ile Glu
            115                 120                 125

Asn Asn Gly Gly Arg Val Ser
130                 135

<210> SEQ ID NO 15
<211> LENGTH: 37
<212> TYPE: PRT
<213> ORGANISM: Mouse

<400> SEQUENCE: 15

Arg Val Glu Tyr Gly Ser Glu Gly Arg His Asn Ser Thr Ile Asp Val
1               5                   10                  15

Gly Gly Gln Lys Phe Val Val Leu Pro Thr Gly Asp Val Trp Ser Arg
            20                  25                  30

Pro Asp Gly Ser Tyr
        35
```

<210> SEQ ID NO 16
<211> LENGTH: 1515
<212> TYPE: DNA
<213> ORGANISM: Human

<400> SEQUENCE: 16

```
atgacgccga gccccctgtt gctgctcctg ctgccgccgc tgctgctggg ggccttccca      60
ccggccgccg ccgcccgagg ccccccaaag atggcggaca aggtggtccc acggcaggtg     120
gcccggctgg gccgcactgt gcggctgcag tgcccagtgg aggggaccc gccgccgctg      180
accatgtgga ccaaggatgg ccgcaccatc cacagcggct ggagccgctt ccgcgtgctg     240
ccgcaggggc tgaaggtgaa gcaggtggag cgggaggatg ccggcgtgta cgtgtgcaag     300
gccaccaacg gcttcggcag ccttagcgtc aactacaccc tcgtcgtgct ggatgacatt     360
agcccaggga aggagagcct ggggcccgac agctcctctg ggggtcaaga ggaccccgcc     420
agccagcagt gggcacgacc gcgcttcaca cagccctcca agatgaggcg ccgggtgatc     480
gcacggcccg tgggtagctc cgtgcggctc aagtgcgtgg ccagcgggca ccctcggccc     540
gacatcacgt ggatgaagga cgaccaggcc ttgacgcgcc agaggccgc tgagcccagg      600
aagaagaagt ggacactgag cctgaagaac ctgcggccgg aggacagcgg caaatacacc     660
tgccgcgtgt cgaaccgcgc gggcgccatc aacgccacct acaaggtgga tgtgatccag     720
cggacccgtt ccaagcccgt gctcacaggc acgcaccccg tgaacacgac ggtggacttc     780
gggggggacca cgtccttcca gtgcaaggtg cgcagcgacg tgaagccggt gatccagtgg     840
ctgaagcgcg tggagtacgg cgccgagggc cgccacaact ccaccatcga tgtgggcggc     900
cagaagtttg tggtgctgcc cacgggtgac gtgtggtcgc ggcccgacgg ctcctacctc     960
aataagctgc tcatcacccg tgcccgccag gacgatgcgg gcatgtacat ctgccttggc    1020
gccaacacca tgggctacag cttccgcagc gccttcctca ccgtgctgcc agacccaaaa    1080
ccgcaagggc cacctgtggc ctcctcgtcc tcggccacta gcctgccgtg gcccgtggtc    1140
atcggcatcc cagccggcgc tgtcttcatc ctgggcaccc tgctcctgtg gctttgccag    1200
gcccagaaga agccgtgcac ccccgcgcct gcccctcccc tgcctgggca ccgccgccg    1260
gggacggccc gcgaccgcag cggagacaag gaccttccct cgttggccgc cctcagcgct    1320
ggccctggtg tggggctgtg tgaggagcat gggtctccgg cagcccccca gcacttactg    1380
ggccaggcc cagttgctgg ccctaagttg taccccaaac tctacacaga catccacaca    1440
cacacacaca cacactctca cacacactca cacgtggagg gcaaggtcca ccagcacatc    1500
cactatcagt gctag                                                   1515
```

<210> SEQ ID NO 17
<211> LENGTH: 504
<212> TYPE: PRT
<213> ORGANISM: Human

<400> SEQUENCE: 17

Met Thr Pro Ser Pro Leu Leu Leu Leu Leu Pro Pro Leu Leu Leu
1               5                   10                  15

Gly Ala Phe Pro Pro Ala Ala Ala Arg Gly Pro Pro Lys Met Ala
                20                  25                  30

Asp Lys Val Val Pro Arg Gln Val Ala Arg Leu Gly Arg Thr Val Arg
            35                  40                  45

Leu Gln Cys Pro Val Glu Gly Asp Pro Pro Leu Thr Met Trp Thr
        50                  55                  60

-continued

```
Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
                 85                  90                  95

Tyr Val Cys Lys Ala Thr Asn Gly Phe Gly Ser Leu Ser Val Asn Tyr
            100                 105                 110

Thr Leu Val Val Leu Asp Asp Ile Ser Pro Gly Lys Glu Ser Leu Gly
            115                 120                 125

Pro Asp Ser Ser Gly Gly Gln Glu Asp Pro Ala Ser Gln Gln Trp
    130                 135                 140

Ala Arg Pro Arg Phe Thr Gln Pro Ser Lys Met Arg Arg Val Ile
145                 150                 155                 160

Ala Arg Pro Val Gly Ser Ser Val Arg Leu Lys Cys Val Ala Ser Gly
                165                 170                 175

His Pro Arg Pro Asp Ile Thr Trp Met Lys Asp Asp Gln Ala Leu Thr
            180                 185                 190

Arg Pro Glu Ala Ala Glu Pro Arg Lys Lys Lys Trp Thr Leu Ser Leu
            195                 200                 205

Lys Asn Leu Arg Pro Glu Asp Ser Gly Lys Tyr Thr Cys Arg Val Ser
    210                 215                 220

Asn Arg Ala Gly Ala Ile Asn Ala Thr Tyr Lys Val Asp Val Ile Gln
225                 230                 235                 240

Arg Thr Arg Ser Lys Pro Val Leu Thr Gly Thr His Pro Val Asn Thr
                245                 250                 255

Thr Val Asp Phe Gly Gly Thr Thr Ser Phe Gln Cys Lys Val Arg Ser
            260                 265                 270

Asp Val Lys Pro Val Ile Gln Trp Leu Lys Arg Val Glu Tyr Gly Ala
            275                 280                 285

Glu Gly Arg His Asn Ser Thr Ile Asp Val Gly Gly Gln Lys Phe Val
    290                 295                 300

Val Leu Pro Thr Gly Asp Val Trp Ser Arg Pro Asp Gly Ser Tyr Leu
305                 310                 315                 320

Asn Lys Leu Leu Ile Thr Arg Ala Arg Gln Asp Asp Ala Gly Met Tyr
                325                 330                 335

Ile Cys Leu Gly Ala Asn Thr Met Gly Tyr Ser Phe Arg Ser Ala Phe
            340                 345                 350

Leu Thr Val Leu Pro Asp Pro Lys Pro Gln Gly Pro Val Ala Ser
            355                 360                 365

Ser Ser Ser Ala Thr Ser Leu Pro Trp Pro Val Val Ile Gly Ile Pro
    370                 375                 380

Ala Gly Ala Val Phe Ile Leu Gly Thr Leu Leu Leu Trp Leu Cys Gln
385                 390                 395                 400

Ala Gln Lys Lys Pro Cys Thr Pro Ala Pro Ala Pro Pro Leu Pro Gly
                405                 410                 415

His Arg Pro Pro Gly Thr Ala Arg Asp Arg Ser Gly Asp Lys Asp Leu
            420                 425                 430

Pro Ser Leu Ala Ala Leu Ser Ala Gly Pro Gly Val Gly Leu Cys Glu
            435                 440                 445

Glu His Gly Ser Pro Ala Ala Pro Gln His Leu Leu Gly Pro Gly Pro
    450                 455                 460

Val Ala Gly Pro Lys Leu Tyr Pro Lys Leu Tyr Thr Asp Ile His Thr
465                 470                 475                 480
```

```
His Thr His Thr His Ser His Thr Ser His Val Glu Gly Lys Val
            485                 490                 495
His Gln His Ile His Tyr Gln Cys
        500
```

<210> SEQ ID NO 18
<211> LENGTH: 1161
<212> TYPE: DNA
<213> ORGANISM: Human

<400> SEQUENCE: 18

```
atgacgccga gcccctgtt gctgctcctg ctgccgccgc tgctgctggg ggccttccca     60
ccggccgccg ccgcccgagg ccccccaaag atggcggaca aggtggtccc acggcaggtg    120
gcccggctgg gccgcactgt gcggctgcag tgcccagtgg aggggacccc gccgccgctg    180
accatgtgga ccaaggatgg ccgcaccatc acagcggct ggagccgctt ccgcgtgctg     240
ccgcagggc tgaaggtgaa gcaggtggag cgggaggatg ccggcgtgta cgtgtgcaag     300
gccaccaacg gcttcggcag ccttagcgtc aactacaccc tcgtcgtgct ggatgacatt    360
agcccaggga aggagagcct ggggcccgac agctcctctg ggggtcaaga ggaccccgcc    420
agccagcagt gggcacgacc gcgcttcaca cagccctcca agatgaggcg ccgggtgatc    480
gcacggcccg tgggtagctc cgtgcggctc aagtgcgtgg ccagcgggca ccctcggccc    540
gacatcacgt ggatgaagga cgaccaggcc ttgacgcgcc agaggccgc tgagcccagg     600
aagaagaagt ggacactgag cctgaagaac ctgcggccgg aggacagcgg caaatacacc    660
tgccgcgtgt cgaaccgcgc gggcgccatc aacgccacct acaaggtgga tgtgatccac    720
ccaaaaccgc aagggccacc tgtggcctcc tcgtcctcgg ccactagcct gccgtggccc    780
gtggtcatcg gcatcccagc cggcgctgtc ttcatcctgg caccctgct cctgtggctt     840
tgccaggccc agaagaagcc gtgcacccc gcgcctgccc ctcccctgcc tgggcaccgc     900
ccgccgggga cggccgcga ccgcagcgga gacaaggacc ttccctcgtt ggccgccctc    960
agcgctggcc ctggtgtggg gctgtgtgag gagcatgggt ctccggcagc cccccagcac   1020
ttactgggcc caggcccagt tgctggccct aagttgtacc ccaaactcta cacagacatc   1080
cacacacaca cacacacaca ctctcacaca cactcacacg tggagggcaa ggtccaccag   1140
cacatccact atcagtgcta g                                              1161
```

<210> SEQ ID NO 19
<211> LENGTH: 386
<212> TYPE: PRT
<213> ORGANISM: Human

<400> SEQUENCE: 19

```
Met Thr Pro Ser Pro Leu Leu Leu Leu Leu Pro Leu Leu Leu
 1               5                  10                  15

Gly Ala Phe Pro Pro Ala Ala Ala Arg Gly Pro Pro Lys Met Ala
             20                  25                  30

Asp Lys Val Val Pro Arg Gln Val Ala Arg Leu Gly Arg Thr Val Arg
             35                  40                  45

Leu Gln Cys Pro Val Glu Gly Asp Pro Pro Leu Thr Met Trp Thr
 50                  55                  60

Lys Asp Gly Arg Thr Ile His Ser Gly Trp Ser Arg Phe Arg Val Leu
65                  70                  75                  80

Pro Gln Gly Leu Lys Val Lys Gln Val Glu Arg Glu Asp Ala Gly Val
                 85                  90                  95
```

```
Tyr Val Cys Lys Ala Thr Asn Gly Phe Gly Ser Leu Ser Val Asn Tyr
                100                 105                 110
Thr Leu Val Leu Asp Asp Ile Ser Pro Gly Lys Glu Ser Leu Gly
            115                 120                 125
Pro Asp Ser Ser Gly Gly Gln Glu Asp Pro Ala Ser Gln Gln Trp
        130                 135                 140
Ala Arg Pro Arg Phe Thr Gln Pro Ser Lys Met Arg Arg Val Ile
145                 150                 155                 160
Ala Arg Pro Val Gly Ser Ser Val Arg Leu Lys Cys Val Ala Ser Gly
                165                 170                 175
His Pro Arg Pro Asp Ile Thr Trp Met Lys Asp Asp Gln Ala Leu Thr
                180                 185                 190
Arg Pro Glu Ala Ala Glu Pro Arg Lys Lys Lys Trp Thr Leu Ser Leu
                195                 200                 205
Lys Asn Leu Arg Pro Glu Asp Ser Gly Lys Tyr Thr Cys Arg Val Ser
                210                 215                 220
Asn Arg Ala Gly Ala Ile Asn Ala Thr Tyr Lys Val Asp Val Ile His
225                 230                 235                 240
Pro Lys Pro Gln Gly Pro Pro Val Ala Ser Ser Ser Ala Thr Ser
                245                 250                 255
Leu Pro Trp Pro Val Val Ile Gly Ile Pro Ala Gly Ala Val Phe Ile
                260                 265                 270
Leu Gly Thr Leu Leu Leu Trp Leu Cys Gln Ala Gln Lys Lys Pro Cys
                275                 280                 285
Thr Pro Ala Pro Ala Pro Pro Leu Pro Gly His Arg Pro Pro Gly Thr
                290                 295                 300
Ala Arg Asp Arg Ser Gly Asp Lys Asp Leu Pro Ser Leu Ala Ala Leu
305                 310                 315                 320
Ser Ala Gly Pro Gly Val Gly Leu Cys Glu Glu His Gly Ser Pro Ala
                325                 330                 335
Ala Pro Gln His Leu Leu Gly Pro Gly Pro Val Ala Gly Pro Lys Leu
                340                 345                 350
Tyr Pro Lys Leu Tyr Thr Asp Ile His Thr His Thr His Thr His Ser
                355                 360                 365
His Thr His Ser His Val Glu Gly Lys Val His Gln His Ile His Tyr
            370                 375                 380
Gln Cys
385

<210> SEQ ID NO 20
<211> LENGTH: 1230
<212> TYPE: DNA
<213> ORGANISM: Human

<400> SEQUENCE: 20
atgacgccga gcccctgtt gctgctcctg ctgccgccgc tgctgctggg ggccttccca      60
ccggccgccg ccgcccgagg ccccccaaag atggcggaca ggtggtccc acggcaggtg     120 gcccggctgg ccgcactgt gcggctgcag tgcccagtgg aggggaccc gccgccgctg     180 accatgtgga ccaaggatgg ccgcaccatc acagcggct ggagccgctt ccgcgtgctg     240 ccgcagggc tgaaggtgaa gcaggtggag cgggaggatg ccggcgtgta cgtgtgcaag     300
gccaccaacg gcttcggcag ccttagcgtc aactacaccc tcgtcgtgct ggatgacatt    360
agcccaggga aggagagcct ggggcccgac agctcctctg ggggtcaaga ggaccccgcc    420
```

```
agccagcagt gggagcggac ccgttccaag cccgtgctca caggcacgca ccccgtgaac    480
acgacggtgg acttcggggg gaccacgtcc ttccagtgca aggtgcgcag cgacgtgaag    540
ccggtgatcc agtggctgaa gcgcgtggag tacggcgccg agggccgcca caactccacc    600
atcgatgtgg gcggccagaa gtttgtggtg ctgcccacgg gtgacgtgtg gtcgcggccc    660
gacggctcct acctcaataa gctgctcatc acccgtgccc gccaggacga tgcgggcatg    720
tacatctgcc ttggcgccaa caccatgggc tacagcttcc gcagcgcctt cctcaccgtg    780
ctgccagacc caaaaccgca agggccacct gtggcctcct cgtcctcggc cactagcctg    840
ccgtggcccg tggtcatcgg catcccagcc ggcgctgtct tcatcctggg caccctgctc    900
ctgtggcttt gccaggccca gaagaagccg tgcaccccg cgcctgcccc tcccctgcct    960
gggcaccgcc cgccgggac ggcccgcgac cgcagcggag acaaggacct tccctcgttg    1020
gccgccctca gcgctggccc tggtgtgggg ctgtgtgagg agcatgggtc tccggcagcc    1080
ccccagcact tactgggccc aggcccagtt gctggcccta agttgtaccc caaactctac    1140
acagacatcc acacacacac acacacacac tctcacacac actcacacgt ggagggcaag    1200
gtccaccagc acatccacta tcagtgctag                                    1230
```

<210> SEQ ID NO 21
<211> LENGTH: 409
<212> TYPE: PRT
<213> ORGANISM: Human

<400> SEQUENCE: 21

```
Met Thr Pro Ser Pro Leu Leu Leu Leu Leu Pro Leu Leu Leu
  1               5                  10                  15

Gly Ala Phe Pro Pro Ala Ala Ala Arg Gly Pro Pro Lys Met Ala
             20                  25                  30

Asp Lys Val Val Pro Arg Gln Val Ala Arg Leu Gly Arg Thr Val Arg
             35                  40                  45

Leu Gln Cys Pro Val Glu Gly Asp Pro Pro Leu Thr Met Trp Thr
  50                  55                  60

Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
                 85                  90                  95

Tyr Val Cys Lys Ala Thr Asn Gly Phe Gly Ser Leu Ser Val Asn Tyr
                100                 105                 110

Thr Leu Val Val Leu Asp Asp Ile Ser Pro Gly Lys Glu Ser Leu Gly
            115                 120                 125

Pro Asp Ser Ser Gly Gly Gln Glu Asp Pro Ala Ser Gln Gln Trp
        130                 135                 140

Glu Arg Thr Arg Ser Lys Pro Val Leu Thr Gly Thr His Pro Val Asn
145                 150                 155                 160

Thr Thr Val Asp Phe Gly Gly Thr Thr Ser Phe Gln Cys Lys Val Arg
                165                 170                 175

Ser Asp Val Lys Pro Val Ile Gln Trp Leu Lys Arg Val Glu Tyr Gly
                180                 185                 190

Ala Glu Gly Arg His Asn Ser Thr Ile Asp Val Gly Gly Gln Lys Phe
            195                 200                 205

Val Val Leu Pro Thr Gly Asp Val Trp Ser Arg Pro Asp Gly Ser Tyr
        210                 215                 220
```

-continued

```
Leu Asn Lys Leu Leu Ile Thr Arg Ala Arg Gln Asp Asp Ala Gly Met
225                 230                 235                 240

Tyr Ile Cys Leu Gly Ala Asn Thr Met Gly Tyr Ser Phe Arg Ser Ala
            245                 250                 255

Phe Leu Thr Val Leu Pro Asp Pro Lys Pro Gln Gly Pro Pro Val Ala
        260                 265                 270

Ser Ser Ser Ala Thr Ser Leu Pro Trp Pro Val Val Ile Gly Ile
    275                 280                 285

Pro Ala Gly Ala Val Phe Ile Leu Gly Thr Leu Leu Leu Trp Leu Cys
290                 295                 300

Gln Ala Gln Lys Lys Pro Cys Thr Pro Ala Pro Ala Pro Pro Leu Pro
305                 310                 315                 320

Gly His Arg Pro Pro Gly Thr Ala Arg Asp Arg Ser Gly Asp Lys Asp
                325                 330                 335

Leu Pro Ser Leu Ala Ala Leu Ser Ala Gly Pro Gly Val Gly Leu Cys
            340                 345                 350

Glu Glu His Gly Ser Pro Ala Ala Pro Gln His Leu Leu Gly Pro Gly
        355                 360                 365

Pro Val Ala Gly Pro Lys Leu Tyr Pro Lys Leu Tyr Thr Asp Ile His
    370                 375                 380

Thr His Thr His Thr His Ser His Thr His Ser His Val Glu Gly Lys
385                 390                 395                 400

Val His Gln His Ile His Tyr Gln Cys
                405
```

<210> SEQ ID NO 22
<211> LENGTH: 1434
<212> TYPE: DNA
<213> ORGANISM: Human

<400> SEQUENCE: 22

| | | |
|---|---|---|
| atgacgccga gccccctgtt gctgctcctg ctgccgccgc tgctgctggg ggccttccca | 60 |
| ccggccgccg ccgcccgagg ccccccaaag atggcggaca ggtggtccc acggcaggtg | 120 |
| gcccggctgg gccgcactgt gcggctgcag tgcccagtgg aggggaccc gccgccgctg | 180 |
| accatgtgga ccaaggatgg ccgcaccatc cacagcggct ggagccgctt ccgcgtgctg | 240 |
| ccgcagggc tgaaggtgaa gcaggtggag cgggaggatg ccggcgtgta cgtgtgcaag | 300 |
| gccaccaacg gcttcggcag ccttagcgtc aactacaccc tcgtcgtgct ggcacgaccg | 360 |
| cgcttcacac agccctccaa gatgaggcgc cgggtgatcg cacggcccgt gggtagctcc | 420 |
| gtgcggctca gtgcgtggc cagcgggcac cctcggcccg acatcacgtg gatgaaggac | 480 |
| gaccaggcct tgacgcgccc agaggccgct gagcccagga agaagaagtg acactgagc | 540 |
| ctgaagaacc tgcggccgga ggacagcggc aaatacacct gccgcgtgtc gaaccgcgcg | 600 |
| ggcgccatca acgccaccta caaggtggat gtgatccagc ggacccgttc caagcccgtg | 660 |
| ctcacaggca cgcaccccgt gaacacgacg gtggacttcg gggggaccac gtccttccag | 720 |
| tgcaaggtgc gcagcgacgt gaagccggtg atccagtggc tgaagcgcgt ggagtacggc | 780 |
| gccgagggcc gccacaactc caccatcgat gtgggcggcc agaagtttgt ggtgctgccc | 840 |
| acgggtgacg tgtggtcgcg gcccgacggc tcctacctca ataagctgct catcacccgt | 900 |
| gcccgccagg acgatgcggg catgtacatc tgccttggcg ccaacaccat gggctacagc | 960 |
| ttccgcagcg ccttcctcac cgtgctgcca gaccaaaaac cgcaagggcc acctgtggcc | 1020 |
| tcctcgtcct cggccactag cctgccgtgg cccgtggtca tcggcatccc agccggcgct | 1080 |

```
gtcttcatcc tgggcaccct gctcctgtgg ctttgccagg cccagaagaa gccgtgcacc    1140
cccgcgcctg cccctcccct gcctgggcac cgcccgccgg ggacggcccg cgaccgcagc    1200
ggagacaagg accttccctc gttggccgcc ctcagcgctg gccctggtgt ggggctgtgt    1260
gaggagcatg ggtctccggc agccccccag cacttactgg gcccaggccc agttgctggc    1320
cctaagttgt accccaaact ctacacagac atccacacac acacacacac acactctcac    1380
acacactcac acgtggaggg caaggtccac cagcacatcc actatcagtg ctag          1434
```

<210> SEQ ID NO 23
<211> LENGTH: 477
<212> TYPE: PRT
<213> ORGANISM: Human

<400> SEQUENCE: 23

```
Met Thr Pro Ser Pro Leu Leu Leu Leu Leu Pro Pro Leu Leu Leu
 1               5                  10                  15

Gly Ala Phe Pro Pro Ala Ala Ala Arg Gly Pro Pro Lys Met Ala
                20                  25                  30

Asp Lys Val Val Pro Arg Gln Val Ala Arg Leu Gly Arg Thr Val Arg
            35                  40                  45

Leu Gln Cys Pro Val Glu Gly Asp Pro Pro Pro Leu Thr Met Trp Thr
50                  55                  60

Lys Asp Gly Arg Thr Ile His Ser Gly Trp Ser Arg Phe Arg Val Leu
65                  70                  75                  80

Pro Gln Gly Leu Lys Val Lys Gln Val Glu Arg Glu Asp Ala Gly Val
                85                  90                  95

Tyr Val Cys Lys Ala Thr Asn Gly Phe Gly Ser Leu Ser Val Asn Tyr
            100                 105                 110

Thr Leu Val Val Leu Ala Arg Pro Arg Phe Thr Gln Pro Ser Lys Met
        115                 120                 125

Arg Arg Arg Val Ile Ala Arg Pro Val Gly Ser Ser Val Arg Leu Lys
130                 135                 140

Cys Val Ala Ser Gly His Pro Arg Pro Asp Ile Thr Trp Met Lys Asp
145                 150                 155                 160

Asp Gln Ala Leu Thr Arg Pro Glu Ala Ala Glu Pro Arg Lys Lys Lys
                165                 170                 175

Trp Thr Leu Ser Leu Lys Asn Leu Arg Pro Glu Asp Ser Gly Lys Tyr
            180                 185                 190

Thr Cys Arg Val Ser Asn Arg Ala Gly Ala Ile Asn Ala Thr Tyr Lys
        195                 200                 205

Val Asp Val Ile Gln Arg Thr Arg Ser Lys Pro Val Leu Thr Gly Thr
    210                 215                 220

His Pro Val Asn Thr Thr Val Asp Phe Gly Gly Thr Thr Ser Phe Gln
225                 230                 235                 240

Cys Lys Val Arg Ser Asp Val Lys Pro Val Ile Gln Trp Leu Lys Arg
                245                 250                 255

Val Glu Tyr Gly Ala Glu Gly Arg His Asn Ser Thr Ile Asp Val Gly
            260                 265                 270

Gly Gln Lys Phe Val Val Leu Pro Thr Gly Asp Val Trp Ser Arg Pro
        275                 280                 285

Asp Gly Ser Tyr Leu Asn Lys Leu Leu Ile Thr Arg Ala Arg Gln Asp
    290                 295                 300

Asp Ala Gly Met Tyr Ile Cys Leu Gly Ala Asn Thr Met Gly Tyr Ser
```

```
                305                 310                 315                 320
Phe Arg Ser Ala Phe Leu Thr Val Leu Pro Asp Pro Lys Pro Gln Gly
                325                 330                 335
Pro Pro Val Ala Ser Ser Ser Ala Thr Ser Leu Pro Trp Pro Val
            340                 345                 350
Val Ile Gly Ile Pro Ala Gly Ala Val Phe Ile Leu Gly Thr Leu Leu
                355                 360                 365
Leu Trp Leu Cys Gln Ala Gln Lys Lys Pro Cys Thr Pro Ala Pro Ala
        370                 375                 380
Pro Pro Leu Pro Gly His Arg Pro Gly Thr Ala Arg Asp Arg Ser
385                 390                 395                 400
Gly Asp Lys Asp Leu Pro Ser Leu Ala Ala Leu Ser Ala Gly Pro Gly
                405                 410                 415
Val Gly Leu Cys Glu Glu His Gly Ser Pro Ala Ala Pro Gln His Leu
            420                 425                 430
Leu Gly Pro Gly Pro Val Ala Gly Pro Lys Leu Tyr Pro Lys Leu Tyr
            435                 440                 445
Thr Asp Ile His Thr His Thr His Thr His Ser His Thr His Ser His
        450                 455                 460
Val Glu Gly Lys Val His Gln His Ile His Tyr Gln Cys
465                 470                 475

<210> SEQ ID NO 24
<211> LENGTH: 1242
<212> TYPE: DNA
<213> ORGANISM: Human

<400> SEQUENCE: 24
atgacgccga gccccctgtt gctgctcctg ctgccgccgc tgctgctggg ggccttccca      60
ccggccgccg ccgcccgaga tgacattagc cagggaagg agagcctggg gcccgacagc     120
tcctctgggg gtcaagagga ccccgccagc cagcagtggg cacgaccgcg cttcacacag     180
ccctccaaga tgaggcgccg ggtgatcgca cggcccgtgg gtagctccgt gcggctcaag     240
tgcgtggcca gcgggcaccc tcggcccgac atcacgtgga tgaaggacga ccaggccttg     300
acgcgcccag aggccgctga gcccaggaag aagaagtgga cactgagcct gaagaacctg     360
cggccggagg acagcggcaa atacacctgc gcgtgtcga accgcgcggg cgccatcaac     420
gccacctaca aggtggatgt gatccagcgg acccgttcca gcccgtgct cacaggcacg     480
caccccgtga acacgacggt ggacttcggg gggaccacgt ccttccagtg caaggtgcgc     540
agcgacgtga agccggtgat ccagtggctg aagcgcgtgg agtacggcgc cgagggccgc     600
cacaactcca ccatcgatgt gggcggccag aagtttgtgg tgctgcccac gggtgacgtg     660
tggtcgcggc ccgacggctc ctacctcaat aagctgctca tcacccgtgc ccgccaggac     720
gatgcgggca tgtacatctg ccttggcgcc aacaccatgg gctacagctt ccgcagcgcc     780
ttcctcaccg tgctgccaga cccaaaaccg caagggccac ctgtggcctc ctcgtcctcg     840
gccactagcc tgccgtggcc cgtggtcatc ggcatcccag ccggcgctgt cttcatcctg     900
ggcaccctgc tcctgtggct tgccaggcc agaagaagc cgtgcacccc cgcgcctgcc      960
cctcccctgc ctgggcaccg cccgccgggg acgccccgcg accgcagcgg agacaaggac    1020
cttccctcgt tggccgccct cagcgctggc cctggtgtgg gctgtgtga ggagcatggg    1080
tctccggcag cccccagca cttactgggc ccaggcccag ttgctggccc taagttgtac    1140
cccaaactct acacagacat ccacacacac acacacacac actctcacac acactcacac    1200
```

```
gtggagggca aggtccacca gcacatccac tatcagtgct ag                    1242
```

<210> SEQ ID NO 25
<211> LENGTH: 413
<212> TYPE: PRT
<213> ORGANISM: Human

<400> SEQUENCE: 25

```
Met Thr Pro Ser Pro Leu Leu Leu Leu Leu Pro Leu Leu Leu
 1               5                  10                  15

Gly Ala Phe Pro Pro Ala Ala Ala Arg Asp Asp Ile Ser Pro Gly
                20                  25                  30

Lys Glu Ser Leu Gly Pro Asp Ser Ser Gly Gly Gln Glu Asp Pro
                35                  40                  45

Ala Ser Gln Gln Trp Ala Arg Pro Arg Phe Thr Gln Pro Ser Lys Met
         50                  55                  60

Arg Arg Arg Val Ile Ala Arg Pro Val Gly Ser Val Arg Leu Lys
 65                  70                  75                  80

Cys Val Ala Ser Gly His Pro Arg Pro Asp Ile Thr Trp Met Lys Asp
                    85                  90                  95

Asp Gln Ala Leu Thr Arg Pro Glu Ala Ala Glu Pro Arg Lys Lys Lys
                    100                 105                 110

Trp Thr Leu Ser Leu Lys Asn Leu Arg Pro Glu Asp Ser Gly Lys Tyr
                    115                 120                 125

Thr Cys Arg Val Ser Asn Arg Ala Gly Ala Ile Asn Ala Thr Tyr Lys
                    130                 135                 140

Val Asp Val Ile Gln Arg Thr Arg Ser Lys Pro Val Leu Thr Gly Thr
145                 150                 155                 160

His Pro Val Asn Thr Thr Val Asp Phe Gly Gly Thr Thr Ser Phe Gln
                    165                 170                 175

Cys Lys Val Arg Ser Asp Val Lys Pro Val Ile Gln Trp Leu Lys Arg
                    180                 185                 190

Val Glu Tyr Gly Ala Glu Gly Arg His Asn Ser Thr Ile Asp Val Gly
                    195                 200                 205

Gly Gln Lys Phe Val Val Leu Pro Thr Gly Asp Val Trp Ser Arg Pro
                    210                 215                 220

Asp Gly Ser Tyr Leu Asn Lys Leu Leu Ile Thr Arg Ala Arg Gln Asp
225                 230                 235                 240

Asp Ala Gly Met Tyr Ile Cys Leu Gly Ala Asn Thr Met Gly Tyr Ser
                    245                 250                 255

Phe Arg Ser Ala Phe Leu Thr Val Leu Pro Asp Pro Lys Pro Gln Gly
                    260                 265                 270

Pro Pro Val Ala Ser Ser Ser Ala Thr Ser Leu Pro Trp Pro Val
                    275                 280                 285

Val Ile Gly Ile Pro Ala Gly Ala Val Phe Ile Leu Gly Thr Leu Leu
                    290                 295                 300

Leu Trp Leu Cys Gln Ala Gln Lys Lys Pro Cys Thr Pro Ala Pro Ala
305                 310                 315                 320

Pro Pro Leu Pro Gly His Arg Pro Pro Gly Thr Ala Arg Asp Arg Ser
                    325                 330                 335

Gly Asp Lys Asp Leu Pro Ser Leu Ala Ala Leu Ser Ala Gly Pro Gly
                    340                 345                 350

Val Gly Leu Cys Glu Glu His Gly Ser Pro Ala Ala Pro Gln His Leu
                    355                 360                 365
```

Leu Gly Pro Gly Pro Val Ala Gly Pro Lys Leu Tyr Pro Lys Leu Tyr
            370                 375                 380

Thr Asp Ile His Thr His Thr His Thr His Ser His Thr His Ser His
385                 390                 395                 400

Val Glu Gly Lys Val His Gln His Ile His Tyr Gln Cys
                405                 410

<210> SEQ ID NO 26
<211> LENGTH: 876
<212> TYPE: DNA
<213> ORGANISM: Human

<400> SEQUENCE: 26

```
atgacgccga gcccctgtt gctgctcctg ctgccgccgc tgctgctggg ggccttccca     60
ccggccgccg ccgcccgagg cccccaaag atggcggaca aggtggtccc acggcaggtg    120
gcccggctgg gccgcactgt gcggctgcag tgcccagtgg aggggacccc gccgccgctg    180
accatgtgga ccaaggatgg ccgcaccatc acagcggct ggagccgctt ccgcgtgctg    240
ccgcaggggc tgaaggtgaa gcaggtggag cgggaggatg ccggcgtgta cgtgtgcaag    300
gccaccaacg gcttcggcag ccttagcgtc aactacaccc tcgtcgtgct ggatgacatt    360
agcccaggga aggagagcct ggggcccgac agctcctctg ggggtcaaga ggaccccgcc    420
agccagcagt gggacccaaa accgcaaggg ccacctgtgg cctcctcgtc ctcggccact    480
agcctgccgt ggcccgtggt catcggcatc ccagccggcg ctgtcttcat cctgggcacc    540
ctgctcctgt ggctttgcca ggcccagaag aagccgtgca ccccgcgcc tgcccctccc    600
ctgcctgggc accgcccgcc ggggacggcc cgcgaccgca gcggagacaa ggaccttccc    660
tcgttggccg ccctcagcgc tggccctggt gtggggctgt gtgaggagca tgggtctccg    720
gcagcccccc agcacttact gggcccaggc ccagttgctg ccctaagtt gtaccccaaa    780
ctctacacag acatccacac acacacacac acacactctc acacacactc acacgtggag    840
ggcaaggtcc accagcacat ccactatcag tgctag                             876
```

<210> SEQ ID NO 27
<211> LENGTH: 291
<212> TYPE: PRT
<213> ORGANISM: Human

<400> SEQUENCE: 27

Met Thr Pro Ser Pro Leu Leu Leu Leu Pro Pro Leu Leu Leu
  1               5                  10                  15

Gly Ala Phe Pro Pro Ala Ala Ala Arg Gly Pro Pro Lys Met Ala
                20                  25                  30

Asp Lys Val Val Pro Arg Gln Val Ala Arg Leu Gly Arg Thr Val Arg
            35                  40                  45

Leu Gln Cys Pro Val Glu Gly Asp Pro Pro Leu Thr Met Trp Thr
    50                  55                  60

Lys Asp Gly Arg Thr Ile His Ser Gly Trp Ser Arg Phe Arg Val Leu
65                  70                  75                  80

Pro Gln Gly Leu Lys Val Lys Gln Val Glu Arg Glu Asp Ala Gly Val
                85                  90                  95

Tyr Val Cys Lys Ala Thr Asn Gly Phe Gly Ser Leu Ser Val Asn Tyr
                100                 105                 110

Thr Leu Val Val Leu Asp Asp Ile Ser Pro Gly Lys Glu Ser Leu Gly
            115                 120                 125

```
Pro Asp Ser Ser Ser Gly Gly Gln Glu Asp Pro Ala Ser Gln Gln Trp
    130                 135                 140

Asp Pro Lys Pro Gln Gly Pro Pro Val Ala Ser Ser Ser Ala Thr
145                 150                 155                 160

Ser Leu Pro Trp Pro Val Val Ile Gly Ile Pro Ala Gly Ala Val Phe
                165                 170                 175

Ile Leu Gly Thr Leu Leu Leu Trp Leu Cys Gln Ala Gln Lys Lys Pro
            180                 185                 190

Cys Thr Pro Ala Pro Ala Pro Leu Pro Gly His Arg Pro Pro Gly
        195                 200                 205

Thr Ala Arg Asp Arg Ser Gly Asp Lys Asp Leu Pro Ser Leu Ala Ala
    210                 215                 220

Leu Ser Ala Gly Pro Gly Val Gly Leu Cys Glu His Gly Ser Pro
225                 230                 235                 240

Ala Ala Pro Gln His Leu Leu Gly Pro Gly Pro Val Ala Gly Pro Lys
                245                 250                 255

Leu Tyr Pro Lys Leu Tyr Thr Asp Ile His Thr His Thr His Thr His
            260                 265                 270

Ser His Thr His Ser His Val Glu Gly Lys Val His Gln His Ile His
        275                 280                 285

Tyr Gln Cys
    290

<210> SEQ ID NO 28
<211> LENGTH: 1080
<212> TYPE: DNA
<213> ORGANISM: Human

<400> SEQUENCE: 28
atgacgccga gcccctgtt gctgctcctg ctgccgccgc tgctgctggg ggccttccca     60
ccggccgccg ccgcccgagg ccccccaaag atggcggaca aggtggtccc acggcaggtg    120
gcccggctgg gccgcactgt gcggctgcag tgcccagtgg aggggaccc gccgccgctg    180
accatgtgga ccaaggatgg ccgcaccatc acagcggct ggagccgctt ccgcgtgctg    240
ccgcaggggc tgaaggtgaa gcaggtggag cgggaggatg ccggcgtgta cgtgtgcaag    300
gccaccaacg gcttcggcag ccttagcgtc aactacaccc tcgtcgtgct ggcacgaccg    360
cgcttcacac agccctccaa gatgaggcgc cgggtgatcg cacggcccgt gggtagctcc    420
gtgcggctca agtgcgtggc cagcgggcac cctcggcccg acatcacgtg gatgaaggac    480
gaccaggcct tgacgcgccc agaggccgct gagcccagga agaagaagtg gacactgagc    540
ctgaagaacc tgcggccgga ggacagcggc aaatacacct gccgcgtgtc gaaccgcgcg    600
ggcgccatca cgccaccta caaggtggat gtgatccacc caaaccgca agggccacct    660
gtggcctcct cgtcctcggc cactagcctg ccgtggcccg tggtcatcgg catcccagcc    720
ggcgctgtct tcatcctggg caccctgctc ctgtggcttt gccaggccca gaagaagccg    780
tgcaccccg cgcctgcccc tcccctgcct gggcaccgcc cgccgggac ggcccgcgac    840
cgcagcggag acaaggacct tccctcgttg gccgccctca gcgctggccc tggtgtgggg    900
ctgtgtgagg agcatgggtc tccggcagcc cccagcact actgggccc aggcccagtt    960
gctggcccta agttgtaccc caaactctac acagacatcc acacacacac acacacacac   1020
tctcacacac actcacacgt ggagggcaag gtccaccagc acatccacta tcagtgctag   1080
```

```
<210> SEQ ID NO 29
<211> LENGTH: 359
<212> TYPE: PRT
<213> ORGANISM: Human

<400> SEQUENCE: 29
```

| | | | | | | | | | | | | | | |
|---|---|---|---|---|---|---|---|---|---|---|---|---|---|---|
|Met|Thr|Pro|Ser|Pro|Leu|Leu|Leu|Leu|Leu|Pro|Leu|Leu|Leu|
|1| | | |5| | | | |10| | | | |15|
|Gly|Ala|Phe|Pro|Pro|Ala|Ala|Ala|Arg|Gly|Pro|Pro|Lys|Met|Ala|
| | | |20| | | | |25| | | | |30| |
|Asp|Lys|Val|Val|Pro|Arg|Gln|Val|Ala|Arg|Leu|Gly|Arg|Thr|Val|Arg|
| | | |35| | | | |40| | | | |45| | |
|Leu|Gln|Cys|Pro|Val|Glu|Gly|Asp|Pro|Pro|Leu|Thr|Met|Trp|Thr|
| |50| | | | |55| | | | |60| | | |
|Lys|Asp|Gly|Arg|Thr|Ile|His|Ser|Gly|Trp|Ser|Arg|Phe|Arg|Val|Leu|
|65| | | | |70| | | | |75| | | | |80|
|Pro|Gln|Gly|Leu|Lys|Val|Lys|Gln|Val|Glu|Arg|Glu|Asp|Ala|Gly|Val|
| | | | |85| | | | |90| | | | |95| |
|Tyr|Val|Cys|Lys|Ala|Thr|Asn|Gly|Phe|Gly|Ser|Leu|Ser|Val|Asn|Tyr|
| | | |100| | | | |105| | | | |110| | |
|Thr|Leu|Val|Val|Leu|Ala|Arg|Pro|Arg|Phe|Thr|Gln|Pro|Ser|Lys|Met|
| | |115| | | | |120| | | | |125| | | |
|Arg|Arg|Arg|Val|Ile|Ala|Arg|Pro|Val|Gly|Ser|Ser|Val|Arg|Leu|Lys|
| |130| | | | |135| | | | |140| | | | |
|Cys|Val|Ala|Ser|Gly|His|Pro|Arg|Pro|Asp|Ile|Thr|Trp|Met|Lys|Asp|
|145| | | | |150| | | | |155| | | | |160|
|Asp|Gln|Ala|Leu|Thr|Arg|Pro|Glu|Ala|Ala|Glu|Pro|Arg|Lys|Lys|Lys|
| | | | |165| | | | |170| | | | |175| |
|Trp|Thr|Leu|Ser|Leu|Lys|Asn|Leu|Arg|Pro|Glu|Asp|Ser|Gly|Lys|Tyr|
| | | |180| | | | |185| | | | |190| | |
|Thr|Cys|Arg|Val|Ser|Asn|Arg|Ala|Gly|Ala|Ile|Asn|Ala|Thr|Tyr|Lys|
| | |195| | | | |200| | | | |205| | | |
|Val|Asp|Val|Ile|His|Pro|Lys|Pro|Gln|Gly|Pro|Pro|Val|Ala|Ser|Ser|
| |210| | | | |215| | | | |220| | | | |
|Ser|Ser|Ala|Thr|Ser|Leu|Pro|Trp|Pro|Val|Val|Ile|Gly|Ile|Pro|Ala|
|225| | | | |230| | | | |235| | | | |240|
|Gly|Ala|Val|Phe|Ile|Leu|Gly|Thr|Leu|Leu|Leu|Trp|Leu|Cys|Gln|Ala|
| | | | |245| | | | |250| | | | |255| |
|Gln|Lys|Lys|Pro|Cys|Thr|Pro|Ala|Pro|Ala|Pro|Pro|Leu|Pro|Gly|His|
| | | |260| | | | |265| | | | |270| | |
|Arg|Pro|Pro|Gly|Thr|Ala|Arg|Asp|Arg|Ser|Gly|Asp|Lys|Asp|Leu|Pro|
| |275| | | | |280| | | | |285| | | | |
|Ser|Leu|Ala|Ala|Leu|Ser|Ala|Gly|Pro|Gly|Val|Gly|Leu|Cys|Glu|Glu|
| |290| | | | |295| | | | |300| | | | |
|His|Gly|Ser|Pro|Ala|Ala|Pro|Gln|His|Leu|Leu|Gly|Pro|Gly|Pro|Val|
|305| | | | |310| | | | |315| | | | |320|
|Ala|Gly|Pro|Lys|Leu|Tyr|Pro|Lys|Leu|Tyr|Thr|Asp|Ile|His|Thr|His|
| | | | |325| | | | |330| | | | |335| |
|Thr|His|Thr|His|Ser|His|Thr|His|Ser|His|Val|Glu|Gly|Lys|Val|His|
| | | |340| | | | |345| | | | |350| | |
|Gln|His|Ile|His|Tyr|Gln|Cys|
| | |355| | | | |

```
<210> SEQ ID NO 30
<211> LENGTH: 1149
```

<212> TYPE: DNA
<213> ORGANISM: Human

<400> SEQUENCE: 30

```
atgacgccga gcccctgtt gctgctcctg ctgccgccgc tgctgctggg ggccttccca      60
ccggccgccg ccgcccgagg cccccaaag atggcggaca aggtggtccc acggcaggtg    120
gcccggctgg ccgcactgt gcggctgcag tgcccagtgg aggggaccc gccgccgctg     180
accatgtgga ccaaggatgg ccgcaccatc acagcggct ggagccgctt ccgcgtgctg    240
ccgcaggggc tgaaggtgaa gcaggtggag cgggaggatg ccggcgtgta cgtgtgcaag   300
gccaccaacg gcttcggcag ccttagcgtc aactacaccc tcgtcgtgct ggagcggacc   360
cgttccaagc ccgtgctcac aggcacgcac cccgtgaaca cgacggtgga cttcgggggg   420
accacgtcct tccagtgcaa ggtgcgcagc gacgtgaagc cggtgatcca gtggctgaag   480
cgcgtggagt acggcgccga gggccgccac aactccacca tcgatgtggg cggccagaag   540
tttgtggtgc tgcccacggg tgacgtgtgg tcgcggcccg acggctccta cctcaataag   600
ctgctcatca cccgtgcccg ccaggacgat gcgggcatgt acatctgcct ggcgccaac    660
accatgggct acagcttccg cagcgccttc ctcaccgtgc tgccagaccc aaaaccgcaa   720
gggccacctg tggcctcctc gtcctcggcc actagcctgc cgtggcccgt ggtcatcggc   780
atcccagccg gcgctgtctt catcctgggc accctgctcc tgtggctttg ccaggcccag   840
aagaagccgt gcacccccgc gcctgccct cccctgcctg gcaccgccc gccggggacg     900
gcccgcgacc gcagcggaga caaggacctt ccctcgttgg ccgccctcag cgctggcccct  960
ggtgtggggc tgtgtgagga gcatgggtct ccggcagccc cccagcactt actgggccca  1020
ggcccagttg ctggccctaa gttgtacccc aaactctaca cagacatcca cacacacaca  1080
cacacacact ctcacacaca ctcacacgtg gagggcaagg tccaccagca catccactat  1140
cagtgctag                                                          1149
```

<210> SEQ ID NO 31
<211> LENGTH: 382
<212> TYPE: PRT
<213> ORGANISM: Human

<400> SEQUENCE: 31

```
Met Thr Pro Ser Pro Leu Leu Leu Leu Leu Pro Leu Leu Leu
 1               5                  10                  15

Gly Ala Phe Pro Pro Ala Ala Ala Arg Gly Pro Pro Lys Met Ala
             20                  25                  30

Asp Lys Val Val Pro Arg Gln Val Ala Arg Leu Gly Arg Thr Val Arg
             35                  40                  45

Leu Gln Cys Pro Val Glu Gly Asp Pro Pro Leu Thr Met Trp Thr
 50                  55                  60

Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
                 85                  90                  95

Tyr Val Cys Lys Ala Thr Asn Gly Phe Gly Ser Leu Ser Val Asn Tyr
                100                 105                 110

Thr Leu Val Val Leu Glu Arg Thr Arg Ser Lys Pro Val Leu Thr Gly
             115                 120                 125

Thr His Pro Val Asn Thr Thr Val Asp Phe Gly Gly Thr Thr Ser Phe
         130                 135                 140
```

```
Gln Cys Lys Val Arg Ser Asp Val Lys Pro Val Ile Gln Trp Leu Lys
145                 150                 155                 160

Arg Val Glu Tyr Gly Ala Glu Gly Arg His Asn Ser Thr Ile Asp Val
                165                 170                 175

Gly Gly Gln Lys Phe Val Leu Pro Thr Gly Asp Val Trp Ser Arg
            180                 185                 190

Pro Asp Gly Ser Tyr Leu Asn Lys Leu Leu Ile Thr Arg Ala Arg Gln
            195                 200                 205

Asp Asp Ala Gly Met Tyr Ile Cys Leu Gly Ala Asn Thr Met Gly Tyr
210                 215                 220

Ser Phe Arg Ser Ala Phe Leu Thr Val Leu Pro Asp Pro Lys Pro Gln
225                 230                 235                 240

Gly Pro Pro Val Ala Ser Ser Ser Ala Thr Ser Leu Pro Trp Pro
                245                 250                 255

Val Val Ile Gly Ile Pro Ala Gly Ala Val Phe Ile Leu Gly Thr Leu
                260                 265                 270

Leu Leu Trp Leu Cys Gln Ala Gln Lys Lys Pro Cys Thr Pro Ala Pro
            275                 280                 285

Ala Pro Pro Leu Pro Gly His Arg Pro Pro Gly Thr Ala Arg Asp Arg
290                 295                 300

Ser Gly Asp Lys Asp Leu Pro Ser Leu Ala Ala Leu Ser Ala Gly Pro
305                 310                 315                 320

Gly Val Gly Leu Cys Glu Glu His Gly Ser Pro Ala Ala Pro Gln His
                325                 330                 335

Leu Leu Gly Pro Gly Pro Val Ala Gly Pro Lys Leu Tyr Pro Lys Leu
            340                 345                 350

Tyr Thr Asp Ile His Thr His Thr His Ser His Thr His Ser
            355                 360                 365

His Val Glu Gly Lys Val His Gln His Ile His Tyr Gln Cys
370                 375                 380

<210> SEQ ID NO 32
<211> LENGTH: 888
<212> TYPE: DNA
<213> ORGANISM: Human

<400> SEQUENCE: 32
atgacgccga gccccctgtt gctgctcctg ctgccgccgc tgctgctggg ggccttccca      60
ccggccgccg ccgcccgaga tgacattagc cagggaagg agagcctggg gcccgacagc     120
tcctctgggg gtcaagagga ccccgccagc cagcagtggg cacgaccgcg cttcacacag     180
ccctccaaga tgaggcgccg ggtgatcgca cggcccgtgg gtagctccgt gcggctcaag     240
tgcgtggcca gcgggcaccc tcggcccgac atcacgtgga tgaaggacga ccaggccttg     300
acgcgcccag aggccgctga gcccaggaag aagaagtgga cactgagcct gaagaacctg     360
cggccggagg acagcggcaa atacacctgc gcgtgtcga accgcgcggg cgccatcaac     420
gccacctaca aggtggatgt gatccaccca aaaccgcaag ggccacctgt ggcctcctcg     480
tcctcggcca ctagcctgcc gtggcccgtg gtcatcggca tcccagccgg cgctgtcttc     540
atcctgggca ccctgctcct gtggctttgc caggcccaga gaagcgtg cacccccgcg      600 cctgccctc ccctgcctgg gcaccgcccg ccggggacgg cccgcgaccg cagcggagac     660 aaggacctc cctcgttggc cgccctcagc gctggccctg tgtgggggct gtgtgaggag     720
```

```
catgggtctc cggcagcccc ccagcactta ctgggcccag gcccagttgc tggccctaag        780
ttgtacccca aactctacac agacatccac acacacacac acacacactc tcacacacac        840
tcacacgtgg agggcaaggt ccaccagcac atccactatc agtgctag                     888
```

<210> SEQ ID NO 33
<211> LENGTH: 295
<212> TYPE: PRT
<213> ORGANISM: Human

<400> SEQUENCE: 33

```
Met Thr Pro Ser Pro Leu Leu Leu Leu Pro Pro Leu Leu Leu
 1               5                  10                  15

Gly Ala Phe Pro Pro Ala Ala Ala Arg Asp Asp Ile Ser Pro Gly
                20                  25                  30

Lys Glu Ser Leu Gly Pro Asp Ser Ser Gly Gly Gln Glu Asp Pro
                35                  40                  45

Ala Ser Gln Gln Trp Ala Arg Pro Arg Phe Thr Gln Pro Ser Lys Met
 50                  55                  60

Arg Arg Arg Val Ile Ala Arg Pro Val Gly Ser Ser Val Arg Leu Lys
 65                  70                  75                  80

Cys Val Ala Ser Gly His Pro Arg Pro Asp Ile Thr Trp Met Lys Asp
                    85                  90                  95

Asp Gln Ala Leu Thr Arg Pro Glu Ala Ala Glu Pro Arg Lys Lys Lys
                    100                 105                 110

Trp Thr Leu Ser Leu Lys Asn Leu Arg Pro Glu Asp Ser Gly Lys Tyr
                    115                 120                 125

Thr Cys Arg Val Ser Asn Arg Ala Gly Ala Ile Asn Ala Thr Tyr Lys
                    130                 135                 140

Val Asp Val Ile His Pro Lys Pro Gln Gly Pro Val Ala Ser Ser
 145                 150                 155                 160

Ser Ser Ala Thr Ser Leu Pro Trp Pro Val Ile Gly Ile Pro Ala
                    165                 170                 175

Gly Ala Val Phe Ile Leu Gly Thr Leu Leu Leu Trp Leu Cys Gln Ala
                    180                 185                 190

Gln Lys Lys Pro Cys Thr Pro Ala Pro Ala Pro Pro Leu Pro Gly His
                    195                 200                 205

Arg Pro Pro Gly Thr Ala Arg Asp Arg Ser Gly Asp Lys Asp Leu Pro
 210                 215                 220

Ser Leu Ala Ala Leu Ser Ala Gly Pro Gly Val Gly Leu Cys Glu Glu
 225                 230                 235                 240

His Gly Ser Pro Ala Ala Pro Gln His Leu Leu Gly Pro Gly Pro Val
                    245                 250                 255

Ala Gly Pro Lys Leu Tyr Pro Lys Leu Tyr Thr Asp Ile His Thr His
                    260                 265                 270

Thr His Thr His Ser His Thr His Ser His Val Glu Gly Lys Val His
                    275                 280                 285

Gln His Ile His Tyr Gln Cys
                    290                 295
```

<210> SEQ ID NO 34
<211> LENGTH: 957
<212> TYPE: DNA
<213> ORGANISM: Human

<400> SEQUENCE: 34

```
atgacgccga gcccctgtt gctgctcctg ctgccgccgc tgctgctggg ggccttccca      60
ccggccgccg ccgcccgaga tgacattagc ccagggaagg agagcctggg gcccgacagc     120
tcctctgggg gtcaagagga ccccgccagc cagcagtggg agcggacccg ttccaagccc     180
gtgctcacag gcacgcaccc cgtgaacacg acggtggact cgggggggac cacgtccttc     240
cagtgcaagg tgcgcagcga cgtgaagccg gtgatccagt ggctgaagcg cgtggagtac     300
ggcgccgagg gccgccacaa ctccaccatc gatgtgggcg ccagaagtt tgtggtgctg      360 cccacgggtg acgtgtggtc gcggcccgac ggctcctacc tcaataagct gctcatcacc     420
cgtgcccgcc aggacgatgc gggcatgtac atctgccttg cgccaacac catgggctac      480 agcttccgca gcgccttcct caccgtgctg ccagacccaa accgcaagg gccacctgtg      540 gcctcctcgt cctcggccac tagcctgccg tggcccgtgg tcatcggcat cccagccggc     600
gctgtcttca tcctgggcac cctgctcctg tggctttgcc aggcccagaa gaagccgtgc     660
acccccgcgc ctgcccctcc cctgcctggg caccgcccgc cggggacggc ccgcgaccgc     720
agcggagaca aggaccttcc ctcgttggcc gccctcagcg ctggccctgg tgtggggctg     780
tgtgaggagc atgggtctcc ggcagccccc cagcacttac tgggcccagg cccagttgct     840
ggccctaagt tgtaccccaa actctacaca gacatccaca cacacacaca cacacactct     900
cacacacact cacacgtgga gggcaaggtc caccagcaca tccactatca gtgctag        957
```

<210> SEQ ID NO 35
<211> LENGTH: 318
<212> TYPE: PRT
<213> ORGANISM: Human

<400> SEQUENCE: 35

```
Met Thr Pro Ser Pro Leu Leu Leu Leu Leu Pro Pro Leu Leu Leu
 1               5                  10                  15

Gly Ala Phe Pro Pro Ala Ala Ala Arg Asp Asp Ile Ser Pro Gly
                20                  25                  30

Lys Glu Ser Leu Gly Pro Asp Ser Ser Gly Gly Gln Glu Asp Pro
             35                  40                  45

Ala Ser Gln Gln Trp Glu Arg Thr Arg Ser Lys Pro Val Leu Thr Gly
 50                  55                  60

Thr His Pro Val Asn Thr Thr Val Asp Phe Gly Gly Thr Thr Ser Phe
 65                  70                  75                  80

Gln Cys Lys Val Arg Ser Asp Val Lys Pro Val Ile Gln Trp Leu Lys
                 85                  90                  95

Arg Val Glu Tyr Gly Ala Glu Gly Arg His Asn Ser Thr Ile Asp Val
                100                 105                 110

Gly Gly Gln Lys Phe Val Val Leu Pro Thr Gly Asp Val Trp Ser Arg
            115                 120                 125

Pro Asp Gly Ser Tyr Leu Asn Lys Leu Leu Ile Thr Arg Ala Arg Gln
        130                 135                 140

Asp Asp Ala Gly Met Tyr Ile Cys Leu Gly Ala Asn Thr Met Gly Tyr
145                 150                 155                 160

Ser Phe Arg Ser Ala Phe Leu Thr Val Leu Pro Asp Pro Lys Pro Gln
                165                 170                 175

Gly Pro Pro Val Ala Ser Ser Ser Ala Thr Ser Leu Pro Trp Pro
            180                 185                 190

Val Val Ile Gly Ile Pro Ala Gly Ala Val Phe Ile Leu Gly Thr Leu
        195                 200                 205
```

```
Leu Leu Trp Leu Cys Gln Ala Gln Lys Lys Pro Cys Thr Pro Ala Pro
        210                 215                 220
Ala Pro Pro Leu Pro Gly His Arg Pro Gly Thr Ala Arg Asp Arg
225                 230                 235                 240
Ser Gly Asp Lys Asp Leu Pro Ser Leu Ala Ala Leu Ser Ala Gly Pro
                245                 250                 255
Gly Val Gly Leu Cys Glu Glu His Gly Ser Pro Ala Ala Pro Gln His
                260                 265                 270
Leu Leu Gly Pro Gly Pro Val Ala Gly Pro Lys Leu Tyr Pro Lys Leu
            275                 280                 285
Tyr Thr Asp Ile His Thr His Thr His Ser His Thr His Ser
    290                 295                 300
His Val Glu Gly Lys Val His Gln His Ile His Tyr Gln Cys
305                 310                 315
```

<210> SEQ ID NO 36
<211> LENGTH: 1161
<212> TYPE: DNA
<213> ORGANISM: Human

<400> SEQUENCE: 36

| | | | | | |
|---|---|---|---|---|---|
| atgacgccga | gccccctgtt | gctgctcctg | ctgccgccgc | tgctgctggg | ggccttccca | 60 |
| ccggccgccg | ccgcccgagc | acgaccgcgc | ttcacacagc | cctccaagat | gaggcgccgg | 120 |
| gtgatcgcac | ggcccgtggg | tagctccgtg | cggctcaagt | gcgtggccag | cgggcaccct | 180 |
| cggcccgaca | tcacgtggat | gaaggacgac | caggccttga | cgcgcccaga | ggccgctgag | 240 |
| cccaggaaga | agaagtggac | actgagcctg | aagaacctgc | ggccggagga | cagcggcaaa | 300 |
| tacacctgcc | gcgtgtcgaa | ccgcgcgggc | gccatcaacg | ccacctacaa | ggtggatgtg | 360 |
| atccagcgga | cccgttccaa | gcccgtgctc | acaggcacgc | accccgtgaa | cacgacggtg | 420 |
| gacttcgggg | ggaccacgtc | cttccagtgc | aaggtgcgca | cgacgtgaa | gccggtgatc | 480 |
| cagtggctga | gcgcgtgga | gtacggcgcc | gagggccgcc | acaactccac | catcgatgtg | 540 |
| ggcggccaga | agtttgtggt | gctgcccacg | ggtgacgtgt | ggtcgcggcc | cgacggctcc | 600 |
| tacctcaata | agctgctcat | cacccgtgcc | cgccaggacg | atgcgggcat | gtacatctgc | 660 |
| cttggcgcca | acaccatggg | ctacagcttc | cgcagcgcct | tcctcaccgt | gctgccagac | 720 |
| ccaaaaccgc | aagggccacc | tgtggcctcc | tcgtcctcgg | ccactagcct | gccgtggccc | 780 |
| gtggtcatcg | gcatcccagc | cggcgctgtc | ttcatcctgg | gcaccctgct | cctgtggctt | 840 |
| tgccaggccc | agaagaagcc | gtgcacccccc | gcgcctgccc | ctccctgcc | tgggcaccgc | 900 |
| ccgccgggga | cggcccgcga | ccgcagcgga | gacaaggacc | ttccctcgtt | ggccgccctc | 960 |
| agcgctggcc | ctggtgtggg | gctgtgtgag | gagcatgggt | ctccggcagc | ccccagcac | 1020 |
| ttactgggcc | caggcccagt | tgctggccct | aagttgtacc | ccaaactcta | cacagacatc | 1080 |
| cacacacaca | cacacacaca | ctctcacaca | cactcacacg | tggagggcaa | ggtccaccag | 1140 |
| cacatccact | atcagtgcta | g | | | | 1161 |

<210> SEQ ID NO 37
<211> LENGTH: 386
<212> TYPE: PRT
<213> ORGANISM: Human

<400> SEQUENCE: 37

```
Met Thr Pro Ser Pro Leu Leu Leu Leu Leu Pro Pro Leu Leu Leu
1               5                   10                  15
```

-continued

Gly Ala Phe Pro Pro Ala Ala Ala Arg Ala Arg Pro Arg Phe Thr
            20                  25                  30

Gln Pro Ser Lys Met Arg Arg Val Ile Ala Arg Pro Val Gly Ser
        35                  40                  45

Ser Val Arg Leu Lys Cys Val Ala Ser Gly His Pro Arg Pro Asp Ile
    50                  55                  60

Thr Trp Met Lys Asp Asp Gln Ala Leu Thr Arg Pro Glu Ala Ala Glu
65                  70                  75                  80

Pro Arg Lys Lys Lys Trp Thr Leu Ser Leu Lys Asn Leu Arg Pro Glu
                85                  90                  95

Asp Ser Gly Lys Tyr Thr Cys Arg Val Ser Asn Arg Ala Gly Ala Ile
            100                 105                 110

Asn Ala Thr Tyr Lys Val Asp Val Ile Gln Arg Thr Arg Ser Lys Pro
        115                 120                 125

Val Leu Thr Gly Thr His Pro Val Asn Thr Thr Val Asp Phe Gly Gly
    130                 135                 140

Thr Thr Ser Phe Gln Cys Lys Val Arg Ser Asp Val Lys Pro Val Ile
145                 150                 155                 160

Gln Trp Leu Lys Arg Val Glu Tyr Gly Ala Glu Gly Arg His Asn Ser
                165                 170                 175

Thr Ile Asp Val Gly Gly Gln Lys Phe Val Val Leu Pro Thr Gly Asp
            180                 185                 190

Val Trp Ser Arg Pro Asp Gly Ser Tyr Leu Asn Lys Leu Leu Ile Thr
        195                 200                 205

Arg Ala Arg Gln Asp Asp Ala Gly Met Tyr Ile Cys Leu Gly Ala Asn
    210                 215                 220

Thr Met Gly Tyr Ser Phe Arg Ser Ala Phe Leu Thr Val Leu Pro Asp
225                 230                 235                 240

Pro Lys Pro Gln Gly Pro Pro Val Ala Ser Ser Ser Ala Thr Ser
                245                 250                 255

Leu Pro Trp Pro Val Val Ile Gly Ile Pro Ala Gly Ala Val Phe Ile
            260                 265                 270

Leu Gly Thr Leu Leu Leu Trp Leu Cys Gln Ala Gln Lys Lys Pro Cys
        275                 280                 285

Thr Pro Ala Pro Ala Pro Pro Leu Pro Gly His Arg Pro Pro Gly Thr
    290                 295                 300

Ala Arg Asp Arg Ser Gly Asp Lys Asp Leu Pro Ser Leu Ala Ala Leu
305                 310                 315                 320

Ser Ala Gly Pro Gly Val Gly Leu Cys Glu Glu His Gly Ser Pro Ala
                325                 330                 335

Ala Pro Gln His Leu Leu Gly Pro Gly Pro Val Ala Gly Pro Lys Leu
            340                 345                 350

Tyr Pro Lys Leu Tyr Thr Asp Ile His Thr His Thr His Thr His Ser
        355                 360                 365

His Thr His Ser His Val Glu Gly Lys Val His Gln His Ile His Tyr
    370                 375                 380

Gln Cys
385

<210> SEQ ID NO 38
<211> LENGTH: 795
<212> TYPE: DNA
<213> ORGANISM: Human

-continued

```
<400> SEQUENCE: 38
atgacgccga gcccctgtt gctgctcctg ctgccgccgc tgctgctggg ggccttccca      60
ccggccgccg ccgcccgagg cccccaaag atggcggaca aggtggtccc acggcaggtg    120
gcccggctgg gccgcactgt gcggctgcag tgcccagtgg aggggaccc gccgccgctg    180 accatgtgga ccaaggatgg ccgcaccatc cacagcggct ggagccgctt ccgcgtgctg    240 ccgcagggc tgaaggtgaa gcaggtggag cgggaggatg ccggcgtgta cgtgtgcaag    300
gccaccaacg gcttcggcag ccttagcgtc aactacaccc tcgtcgtgct ggacccaaaa    360
ccgcaagggc cacctgtggc ctcctcgtcc tcggccacta gcctgccgtg gcccgtggtc    420
atcggcatcc cagccggcgc tgtcttcatc ctgggcaccc tgctcctgtg gctttgccag    480
gcccagaaga agccgtgcac ccccgcgcct gcccctcccc tgcctgggca ccgcccgccg    540
gggacggccc gcgaccgcag cggagacaag gaccttccct cgttggccgc cctcagcgct    600
ggccctggtg tggggctgtg tgaggagcat gggtctccgg cagccccca gcacttactg    660 ggcccaggcc cagttgctgg ccctaagttg taccccaaac tctacacaga catccacaca    720
cacacacaca cacactctca cacacactca cacgtggagg gcaaggtcca ccagcacatc    780
cactatcagt gctag                                                     795

<210> SEQ ID NO 39
<211> LENGTH: 264
<212> TYPE: PRT
<213> ORGANISM: Human

<400> SEQUENCE: 39

Met Thr Pro Ser Pro Leu Leu Leu Leu Leu Pro Pro Leu Leu Leu
  1               5                  10                  15

Gly Ala Phe Pro Pro Ala Ala Ala Arg Gly Pro Pro Lys Met Ala
                 20                  25                  30

Asp Lys Val Val Pro Arg Gln Val Ala Arg Leu Gly Arg Thr Val Arg
             35                  40                  45

Leu Gln Cys Pro Val Glu Gly Asp Pro Pro Leu Thr Met Trp Thr
 50                      55                  60

Lys Asp Gly Arg Thr Ile His Ser Gly Trp Ser Arg Phe Arg Val Leu
 65                  70                  75                  80

Pro Gln Gly Leu Lys Val Lys Val Glu Arg Glu Asp Ala Gly Val
                 85                  90                  95

Tyr Val Cys Lys Ala Thr Asn Gly Phe Gly Ser Leu Ser Val Asn Tyr
                100                 105                 110

Thr Leu Val Val Leu Asp Pro Lys Pro Gln Gly Pro Val Ala Ser
             115                 120                 125

Ser Ser Ser Ala Thr Ser Leu Pro Trp Pro Val Val Ile Gly Ile Pro
130                 135                 140

Ala Gly Ala Val Phe Ile Leu Gly Thr Leu Leu Leu Trp Leu Cys Gln
145                 150                 155                 160

Ala Gln Lys Lys Pro Cys Thr Pro Ala Pro Ala Pro Leu Pro Gly
                165                 170                 175

His Arg Pro Pro Gly Thr Ala Arg Asp Arg Ser Gly Asp Lys Asp Leu
                180                 185                 190

Pro Ser Leu Ala Ala Leu Ser Ala Gly Pro Gly Val Gly Leu Cys Glu
            195                 200                 205

Glu His Gly Ser Pro Ala Ala Pro Gln His Leu Leu Gly Pro Gly Pro
            210                 215                 220
```

| Val | Ala | Gly | Pro | Lys | Leu | Tyr | Pro | Lys | Leu | Tyr | Thr | Asp | Ile | His | Thr |
| 225 | | | | 230 | | | | | 235 | | | | | 240 | |

| His | Thr | His | Thr | His | Ser | His | Thr | His | Ser | His | Val | Glu | Gly | Lys | Val |
| | | | | 245 | | | | | 250 | | | | | 255 | |

His Gln His Ile His Tyr Gln Cys
          260

<210> SEQ ID NO 40
<211> LENGTH: 603
<212> TYPE: DNA
<213> ORGANISM: Human

<400> SEQUENCE: 40

```
atgacgccga gcccctgtt gctgctcctg ctgccgccgc tgctgctggg ggccttccca      60
ccggccgccg ccgcccgaga tgacattagc cagggaagg agagcctggg gcccgacagc     120
tcctctgggg gtcaagagga ccccgccagc cagcagtggg acccaaaacc gcaagggcca    180
cctgtggcct cctcgtcctc ggccactagc ctgccgtggc ccgtggtcat cggcatccca    240
gccggcgctg tcttcatcct gggcacccct ctcctgtggc tttgccaggc cagaagaag    300
ccgtgcaccc ccgcgcctgc ccctcccctg cctgggcacc gcccgccggg gacggcccgc    360
gaccgcagcg gagacaagga ccttccctcg ttggccgccc tcagcgctgg ccctggtgtg    420
gggctgtgtg aggagcatgg gtctccggca gccccccagc acttactggg cccaggccca    480
gttgctggcc ctaagttgta ccccaaactc tacacagaca tccacacaca cacacacaca    540
cactctcaca cacactcaca cgtggagggc aaggtccacc agcacatcca ctatcagtgc    600
tag                                                                   603
```

<210> SEQ ID NO 41
<211> LENGTH: 200
<212> TYPE: PRT
<213> ORGANISM: Human

<400> SEQUENCE: 41

| Met | Thr | Pro | Ser | Pro | Leu | Leu | Leu | Leu | Leu | Pro | Pro | Leu | Leu | Leu |
| 1 | | | | 5 | | | | | 10 | | | | | 15 |

| Gly | Ala | Phe | Pro | Pro | Ala | Ala | Ala | Arg | Asp | Asp | Ile | Ser | Pro | Gly |
| | | | 20 | | | | | 25 | | | | | 30 | |

| Lys | Glu | Ser | Leu | Gly | Pro | Asp | Ser | Ser | Gly | Gly | Gln | Glu | Asp | Pro |
| | | | 35 | | | | | 40 | | | | | 45 | |

| Ala | Ser | Gln | Gln | Trp | Asp | Pro | Lys | Pro | Gln | Gly | Pro | Pro | Val | Ala | Ser |
| 50 | | | | | 55 | | | | | 60 | | | | | |

| Ser | Ser | Ser | Ala | Thr | Ser | Leu | Pro | Trp | Pro | Val | Val | Ile | Gly | Ile | Pro |
| 65 | | | | | 70 | | | | | 75 | | | | | 80 |

| Ala | Gly | Ala | Val | Phe | Ile | Leu | Gly | Thr | Leu | Leu | Leu | Trp | Leu | Cys | Gln |
| | | | | 85 | | | | | 90 | | | | | 95 | |

| Ala | Gln | Lys | Lys | Pro | Cys | Thr | Pro | Ala | Pro | Ala | Pro | Pro | Leu | Pro | Gly |
| | | | 100 | | | | | 105 | | | | | 110 | | |

| His | Arg | Pro | Pro | Gly | Thr | Ala | Arg | Asp | Arg | Ser | Gly | Asp | Lys | Asp | Leu |
| | | | 115 | | | | | 120 | | | | | 125 | | |

| Pro | Ser | Leu | Ala | Ala | Leu | Ser | Ala | Gly | Pro | Gly | Val | Gly | Leu | Cys | Glu |
| | | | 130 | | | | | 135 | | | | | 140 | | |

| Glu | His | Gly | Ser | Pro | Ala | Ala | Pro | Gln | His | Leu | Leu | Gly | Pro | Gly | Pro |
| 145 | | | | | 150 | | | | | 155 | | | | | 160 |

Val Ala Gly Pro Lys Leu Tyr Pro Lys Leu Tyr Thr Asp Ile His Thr

```
                  165                 170                 175
   His Thr His Thr His Ser His Thr His Ser His Val Glu Gly Lys Val
                180                 185                 190

His Gln His Ile His Tyr Gln Cys
             195                 200

<210> SEQ ID NO 42
<211> LENGTH: 807
<212> TYPE: DNA
<213> ORGANISM: Human

<400> SEQUENCE: 42
atgacgccga gcccctgtt gctgctcctg ctgccgccgc tgctgctggg ggccttccca      60
ccggccgccg ccgcccgagc acgaccgcgc ttcacacagc cctccaagat gaggcgccgg    120
gtgatcgcac ggcccgtggg tagctccgtg cggctcaagt gcgtggccag cgggcaccct    180
cggcccgaca tcacgtggat gaaggacgac caggccttga cgcgcccaga ggccgctgag    240
cccaggaaga agaagtggac actgagcctg aagaacctgc ggccggagga cagcggcaaa    300
tacacctgcc gcgtgtcgaa ccgcgcgggc gccatcaacg ccacctacaa ggtggatgtg    360
atccacccaa aaccgcaagg gccacctgtg gcctcctcgt cctcggccac tagcctgccg    420
tggcccgtgg tcatcggcat cccagccggc gctgtcttca tcctgggcac cctgctcctg    480
tggctttgcc aggcccagaa gaagccgtgc accccgcgc ctgcccctcc cctgcctggg    540
caccgcccgc cggggacggc ccgcgaccgc agcggagaca aggaccttcc ctcgttggcc    600
gccctcagcg ctggccctgg tgtggggctg tgtgaggagc atgggtctcc ggcagccccc    660
cagcacttac tgggcccagg cccagttgct ggcctaagt tgtacccccaa actctacaca    720 gacatccaca cacacacaca cacacactct cacacacact cacacgtgga gggcaaggtc    780
caccagcaca tccactatca gtgctag                                        807

<210> SEQ ID NO 43
<211> LENGTH: 268
<212> TYPE: PRT
<213> ORGANISM: Human

<400> SEQUENCE: 43

Met Thr Pro Ser Pro Leu Leu Leu Leu Leu Pro Pro Leu Leu Leu
 1               5                  10                  15

Gly Ala Phe Pro Pro Ala Ala Ala Arg Ala Arg Pro Arg Phe Thr
              20                  25                  30

Gln Pro Ser Lys Met Arg Arg Val Ile Ala Arg Pro Val Gly Ser
            35                  40                  45

Ser Val Arg Leu Lys Cys Val Ala Ser Gly His Pro Arg Pro Asp Ile
     50                  55                  60

Thr Trp Met Lys Asp Asp Gln Ala Leu Thr Arg Pro Glu Ala Ala Glu
 65                  70                  75                  80

Pro Arg Lys Lys Lys Trp Thr Leu Ser Leu Lys Asn Leu Arg Pro Glu
                 85                  90                  95

Asp Ser Gly Lys Tyr Thr Cys Arg Val Ser Asn Arg Ala Gly Ala Ile
               100                 105                 110

Asn Ala Thr Tyr Lys Val Asp Val Ile His Pro Lys Pro Gln Gly Pro
             115                 120                 125

Pro Val Ala Ser Ser Ser Ala Thr Ser Leu Pro Trp Pro Val Val
           130                 135                 140
```

Ile Gly Ile Pro Ala Gly Ala Val Phe Ile Leu Gly Thr Leu Leu Leu
145                 150                 155                 160

Trp Leu Cys Gln Ala Gln Lys Lys Pro Cys Thr Pro Ala Pro Ala Pro
                165                 170                 175

Pro Leu Pro Gly His Arg Pro Pro Gly Thr Ala Arg Asp Arg Ser Gly
            180                 185                 190

Asp Lys Asp Leu Pro Ser Leu Ala Ala Leu Ser Ala Gly Pro Gly Val
        195                 200                 205

Gly Leu Cys Glu Glu His Gly Ser Pro Ala Ala Pro Gln His Leu Leu
    210                 215                 220

Gly Pro Gly Pro Val Ala Gly Pro Lys Leu Tyr Pro Lys Leu Tyr Thr
225                 230                 235                 240

Asp Ile His Thr His Thr His Thr His Ser His Thr His Ser His Val
                245                 250                 255

Glu Gly Lys Val His Gln His Ile His Tyr Gln Cys
            260                 265

<210> SEQ ID NO 44
<211> LENGTH: 876
<212> TYPE: DNA
<213> ORGANISM: Human

<400> SEQUENCE: 44
atgacgccga gcccctgtt gctgctcctg ctgccgccgc tgctgctggg ggccttccca      60
ccggccgccg ccgcccgaga gcggacccgt tccaagcccg tgctcacagg cacgcacccc    120
gtgaacacga cggtggactt cggggggacc acgtccttcc agtgcaaggt gcgcagcgac    180
gtgaagccgg tgatccagtg gctgaagcgc gtggagtacg cgccgagggg ccgccacaac    240
tccaccatcg atgtgggcgg ccagaagttt gtggtgctgc ccacgggtga cgtgtggtcg    300
cggcccgacg gctcctacct caataagctg ctcatcaccc gtgcccgcca ggacgatgcg    360
ggcatgtaca tctgccttgg cgccaacacc atgggctaca gcttccgcag cgccttcctc    420
accgtgctgc cagacccaaa accgcaaggg ccacctgtgg cctcctcgtc tcggccact     480
agcctgccgt ggcccgtggt catcggcatc ccagccggcg ctgtcttcat cctgggcacc    540
ctgctcctgt ggctttgcca ggcccagaag aagccgtgca cccccgcgcc tgcccctccc    600
ctgcctgggc accgccgcc ggggacggcc cgcgaccgca gcggagacaa ggaccttccc    660
tcgttggccg ccctcagcgc tggccctggt gtgggctgt gtgaggagca tgggtctccg    720
gcagccccc agcacttact gggcccaggc ccagttgctg gccctaagtt gtaccccaaa    780
ctctacacag acatccacac acacacacac acactctc acacacactc acacgtggag     840
ggcaaggtcc accagcacat ccactatcag tgctag                              876

<210> SEQ ID NO 45
<211> LENGTH: 291
<212> TYPE: PRT
<213> ORGANISM: Human

<400> SEQUENCE: 45

Met Thr Pro Ser Pro Leu Leu Leu Leu Leu Pro Pro Leu Leu Leu
1               5                   10                  15

Gly Ala Phe Pro Pro Ala Ala Ala Ala Arg Glu Arg Thr Arg Ser Lys
                20                  25                  30

Pro Val Leu Thr Gly Thr His Pro Val Asn Thr Thr Val Asp Phe Gly
            35                  40                  45

```
Gly Thr Thr Ser Phe Gln Cys Lys Val Arg Ser Asp Val Lys Pro Val
 50                  55                  60
Ile Gln Trp Leu Lys Arg Val Glu Tyr Gly Ala Glu Gly Arg His Asn
 65                  70                  75                  80
Ser Thr Ile Asp Val Gly Gly Gln Lys Phe Val Val Leu Pro Thr Gly
                 85                  90                  95
Asp Val Trp Ser Arg Pro Asp Gly Ser Tyr Leu Asn Lys Leu Leu Ile
                100                 105                 110
Thr Arg Ala Arg Gln Asp Asp Ala Gly Met Tyr Ile Cys Leu Gly Ala
                115                 120                 125
Asn Thr Met Gly Tyr Ser Phe Arg Ser Ala Phe Leu Thr Val Leu Pro
130                 135                 140
Asp Pro Lys Pro Gln Gly Pro Pro Val Ala Ser Ser Ser Ala Thr
145                 150                 155                 160
Ser Leu Pro Trp Pro Val Val Ile Gly Ile Pro Ala Gly Ala Val Phe
                165                 170                 175
Ile Leu Gly Thr Leu Leu Leu Trp Leu Cys Gln Ala Gln Lys Lys Pro
                180                 185                 190
Cys Thr Pro Ala Pro Ala Pro Pro Leu Pro Gly His Arg Pro Pro Gly
                195                 200                 205
Thr Ala Arg Asp Arg Ser Gly Asp Lys Asp Leu Pro Ser Leu Ala Ala
210                 215                 220
Leu Ser Ala Gly Pro Gly Val Gly Leu Cys Glu Glu His Gly Ser Pro
225                 230                 235                 240
Ala Ala Pro Gln His Leu Leu Gly Pro Gly Pro Val Ala Gly Pro Lys
                245                 250                 255
Leu Tyr Pro Lys Leu Tyr Thr Asp Ile His Thr His Thr His Thr His
                260                 265                 270
Ser His Thr His Ser His Val Glu Gly Lys Val His Gln His Ile His
                275                 280                 285
Tyr Gln Cys
290

<210> SEQ ID NO 46
<211> LENGTH: 522
<212> TYPE: DNA
<213> ORGANISM: Human

<400> SEQUENCE: 46
atgacgccga gccccctgtt gctgctcctg ctgccgccgc tgctgctggg ggccttccca      60
ccggccgccg ccgcccgaga cccaaaaccg caagggccac ctgtggcctc ctcgtcctcg     120
gccactagcc tgccgtggcc cgtggtcatc ggcatcccag ccggcgctgt cttcatcctg     180
ggcaccctgc tcctgtggct ttgccaggcc cagaagaagc cgtgcacccc cgcgcctgcc     240
cctcccctgc ctgggcaccg cccgccgggg acggccgcg accgcagcgg agacaaggac      300
cttccctcgt tggccgccct cagcgctggc cctggtgtgg gctgtgtga ggagcatggg      360 tctccggcag ccccccagca cttactgggc ccaggcccca ttgctggccc taagttgtac     420
cccaaactct acacagacat ccacacacac acacacacac actctcacac acactcacac     480
gtggagggca aggtccacca gcacatccac tatcagtgct ag                        522

<210> SEQ ID NO 47
<211> LENGTH: 173
<212> TYPE: PRT
<213> ORGANISM: Human
```

<400> SEQUENCE: 47

| | | | | | | | | | | | | | | |
|---|---|---|---|---|---|---|---|---|---|---|---|---|---|---|
|Met|Thr|Pro|Ser|Pro|Leu|Leu|Leu|Leu|Leu|Pro|Leu|Leu|Leu| |
|1| | | |5| | | | |10| | | | |15|

Gly Ala Phe Pro Pro Ala Ala Ala Arg Asp Pro Lys Pro Gln Gly
     20     25     30

Pro Pro Val Ala Ser Ser Ser Ala Thr Ser Leu Pro Trp Pro Val
    35     40     45

Val Ile Gly Ile Pro Ala Gly Ala Val Phe Ile Leu Gly Thr Leu Leu
   50     55     60

Leu Trp Leu Cys Gln Ala Gln Lys Lys Pro Cys Thr Pro Ala Pro Ala
65     70     75     80

Pro Pro Leu Pro Gly His Arg Pro Pro Gly Thr Ala Arg Asp Arg Ser
    85     90     95

Gly Asp Lys Asp Leu Pro Ser Leu Ala Ala Leu Ser Ala Gly Pro Gly
    100     105     110

Val Gly Leu Cys Glu Glu His Gly Ser Pro Ala Ala Pro Gln His Leu
   115     120     125

Leu Gly Pro Gly Pro Val Ala Gly Pro Lys Leu Tyr Pro Lys Leu Tyr
   130     135     140

Thr Asp Ile His Thr His Thr His Thr His Ser His Thr His Ser His
145     150     155     160

Val Glu Gly Lys Val His Gln His Ile His Tyr Gln Cys
    165     170

<210> SEQ ID NO 48
<211> LENGTH: 1072
<212> TYPE: DNA
<213> ORGANISM: Human

<400> SEQUENCE: 48

```
atgacgccga gccccctgtt gctgctcctg ctgccgccgc tgctgctggg ggccttccca      60
ccggccgccg ccgcccgagg cccccccaaag atggcggaca aggtggtccc acggcaggtg     120
gcccggctgg gccgcactgt gcggctgcag tgcccagtgg aggggaccc gccgccgctg       180
accatgtgga ccaaggatgg ccgcaccatc acacagcggct ggagccgctt cgcgtgctg      240
ccgcagggc tgaaggtgaa gcaggtggag cgggaggatg ccggcgtgta cgtgtgcaag       300
gccaccaacg gcttcggcag ccttagcgtc aactacaccc tcgtcgtgct ggatgacatt      360
agcccaggga aggagagcct ggggcccgac agctcctctg ggggtcaaga ggaccccgcc      420
agccagcagt gggcacgacc gcgcttcaca cagccctcca agatgaggcg ccgggtgatc      480
gcacggcccg tgggtagctc cgtgcggctc aagtgcgtgg ccagcgggca ccctcggccc      540
gacatcacgt ggatgaagga cgaccaggcc ttgacgcgcc agaggccgc tgagcccagg      600
aagaagaagt ggacactgag cctgaagaac ctgcggccgg aggacagcgg caaatacacc      660
tgccgcgtgt cgaaccgcgc gggcgccatc aacgccacct acaaggtgga tgtgatccag      720
cggacccgtt ccaagcccgt gctcacaggc acgcacccg tgaacacgac ggtggacttc      780
gggggggacca cgtccttcca gtgcaaggtg cgcagcgacg tgaagccggt gatccagtgg      840
ctgaagcgcg tggagtacgg cgccgagggc cgccacaact ccaccatcga tgtgggcggc      900
cagaagtttg tggtgctgcc cacgggtgac gtgtggtcgc ggcccgacgg ctcctacctc      960
aataagctgc tcatcacccg tgcccgccag gacgatgcgg gcatgtacat ctgccttggc     1020
gccaacacca tgggctacag cttccgcagc gccttcctca ccgtgctgcc ag            1072
```

<210> SEQ ID NO 49
<211> LENGTH: 357
<212> TYPE: PRT
<213> ORGANISM: Human

<400> SEQUENCE: 49

```
Met Thr Pro Ser Pro Leu Leu Leu Leu Pro Pro Leu Leu Leu
 1               5                  10                  15

Gly Ala Phe Pro Pro Ala Ala Ala Arg Gly Pro Pro Lys Met Ala
                20              25                  30

Asp Lys Val Val Pro Arg Gln Val Ala Arg Leu Gly Arg Thr Val Arg
            35                  40                  45

Leu Gln Cys Pro Val Glu Gly Asp Pro Pro Pro Leu Thr Met Trp Thr
 50                      55                  60

Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
                85                  90                  95

Tyr Val Cys Lys Ala Thr Asn Gly Phe Gly Ser Leu Ser Val Asn Tyr
                100                 105                 110

Thr Leu Val Val Leu Asp Asp Ile Ser Pro Gly Lys Glu Ser Leu Gly
                115                 120                 125

Pro Asp Ser Ser Ser Gly Gly Gln Glu Asp Pro Ala Ser Gln Gln Trp
 130                 135                 140

Ala Arg Pro Arg Phe Thr Gln Pro Ser Lys Met Arg Arg Arg Val Ile
145                 150                 155                 160

Ala Arg Pro Val Gly Ser Ser Val Arg Leu Lys Cys Val Ala Ser Gly
                165                 170                 175

His Pro Arg Pro Asp Ile Thr Trp Met Lys Asp Asp Gln Ala Leu Thr
                180                 185                 190

Arg Pro Glu Ala Ala Glu Pro Arg Lys Lys Trp Thr Leu Ser Leu
                195                 200                 205

Lys Asn Leu Arg Pro Glu Asp Ser Gly Lys Tyr Thr Cys Arg Val Ser
                210                 215                 220

Asn Arg Ala Gly Ala Ile Asn Ala Thr Tyr Lys Val Asp Val Ile Gln
225                 230                 235                 240

Arg Thr Arg Ser Lys Pro Val Leu Thr Gly Thr His Pro Val Asn Thr
                245                 250                 255

Thr Val Asp Phe Gly Gly Thr Thr Ser Phe Gln Cys Lys Val Arg Ser
                260                 265                 270

Asp Val Lys Pro Val Ile Gln Trp Leu Lys Arg Val Glu Tyr Gly Ala
                275                 280                 285

Glu Gly Arg His Asn Ser Thr Ile Asp Val Gly Gly Gln Lys Phe Val
                290                 295                 300

Val Leu Pro Thr Gly Asp Val Trp Ser Arg Pro Asp Gly Ser Tyr Leu
305                 310                 315                 320

Asn Lys Leu Leu Ile Thr Arg Ala Arg Gln Asp Asp Ala Gly Met Tyr
                325                 330                 335

Ile Cys Leu Gly Ala Asn Thr Met Gly Tyr Ser Phe Arg Ser Ala Phe
                340                 345                 350

Leu Thr Val Leu Pro
                355
```

```
<210> SEQ ID NO 50
<211> LENGTH: 718
<212> TYPE: DNA
<213> ORGANISM: Human

<400> SEQUENCE: 50
atgacgccga gccccctgtt gctgctcctg ctgccgccgc tgctgctggg ggccttccca      60
ccggccgccg ccgcccgagg ccccccaaag atggcggaca aggtggtccc acggcaggtg     120
gcccggctgg gccgcactgt gcggctgcag tgcccagtgg aggggaccc gccgccgctg      180 accatgtgga ccaaggatgg ccgcaccatc acagcggct ggagccgctt ccgcgtgctg      240 ccgcagggc tgaaggtgaa gcaggtggag cgggaggatg ccggcgtgta cgtgtgcaag     300
gccaccaacg gcttcggcag ccttagcgtc aactacaccc tcgtcgtgct ggatgacatt     360
agcccaggga aggagagcct ggggcccgac agctcctctg ggggtcaaga ggaccccgcc     420
agccagcagt gggcacgacc gcgcttcaca cagccctcca agatgaggcg ccgggtgatc     480
gcacggcccg tgggtagctc cgtgcggctc aagtgcgtgg ccagcgggca ccctcggccc     540
gacatcacgt ggatgaagga cgaccaggcc ttgacgcgcc cagaggccgc tgagcccagg     600
aagaagaagt ggacactgag cctgaagaac ctgcggccgg aggacagcgg caaatacacc     660
tgccgcgtgt cgaaccgcgc gggcgccatc aacgccacct acaaggtgga tgtgatcc     718

<210> SEQ ID NO 51
<211> LENGTH: 239
<212> TYPE: PRT
<213> ORGANISM: Human

<400> SEQUENCE: 51
```

Met Thr Pro Ser Pro Leu Leu Leu Leu Leu Pro Pro Leu Leu
1               5                   10                  15

Gly Ala Phe Pro Pro Ala Ala Ala Arg Gly Pro Pro Lys Met Ala
            20                  25                  30

Asp Lys Val Val Pro Arg Gln Val Ala Arg Leu Gly Arg Thr Val Arg
        35                  40                  45

Leu Gln Cys Pro Val Glu Gly Asp Pro Pro Leu Thr Met Trp Thr
    50                  55                  60

Lys Asp Gly Arg Thr Ile His Ser Gly Trp Ser Arg Phe Arg Val Leu
65                  70                  75                  80

Pro Gln Gly Leu Lys Val Lys Gln Val Glu Arg Glu Asp Ala Gly Val
                85                  90                  95

Tyr Val Cys Lys Ala Thr Asn Gly Phe Gly Ser Leu Ser Val Asn Tyr
            100                 105                 110

Thr Leu Val Val Leu Asp Asp Ile Ser Pro Gly Lys Glu Ser Leu Gly
        115                 120                 125

Pro Asp Ser Ser Ser Gly Gly Gln Glu Asp Pro Ala Ser Gln Gln Trp
    130                 135                 140

Ala Arg Pro Arg Phe Thr Gln Pro Ser Lys Met Arg Arg Val Ile
145                 150                 155                 160

Ala Arg Pro Val Gly Ser Ser Val Arg Leu Lys Cys Val Ala Ser Gly
                165                 170                 175

His Pro Arg Pro Asp Ile Thr Trp Met Lys Asp Gln Ala Leu Thr
            180                 185                 190

Arg Pro Glu Ala Ala Glu Pro Arg Lys Lys Trp Thr Leu Ser Leu
        195                 200                 205

Lys Asn Leu Arg Pro Glu Asp Ser Gly Lys Tyr Thr Cys Arg Val Ser

```
                    210                 215                 220
Asn Arg Ala Gly Ala Ile Asn Ala Thr Tyr Lys Val Asp Val Ile
225                 230                 235
```

<210> SEQ ID NO 52
<211> LENGTH: 787
<212> TYPE: DNA
<213> ORGANISM: Human

<400> SEQUENCE: 52

| | | |
|---|---|---|
| atgacgccga gccccctgtt gctgctcctg ctgccgccgc tgctgctggg ggccttccca | 60 |
| ccggccgccg ccgcccgagg cccccccaaag atggcggaca aggtggtccc acggcaggtg | 120 |
| gcccggctgg gccgcactgt gcggctgcag tgcccagtgg aggggacccc gccgccgctg | 180 |
| accatgtgga ccaaggatgg ccgcaccatc acagcggct ggagccgctt ccgcgtgctg | 240 |
| ccgcaggggc tgaaggtgaa gcaggtggag cgggaggatg ccggcgtgta cgtgtgcaag | 300 |
| gccaccaacg gcttcggcag ccttagcgtc aactacaccc tcgtcgtgct ggatgacatt | 360 |
| agcccaggga aggagagcct ggggcccgac agctcctctg ggggtcaaga ggaccccgcc | 420 |
| agccagcagt gggagcggac ccgttccaag cccgtgctca caggcacgca ccccgtgaac | 480 |
| acgacggtgg acttcggggg gaccacgtcc ttccagtgca aggtgcgcag cgacgtgaag | 540 |
| ccggtgatcc agtggctgaa gcgcgtggag tacgcgccg agggccgcca caactccacc | 600 |
| atcgatgtgg gcggccagaa gtttgtggtg ctgcccacgg tgacgtgtg gtcgcggccc | 660 |
| gacggctcct acctcaataa gctgctcatc acccgtgccc gccaggacga tgcgggcatg | 720 |
| tacatctgcc ttggcgccaa caccatgggc tacagcttcc gcagcgcctt cctcaccgtg | 780 |
| ctgccag | 787 |

<210> SEQ ID NO 53
<211> LENGTH: 262
<212> TYPE: PRT
<213> ORGANISM: Human

<400> SEQUENCE: 53

```
Met Thr Pro Ser Pro Leu Leu Leu Leu Leu Pro Pro Leu Leu Leu
  1               5                  10                  15

Gly Ala Phe Pro Pro Ala Ala Ala Arg Gly Pro Pro Lys Met Ala
                 20                  25                  30

Asp Lys Val Val Pro Arg Gln Val Ala Arg Leu Gly Arg Thr Val Arg
                 35                  40                  45

Leu Gln Cys Pro Val Glu Gly Asp Pro Pro Leu Thr Met Trp Thr
 50                  55                  60

Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
                 85                  90                  95

Tyr Val Cys Lys Ala Thr Asn Gly Phe Gly Ser Leu Ser Val Asn Tyr
                100                 105                 110

Thr Leu Val Val Leu Asp Asp Ile Ser Pro Gly Lys Glu Ser Leu Gly
                115                 120                 125

Pro Asp Ser Ser Ser Gly Gly Gln Glu Asp Pro Ala Ser Gln Gln Trp
                130                 135                 140

Glu Arg Thr Arg Ser Lys Pro Val Leu Thr Gly Thr His Pro Val Asn
145                 150                 155                 160
```

| | | | | | | | | | | | |
|---|---|---|---|---|---|---|---|---|---|---|---|
|Thr|Thr|Val|Asp|Phe|Gly|Gly|Thr|Thr|Ser|Phe|Gln|Cys|Lys|Val|Arg|
| | | |165| | | |170| | | |175| | | | |

Ser Asp Val Lys Pro Val Ile Gln Trp Leu Lys Arg Val Glu Tyr Gly
            180                 185                 190

Ala Glu Gly Arg His Asn Ser Thr Ile Asp Val Gly Gln Lys Phe
        195                 200                 205

Val Val Leu Pro Thr Gly Asp Val Trp Ser Arg Pro Asp Gly Ser Tyr
    210                 215                 220

Leu Asn Lys Leu Leu Ile Thr Arg Ala Arg Gln Asp Asp Ala Gly Met
225                 230                 235                 240

Tyr Ile Cys Leu Gly Ala Asn Thr Met Gly Tyr Ser Phe Arg Ser Ala
                245                 250                 255

Phe Leu Thr Val Leu Pro
            260

<210> SEQ ID NO 54
<211> LENGTH: 991
<212> TYPE: DNA
<213> ORGANISM: Human

<400> SEQUENCE: 54
atgacgccga gcccctgtt gctgctcctg ctgccgccgc tgctgctggg ggccttccca      60
ccggccgccg ccgcccgagg ccccccaaag atggcggaca aggtggtccc acggcaggtg     120
gcccggctgg gccgcactgt gcggctgcag tgcccagtgg aggggaccc gccgccgctg     180
accatgtgga ccaaggatgg ccgcaccatc cacagcggct ggagccgctt ccgcgtgctg     240
ccgcagggc tgaaggtgaa gcaggtggag cgggaggatg ccggcgtgta cgtgtgcaag     300
gccaccaacg gcttcggcag ccttagcgtc aactacaccc tcgtcgtgct ggcacgaccg     360
cgcttcacac agccctccaa gatgaggcgc cgggtgatcg cacggcccgt gggtagctcc     420
gtgcggctca gtgcgtggc cagcgggcac cctcggcccg acatcacgtg gatgaaggac     480
gaccaggcct tgacgcgccc agaggccgct gagcccagga agaagaagtg gacactgagc     540
ctgaagaacc tgcggccgga ggacagcggc aaatacacct gccgcgtgtc gaaccgcgcg     600
ggcgccatca acgccaccta caagtggat gtgatccagc ggacccgttc aagcccgtg     660
ctcacaggca cgcaccccgt gaacacgacg gtggacttcg ggggaccac gtccttccag     720
tgcaaggtgc gcagcgacgt gaagccggtg atccagtggc tgaagcgcgt ggagtacggc     780
gccgagggcc gccacaactc caccatcgat gtgggcggcc agaagtttgt ggtgctgccc     840
acgggtgacg tgtggtcgcg gcccgacggc tcctacctca ataagctgct catcacccgt     900
gcccgccagg acgatgcggg catgtacatc tgccttggcg ccaacaccat gggctacagc     960
ttccgcagcg ccttcctcac cgtgctgcca g                                    991

<210> SEQ ID NO 55
<211> LENGTH: 330
<212> TYPE: PRT
<213> ORGANISM: Human

<400> SEQUENCE: 55

Met Thr Pro Ser Pro Leu Leu Leu Leu Leu Pro Pro Leu Leu Leu
1               5                   10                  15

Gly Ala Phe Pro Pro Ala Ala Ala Arg Gly Pro Pro Lys Met Ala
            20                  25                  30

Asp Lys Val Val Pro Arg Gln Val Ala Arg Leu Gly Arg Thr Val Arg
        35                  40                  45

```
Leu Gln Cys Pro Val Glu Gly Asp Pro Pro Leu Thr Met Trp Thr
    50                  55                  60

Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
                 85                  90                  95

Tyr Val Cys Lys Ala Thr Asn Gly Phe Gly Ser Leu Ser Val Asn Tyr
                100                 105                 110

Thr Leu Val Val Leu Ala Arg Pro Arg Phe Thr Gln Pro Ser Lys Met
            115                 120                 125

Arg Arg Arg Val Ile Ala Arg Pro Val Gly Ser Ser Val Arg Leu Lys
        130                 135                 140

Cys Val Ala Ser Gly His Pro Arg Pro Asp Ile Thr Trp Met Lys Asp
145                 150                 155                 160

Asp Gln Ala Leu Thr Arg Pro Glu Ala Ala Glu Pro Arg Lys Lys Lys
                165                 170                 175

Trp Thr Leu Ser Leu Lys Asn Leu Arg Pro Glu Asp Ser Gly Lys Tyr
                180                 185                 190

Thr Cys Arg Val Ser Asn Arg Ala Gly Ala Ile Asn Ala Thr Tyr Lys
            195                 200                 205

Val Asp Val Ile Gln Arg Thr Arg Ser Lys Pro Val Leu Thr Gly Thr
210                 215                 220

His Pro Val Asn Thr Thr Val Asp Phe Gly Gly Thr Thr Ser Phe Gln
225                 230                 235                 240

Cys Lys Val Arg Ser Asp Val Lys Pro Val Ile Gln Trp Leu Lys Arg
                245                 250                 255

Val Glu Tyr Gly Ala Glu Gly Arg His Asn Ser Thr Ile Asp Val Gly
            260                 265                 270

Gly Gln Lys Phe Val Val Leu Pro Thr Gly Asp Val Trp Ser Arg Pro
            275                 280                 285

Asp Gly Ser Tyr Leu Asn Lys Leu Leu Ile Thr Arg Ala Arg Gln Asp
290                 295                 300

Asp Ala Gly Met Tyr Ile Cys Leu Gly Ala Asn Thr Met Gly Tyr Ser
305                 310                 315                 320

Phe Arg Ser Ala Phe Leu Thr Val Leu Pro
                325                 330

<210> SEQ ID NO 56
<211> LENGTH: 799
<212> TYPE: DNA
<213> ORGANISM: Human

<400> SEQUENCE: 56
atgacgccga gcccctgtt gctgctcctg ctgccgccgc tgctgctggg ggccttccca      60
ccggccgccg ccgcccgaga tgacattagc ccagggaagg agagcctggg gcccgacagc    120
tcctctgggg gtcaagagga ccccgccagc cagcagtggg cacgaccgcg cttcacacag    180
ccctccaaga tgaggcgccg ggtgatcgca cggcccgtgg gtagctccgt gcggctcaag    240
tgcgtggcca gcgggcaccc tcggcccgac atcacgtgga tgaaggacga ccaggccttg    300
acgcgcccag aggccgctga gcccaggaag aagaagtgga cactgagcct gaagaacctg    360
cggccggagg acagcggcaa atacacctgc cgcgtgtcga accgcgcggg cgccatcaac    420
gccacctaca aggtggatgt gatccagcgg acccgttcca gcccgtgct cacaggcacg    480
```

-continued

```
caccccgtga acacgacggt ggacttcggg gggaccacgt ccttccagtg caaggtgcgc    540
agcgacgtga agccggtgat ccagtggctg aagcgcgtgg agtacggcgc cgagggccgc    600
cacaactcca ccatcgatgt gggcggccag aagtttgtgg tgctgcccac gggtgacgtg    660
tggtcgcggc ccgacggctc ctacctcaat aagctgctca tcacccgtgc ccgccaggac    720
gatgcgggca tgtacatctg ccttggcgcc aacaccatgg gctacagctt ccgcagcgcc    780
ttcctcaccg tgctgccag                                                  799
```

<210> SEQ ID NO 57
<211> LENGTH: 266
<212> TYPE: PRT
<213> ORGANISM: Human

<400> SEQUENCE: 57

```
Met Thr Pro Ser Pro Leu Leu Leu Leu Leu Pro Pro Leu Leu Leu
 1               5                  10                  15

Gly Ala Phe Pro Pro Ala Ala Ala Arg Asp Asp Ile Ser Pro Gly
                20                  25                  30

Lys Glu Ser Leu Gly Pro Asp Ser Ser Gly Gly Gln Glu Asp Pro
            35                  40                  45

Ala Ser Gln Gln Trp Ala Arg Pro Arg Phe Thr Gln Pro Ser Lys Met
    50                  55                  60

Arg Arg Arg Val Ile Ala Arg Pro Val Gly Ser Ser Val Arg Leu Lys
65                  70                  75                  80

Cys Val Ala Ser Gly His Pro Arg Pro Asp Ile Thr Trp Met Lys Asp
                85                  90                  95

Asp Gln Ala Leu Thr Arg Pro Glu Ala Ala Glu Pro Arg Lys Lys Lys
            100                 105                 110

Trp Thr Leu Ser Leu Lys Asn Leu Arg Pro Glu Asp Ser Gly Lys Tyr
        115                 120                 125

Thr Cys Arg Val Ser Asn Arg Ala Gly Ala Ile Asn Ala Thr Tyr Lys
    130                 135                 140

Val Asp Val Ile Gln Arg Thr Arg Ser Lys Pro Val Leu Thr Gly Thr
145                 150                 155                 160

His Pro Val Asn Thr Thr Val Asp Phe Gly Gly Thr Thr Ser Phe Gln
                165                 170                 175

Cys Lys Val Arg Ser Asp Val Lys Pro Val Ile Gln Trp Leu Lys Arg
            180                 185                 190

Val Glu Tyr Gly Ala Glu Gly Arg His Asn Ser Thr Ile Asp Val Gly
        195                 200                 205

Gly Gln Lys Phe Val Val Leu Pro Thr Gly Asp Val Trp Ser Arg Pro
    210                 215                 220

Asp Gly Ser Tyr Leu Asn Lys Leu Leu Ile Thr Arg Ala Arg Gln Asp
225                 230                 235                 240

Asp Ala Gly Met Tyr Ile Cys Leu Gly Ala Asn Thr Met Gly Tyr Ser
                245                 250                 255

Phe Arg Ser Ala Phe Leu Thr Val Leu Pro
            260                 265
```

<210> SEQ ID NO 58
<211> LENGTH: 433
<212> TYPE: DNA
<213> ORGANISM: Human

<400> SEQUENCE: 58

-continued

| | |
|---|---|
| atgacgccga gccccctgtt gctgctcctg ctgccgccgc tgctgctggg ggccttccca | 60 |
| ccggccgccg ccgcccgagg ccccccaaag atggcggaca aggtggtccc acggcaggtg | 120 |
| gcccggctgg gccgcactgt gcggctgcag tgcccagtgg aggggaccc gccgccgctg | 180 |
| accatgtgga ccaaggatgg ccgcaccatc cacagcggct ggagccgctt ccgcgtgctg | 240 |
| ccgcaggggc tgaaggtgaa gcaggtggag cgggaggatg ccggcgtgta cgtgtgcaag | 300 |
| gccaccaacg gcttcggcag ccttagcgtc aactacaccc tcgtcgtgct ggatgacatt | 360 |
| agcccaggga aggagagcct ggggcccgac agctcctctg ggggtcaaga ggaccccgcc | 420 |
| agccagcagt ggg | 433 |

<210> SEQ ID NO 59
<211> LENGTH: 144
<212> TYPE: PRT
<213> ORGANISM: Human

<400> SEQUENCE: 59

```
Met Thr Pro Ser Pro Leu Leu Leu Leu Leu Pro Pro Leu Leu Leu
 1               5                  10                  15
Gly Ala Phe Pro Pro Ala Ala Ala Arg Gly Pro Pro Lys Met Ala
            20                  25                  30
Asp Lys Val Val Pro Arg Gln Val Ala Arg Leu Gly Arg Thr Val Arg
        35                  40                  45
Leu Gln Cys Pro Val Glu Gly Asp Pro Pro Leu Thr Met Trp Thr
    50                  55                  60
Lys Asp Gly Arg Thr Ile His Ser Gly Trp Ser Arg Phe Arg Val Leu
65                  70                  75                  80
Pro Gln Gly Leu Lys Val Lys Gln Val Glu Arg Glu Asp Ala Gly Val
                85                  90                  95
Tyr Val Cys Lys Ala Thr Asn Gly Phe Gly Ser Leu Ser Val Asn Tyr
            100                 105                 110
Thr Leu Val Val Leu Asp Asp Ile Ser Pro Gly Lys Glu Ser Leu Gly
        115                 120                 125
Pro Asp Ser Ser Ser Gly Gly Gln Glu Asp Pro Ala Ser Gln Gln Trp
    130                 135                 140
```

<210> SEQ ID NO 60
<211> LENGTH: 637
<212> TYPE: DNA
<213> ORGANISM: Human

<400> SEQUENCE: 60

| | |
|---|---|
| atgacgccga gccccctgtt gctgctcctg ctgccgccgc tgctgctggg ggccttccca | 60 |
| ccggccgccg ccgcccgagg ccccccaaag atggcggaca aggtggtccc acggcaggtg | 120 |
| gcccggctgg gccgcactgt gcggctgcag tgcccagtgg aggggaccc gccgccgctg | 180 |
| accatgtgga ccaaggatgg ccgcaccatc cacagcggct ggagccgctt ccgcgtgctg | 240 |
| ccgcaggggc tgaaggtgaa gcaggtggag cgggaggatg ccggcgtgta cgtgtgcaag | 300 |
| gccaccaacg gcttcggcag ccttagcgtc aactacaccc tcgtcgtgct ggcacgaccg | 360 |
| cgcttcacac agccctccaa gatgaggcgc cgggtgatcg cacggcccgt gggtagctcc | 420 |
| gtgcggctca agtgcgtggc cagcgggcac cctcggcccg acatcacgtg gatgaaggac | 480 |
| gaccaggcct tgacgcgccc agaggccgct gagcccagga agaagaagtg gacactgagc | 540 |
| ctgaagaacc tgcggccgga ggacagcggc aaatacacct gccgcgtgtc gaaccgcgcg | 600 |

```
ggcgccatca acgccaccta caaggtggat gtgatcc                              637
```

<210> SEQ ID NO 61
<211> LENGTH: 212
<212> TYPE: PRT
<213> ORGANISM: Human

<400> SEQUENCE: 61

```
Met Thr Pro Ser Pro Leu Leu Leu Leu Pro Pro Leu Leu
 1               5                  10              15

Gly Ala Phe Pro Pro Ala Ala Ala Arg Gly Pro Lys Met Ala
            20              25              30

Asp Lys Val Val Pro Arg Gln Val Ala Arg Leu Gly Arg Thr Val Arg
            35              40              45

Leu Gln Cys Pro Val Glu Gly Asp Pro Pro Leu Thr Met Trp Thr
    50              55                  60

Lys Asp Gly Arg Thr Ile His Ser Gly Trp Ser Arg Phe Arg Val Leu
65              70                  75                  80

Pro Gln Gly Leu Lys Val Lys Gln Val Glu Arg Glu Asp Ala Gly Val
                85              90                  95

Tyr Val Cys Lys Ala Thr Asn Gly Phe Gly Ser Leu Ser Val Asn Tyr
            100             105             110

Thr Leu Val Val Leu Ala Arg Pro Arg Phe Thr Gln Pro Ser Lys Met
        115             120             125

Arg Arg Arg Val Ile Ala Arg Pro Val Gly Ser Ser Val Arg Leu Lys
    130             135             140

Cys Val Ala Ser Gly His Pro Arg Pro Asp Ile Thr Trp Met Lys Asp
145             150             155             160

Asp Gln Ala Leu Thr Arg Pro Glu Ala Ala Glu Pro Arg Lys Lys Lys
                165             170             175

Trp Thr Leu Ser Leu Lys Asn Leu Arg Pro Glu Asp Ser Gly Lys Tyr
            180             185             190

Thr Cys Arg Val Ser Asn Arg Ala Gly Ala Ile Asn Ala Thr Tyr Lys
        195             200             205

Val Asp Val Ile
    210
```

<210> SEQ ID NO 62
<211> LENGTH: 706
<212> TYPE: DNA
<213> ORGANISM: Human

<400> SEQUENCE: 62

```
atgacgccga gcccctgtt gctgctcctg ctgccgccgc tgctgctggg ggccttccca      60
ccggccgccg ccgcccgagg ccccccaaag atggcggaca aggtggtccc acggcaggtg    120
gcccggctgg gccgcactgt gcggctgcag tgcccagtgg aggggacccg ccgccgctg     180 accatgtgga ccaaggatgg ccgcaccatc acagcggct ggagccgctt ccgcgtgctg     240
ccgcaggggc tgaaggtgaa gcaggtggag cgggaggatg ccggcgtgta cgtgtgcaag    300
gccaccaacg gcttcggcag ccttagcgtc aactacaccc tcgtcgtgct ggagcggacc    360
cgttccaagc ccgtgctcac aggcacgcac cccgtgaaca cgacggtgga cttcgggggg    420
accacgtcct tccagtgcaa ggtgcgcagc gacgtgaagc cggtgatcca gtggctgaag    480
cgcgtggagt acgcgccga gggccgccac aactccacca tcgatgtggg cggccagaag    540
tttgtggtgc tgcccacggg tgacgtgtgg tcgcggcccg acggctccta cctcaataag    600
```

```
ctgctcatca cccgtgcccg ccaggacgat gcgggcatgt acatctgcct tggcgccaac    660
accatgggct acagcttccg cagcgccttc ctcaccgtgc tgccag                   706
```

<210> SEQ ID NO 63
<211> LENGTH: 235
<212> TYPE: PRT
<213> ORGANISM: Human

<400> SEQUENCE: 63

```
Met Thr Pro Ser Pro Leu Leu Leu Leu Leu Pro Pro Leu Leu Leu
  1               5                  10                  15

Gly Ala Phe Pro Pro Ala Ala Ala Arg Gly Pro Pro Lys Met Ala
                 20                  25                  30

Asp Lys Val Val Pro Arg Gln Val Ala Arg Leu Gly Arg Thr Val Arg
                 35                  40                  45

Leu Gln Cys Pro Val Glu Gly Asp Pro Pro Pro Leu Thr Met Trp Thr
 50                  55                      60

Lys Asp Gly Arg Thr Ile His Ser Gly Trp Ser Arg Phe Arg Val Leu
 65                  70                      75                  80

Pro Gln Gly Leu Lys Val Lys Gln Val Glu Arg Glu Asp Ala Gly Val
                 85                  90                  95

Tyr Val Cys Lys Ala Thr Asn Gly Phe Gly Ser Leu Ser Val Asn Tyr
                100                 105                 110

Thr Leu Val Val Leu Glu Arg Thr Arg Ser Lys Pro Val Leu Thr Gly
                115                 120                 125

Thr His Pro Val Asn Thr Thr Val Asp Phe Gly Gly Thr Thr Ser Phe
            130                 135                 140

Gln Cys Lys Val Arg Ser Asp Val Lys Pro Val Ile Gln Trp Leu Lys
145                 150                 155                 160

Arg Val Glu Tyr Gly Ala Glu Gly Arg His Asn Ser Thr Ile Asp Val
                165                 170                 175

Gly Gly Gln Lys Phe Val Val Leu Pro Thr Gly Asp Val Trp Ser Arg
                180                 185                 190

Pro Asp Gly Ser Tyr Leu Asn Lys Leu Leu Ile Thr Arg Ala Arg Gln
                195                 200                 205

Asp Asp Ala Gly Met Tyr Ile Cys Leu Gly Ala Asn Thr Met Gly Tyr
            210                 215                 220

Ser Phe Arg Ser Ala Phe Leu Thr Val Leu Pro
225                 230                 235
```

<210> SEQ ID NO 64
<211> LENGTH: 445
<212> TYPE: DNA
<213> ORGANISM: Human

<400> SEQUENCE: 64

```
atgacgccga gccccctgtt gctgctcctg ctgccgccgc tgctgctggg ggccttccca    60
ccggccgccg ccgcccgaga tgacattagc cagggaagg agagcctggg gcccgacagc    120
tcctctgggg gtcaagagga ccccgccagc cagcagtggg cacgaccgcg cttcacacag    180
ccctccaaga tgaggcgccg ggtgatcgca cggcccgtgg gtagctccgt gcggctcaag    240
tgcgtggcca gcgggcaccc tcggcccgac atcacgtgga tgaaggacga ccaggccttg    300
acgcgcccag aggccgctga gcccaggaag aagaagtgga cactgagcct gaagaacctg    360
cggccggagg acagcggcaa atacacctgc gcgtgtcga accgcgcggg cgccatcaac    420
```

```
gccacctaca aggtggatgt gatcc                                          445
```

<210> SEQ ID NO 65
<211> LENGTH: 148
<212> TYPE: PRT
<213> ORGANISM: Human

<400> SEQUENCE: 65

```
Met Thr Pro Ser Pro Leu Leu Leu Leu Leu Pro Pro Leu Leu Leu
1               5                   10                  15

Gly Ala Phe Pro Pro Ala Ala Ala Ala Arg Asp Asp Ile Ser Pro Gly
            20                  25                  30

Lys Glu Ser Leu Gly Pro Asp Ser Ser Gly Gly Gln Glu Asp Pro
            35                  40                  45

Ala Ser Gln Gln Trp Ala Arg Pro Arg Phe Thr Gln Pro Ser Lys Met
        50                  55                  60

Arg Arg Arg Val Ile Ala Arg Pro Val Gly Ser Val Arg Leu Lys
65                  70                  75                  80

Cys Val Ala Ser Gly His Pro Arg Pro Asp Ile Thr Trp Met Lys Asp
                85                  90                  95

Asp Gln Ala Leu Thr Arg Pro Glu Ala Ala Glu Pro Arg Lys Lys Lys
                100                 105                 110

Trp Thr Leu Ser Leu Lys Asn Leu Arg Pro Glu Asp Ser Gly Lys Tyr
            115                 120                 125

Thr Cys Arg Val Ser Asn Arg Ala Gly Ala Ile Asn Ala Thr Tyr Lys
            130                 135                 140

Val Asp Val Ile
145
```

<210> SEQ ID NO 66
<211> LENGTH: 514
<212> TYPE: DNA
<213> ORGANISM: Human

<400> SEQUENCE: 66

```
atgacgccga gccccctgtt gctgctcctg ctgccgccgc tgctgctggg ggccttccca     60
ccggccgccg ccgcccgaga tgacattagc ccagggaagg agagcctggg gcccgacagc    120
tcctctgggg gtcaagagga ccccgccagc cagcagtggg agcggacccg ttccaagccc    180
gtgctcacag gcacgcaccc cgtgaacacg acggtggact cgggggggac cacgtccttc    240
cagtgcaagg tgcgcagcga cgtgaagccg gtgatccagt ggctgaagcg cgtggagtac    300
ggcgccgagg gccgccacaa ctccaccatc gatgtgggcg ccagaagtt tgtggtgctg    360 cccacggggtg acgtgtggtc gcggcccgac ggctcctacc tcaataagct gctcatcacc    420
cgtgcccgcc aggacgatgc gggcatgtac atctgccttg cgccaacac catgggctac    480 agcttccgca gcgccttcct caccgtgctg ccag                                 514
```

<210> SEQ ID NO 67
<211> LENGTH: 171
<212> TYPE: PRT
<213> ORGANISM: Human

<400> SEQUENCE: 67

```
Met Thr Pro Ser Pro Leu Leu Leu Leu Leu Pro Pro Leu Leu Leu
1               5                   10                  15

Gly Ala Phe Pro Pro Ala Ala Ala Ala Arg Asp Asp Ile Ser Pro Gly
```

```
                20                  25                  30
Lys Glu Ser Leu Gly Pro Asp Ser Ser Gly Gln Glu Asp Pro
             35                  40                  45

Ala Ser Gln Gln Trp Glu Arg Thr Arg Ser Lys Pro Val Leu Thr Gly
 50                  55                  60

Thr His Pro Val Asn Thr Thr Val Asp Phe Gly Gly Thr Thr Ser Phe
 65                  70                  75                  80

Gln Cys Lys Val Arg Ser Asp Val Lys Pro Val Ile Gln Trp Leu Lys
                 85                  90                  95

Arg Val Glu Tyr Gly Ala Glu Gly Arg His Asn Ser Thr Ile Asp Val
                100                 105                 110

Gly Gly Gln Lys Phe Val Val Leu Pro Thr Gly Asp Val Trp Ser Arg
             115                 120                 125

Pro Asp Gly Ser Tyr Leu Asn Lys Leu Leu Ile Thr Arg Ala Arg Gln
130                 135                 140

Asp Asp Ala Gly Met Tyr Ile Cys Leu Gly Ala Asn Thr Met Gly Tyr
145                 150                 155                 160

Ser Phe Arg Ser Ala Phe Leu Thr Val Leu Pro
                165                 170
```

<210> SEQ ID NO 68
<211> LENGTH: 718
<212> TYPE: DNA
<213> ORGANISM: Human

<400> SEQUENCE: 68

```
atgacgccga gcccctgtt gctgctcctg ctgccgccgc tgctgctggg ggccttccca      60
ccggccgccg ccgcccgagc acgaccgcgc ttcacacagc cctccaagat gaggcgccgg    120
gtgatcgcac ggcccgtggg tagctccgtg cggctcaagt gcgtggccag cgggcaccct    180
cggcccgaca tcacgtggat gaaggacgac caggccttga cgcgcccaga ggccgctgag    240
cccaggaaga agaagtggac actgagcctg aagaacctgc ggccggagga cagcggcaaa    300
tacacctgcc gcgtgtcgaa ccgcgcgggc gccatcaacg ccacctacaa ggtggatgtg    360
atccagcgga cccgttccaa gcccgtgctc acaggcacgc accccgtgaa cacgacggtg    420
gacttcgggg ggaccacgtc cttccagtgc aaggtgcgca cgacgtgaa gccggtgatc    480
cagtggctga agcgcgtgga gtacggcgcc gagggccgcc acaactccac catcgatgtg    540
ggcggccaga agtttgtggt gctgcccacg ggtgacgtgt ggtcgcggcc cgacggctcc    600
tacctcaata agctgctcat cacccgtgcc cgccaggacg atgcgggcat gtacatctgc    660
cttggcgcca acaccatggg ctacagcttc cgcagcgcct tcctcaccgt gctgccag     718
```

<210> SEQ ID NO 69
<211> LENGTH: 239
<212> TYPE: PRT
<213> ORGANISM: Human

<400> SEQUENCE: 69

```
Met Thr Pro Ser Pro Leu Leu Leu Leu Leu Pro Pro Leu Leu Leu
 1               5                  10                  15

Gly Ala Phe Pro Pro Ala Ala Ala Ala Arg Ala Arg Pro Arg Phe Thr
                 20                  25                  30

Gln Pro Ser Lys Met Arg Arg Arg Val Ile Ala Arg Pro Val Gly Ser
             35                  40                  45

Ser Val Arg Leu Lys Cys Val Ala Ser Gly His Pro Arg Pro Asp Ile
```

-continued

```
                50                  55                  60
Thr Trp Met Lys Asp Asp Gln Ala Leu Thr Arg Pro Glu Ala Ala Glu
 65                  70                  75                  80

Pro Arg Lys Lys Lys Trp Thr Leu Ser Leu Lys Asn Leu Arg Pro Glu
                 85                  90                  95

Asp Ser Gly Lys Tyr Thr Cys Arg Val Ser Asn Arg Ala Gly Ala Ile
            100                 105                 110

Asn Ala Thr Tyr Lys Val Asp Val Ile Gln Arg Thr Arg Ser Lys Pro
        115                 120                 125

Val Leu Thr Gly Thr His Pro Val Asn Thr Thr Val Asp Phe Gly Gly
130                 135                 140

Thr Thr Ser Phe Gln Cys Lys Val Arg Ser Asp Val Lys Pro Val Ile
145                 150                 155                 160

Gln Trp Leu Lys Arg Val Glu Tyr Gly Ala Glu Gly Arg His Asn Ser
                165                 170                 175

Thr Ile Asp Val Gly Gly Gln Lys Phe Val Val Leu Pro Thr Gly Asp
            180                 185                 190

Val Trp Ser Arg Pro Asp Gly Ser Tyr Leu Asn Lys Leu Leu Ile Thr
        195                 200                 205

Arg Ala Arg Gln Asp Asp Ala Gly Met Tyr Ile Cys Leu Gly Ala Asn
    210                 215                 220

Thr Met Gly Tyr Ser Phe Arg Ser Ala Phe Leu Thr Val Leu Pro
225                 230                 235

<210> SEQ ID NO 70
<211> LENGTH: 352
<212> TYPE: DNA
<213> ORGANISM: Human

<400> SEQUENCE: 70
atgacgccga gccccctgtt gctgctcctg ctgccgccgc tgctgctggg ggccttccca      60
ccggccgccg ccgcccgagg ccccccaaag atggcggaca aggtggtccc acggcaggtg     120
gcccggctgg gccgcactgt gcggctgcag tgcccagtgg aggggacccg ccgccgctg     180 accatgtgga ccaaggatgg ccgcaccatc acagcggct ggagccgctt ccgcgtgctg     240
ccgcaggggc tgaaggtgaa gcaggtggag cgggaggatg ccggcgtgta cgtgtgcaag     300
gccaccaacg gcttcggcag ccttagcgtc aactacaccc tcgtcgtgct gg             352

<210> SEQ ID NO 71
<211> LENGTH: 117
<212> TYPE: PRT
<213> ORGANISM: Human

<400> SEQUENCE: 71

Met Thr Pro Ser Pro Leu Leu Leu Leu Leu Pro Pro Leu Leu Leu
  1               5                  10                  15

Gly Ala Phe Pro Pro Ala Ala Ala Arg Gly Pro Pro Lys Met Ala
             20                  25                  30

Asp Lys Val Val Pro Arg Gln Val Ala Arg Leu Gly Arg Thr Val Arg
         35                  40                  45

Leu Gln Cys Pro Val Glu Gly Asp Pro Pro Leu Thr Met Trp Thr
    50                  55                  60

Lys Asp Gly Arg Thr Ile His Ser Gly Trp Ser Arg Phe Arg Val Leu
 65                  70                  75                  80

Pro Gln Gly Leu Lys Val Lys Gln Val Glu Arg Glu Asp Ala Gly Val
```

```
                     85                   90                   95
Tyr Val Cys Lys Ala Thr Asn Gly Phe Gly Ser Leu Ser Val Asn Tyr
            100                 105                 110

Thr Leu Val Val Leu
        115

<210> SEQ ID NO 72
<211> LENGTH: 160
<212> TYPE: DNA
<213> ORGANISM: Human

<400> SEQUENCE: 72
atgacgccga gcccctgtt gctgctcctg ctgccgccgc tgctgctggg ggccttccca      60
ccggccgccg ccgcccgaga tgacattagc ccagggaagg agagcctggg gcccgacagc     120
tcctctgggg gtcaagagga ccccgccagc cagcagtggg                          160

<210> SEQ ID NO 73
<211> LENGTH: 53
<212> TYPE: PRT
<213> ORGANISM: Human

<400> SEQUENCE: 73

Met Thr Pro Ser Pro Leu Leu Leu Leu Leu Pro Pro Leu Leu Leu
  1               5                  10                  15

Gly Ala Phe Pro Pro Ala Ala Ala Arg Asp Asp Ile Ser Pro Gly
             20                  25                  30

Lys Glu Ser Leu Gly Pro Asp Ser Ser Gly Gly Gln Glu Asp Pro
             35                  40                  45

Ala Ser Gln Gln Trp
         50

<210> SEQ ID NO 74
<211> LENGTH: 364
<212> TYPE: DNA
<213> ORGANISM: Human

<400> SEQUENCE: 74
atgacgccga gcccctgtt gctgctcctg ctgccgccgc tgctgctggg ggccttccca      60
ccggccgccg ccgcccgagc acgaccgcgc ttcacacagc cctccaagat gaggcgccgg    120
gtgatcgcac ggcccgtggg tagctccgtg cggctcaagt gcgtggccag cgggcaccct    180
cggcccgaca tcacgtggat gaaggacgac caggccttga cgcgcccaga ggccgctgag    240
cccaggaaga agaagtggac actgagcctg aagaacctgc ggccggagga cagcggcaaa    300
tacacctgcc gcgtgtcgaa ccgcgcgggc gccatcaacg ccacctacaa ggtggatgtg    360
atcc                                                                364

<210> SEQ ID NO 75
<211> LENGTH: 121
<212> TYPE: PRT
<213> ORGANISM: Human

<400> SEQUENCE: 75

Met Thr Pro Ser Pro Leu Leu Leu Leu Leu Pro Pro Leu Leu Leu
  1               5                  10                  15

Gly Ala Phe Pro Pro Ala Ala Ala Arg Ala Arg Pro Arg Phe Thr
             20                  25                  30

Gln Pro Ser Lys Met Arg Arg Arg Val Ile Ala Arg Pro Val Gly Ser
```

-continued

```
                 35                  40                  45
Ser Val Arg Leu Lys Cys Val Ala Ser Gly His Pro Arg Pro Asp Ile
     50                  55                  60

Thr Trp Met Lys Asp Asp Gln Ala Leu Thr Arg Pro Glu Ala Ala Glu
 65                  70                  75                  80

Pro Arg Lys Lys Lys Trp Thr Leu Ser Leu Lys Asn Leu Arg Pro Glu
                 85                  90                  95

Asp Ser Gly Lys Tyr Thr Cys Arg Val Ser Asn Arg Ala Gly Ala Ile
            100                 105                 110

Asn Ala Thr Tyr Lys Val Asp Val Ile
        115                 120
```

<210> SEQ ID NO 76
<211> LENGTH: 433
<212> TYPE: DNA
<213> ORGANISM: Human

<400> SEQUENCE: 76

```
atgacgccga gcccctgtt gctgctcctg ctgccgccgc tgctgctggg ggccttccca      60
ccggccgccg ccgcccgaga gcggacccgt tccaagcccg tgctcacagg cacgcacccc   120
gtgaacacga cggtggactt cgggggacc acgtccttcc agtgcaaggt gcgcagcgac   180
gtgaagccgg tgatccagtg gctgaagcgc gtggagtacg gcgccgaggg ccgccacaac   240
tccaccatcg atgtgggcgg ccagaagttt gtggtgctgc ccacgggtga cgtgtggtcg   300
cggcccgacg gctcctacct caataagctg ctcatcaccc gtgcccgcca ggacgatgcg   360
ggcatgtaca tctgccttgg cgccaacacc atgggctaca gcttccgcag cgccttcctc   420
accgtgctgc cag                                                      433
```

<210> SEQ ID NO 77
<211> LENGTH: 144
<212> TYPE: PRT
<213> ORGANISM: Human

<400> SEQUENCE: 77

```
Met Thr Pro Ser Pro Leu Leu Leu Leu Leu Pro Pro Leu Leu Leu
 1               5                  10                  15

Gly Ala Phe Pro Pro Ala Ala Ala Ala Arg Glu Arg Thr Arg Ser Lys
                 20                  25                  30

Pro Val Leu Thr Gly Thr His Pro Val Asn Thr Thr Val Asp Phe Gly
             35                  40                  45

Gly Thr Thr Ser Phe Gln Cys Lys Val Arg Ser Asp Val Lys Pro Val
         50                  55                  60

Ile Gln Trp Leu Lys Arg Val Glu Tyr Gly Ala Glu Gly Arg His Asn
 65                  70                  75                  80

Ser Thr Ile Asp Val Gly Gly Gln Lys Phe Val Val Leu Pro Thr Gly
                 85                  90                  95

Asp Val Trp Ser Arg Pro Asp Gly Ser Tyr Leu Asn Lys Leu Leu Ile
            100                 105                 110

Thr Arg Ala Arg Gln Asp Asp Ala Gly Met Tyr Ile Cys Leu Gly Ala
        115                 120                 125

Asn Thr Met Gly Tyr Ser Phe Arg Ser Ala Phe Leu Thr Val Leu Pro
    130                 135                 140
```

<210> SEQ ID NO 78
<211> LENGTH: 79

-continued

```
<212> TYPE: DNA
<213> ORGANISM: Human

<400> SEQUENCE: 78
atgacgccga gccccctgtt gctgctcctg ctgccgccgc tgctgctggg ggccttccca      60
ccggccgccg ccgcccgag                                                  79

<210> SEQ ID NO 79
<211> LENGTH: 26
<212> TYPE: PRT
<213> ORGANISM: Human

<400> SEQUENCE: 79

Met Thr Pro Ser Pro Leu Leu Leu Leu Leu Pro Pro Leu Leu Leu
 1               5                  10                  15

Gly Ala Phe Pro Pro Ala Ala Ala Arg
            20                  25

<210> SEQ ID NO 80
<211> LENGTH: 1590
<212> TYPE: DNA
<213> ORGANISM: Mouse

<400> SEQUENCE: 80
atgacgcgga gccccgcgct gctgctgctg ctattggggg ccctcccgtc ggctgaggcg      60
gcgcgaggac ccccaagaat ggcagacaaa gtggtcccac ggcaggtggc ccgcctgggc     120
cgcactgtgc ggctacagtg cccagtgagg gggacccac accgttgac catgtggacc       180 aaagatggcc gcacaatcca cagtggctgg agccgcttcc gtgtgctgcc ccagggtctg     240
aaggtgaagg aggtggaggc cgaggatgcc ggtgtttatg tgtgcaaggc caccaatggc     300
tttggcagcc tcagcgtcaa ctacactctc atcatcatgg atgatattag tccagggaag     360
gagagccctg ggcaggtgg ttcttcgggg gccaggagg acccagccag ccagcagtgg       420
gcacggcctc gcttcacaca gccctccaag atgaggcgcc gagtgattgc acggcctgtg     480
ggtagctctg tgcggctcaa gtgtgtggcc agtgggcacc acggccaga catcatgtgg     540 atgaaggatg accagacctt gacgcatcta gaggctagtg aacacagaaa gaagaagtgg    600
acactgagct tgaagaacct gaagcctgaa gacagtggca agtacacgtg ccgtgtatct    660
aacaaggccg gtgccatcaa cgccacctac aaagtggatg taatccagcg gactcgttcc    720
aagcctgtgc tcacagggac acaccctgtg aacacaacgg tggacttcgg tgggacaacg    780
tccttccagt gcaaggtgcg cagtgacgtg aagcctgtga tccagtggct gaagcgggtg    840
gagtacggct ccgagggacg ccacaactcc accattgatg tgggtggcca aagtttgtg     900 gtgttgccca cgggtgatgt gtggtcacgg cctgatggct cctacctcaa caagctgctc    960
atctctcggg cccgccagga tgatgctggc atgtacatct gcctaggtgc aaataccatg   1020
ggctacagtt ccgtagcgc cttcctcact gtattaccag accccaaacc tccagggcct    1080
cctatggctt cttcatcgtc atccacaagc ctgccatggc ctgtggtgat cggcatccca   1140
gctggtgctg tcttcatcct aggcactgtg ctgctctggc tttgccagac caagaagaag   1200
ccatgtgccc cagcatctac acttcctgtg cctgggcatc gtcccccagg acatcccga    1260 gaacgcagtg gtgacaagga cctgccctca ttggctgtgg gcatatgtga ggagcatgga   1320
tccgccatgg cccccagca catcctggcc tctggctcaa ctgctggccc caagctgtac    1380
cccaagctat acacagatgt gcacacacac acacatacac acacctgcac tcacacgctc    1440
```

-continued

```
tcatgtggag ggcaaggttc atcaacacca gcatgtccac tatcagtgct aaatacagcg  1500
aatctccaag cactgtgtcc tgaggtaggc atttgggggc caaggcaaca ggttgggaga  1560
attgagaaca atggaggaag agtatcttag                                   1590
```

<210> SEQ ID NO 81
<211> LENGTH: 529
<212> TYPE: PRT
<213> ORGANISM: Mouse

<400> SEQUENCE: 81

```
Met Thr Arg Ser Pro Ala Leu Leu Leu Leu Gly Ala Leu Pro
 1               5                  10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
             35                  40                  45

Val Glu Gly Asp Pro Pro Leu Thr Met Trp Thr Lys Asp Gly Arg
 50                  55                  60

Thr Ile His Ser Gly Trp Ser Arg Phe Arg Val Leu Pro Gln Gly Leu
 65                  70                  75                  80

Lys Val Lys Glu Val Glu Ala Glu Asp Ala Gly Val Tyr Val Cys Lys
                 85                  90                  95

Ala Thr Asn Gly Phe Gly Ser Leu Ser Val Asn Tyr Thr Leu Ile Ile
                100                 105                 110

Met Asp Asp Ile Ser Pro Gly Lys Glu Ser Pro Gly Pro Gly Gly Ser
             115                 120                 125

Ser Gly Gly Gln Glu Asp Pro Ala Ser Gln Gln Trp Ala Arg Pro Arg
130                 135                 140

Phe Thr Gln Pro Ser Lys Met Arg Arg Val Ile Ala Arg Pro Val
145                 150                 155                 160

Gly Ser Ser Val Arg Leu Lys Cys Val Ala Ser Gly His Pro Arg Pro
                165                 170                 175

Asp Ile Met Trp Met Lys Asp Asp Gln Thr Leu Thr His Leu Glu Ala
             180                 185                 190

Ser Glu His Arg Lys Lys Lys Trp Thr Leu Ser Leu Lys Asn Leu Lys
             195                 200                 205

Pro Glu Asp Ser Gly Lys Tyr Thr Cys Arg Val Ser Asn Lys Ala Gly
210                 215                 220

Ala Ile Asn Ala Thr Tyr Lys Val Asp Val Ile Gln Arg Thr Arg Ser
225                 230                 235                 240

Lys Pro Val Leu Thr Gly Thr His Pro Val Asn Thr Thr Val Asp Phe
                245                 250                 255

Gly Gly Thr Thr Ser Phe Gln Cys Lys Val Arg Ser Asp Val Lys Pro
             260                 265                 270

Val Ile Gln Trp Leu Lys Arg Val Glu Tyr Gly Ser Glu Gly Arg His
             275                 280                 285

Asn Ser Thr Ile Asp Val Gly Gly Gln Lys Phe Val Val Leu Pro Thr
290                 295                 300

Gly Asp Val Trp Ser Arg Pro Asp Gly Ser Tyr Leu Asn Lys Leu Leu
305                 310                 315                 320

Ile Ser Arg Ala Arg Gln Asp Asp Ala Gly Met Tyr Ile Cys Leu Gly
                325                 330                 335

Ala Asn Thr Met Gly Tyr Ser Phe Arg Ser Ala Phe Leu Thr Val Leu
             340                 345                 350
```

-continued

```
Pro Asp Pro Lys Pro Gly Pro Met Ala Ser Ser Ser Ser Ser
        355                 360                 365

Thr Ser Leu Pro Trp Pro Val Val Ile Gly Ile Pro Ala Gly Ala Val
    370                 375                 380

Phe Ile Leu Gly Thr Val Leu Leu Trp Leu Cys Gln Thr Lys Lys Lys
385                 390                 395                 400

Pro Cys Ala Pro Ala Ser Thr Leu Pro Val Pro Gly His Arg Pro Pro
                405                 410                 415

Gly Thr Ser Arg Glu Arg Ser Gly Asp Lys Asp Leu Pro Ser Leu Ala
            420                 425                 430

Val Gly Ile Cys Glu Glu His Gly Ser Ala Met Ala Pro Gln His Ile
        435                 440                 445

Leu Ala Ser Gly Ser Thr Ala Gly Pro Lys Leu Tyr Pro Lys Leu Tyr
    450                 455                 460

Thr Asp Val His Thr His Thr His Thr His Thr Cys Thr His Thr Leu
465                 470                 475                 480

Ser Cys Gly Gly Gln Gly Ser Ser Thr Pro Ala Cys Pro Leu Ser Val
                485                 490                 495

Leu Asn Thr Ala Asn Leu Gln Ala Leu Cys Pro Glu Val Gly Ile Trp
            500                 505                 510

Gly Pro Arg Gln Gln Val Gly Arg Ile Glu Asn Asn Gly Gly Arg Val
        515                 520                 525

Ser
```

<210> SEQ ID NO 82
<211> LENGTH: 1236
<212> TYPE: DNA
<213> ORGANISM: Mouse

<400> SEQUENCE: 82

| | |
|---|---|
| atgacgcgga gccccgcgct gctgctgctg ctattggggg ccctcccgtc ggctgaggcg | 60 |
| gcgcgaggac ccccaagaat ggcagacaaa gtggtccac ggcaggtggc ccgcctgggc | 120 |
| cgcactgtgc ggctacagtg cccagtggag ggggacccca caccgttgac catgtggacc | 180 |
| aaagatggcc gcacaatcca cagtggctgg agccgcttcc gtgtgctgcc ccagggtctg | 240 |
| aaggtgaagg aggtggaggc cgaggatgcc ggtgtttatg tgtgcaaggc caccaatggc | 300 |
| tttggcagcc tcagcgtcaa ctacactctc atcatcatgg atgatattag tccagggaag | 360 |
| gagagccctg gccaggtgg ttcttcgggg gccaggagg acccagccag ccagcagtgg | 420 |
| gcacggcctc gcttcacaca gccctccaag atgaggcgcc gagtgattgc acggcctgtg | 480 |
| ggtagctctg tgcggctcaa gtgtgtggcc agtgggcacc cacggccaga catcatgtgg | 540 |
| atgaaggatg accagacctt gacgcatcta gaggctagtg aacacagaaa gaagaagtgg | 600 |
| acactgagct tgaagaacct gaagcctgaa gacagtggca agtacacgtg ccgtgtatct | 660 |
| aacaaggccg gtgccatcaa cgccacctac aaagtggatg taatccaccc caaacctcca | 720 |
| gggcctccta tggcttcttc atcgtcatcc acaagcctgc catggcctgt ggtgatcggc | 780 |
| atcccagctg gtgctgtctt catcctaggc actgtgctgc tctggctttg ccagaccaag | 840 |
| aagaagccat gtgccccagc atctacactt cctgtgcctg gcatcgtcc cccagggaca | 900 |
| tcccgagaac gcagtggtga caaggacctg ccctcattgg ctgtgggcat atgtgaggag | 960 |
| catggatccg ccatgccccc ccagcacatc ctggcctctg gctcaactgc tggccccaag | 1020 |
| ctgtaccccca agctatacac agatgtgcac acacacacac atacacacac ctgcactcac | 1080 |

```
acgctctcat gtggagggca aggttcatca acaccagcat gtccactatc agtgctaaat    1140
acagcgaatc tccaagcact gtgtcctgag gtaggcattt gggggccaag gcaacaggtt    1200
gggagaattg agaacaatgg aggaagagta tcttag                              1236
```

<210> SEQ ID NO 83
<211> LENGTH: 411
<212> TYPE: PRT
<213> ORGANISM: Mouse

<400> SEQUENCE: 83

```
Met Thr Arg Ser Pro Ala Leu Leu Leu Leu Leu Gly Ala Leu Pro
 1               5                  10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Leu Thr Met Trp Thr Lys Asp Gly Arg
50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
            100                 105                 110

Met Asp Asp Ile Ser Pro Gly Lys Glu Ser Pro Gly Pro Gly Gly Ser
        115                 120                 125

Ser Gly Gly Gln Glu Asp Pro Ala Ser Gln Gln Trp Ala Arg Pro Arg
    130                 135                 140

Phe Thr Gln Pro Ser Lys Met Arg Arg Arg Val Ile Ala Arg Pro Val
145                 150                 155                 160

Gly Ser Ser Val Arg Leu Lys Cys Val Ala Ser Gly His Pro Arg Pro
                165                 170                 175

Asp Ile Met Trp Met Lys Asp Asp Gln Thr Leu Thr His Leu Glu Ala
            180                 185                 190

Ser Glu His Arg Lys Lys Lys Trp Thr Leu Ser Leu Lys Asn Leu Lys
        195                 200                 205

Pro Glu Asp Ser Gly Lys Tyr Thr Cys Arg Val Ser Asn Lys Ala Gly
    210                 215                 220

Ala Ile Asn Ala Thr Tyr Lys Val Asp Val Ile His Pro Lys Pro Pro
225                 230                 235                 240

Gly Pro Pro Met Ala Ser Ser Ser Ser Thr Ser Leu Pro Trp Pro
                245                 250                 255

Val Val Ile Gly Ile Pro Ala Gly Ala Val Phe Ile Leu Gly Thr Val
            260                 265                 270

Leu Leu Trp Leu Cys Gln Thr Lys Lys Pro Cys Ala Pro Ala Ser
        275                 280                 285

Thr Leu Pro Val Pro Gly His Arg Pro Pro Gly Thr Ser Arg Glu Arg
    290                 295                 300

Ser Gly Asp Lys Asp Leu Pro Ser Leu Ala Val Gly Ile Cys Glu Glu
305                 310                 315                 320

His Gly Ser Ala Met Ala Pro Gln His Ile Leu Ala Ser Gly Ser Thr
                325                 330                 335

Ala Gly Pro Lys Leu Tyr Pro Lys Leu Tyr Thr Asp Val His Thr His
```

-continued

```
            340                 345                 350
Thr His Thr His Thr Cys Thr His Thr Leu Ser Cys Gly Gly Gln Gly
            355                 360                 365

Ser Ser Thr Pro Ala Cys Pro Leu Ser Val Leu Asn Thr Ala Asn Leu
    370                 375                 380

Gln Ala Leu Cys Pro Glu Val Gly Ile Trp Gly Pro Arg Gln Val
385                 390                 395                 400

Gly Arg Ile Glu Asn Asn Gly Gly Arg Val Ser
                405                 410
```

```
<210> SEQ ID NO 84
<211> LENGTH: 1305
<212> TYPE: DNA
<213> ORGANISM: Mouse

<400> SEQUENCE: 84
atgacgcgga gccccgcgct gctgctgctg ctattggggg ccctcccgtc ggctgaggcg     60
gcgcgaggac ccccaagaat ggcagacaaa gtggtcccac ggcaggtggc ccgcctgggc    120
cgcactgtgc ggctacagtg cccagtggag ggggacccac accgttgac catgtggacc     180 aaagatggcc gcacaatcca cagtggctgg agccgcttcc gtgtgctgcc ccagggtctg    240
aaggtgaagg aggtggaggc cgaggatgcc ggtgtttatg tgtgcaaggc caccaatggc    300
tttggcagcc tcagcgtcaa ctacactctc atcatcatgg atgatattag tccagggaag    360
gagagccctg ggccaggtgg ttcttcgggg gccaggagg acccagccag ccagcagtgg     420
gagcggactc gttccaagcc tgtgctcaca gggacacacc ctgtgaacac aacggtggac    480
ttcggtggga caacgtcctt ccagtgcaag gtgcgcagtg acgtgaagcc tgtgatccag    540
tggctgaagc gggtggagta cggctccgag ggacgccaca actccaccat tgatgtgggt    600
ggccagaagt ttgtggtgtt gcccacgggt gatgtgtggt cacggcctga tggctcctac    660
ctcaacaagc tgctcatctc tcgggcccgc caggatgatg ctggcatgta catctgccta    720
ggtgcaaata ccatgggcta cagttttccgt agcgccttcc tcactgtatt accgaccccc    780
aaacctccag ggcctcctat ggcttcttca tcgtcatcca aagcctgcc atggcctgtg     840 gtgatcggca tcccagctgg tgctgtcttc atcctaggca ctgtgctgct ctggcttttgc    900 cagaccaaga agaagccatg tgccccagca tctacacttc ctgtgcctgg gcatcgtccc    960
ccagggacat cccgagaacg cagtggtgac aaggacctgc cctcattggc tgtgggcata    1020
tgtgaggagc atggatccgc catggccccc cagcacatcc tggcctctgg ctcaactgct    1080
ggccccaagc tgtaccccaa gctatacaca gatgtgcaca cacacacaca tacacacacc    1140
tgcactcaca cgctctcatg tggagggcaa ggttcatcaa caccagcatg tccactatca    1200
gtgctaaata cagcgaatct ccaagcactg tgtcctgagg taggcatttg ggggccaagg    1260
caacaggttg ggagaattga gaacaatgga ggaagagtat cttag                    1305
```

```
<210> SEQ ID NO 85
<211> LENGTH: 434
<212> TYPE: PRT
<213> ORGANISM: Mouse

<400> SEQUENCE: 85

Met Thr Arg Ser Pro Ala Leu Leu Leu Leu Leu Gly Ala Leu Pro
1               5                   10                  15

Ser Ala Glu Ala Ala Arg Gly Pro Pro Arg Met Ala Asp Lys Val Val
            20                  25                  30
```

-continued

```
Pro Arg Gln Val Ala Arg Leu Gly Arg Thr Val Arg Leu Gln Cys Pro
         35                  40                  45
Val Glu Gly Asp Pro Pro Leu Thr Met Trp Thr Lys Asp Gly Arg
 50                  55                  60
Thr Ile His Ser Gly Trp Ser Arg Phe Arg Val Leu Pro Gln Gly Leu
 65                  70                  75                  80
Lys Val Lys Glu Val Glu Ala Glu Asp Ala Gly Val Tyr Val Cys Lys
                 85                  90                  95
Ala Thr Asn Gly Phe Gly Ser Leu Ser Val Asn Tyr Thr Leu Ile Ile
                100                 105                 110
Met Asp Asp Ile Ser Pro Gly Lys Glu Ser Pro Gly Pro Gly Gly Ser
             115                 120                 125
Ser Gly Gly Gln Glu Asp Pro Ala Ser Gln Gln Trp Glu Arg Thr Arg
         130                 135                 140
Ser Lys Pro Val Leu Thr Gly Thr His Pro Val Asn Thr Thr Val Asp
145                 150                 155                 160
Phe Gly Gly Thr Thr Ser Phe Gln Cys Lys Val Arg Ser Asp Val Lys
                165                 170                 175
Pro Val Ile Gln Trp Leu Lys Arg Val Glu Tyr Gly Ser Glu Gly Arg
                180                 185                 190
His Asn Ser Thr Ile Asp Val Gly Gly Gln Lys Phe Val Val Leu Pro
            195                 200                 205
Thr Gly Asp Val Trp Ser Arg Pro Asp Gly Ser Tyr Leu Asn Lys Leu
        210                 215                 220
Leu Ile Ser Arg Ala Arg Gln Asp Asp Ala Gly Met Tyr Ile Cys Leu
225                 230                 235                 240
Gly Ala Asn Thr Met Gly Tyr Ser Phe Arg Ser Ala Phe Leu Thr Val
                245                 250                 255
Leu Pro Asp Pro Lys Pro Pro Gly Pro Pro Met Ala Ser Ser Ser Ser
            260                 265                 270
Ser Thr Ser Leu Pro Trp Pro Val Val Ile Gly Ile Pro Ala Gly Ala
        275                 280                 285
Val Phe Ile Leu Gly Thr Val Leu Leu Trp Leu Cys Gln Thr Lys Lys
        290                 295                 300
Lys Pro Cys Ala Pro Ala Ser Thr Leu Pro Val Pro Gly His Arg Pro
305                 310                 315                 320
Pro Gly Thr Ser Arg Glu Arg Ser Gly Asp Lys Asp Leu Pro Ser Leu
                325                 330                 335
Ala Val Gly Ile Cys Glu Glu His Gly Ser Ala Met Ala Pro Gln His
            340                 345                 350
Ile Leu Ala Ser Gly Ser Thr Ala Gly Pro Lys Leu Tyr Pro Lys Leu
        355                 360                 365
Tyr Thr Asp Val His Thr His Thr His Thr Cys Thr His Thr
        370                 375                 380
Leu Ser Cys Gly Gly Gln Gly Ser Ser Thr Pro Ala Cys Pro Leu Ser
385                 390                 395                 400
Val Leu Asn Thr Ala Asn Leu Gln Ala Leu Cys Pro Glu Val Gly Ile
            405                 410                 415
Trp Gly Pro Arg Gln Gln Val Gly Arg Ile Glu Asn Asn Gly Gly Arg
        420                 425                 430
Val Ser
```

<210> SEQ ID NO 86
<211> LENGTH: 1509
<212> TYPE: DNA
<213> ORGANISM: Mouse

<400> SEQUENCE: 86

| | | | | | |
|---|---|---|---|---|---|
| atgacgcgga | gccccgcgct | gctgctgctg | ctattggggg | ccctcccgtc | ggctgaggcg | 60 |
| gcgcgaggac | ccccaagaat | ggcagacaaa | gtggtcccac | ggcaggtggc | ccgcctgggc | 120 |
| cgcactgtgc | ggctacagtg | cccagtggag | ggggacccac | caccgttgac | catgtggacc | 180 |
| aaagatggcc | gcacaatcca | cagtggctgg | agccgcttcc | gtgtgctgcc | ccagggtctg | 240 |
| aaggtgaagg | aggtggaggc | cgaggatgcc | ggtgtttatg | tgtgcaaggc | caccaatggc | 300 |
| tttggcagcc | tcagcgtcaa | ctacactctc | atcatcatgg | cacggcctcg | cttcacacag | 360 |
| ccctccaaga | tgaggcgccg | agtgattgca | cggcctgtgg | gtagctctgt | gcggctcaag | 420 |
| tgtgtggcca | gtgggcaccc | acggccagac | atcatgtgga | tgaaggatga | ccagaccttg | 480 |
| acgcatctag | aggctagtga | acacagaaag | aagaagtgga | cactgagctt | gaagaacctg | 540 |
| aagcctgaag | acagtggcaa | gtacacgtgc | cgtgtatcta | acaaggccgg | tgccatcaac | 600 |
| gccacctaca | agtggatgt | aatccagcgg | actcgttcca | agcctgtgct | cacagggaca | 660 |
| caccctgtga | acacaacggt | ggacttcggt | gggacaacgt | ccttccagtg | caaggtgcgc | 720 |
| agtgacgtga | agcctgtgat | ccagtggctg | aagcgggtgg | agtacggctc | cgaggacgc | 780 |
| cacaactcca | ccattgatgt | gggtggccag | aagtttgtgg | tgttgcccac | gggtgatgtg | 840 |
| tggtcacggc | ctgatggctc | ctacctcaac | aagctgctca | tctctcgggc | ccgccaggat | 900 |
| gatgctggca | tgtacatctg | cctaggtgca | ataccatgg | gctacagttt | ccgtagcgcc | 960 |
| ttcctcactg | tattaccaga | ccccaaacct | ccagggcctc | ctatggcttc | ttcatcgtca | 1020 |
| tccacaagcc | tgccatggcc | tgtggtgatc | ggcatcccag | ctggtgctgt | cttcatccta | 1080 |
| ggcactgtgc | tgctctggct | tgccagacc | aagaagaagc | catgtgcccc | agcatctaca | 1140 |
| cttcctgtgc | ctgggcatcg | tcccccaggg | acatcccgag | aacgcagtgg | tgacaaggac | 1200 |
| ctgccctcat | ggctgtgggg | catatgtgag | gagcatggat | ccgccatggc | cccccagcac | 1260 |
| atcctggcct | ctggctcaac | tgctggcccc | aagctgtacc | ccaagctata | cacagatgtg | 1320 |
| cacacacaca | cacatacaca | cacctgcact | cacacgctct | catgtggagg | caaggttca | 1380 |
| tcaacaccag | catgtccact | atcagtgcta | aatacagcga | atctccaagc | actgtgtcct | 1440 |
| gaggtaggca | tttgggggcc | aaggcaacag | gttgggagaa | ttgagaacaa | tggaggaaga | 1500 |
| gtatcttag | | | | | 1509 |

<210> SEQ ID NO 87
<211> LENGTH: 502
<212> TYPE: PRT
<213> ORGANISM: Mouse

<400> SEQUENCE: 87

Met Thr Arg Ser Pro Ala Leu Leu Leu Leu Leu Gly Ala Leu Pro
1               5                   10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Pro Leu Thr Met Trp Thr Lys Asp Gly Arg
        50                  55                  60

-continued

```
Thr Ile His Ser Gly Trp Ser Arg Phe Arg Val Leu Pro Gln Gly Leu
 65                  70                  75                  80

Lys Val Lys Glu Val Glu Ala Glu Asp Ala Gly Val Tyr Val Cys Lys
                 85                  90                  95

Ala Thr Asn Gly Phe Gly Ser Leu Ser Val Asn Tyr Thr Leu Ile Ile
            100                 105                 110

Met Ala Arg Pro Arg Phe Thr Gln Pro Ser Lys Met Arg Arg Arg Val
        115                 120                 125

Ile Ala Arg Pro Val Gly Ser Ser Val Arg Leu Lys Cys Val Ala Ser
    130                 135                 140

Gly His Pro Arg Pro Asp Ile Met Trp Met Lys Asp Asp Gln Thr Leu
145                 150                 155                 160

Thr His Leu Glu Ala Ser Glu His Arg Lys Lys Lys Trp Thr Leu Ser
                165                 170                 175

Leu Lys Asn Leu Lys Pro Glu Asp Ser Gly Lys Tyr Thr Cys Arg Val
            180                 185                 190

Ser Asn Lys Ala Gly Ala Ile Asn Ala Thr Tyr Lys Val Asp Val Ile
        195                 200                 205

Gln Arg Thr Arg Ser Lys Pro Val Leu Thr Gly Thr His Pro Val Asn
    210                 215                 220

Thr Thr Val Asp Phe Gly Gly Thr Thr Ser Phe Gln Cys Lys Val Arg
225                 230                 235                 240

Ser Asp Val Lys Pro Val Ile Gln Trp Leu Lys Arg Val Glu Tyr Gly
                245                 250                 255

Ser Glu Gly Arg His Asn Ser Thr Ile Asp Val Gly Gly Gln Lys Phe
            260                 265                 270

Val Val Leu Pro Thr Gly Asp Val Trp Ser Arg Pro Asp Gly Ser Tyr
        275                 280                 285

Leu Asn Lys Leu Leu Ile Ser Arg Ala Arg Gln Asp Asp Ala Gly Met
    290                 295                 300

Tyr Ile Cys Leu Gly Ala Asn Thr Met Gly Tyr Ser Phe Arg Ser Ala
305                 310                 315                 320

Phe Leu Thr Val Leu Pro Asp Pro Lys Pro Gly Pro Pro Met Ala
                325                 330                 335

Ser Ser Ser Ser Ser Thr Ser Leu Pro Trp Pro Val Val Ile Gly Ile
            340                 345                 350

Pro Ala Gly Ala Val Phe Ile Leu Gly Thr Val Leu Leu Trp Leu Cys
        355                 360                 365

Gln Thr Lys Lys Lys Pro Cys Ala Pro Ala Ser Thr Leu Pro Val Pro
    370                 375                 380

Gly His Arg Pro Pro Gly Thr Ser Arg Glu Arg Ser Gly Asp Lys Asp
385                 390                 395                 400

Leu Pro Ser Leu Ala Val Gly Ile Cys Glu Glu His Gly Ser Ala Met
                405                 410                 415

Ala Pro Gln His Ile Leu Ala Ser Gly Ser Thr Ala Gly Pro Lys Leu
            420                 425                 430

Tyr Pro Lys Leu Tyr Thr Asp Val His Thr His Thr His Thr His Thr
        435                 440                 445

Cys Thr His Thr Leu Ser Cys Gly Gly Gln Ser Ser Thr Pro Ala
    450                 455                 460

Cys Pro Leu Ser Val Leu Asn Thr Ala Asn Leu Gln Ala Leu Cys Pro
465                 470                 475                 480

Glu Val Gly Ile Trp Gly Pro Arg Gln Gln Val Gly Arg Ile Glu Asn
```

Asn Gly Gly Arg Val Ser
            500

<210> SEQ ID NO 88
<211> LENGTH: 1317
<212> TYPE: DNA
<213> ORGANISM: Mouse

<400> SEQUENCE: 88

| | | | | | |
|---|---|---|---|---|---|
| atgacgcgga | gccccgcgct | gctgctgctg | ctattggggg | ccctcccgtc | ggctgaggcg | 60 |
| gcgcgagatg | atattagtcc | agggaaggag | agccctgggc | caggtggttc | ttcgggggc | 120 |
| caggaggacc | cagccagcca | gcagtgggca | cggcctcgct | tcacacagcc | ctccaagatg | 180 |
| aggcgccgag | tgattgcacg | gcctgtgggt | agctctgtgc | ggctcaagtg | tgtggccagt | 240 |
| gggcacccac | ggccagacat | catgtggatg | aaggatgacc | agaccttgac | gcatctagag | 300 |
| gctagtgaac | acagaaagaa | gaagtggaca | ctgagcttga | agaacctgaa | gcctgaagac | 360 |
| agtggcaagt | acacgtgccg | tgtatctaac | aaggccggtg | ccatcaacgc | cacctacaaa | 420 |
| gtggatgtaa | tccagcggac | tcgttccaag | cctgtgctca | cagggacaca | ccctgtgaac | 480 |
| acaacggtgg | acttcggtgg | gacaacgtcc | ttccagtgca | aggtgcgcag | tgacgtgaag | 540 |
| cctgtgatcc | agtggctgaa | gcgggtggag | tacggctccg | agggacgcca | caactccacc | 600 |
| attgatgtgg | gtggccagaa | gtttgtggtg | ttgcccacgg | gtgatgtgtg | gtcacggcct | 660 |
| gatggctcct | acctcaacaa | gctgctcatc | tctcgggccc | gccaggatga | tgctggcatg | 720 |
| tacatctgcc | taggtgcaaa | taccatgggc | tacagtttcc | gtagcgcctt | cctcactgta | 780 |
| ttaccagacc | ccaaacctcc | agggcctcct | atggcttctt | catcgtcatc | acaagcctg | 840 |
| ccatggcctg | tggtgatcgg | catcccagct | ggtgctgtct | tcatcctagg | cactgtgctg | 900 |
| ctctggcttt | gccagaccaa | gaagaagcca | tgtgccccag | catctacact | tcctgtgcct | 960 |
| gggcatcgtc | cccagggac | atcccgagaa | cgcagtggtg | acaaggacct | gccctcattg | 1020 |
| gctgtgggca | tatgtgagga | gcatggatcc | gccatggccc | ccagcacat | cctggcctct | 1080 |
| ggctcaactg | ctggcccccaa | gctgtacccc | aagctataca | cagatgtgca | cacacacaca | 1140 |
| catacacaca | cctgcactca | cacgctctca | tgtggagggc | aaggttcatc | aacaccagca | 1200 |
| tgtccactat | cagtgctaaa | tacagcgaat | ctccaagcac | tgtgtcctga | ggtaggcatt | 1260 |
| tgggggccaa | ggcaacaggt | tgggagaatt | gagaacaatg | gaggaagagt | atcttag | 1317 |

<210> SEQ ID NO 89
<211> LENGTH: 438
<212> TYPE: PRT
<213> ORGANISM: Mouse

<400> SEQUENCE: 89

Met Thr Arg Ser Pro Ala Leu Leu Leu Leu Leu Gly Ala Leu Pro
1               5                   10                  15

Ser Ala Glu Ala Ala Arg Asp Asp Ile Ser Pro Gly Lys Glu Ser Pro
                20                  25                  30

Gly Pro Gly Gly Ser Gly Gly Gln Glu Asp Pro Ala Ser Gln Gln
            35                  40                  45

Trp Ala Arg Pro Arg Phe Thr Gln Pro Ser Lys Met Arg Arg Arg Val
    50                  55                  60

Ile Ala Arg Pro Val Gly Ser Ser Val Arg Leu Lys Cys Val Ala Ser
65                  70                  75                  80

```
Gly His Pro Arg Pro Asp Ile Met Trp Met Lys Asp Asp Gln Thr Leu
                85                  90                  95
Thr His Leu Glu Ala Ser Glu His Arg Lys Lys Lys Trp Thr Leu Ser
            100                 105                 110
Leu Lys Asn Leu Lys Pro Glu Asp Ser Gly Lys Tyr Thr Cys Arg Val
        115                 120                 125
Ser Asn Lys Ala Gly Ala Ile Asn Ala Thr Tyr Lys Val Asp Val Ile
    130                 135                 140
Gln Arg Thr Arg Ser Lys Pro Val Leu Thr Gly Thr His Pro Val Asn
145                 150                 155                 160
Thr Thr Val Asp Phe Gly Gly Thr Thr Ser Phe Gln Cys Lys Val Arg
                165                 170                 175
Ser Asp Val Lys Pro Val Ile Gln Trp Leu Lys Arg Val Glu Tyr Gly
                180                 185                 190
Ser Glu Gly Arg His Asn Ser Thr Ile Asp Val Gly Gly Gln Lys Phe
            195                 200                 205
Val Val Leu Pro Thr Gly Asp Val Trp Ser Arg Pro Asp Gly Ser Tyr
        210                 215                 220
Leu Asn Lys Leu Leu Ile Ser Arg Ala Arg Gln Asp Asp Ala Gly Met
225                 230                 235                 240
Tyr Ile Cys Leu Gly Ala Asn Thr Met Gly Tyr Ser Phe Arg Ser Ala
                245                 250                 255
Phe Leu Thr Val Leu Pro Asp Pro Lys Pro Pro Gly Pro Pro Met Ala
                260                 265                 270
Ser Ser Ser Ser Thr Ser Leu Pro Trp Pro Val Val Ile Gly Ile
            275                 280                 285
Pro Ala Gly Ala Val Phe Ile Leu Gly Thr Val Leu Leu Trp Leu Cys
        290                 295                 300
Gln Thr Lys Lys Lys Pro Cys Ala Pro Ala Ser Thr Leu Pro Val Pro
305                 310                 315                 320
Gly His Arg Pro Pro Gly Thr Ser Arg Glu Arg Ser Gly Asp Lys Asp
                325                 330                 335
Leu Pro Ser Leu Ala Val Gly Ile Cys Glu Glu His Gly Ser Ala Met
                340                 345                 350
Ala Pro Gln His Ile Leu Ala Ser Gly Ser Thr Ala Gly Pro Lys Leu
            355                 360                 365
Tyr Pro Lys Leu Tyr Thr Asp Val His Thr His Thr His Thr
        370                 375                 380
Cys Thr His Thr Leu Ser Cys Gly Gln Gly Ser Ser Thr Pro Ala
385                 390                 395                 400
Cys Pro Leu Ser Val Leu Asn Thr Ala Asn Leu Gln Ala Leu Cys Pro
                405                 410                 415
Glu Val Gly Ile Trp Gly Pro Arg Gln Gln Val Gly Arg Ile Glu Asn
                420                 425                 430
Asn Gly Gly Arg Val Ser
            435

<210> SEQ ID NO 90
<211> LENGTH: 951
<212> TYPE: DNA
<213> ORGANISM: Mouse

<400> SEQUENCE: 90
atgacgcgga gccccgcgct gctgctgctg ctattggggg ccctcccgtc ggctgaggcg      60
```

```
gcgcgaggac cccaagaat ggcagacaaa gtggtccac ggcaggtggc ccgcctgggc    120
cgcactgtgc ggctacagtg cccagtggag ggggaccccac caccgttgac catgtggacc   180
aaagatggcc gcacaatcca cagtggctgg agccgcttcc gtgtgctgcc ccagggtctg    240
aaggtgaagg aggtggaggc cgaggatgcc ggtgtttatg tgtgcaaggc caccaatggc    300
tttggcagcc tcagcgtcaa ctacactctc atcatcatgg atgatattag tccagggaag    360
gagagccctg gccaggtgg ttcttcgggg gccaggagg acccagccag ccagcagtgg     420
gaccccaaac ctccagggcc tcctatggct tcttcatcgt catccacaag cctgccatgg    480
cctgtggtga tcggcatccc agctggtgct gtcttcatcc taggcactgt gctgctctgg    540
ctttgccaga ccaagaagaa gccatgtgcc ccagcatcta cacttcctgt gcctgggcat    600
cgtcccccag ggacatcccg agaacgcagt ggtgacaagg acctgccctc attggctgtg    660
ggcatatgtg aggagcatgg atccgccatg gccccccagc acatcctggc ctctggctca    720
actgctggcc ccaagctgta ccccaagcta tacacagatg tgcacacaca cacacataca    780
cacacctgca ctcacacgct tcatgtgga gggcaaggtt catcaacacc agcatgtcca    840
ctatcagtgc taaatacagc gaatctccaa gcactgtgtc ctgaggtagg catttggggg    900
ccaaggcaac aggttgggag aattgagaac aatggaggaa gagtatctta g            951
```

<210> SEQ ID NO 91
<211> LENGTH: 316
<212> TYPE: PRT
<213> ORGANISM: Mouse

<400> SEQUENCE: 91

```
Met Thr Arg Ser Pro Ala Leu Leu Leu Leu Gly Ala Leu Pro
1               5                   10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Leu Thr Met Trp Thr Lys Asp Gly Arg
        50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
                100                 105                 110

Met Asp Asp Ile Ser Pro Gly Lys Glu Ser Pro Gly Pro Gly Gly Ser
            115                 120                 125

Ser Gly Gly Gln Glu Asp Pro Ala Ser Gln Gln Trp Asp Pro Lys Pro
    130                 135                 140

Pro Gly Pro Pro Met Ala Ser Ser Ser Ser Thr Ser Leu Pro Trp
145                 150                 155                 160

Pro Val Val Ile Gly Ile Pro Ala Gly Ala Val Phe Ile Leu Gly Thr
                165                 170                 175

Val Leu Leu Trp Leu Cys Gln Thr Lys Lys Lys Pro Cys Ala Pro Ala
                180                 185                 190

Ser Thr Leu Pro Val Pro Gly His Arg Pro Pro Gly Thr Ser Arg Glu
            195                 200                 205

Arg Ser Gly Asp Lys Asp Leu Pro Ser Leu Ala Val Gly Ile Cys Glu
```

```
                    210                 215                 220
Glu His Gly Ser Ala Met Ala Pro Gln His Ile Leu Ala Ser Gly Ser
225                 230                 235                 240

Thr Ala Gly Pro Lys Leu Tyr Pro Lys Leu Tyr Thr Asp Val His Thr
                245                 250                 255

His Thr His Thr His Thr Cys Thr His Thr Leu Ser Cys Gly Gly Gln
                260                 265                 270

Gly Ser Ser Thr Pro Ala Cys Pro Leu Ser Val Leu Asn Thr Ala Asn
            275                 280                 285

Leu Gln Ala Leu Cys Pro Glu Val Gly Ile Trp Gly Pro Arg Gln Gln
        290                 295                 300

Val Gly Arg Ile Glu Asn Asn Gly Gly Arg Val Ser
305                 310                 315

<210> SEQ ID NO 92
<211> LENGTH: 1155
<212> TYPE: DNA
<213> ORGANISM: Mouse

<400> SEQUENCE: 92
atgacgcgga gccccgcgct gctgctgctg ctattggggg ccctcccgtc ggctgaggcg     60
gcgcgaggac ccccaagaat ggcagacaaa gtggtcccac ggcaggtggc ccgcctgggc    120
cgcactgtgc ggctacagtg cccagtggag ggggaccccac caccgttgac catgtggacc    180
aaagatggcc gcacaatcca cagtggctgg agccgcttcc gtgtgctgcc ccagggtctg    240
aaggtgaagg aggtggaggc cgaggatgcc ggtgtttatg tgtgcaaggc caccaatggc    300
tttggcagcc tcagcgtcaa ctacactctc atcatcatgg cacggcctcg cttcacacag    360
ccctccaaga tgaggcgccg agtgattgca cggcctgtgg gtagctctgt gcggctcaag    420
tgtgtggcca gtgggcaccc acggccagac atcatgtgga tgaaggatga ccagaccttg    480
acgcatctag aggctagtga acacagaaag aagaagtgga cactgagctt gaagaacctg    540
aagcctgaag acagtggcaa gtacacgtgc cgtgtatcta caaggccggt gccatcaac    600 gccacctaca aagtggatgt aatccacccc aaacctccag ggcctcctat ggcttcttca    660
tcgtcatcca caagcctgcc atggcctgtg gtgatcggca tcccagctgg tgctgtcttc    720
atcctaggca ctgtgctgct ctggctttgc cagaccaaga gaagccatg tgccccagca    780 tctacacttc ctgtgcctgg gcatcgtccc caagggacat cccgagaacg cagtggtgac    840
aaggacctgc cctcattggc tgtgggcata tgtgaggagc atggatccgc catggccccc    900
cagcacatcc tggcctctgg ctcaactgct ggccccaagc tgtacccaa gctatacaca    960 gatgtgcaca cacacacaca tacacacacc tgcactcaca cgctctcatg tggagggcaa   1020
ggttcatcaa caccagcatg tccactatca gtgctaaata cagcgaatct ccaagcactg   1080
tgtcctgagg taggcatttg ggggccaagg caacaggttg ggagaattga gaacaatgga   1140
ggaagagtat cttag                                                    1155

<210> SEQ ID NO 93
<211> LENGTH: 384
<212> TYPE: PRT
<213> ORGANISM: Mouse

<400> SEQUENCE: 93

Met Thr Arg Ser Pro Ala Leu Leu Leu Leu Leu Leu Gly Ala Leu Pro
1               5                  10                  15
```

```
Ser Ala Glu Ala Ala Arg Gly Pro Pro Arg Met Ala Asp Lys Val Val
             20                  25                  30

Pro Arg Gln Val Ala Arg Leu Gly Arg Thr Val Arg Leu Gln Cys Pro
         35                  40                  45

Val Glu Gly Asp Pro Pro Leu Thr Met Trp Thr Lys Asp Gly Arg
     50                  55                  60

Thr Ile His Ser Gly Trp Ser Arg Phe Arg Val Leu Pro Gln Gly Leu
 65                  70                  75                  80

Lys Val Lys Glu Val Glu Ala Glu Asp Ala Gly Val Tyr Val Cys Lys
                 85                  90                  95

Ala Thr Asn Gly Phe Gly Ser Leu Ser Val Asn Tyr Thr Leu Ile Ile
             100                 105                 110

Met Ala Arg Pro Arg Phe Thr Gln Pro Ser Lys Met Arg Arg Val
         115                 120                 125

Ile Ala Arg Pro Val Gly Ser Ser Val Arg Leu Lys Cys Val Ala Ser
 130                 135                 140

Gly His Pro Arg Pro Asp Ile Met Trp Met Lys Asp Asp Gln Thr Leu
145                 150                 155                 160

Thr His Leu Glu Ala Ser Glu His Arg Lys Lys Trp Thr Leu Ser
                 165                 170                 175

Leu Lys Asn Leu Lys Pro Glu Asp Ser Gly Lys Tyr Thr Cys Arg Val
             180                 185                 190

Ser Asn Lys Ala Gly Ala Ile Asn Ala Thr Tyr Lys Val Asp Val Ile
         195                 200                 205

His Pro Lys Pro Pro Gly Pro Pro Met Ala Ser Ser Ser Ser Thr
 210                 215                 220

Ser Leu Pro Trp Pro Val Val Ile Gly Ile Pro Ala Gly Ala Val Phe
225                 230                 235                 240

Ile Leu Gly Thr Val Leu Leu Trp Leu Cys Gln Thr Lys Lys Pro
                 245                 250                 255

Cys Ala Pro Ala Ser Thr Leu Pro Val Pro Gly His Arg Pro Pro Gly
             260                 265                 270

Thr Ser Arg Glu Arg Ser Gly Asp Lys Asp Leu Pro Ser Leu Ala Val
         275                 280                 285

Gly Ile Cys Glu Glu His Gly Ser Ala Met Ala Pro Gln His Ile Leu
 290                 295                 300

Ala Ser Gly Ser Thr Ala Gly Pro Lys Leu Tyr Pro Lys Leu Tyr Thr
305                 310                 315                 320

Asp Val His Thr His Thr His Thr Cys Thr His Thr Leu Ser
                 325                 330                 335

Cys Gly Gly Gln Gly Ser Ser Thr Pro Ala Cys Pro Leu Ser Val Leu
             340                 345                 350

Asn Thr Ala Asn Leu Gln Ala Leu Cys Pro Glu Val Gly Ile Trp Gly
         355                 360                 365

Pro Arg Gln Gln Val Gly Arg Ile Glu Asn Asn Gly Gly Arg Val Ser
 370                 375                 380
```

<210> SEQ ID NO 94
<211> LENGTH: 1224
<212> TYPE: DNA
<213> ORGANISM: Mouse

<400> SEQUENCE: 94
atgacgcgga gccccgcgct gctgctgctg ctattggggg ccctccccgtc ggctgaggcg    60

-continued

| | |
|---|---|
| gcgcgaggac cccaagaat ggcagacaaa gtggtccac ggcaggtggc ccgcctggc | 120 |
| cgcactgtgc ggctacagtg cccagtggag ggggacccac caccgttgac catgtggacc | 180 |
| aaagatggcc gcacaatcca cagtggctgg agccgcttcc gtgtgctgcc ccagggtctg | 240 |
| aaggtgaagg aggtggaggc cgaggatgcc ggtgtttatg tgtgcaaggc caccaatggc | 300 |
| tttggcagcc tcagcgtcaa ctacactctc atcatcatgg agcggactcg ttccaagcct | 360 |
| gtgctcacag ggacacaccc tgtgaacaca acggtggact cggtgggac aacgtccttc | 420 |
| cagtgcaagg tgcgcagtga cgtgaagcct gtgatccagt ggctgaagcg ggtggagtac | 480 |
| ggctccgagg gacgccacaa ctccaccatt gatgtgggtg ccagaagtt tgtggtgttg | 540 |
| cccacgggtg atgtgtggtc acggcctgat ggctcctacc tcaacaagct gctcatctct | 600 |
| cgggcccgcc aggatgatgc tggcatgtac atctgcctag gtcaaatac catgggctac | 660 |
| agtttccgta gcgccttcct cactgtatta ccagacccca aacctccagg gcctcctatg | 720 |
| gcttcttcat cgtcatccac aagcctgcca tggcctgtgg tgatcggcat cccagctggt | 780 |
| gctgtcttca tcctaggcac tgtgctgctc tggctttgcc agaccaagaa gaagccatgt | 840 |
| gccccagcat ctacacttcc tgtgcctggg catcgtcccc cagggacatc ccgagaacgc | 900 |
| agtggtgaca aggacctgcc ctcattggct gtgggcatat gtgaggagca tggatccgcc | 960 |
| atggccccc agcacatcct ggcctctggc tcaactgctg gccccaagct gtaccccaag | 1020 |
| ctatacacag atgtgcacac acacacacat acacacacct gcactcacac gctctcatgt | 1080 |
| ggagggcaag gttcatcaac accagcatgt ccactatcag tgctaaatac agcgaatctc | 1140 |
| caagcactgt gtcctgaggt aggcatttgg gggccaaggc aacaggttgg gagaattgag | 1200 |
| aacaatggag gaagagtatc ttag | 1224 |

<210> SEQ ID NO 95
<211> LENGTH: 407
<212> TYPE: PRT
<213> ORGANISM: Mouse

<400> SEQUENCE: 95

Met Thr Arg Ser Pro Ala Leu Leu Leu Leu Gly Ala Leu Pro
1               5                   10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Leu Thr Met Trp Thr Lys Asp Gly Arg
        50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
            100                 105                 110

Met Glu Arg Thr Arg Ser Lys Pro Val Leu Thr Gly Thr His Pro Val
        115                 120                 125

Asn Thr Thr Val Asp Phe Gly Gly Thr Thr Ser Phe Gln Cys Lys Val
    130                 135                 140

Arg Ser Asp Val Lys Pro Val Ile Gln Trp Leu Lys Arg Val Glu Tyr
145                 150                 155                 160

Gly Ser Glu Gly Arg His Asn Ser Thr Ile Asp Val Gly Gly Gln Lys

```
                         165                 170                 175
    Phe Val Leu Pro Thr Gly Asp Val Trp Ser Arg Pro Asp Gly Ser
                    180                 185                 190

Tyr Leu Asn Lys Leu Leu Ile Ser Arg Ala Arg Gln Asp Asp Ala Gly
                195                 200                 205

Met Tyr Ile Cys Leu Gly Ala Asn Thr Met Gly Tyr Ser Phe Arg Ser
                210                 215                 220

Ala Phe Leu Thr Val Leu Pro Asp Pro Lys Pro Gly Pro Pro Met
    225                 230                 235                 240

Ala Ser Ser Ser Ser Thr Ser Leu Pro Trp Pro Val Val Ile Gly
                    245                 250                 255

Ile Pro Ala Gly Ala Val Phe Ile Leu Gly Thr Val Leu Leu Trp Leu
                260                 265                 270

Cys Gln Thr Lys Lys Lys Pro Cys Ala Pro Ala Ser Thr Leu Pro Val
                275                 280                 285

Pro Gly His Arg Pro Pro Gly Thr Ser Arg Glu Arg Ser Gly Asp Lys
                290                 295                 300

Asp Leu Pro Ser Leu Ala Val Gly Ile Cys Glu Glu His Gly Ser Ala
    305                 310                 315                 320

Met Ala Pro Gln His Ile Leu Ala Ser Gly Ser Thr Ala Gly Pro Lys
                325                 330                 335

Leu Tyr Pro Lys Leu Tyr Thr Asp Val His Thr His Thr His
                340                 345                 350

Thr Cys Thr His Thr Leu Ser Cys Gly Gly Gln Gly Ser Ser Thr Pro
                355                 360                 365

Ala Cys Pro Leu Ser Val Leu Asn Thr Ala Asn Leu Gln Ala Leu Cys
                370                 375                 380

Pro Glu Val Gly Ile Trp Gly Pro Arg Gln Gln Val Gly Arg Ile Glu
    385                 390                 395                 400

Asn Asn Gly Gly Arg Val Ser
                    405

<210> SEQ ID NO 96
<211> LENGTH: 963
<212> TYPE: DNA
<213> ORGANISM: Mouse

<400> SEQUENCE: 96
atgacgcgga gccccgcgct gctgctgctg ctattggggg ccctcccgtc ggctgaggcg      60
gcgcgagatg atattagtcc agggaaggag agccctgggc caggtggttc ttcgggggc     120 caggaggacc cagccagcca gcagtgggca cggcctcgct tcacacagcc ctccaagatg     180
aggcgccgag tgattgcacg gcctgtgggt agctctgtgc ggctcaagtg tgtggccagt     240
gggcacccac ggccagacat catgtggatg aaggatgacc agaccttgac gcatctagag     300
gctagtgaac acagaaagaa gaagtggaca ctgagcttga agaacctgaa gcctgaagac     360
agtggcaagt acacgtgccg tgtatctaac aaggccggtg ccatcaacgc cacctacaaa     420
gtggatgtaa tccaccccaa acctccaggg cctcctatgg cttcttcatc gtcatccaca     480
agcctgccat ggcctgtggt gatcggcatc ccagctggtg ctgtcttcat cctaggcact     540
gtgctgctct ggctttgcca gaccaagaag aagccatgtg ccccagcatc tacacttcct     600
gtgcctgggc atcgtccccc agggacatcc cgagaacgca gtggtgacaa ggacctgccc     660
tcattggctg tgggcatatg tgaggagcat ggatccgcca tggccccca gcacatcctg     720
```

-continued

```
gcctctggct caactgctgg ccccaagctg tacccaagc tatacacaga tgtgcacaca      780
cacacacata cacacacctg cactcacacg ctctcatgtg gagggcaagg ttcatcaaca      840
ccagcatgtc cactatcagt gctaaataca gcgaatctcc aagcactgtg tcctgaggta      900
ggcatttggg ggccaaggca acaggttggg agaattgaga caatggagg aagagtatct      960 tag                                                                    963
```

<210> SEQ ID NO 97
<211> LENGTH: 320
<212> TYPE: PRT
<213> ORGANISM: Mouse

<400> SEQUENCE: 97

```
Met Thr Arg Ser Pro Ala Leu Leu Leu Leu Leu Gly Ala Leu Pro
  1               5                  10                  15

Ser Ala Glu Ala Ala Arg Asp Asp Ile Ser Pro Gly Lys Glu Ser Pro
                 20                  25                  30

Gly Pro Gly Gly Ser Gly Gly Gln Glu Asp Pro Ala Ser Gln Gln
             35                  40                  45

Trp Ala Arg Pro Arg Phe Thr Gln Pro Ser Lys Met Arg Arg Val
 50                  55                  60

Ile Ala Arg Pro Val Gly Ser Ser Val Arg Leu Lys Cys Val Ala Ser
 65                  70                  75                  80

Gly His Pro Arg Pro Asp Ile Met Trp Met Lys Asp Gln Thr Leu
                 85                  90                  95

Thr His Leu Glu Ala Ser Glu His Arg Lys Lys Lys Trp Thr Leu Ser
                100                 105                 110

Leu Lys Asn Leu Lys Pro Glu Asp Ser Gly Lys Tyr Thr Cys Arg Val
            115                 120                 125

Ser Asn Lys Ala Gly Ala Ile Asn Ala Thr Tyr Lys Val Asp Val Ile
        130                 135                 140

His Pro Lys Pro Pro Gly Pro Pro Met Ala Ser Ser Ser Ser Thr
145                 150                 155                 160

Ser Leu Pro Trp Pro Val Val Ile Gly Ile Pro Ala Gly Ala Val Phe
                165                 170                 175

Ile Leu Gly Thr Val Leu Leu Trp Leu Cys Gln Thr Lys Lys Lys Pro
            180                 185                 190

Cys Ala Pro Ala Ser Thr Leu Pro Val Pro Gly His Arg Pro Pro Gly
        195                 200                 205

Thr Ser Arg Glu Arg Ser Gly Asp Lys Asp Leu Pro Ser Leu Ala Val
    210                 215                 220

Gly Ile Cys Glu Glu His Gly Ser Ala Met Ala Pro Gln His Ile Leu
225                 230                 235                 240

Ala Ser Gly Ser Thr Ala Gly Pro Lys Leu Tyr Pro Lys Leu Tyr Thr
                245                 250                 255

Asp Val His Thr His Thr His Thr Cys Thr His Thr Leu Ser
            260                 265                 270

Cys Gly Gly Gln Gly Ser Ser Thr Pro Ala Cys Pro Leu Ser Val Leu
        275                 280                 285

Asn Thr Ala Asn Leu Gln Ala Leu Cys Pro Glu Val Gly Ile Trp Gly
    290                 295                 300

Pro Arg Gln Gln Val Gly Arg Ile Glu Asn Asn Gly Gly Arg Val Ser
305                 310                 315                 320
```

<210> SEQ ID NO 98
<211> LENGTH: 1032
<212> TYPE: DNA
<213> ORGANISM: Mouse

<400> SEQUENCE: 98

| | | |
|---|---|---|
| atgacgcgga gccccgcgct gctgctgctg ctattggggg ccctcccgtc ggctgaggcg | 60 |
| gcgcgagatg atattagtcc agggaaggag agccctgggc caggtggttc ttcgggggc | 120 |
| caggaggacc cagccagcca gcagtgggag cggactcgtt ccaagcctgt gctcacaggg | 180 |
| acacaccctg tgaacacaac ggtggacttc ggtgggacaa cgtccttcca gtgcaaggtg | 240 |
| cgcagtgacg tgaagcctgt gatccagtgg ctgaagcggg tggagtacgg ctccgaggga | 300 |
| cgccacaact ccaccattga tgtgggtggc cagaagtttg tggtgttgcc cacgggtgat | 360 |
| gtgtggtcac ggcctgatgg ctcctacctc aacaagctgc tcatctctcg ggcccgccag | 420 |
| gatgatgctg gcatgtacat ctgcctaggt gcaaatacca tgggctacag tttccgtagc | 480 |
| gccttcctca ctgtattacc agaccccaaa cctccagggc tcctatggc ttcttcatcg | 540 |
| tcatccacaa gcctgccatg gcctgtggtg atcggcatcc cagctggtgc tgtcttcatc | 600 |
| ctaggcactg tgctgctctg gctttgccag accaagaaga agccatgtgc cccagcatct | 660 |
| acacttcctg tgcctgggca tcgtccccca gggacatccc gagaacgcag tggtgacaag | 720 |
| gacctgcct cattggctgt gggcatatgt gaggagcatg gatccgccat ggcccccag | 780 |
| cacatcctgg cctctggctc aactgctggc cccaagctgt accccaagct atacacagat | 840 |
| gtgcacacac acacacatac acacacctgc actcacacgc tctcatgtgg agggcaaggt | 900 |
| tcatcaacac cagcatgtcc actatcagtg ctaaatacag cgaatctcca agcactgtgt | 960 |
| cctgaggtag gcatttgggg gccaaggcaa caggttggga gaattgagaa caatggagga | 1020 |
| agagtatctt ag | 1032 |

<210> SEQ ID NO 99
<211> LENGTH: 343
<212> TYPE: PRT
<213> ORGANISM: Mouse

<400> SEQUENCE: 99

Met Thr Arg Ser Pro Ala Leu Leu Leu Leu Leu Gly Ala Leu Pro
1               5                   10                  15

Ser Ala Glu Ala Ala Arg Asp Asp Ile Ser Pro Gly Lys Glu Ser Pro
            20                  25                  30

Gly Pro Gly Gly Ser Gly Gly Gln Glu Asp Pro Ala Ser Gln Gln
        35                  40                  45

Trp Glu Arg Thr Arg Ser Lys Pro Val Leu Thr Gly Thr His Pro Val
    50                  55                  60

Asn Thr Thr Val Asp Phe Gly Gly Thr Thr Ser Phe Gln Cys Lys Val
65                  70                  75                  80

Arg Ser Asp Val Lys Pro Val Ile Gln Trp Leu Lys Arg Val Glu Tyr
                85                  90                  95

Gly Ser Glu Gly Arg His Asn Ser Thr Ile Asp Val Gly Gly Gln Lys
            100                 105                 110

Phe Val Val Leu Pro Thr Gly Asp Val Trp Ser Arg Pro Asp Gly Ser
        115                 120                 125

Tyr Leu Asn Lys Leu Leu Ile Ser Arg Ala Arg Gln Asp Asp Ala Gly
    130                 135                 140

Met Tyr Ile Cys Leu Gly Ala Asn Thr Met Gly Tyr Ser Phe Arg Ser

|   |   |   |   | 145 |   |   |   | 150 |   |   |   | 155 |   |   |   | 160 |
|---|---|---|---|---|---|---|---|---|---|---|---|---|---|---|---|---|

Ala Phe Leu Thr Val Leu Pro Asp Pro Lys Pro Pro Gly Pro Pro Met
              165             170             175

Ala Ser Ser Ser Ser Thr Ser Leu Pro Trp Pro Val Val Ile Gly
        180             185            190

Ile Pro Ala Gly Ala Val Phe Ile Leu Gly Thr Val Leu Leu Trp Leu
        195             200            205

Cys Gln Thr Lys Lys Pro Cys Ala Pro Ala Ser Thr Leu Pro Val
    210             215            220

Pro Gly His Arg Pro Pro Gly Thr Ser Arg Glu Arg Ser Gly Asp Lys
225             230            235           240

Asp Leu Pro Ser Leu Ala Val Gly Ile Cys Glu Glu His Gly Ser Ala
        245             250            255

Met Ala Pro Gln His Ile Leu Ala Ser Gly Ser Thr Ala Gly Pro Lys
        260             265            270

Leu Tyr Pro Lys Leu Tyr Thr Asp Val His Thr His Thr His Thr His
    275             280            285

Thr Cys Thr His Thr Leu Ser Cys Gly Gly Gln Gly Ser Ser Thr Pro
290             295            300

Ala Cys Pro Leu Ser Val Leu Asn Thr Ala Asn Leu Gln Ala Leu Cys
305             310            315           320

Pro Glu Val Gly Ile Trp Gly Pro Arg Gln Gln Val Gly Arg Ile Glu
        325             330            335

Asn Asn Gly Gly Arg Val Ser
        340

<210> SEQ ID NO 100
<211> LENGTH: 1236
<212> TYPE: DNA
<213> ORGANISM: Mouse

<400> SEQUENCE: 100

| | | | | | |
|---|---|---|---|---|---|
| atgacgcgga | gccccgcgct | gctgctgctg | ctattggggg | ccctcccgtc | ggctgaggcg | 60 |
| gcgcgagcac | ggcctcgctt | cacacagccc | tccaagatga | ggcgccgagt | gattgcacgg | 120 |
| cctgtgggta | gctctgtgcg | gctcaagtgt | gtggccagtg | gcacccacg | gccagacatc | 180 |
| atgtggatga | aggatgacca | gaccttgacg | catctagagg | ctagtgaaca | cagaaagaag | 240 |
| aagtggacac | tgagcttgaa | gaacctgaag | cctgaagaca | gtggcaagta | cacgtgccgt | 300 |
| gtatctaaca | aggccggtgc | catcaacgcc | acctacaaag | tggatgtaat | ccagcggact | 360 |
| cgttccaagc | tgtgctcac | agggacacac | cctgtgaaca | caacggtgga | cttcggtggg | 420 |
| acaacgtcct | tccagtgcaa | ggtgcgcagt | gacgtgaagc | tgtgatcca | gtggctgaag | 480 |
| cgggtggagt | acggctccga | gggacgccac | aactccacca | ttgatgtggg | tggccagaag | 540 |
| tttgtggtgt | tgcccacggg | tgatgtgtgg | tcacggcctg | atggctccta | cctcaacaag | 600 |
| ctgctcatct | ctcgggcccg | ccaggatgat | gctggcatgt | acatctgcct | aggtgcaaat | 660 |
| accatgggct | acagtttccg | tagcgccttc | ctcactgtat | accagacccc | aaacctcca | 720 |
| gggcctccta | tggcttcttc | atcgtcatcc | acaagcctgc | catggcctgt | ggtgatcggc | 780 |
| atcccagctg | gtgctgtctt | catcctaggc | actgtgctgc | tctggctttg | ccagaccaag | 840 |
| aagaagccat | gtgccccagc | atctacactt | cctgtgcctg | ggcatcgtcc | cccagggaca | 900 |
| tcccgagaac | gcagtggtga | caaggacctg | ccctcattgg | ctgtgggcat | atgtgaggag | 960 |
| catggatccg | ccatggcccc | ccagcacatc | ctggcctctg | gctcaactgc | tggccccaag | 1020 |

```
ctgtacccca agctatacac agatgtgcac acacacacac atacacacac ctgcactcac    1080
acgctctcat gtggagggca aggttcatca acaccagcat gtccactatc agtgctaaat    1140
acagcgaatc tccaagcact gtgtcctgag gtaggcattt gggggccaag gcaacaggtt    1200
gggagaattg agaacaatgg aggaagagta tcttag                              1236
```

<210> SEQ ID NO 101
<211> LENGTH: 411
<212> TYPE: PRT
<213> ORGANISM: Mouse

<400> SEQUENCE: 101

```
Met Thr Arg Ser Pro Ala Leu Leu Leu Leu Gly Ala Leu Pro
 1               5                  10                  15

Ser Ala Glu Ala Ala Arg Ala Arg Pro Arg Phe Thr Gln Pro Ser Lys
            20                  25                  30

Met Arg Arg Arg Val Ile Ala Arg Pro Val Gly Ser Ser Val Arg Leu
        35                  40                  45

Lys Cys Val Ala Ser Gly His Pro Arg Pro Asp Ile Met Trp Met Lys
 50                  55                  60

Asp Asp Gln Thr Leu Thr His Leu Glu Ala Ser Glu His Arg Lys Lys
65                   70                  75                  80

Lys Trp Thr Leu Ser Leu Lys Asn Leu Lys Pro Glu Asp Ser Gly Lys
                85                  90                  95

Tyr Thr Cys Arg Val Ser Asn Lys Ala Gly Ala Ile Asn Ala Thr Tyr
            100                 105                 110

Lys Val Asp Val Ile Gln Arg Thr Arg Ser Lys Pro Val Leu Thr Gly
        115                 120                 125

Thr His Pro Val Asn Thr Thr Val Asp Phe Gly Gly Thr Thr Ser Phe
130                 135                 140

Gln Cys Lys Val Arg Ser Asp Val Lys Pro Val Ile Gln Trp Leu Lys
145                 150                 155                 160

Arg Val Glu Tyr Gly Ser Glu Gly Arg His Asn Ser Thr Ile Asp Val
                165                 170                 175

Gly Gly Gln Lys Phe Val Val Leu Pro Thr Gly Asp Val Trp Ser Arg
            180                 185                 190

Pro Asp Gly Ser Tyr Leu Asn Lys Leu Leu Ile Ser Arg Ala Arg Gln
        195                 200                 205

Asp Asp Ala Gly Met Tyr Ile Cys Leu Gly Ala Asn Thr Met Gly Tyr
210                 215                 220

Ser Phe Arg Ser Ala Phe Leu Thr Val Leu Pro Asp Pro Lys Pro Pro
225                 230                 235                 240

Gly Pro Pro Met Ala Ser Ser Ser Ser Thr Ser Leu Pro Trp Pro
                245                 250                 255

Val Val Ile Gly Ile Pro Ala Gly Ala Val Phe Ile Leu Gly Thr Val
            260                 265                 270

Leu Leu Trp Leu Cys Gln Thr Lys Lys Lys Pro Cys Ala Pro Ala Ser
        275                 280                 285

Thr Leu Pro Val Pro Gly His Arg Pro Gly Thr Ser Arg Glu Arg
290                 295                 300

Ser Gly Asp Lys Asp Leu Pro Ser Leu Ala Val Gly Ile Cys Glu Glu
305                 310                 315                 320

His Gly Ser Ala Met Ala Pro Gln His Ile Leu Ala Ser Gly Ser Thr
                325                 330                 335
```

Ala Gly Pro Lys Leu Tyr Pro Lys Leu Tyr Thr Asp Val His Thr His
            340                 345                 350

Thr His Thr His Thr Cys Thr His Thr Leu Ser Cys Gly Gly Gln Gly
        355                 360                 365

Ser Ser Thr Pro Ala Cys Pro Leu Ser Val Leu Asn Thr Ala Asn Leu
    370                 375                 380

Gln Ala Leu Cys Pro Glu Val Gly Ile Trp Gly Pro Arg Gln Val
385                 390                 395                 400

Gly Arg Ile Glu Asn Asn Gly Gly Arg Val Ser
                405                 410

<210> SEQ ID NO 102
<211> LENGTH: 870
<212> TYPE: DNA
<213> ORGANISM: Mouse

<400> SEQUENCE: 102
atgacgcgga gccccgcgct gctgctgctg ctattggggg ccctcccgtc ggctgaggcg      60
gcgcgaggac ccccaagaat ggcagacaaa gtggtccacg gcaggtggcc cgcctgggc     120
cgcactgtgc ggctacagtg cccagtggag ggggacccac caccgttgac catgtggacc     180
aaagatggcc gcacaatcca cagtggctgg agccgcttcc gtgtgctgcc ccagggtctg     240
aaggtgaagg aggtggaggc cgaggatgcc ggtgtttatg tgtgcaaggc caccaatggc     300
tttggcagcc tcagcgtcaa ctacactctc atcatcatgg accccaaacc tccagggcct     360
cctatggctt cttcatcgtc atccacaagc ctgccatggc ctgtggtgat cggcatccca     420
gctggtgctg tcttcatcct aggcactgtg ctgctctggc tttgccagac caagaagaag     480
ccatgtgccc agcatctaca cttcctgtg cctgggcatc gtcccccagg acatcccga     540
gaacgcagtg gtgacaagga cctgccctca ttggctgtgg gcatatgtga ggagcatgga     600
tccgccatgg ccccccagca catcctggcc tctggctcaa ctgctggccc caagctgtac     660
cccaagctat acacagatgt gcacacacac acacatacac acacctgcac tcacacgctc     720
tcatgtggag ggcaaggttc atcaacacca gcatgtccac tatcagtgct aaatacagcg     780
aatctccaag cactgtgtcc tgaggtaggc atttgggggc caaggcaaca ggttgggaga     840
attgagaaca atggaggaag agtatcttag                                        870

<210> SEQ ID NO 103
<211> LENGTH: 289
<212> TYPE: PRT
<213> ORGANISM: Mouse

<400> SEQUENCE: 103

Met Thr Arg Ser Pro Ala Leu Leu Leu Leu Leu Gly Ala Leu Pro
1               5                   10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Leu Thr Met Trp Thr Lys Asp Gly Arg
        50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

```
Ala Thr Asn Gly Phe Gly Ser Leu Ser Val Asn Tyr Thr Leu Ile Ile
            100                 105                 110
Met Asp Pro Lys Pro Gly Pro Pro Met Ala Ser Ser Ser Ser
        115                 120                 125
Thr Ser Leu Pro Trp Pro Val Val Ile Gly Ile Pro Ala Gly Ala Val
    130                 135                 140
Phe Ile Leu Gly Thr Val Leu Leu Trp Leu Cys Gln Thr Lys Lys Lys
145                 150                 155                 160
Pro Cys Ala Pro Ala Ser Thr Leu Pro Val Pro Gly His Arg Pro Pro
                165                 170                 175
Gly Thr Ser Arg Glu Arg Ser Gly Asp Lys Asp Leu Pro Ser Leu Ala
            180                 185                 190
Val Gly Ile Cys Glu Glu His Gly Ser Ala Met Ala Pro Gln His Ile
            195                 200                 205
Leu Ala Ser Gly Ser Thr Ala Gly Pro Lys Leu Tyr Pro Lys Leu Tyr
    210                 215                 220
Thr Asp Val His Thr His Thr His Thr His Thr Cys Thr His Thr Leu
225                 230                 235                 240
Ser Cys Gly Gly Gln Gly Ser Ser Thr Pro Ala Cys Pro Leu Ser Val
                245                 250                 255
Leu Asn Thr Ala Asn Leu Gln Ala Leu Cys Pro Glu Val Gly Ile Trp
            260                 265                 270
Gly Pro Arg Gln Gln Val Gly Arg Ile Glu Asn Asn Gly Gly Arg Val
            275                 280                 285
Ser

<210> SEQ ID NO 104
<211> LENGTH: 678
<212> TYPE: DNA
<213> ORGANISM: Mouse

<400> SEQUENCE: 104
atgacgcgga gccccgcgct gctgctgctg ctattggggg ccctcccgtc ggctgaggcg      60
gcgcgagatg atattagtcc agggaaggag agccctgggc aggtggttc ttcgggggc      120 caggaggacc cagccagcca gcagtgggac cccaaacctc agggcctcc tatggcttct      180 tcatcgtcat ccacaagcct gccatggcct gtggtgatcg gcatcccagc tggtgctgtc      240
ttcatcctag gcactgtgct gctctggctt tgccagacca agaagaagcc atgtgccca      300 gcatctacac ttcctgtgcc tgggcatcgt ccccagggga catcccgaga acgcagtggt      360
gacaaggacc tgccctcatt ggctgtgggc atatgtgagg agcatggatc cgccatggcc      420
ccccagcaca tcctggcctc tggctcaact gctggcccca agctgtaccc caagctatac      480
acagatgtgc acacacacac acatacacac acctgcactc acacgctctc atgtggaggg      540
caaggttcat caacaccagc atgtccacta tcagtgctaa atacagcgaa tctccaagca      600
ctgtgtcctg aggtaggcat ttgggggcca aggcaacagg ttgggagaat tgagaacaat      660
ggaggaagag tatcttag                                                    678

<210> SEQ ID NO 105
<211> LENGTH: 225
<212> TYPE: PRT
<213> ORGANISM: Mouse

<400> SEQUENCE: 105
```

-continued

```
Met Thr Arg Ser Pro Ala Leu Leu Leu Leu Leu Gly Ala Leu Pro
 1               5                  10                  15

Ser Ala Glu Ala Ala Arg Asp Asp Ile Ser Pro Gly Lys Glu Ser Pro
                20                  25                  30

Gly Pro Gly Gly Ser Ser Gly Gly Gln Glu Asp Pro Ala Ser Gln Gln
            35                  40                  45

Trp Asp Pro Lys Pro Pro Gly Pro Pro Met Ala Ser Ser Ser Ser
 50                  55                  60

Thr Ser Leu Pro Trp Pro Val Val Ile Gly Ile Pro Ala Gly Ala Val
 65                  70                  75                  80

Phe Ile Leu Gly Thr Val Leu Leu Trp Leu Cys Gln Thr Lys Lys Lys
                85                  90                  95

Pro Cys Ala Pro Ala Ser Thr Leu Pro Val Pro Gly His Arg Pro Pro
                100                 105                 110

Gly Thr Ser Arg Glu Arg Ser Gly Asp Lys Asp Leu Pro Ser Leu Ala
            115                 120                 125

Val Gly Ile Cys Glu Glu His Gly Ser Ala Met Ala Pro Gln His Ile
130                 135                 140

Leu Ala Ser Gly Ser Thr Ala Gly Pro Lys Leu Tyr Pro Lys Leu Tyr
145                 150                 155                 160

Thr Asp Val His Thr His Thr His Thr His Thr Cys Thr His Thr Leu
                165                 170                 175

Ser Cys Gly Gly Gln Gly Ser Ser Thr Pro Ala Cys Pro Leu Ser Val
            180                 185                 190

Leu Asn Thr Ala Asn Leu Gln Ala Leu Cys Pro Glu Val Gly Ile Trp
            195                 200                 205

Gly Pro Arg Gln Gln Val Gly Arg Ile Glu Asn Asn Gly Gly Arg Val
    210                 215                 220

Ser
225
```

<210> SEQ ID NO 106
<211> LENGTH: 882
<212> TYPE: DNA
<213> ORGANISM: Mouse

<400> SEQUENCE: 106

```
atgacgcgga gccccgcgct gctgctgctg ctattggggg ccctccccgtc ggctgaggcg    60
gcgcgagcac ggcctcgctt cacacagccc tccaagatga ggcgccgagt gattgcacgg   120
cctgtgggta gctctgtgcg gctcaagtgt gtggccagtg ggcacccacg gccagacatc   180
atgtggatga aggatgacca gaccttgacg catctagagg ctagtgaaca cagaaagaag   240
aagtggacac tgagcttgaa gaacctgaag cctgaagaca gtggcaagta cacgtgccgt   300
gtatctaaca aggccggtgc catcaacgcc acctacaaag tggatgtaat ccaccccaaa   360
cctccagggc ctcctatggc ttcttcatcg tcatccacaa gcctgccatg gcctgtggtg   420
atcggcatcc cagctggtgc tgtcttcatc ctaggcactg tgctgctctg gctttgccag   480
accaagaaga agccatgtgc cccagcatct acacttcctg tgcctgggca tcgtccccca   540
gggacatccc gagaacgcag tggtgacaag acctgccct cattggctgt gggcatatgt   600
gaggagcatg gatccgccat ggcccccag cacatcctgg cctctggctc aactgctggc   660
cccaagctgt accccaagct atacacagat gtgcacacac acacatac acacacctgc   720
actcacacgc tctcatgtgg agggcaaggt tcatcaacac cagcatgtcc actatcagtg   780
```

-continued

```
ctaaatacag cgaatctcca agcactgtgt cctgaggtag gcatttgggg gccaaggcaa      840
caggttggga gaattgagaa caatggagga agagtatctt ag                         882
```

<210> SEQ ID NO 107
<211> LENGTH: 293
<212> TYPE: PRT
<213> ORGANISM: Mouse

<400> SEQUENCE: 107

| Met | Thr | Arg | Ser | Pro | Ala | Leu | Leu | Leu | Leu | Leu | Gly | Ala | Leu | Pro |
|---|---|---|---|---|---|---|---|---|---|---|---|---|---|---|
| 1 | | | | 5 | | | | | 10 | | | | | 15 |

| Ser | Ala | Glu | Ala | Ala | Arg | Ala | Arg | Pro | Arg | Phe | Thr | Gln | Pro | Ser | Lys |
|---|---|---|---|---|---|---|---|---|---|---|---|---|---|---|---|
| | | 20 | | | | | 25 | | | | | 30 | | | |

Met Arg Arg Arg Val Ile Ala Arg Pro Val Gly Ser Ser Val Arg Leu
                35                  40                  45

Lys Cys Val Ala Ser Gly His Pro Arg Pro Asp Ile Met Trp Met Lys
 50                  55                  60

Asp Asp Gln Thr Leu Thr His Leu Glu Ala Ser Glu His Arg Lys Lys
 65                  70                  75                  80

Lys Trp Thr Leu Ser Leu Lys Asn Leu Lys Pro Glu Asp Ser Gly Lys
                 85                  90                  95

Tyr Thr Cys Arg Val Ser Asn Lys Ala Gly Ala Ile Asn Ala Thr Tyr
            100                 105                 110

Lys Val Asp Val Ile His Pro Lys Pro Pro Gly Pro Pro Met Ala Ser
        115                 120                 125

Ser Ser Ser Ser Thr Ser Leu Pro Trp Pro Val Val Ile Gly Ile Pro
130                 135                 140

Ala Gly Ala Val Phe Ile Leu Gly Thr Val Leu Leu Trp Leu Cys Gln
145                 150                 155                 160

Thr Lys Lys Lys Pro Cys Ala Pro Ala Ser Thr Leu Pro Val Pro Gly
                165                 170                 175

His Arg Pro Pro Gly Thr Ser Arg Glu Arg Ser Gly Asp Lys Asp Leu
            180                 185                 190

Pro Ser Leu Ala Val Gly Ile Cys Glu Glu His Gly Ser Ala Met Ala
        195                 200                 205

Pro Gln His Ile Leu Ala Ser Gly Ser Thr Ala Gly Pro Lys Leu Tyr
    210                 215                 220

Pro Lys Leu Tyr Thr Asp Val His Thr His Thr His Thr His Thr Cys
225                 230                 235                 240

Thr His Thr Leu Ser Cys Gly Gly Gln Gly Ser Ser Thr Pro Ala Cys
                245                 250                 255

Pro Leu Ser Val Leu Asn Thr Ala Asn Leu Gln Ala Leu Cys Pro Glu
            260                 265                 270

Val Gly Ile Trp Gly Pro Arg Gln Gln Val Gly Arg Ile Glu Asn Asn
        275                 280                 285

Gly Gly Arg Val Ser
    290

<210> SEQ ID NO 108
<211> LENGTH: 951
<212> TYPE: DNA
<213> ORGANISM: Mouse

<400> SEQUENCE: 108

```
atgacgcgga gccccgcgct gctgctgctg ctattggggg ccctcccgtc ggctgaggcg      60
```

-continued

```
gcgcgagagc ggactcgttc caagcctgtg ctcacaggga cacaccctgt gaacacaacg      120
gtggacttcg gtgggacaac gtccttccag tgcaaggtgc gcagtgacgt gaagcctgtg      180
atccagtggc tgaagcgggt ggagtacggc tccgagggac gccacaactc caccattgat      240
gtgggtggcc agaagtttgt ggtgttgccc acgggtgatg tgtggtcacg gcctgatggc      300
tcctacctca acaagctgct catctctcgg gcccgccagg atgatgctgg catgtacatc      360
tgcctaggtg caaataccat gggctacagt ttccgtagcg ccttcctcac tgtattacca      420
gaccccaaac ctccagggcc tcctatggct tcttcatcgt catccacaag cctgccatgg      480
cctgtggtga tcgcatccc agctggtgct gtcttcatcc taggcactgt gctgctctgg      540
ctttgccaga ccaagaagaa gccatgtgcc ccagcatcta cacttcctgt gcctgggcat      600
cgtcccccag ggacatcccg agaacgcagt ggtgacaagg acctgccctc attggctgtg      660
ggcatatgtg aggagcatgg atccgccatg gcccccagc acatcctggc ctctggctca      720
actgctggcc ccaagctgta ccccaagcta tacacagatg tgcacacaca cacacataca      780
cacacctgca ctcacacgct ctcatgtgga gggcaaggtt catcaacacc agcatgtcca      840
ctatcagtgc taaatacagc gaatctccaa gcactgtgtc ctgaggtagg catttggggg      900
ccaaggcaac aggttgggag aattgagaac aatggaggaa gagtatctta g              951
```

<210> SEQ ID NO 109
<211> LENGTH: 316
<212> TYPE: PRT
<213> ORGANISM: Mouse

<400> SEQUENCE: 109

```
Met Thr Arg Ser Pro Ala Leu Leu Leu Leu Gly Ala Leu Pro
  1               5                  10                  15

Ser Ala Glu Ala Ala Arg Glu Arg Thr Arg Ser Lys Pro Val Leu Thr
                 20                  25                  30

Gly Thr His Pro Val Asn Thr Thr Val Asp Phe Gly Thr Thr Ser
             35                  40                  45

Phe Gln Cys Lys Val Arg Ser Asp Val Lys Pro Val Ile Gln Trp Leu
 50                  55                  60

Lys Arg Val Glu Tyr Gly Ser Glu Gly Arg His Asn Ser Thr Ile Asp
 65                  70                  75                  80

Val Gly Gly Gln Lys Phe Val Val Leu Pro Thr Gly Asp Val Trp Ser
                 85                  90                  95

Arg Pro Asp Gly Ser Tyr Leu Asn Lys Leu Leu Ile Ser Arg Ala Arg
            100                 105                 110

Gln Asp Asp Ala Gly Met Tyr Ile Cys Leu Gly Ala Asn Thr Met Gly
            115                 120                 125

Tyr Ser Phe Arg Ser Ala Phe Leu Thr Val Leu Pro Asp Pro Lys Pro
130                 135                 140

Pro Gly Pro Pro Met Ala Ser Ser Ser Ser Thr Ser Leu Pro Trp
145                 150                 155                 160

Pro Val Val Ile Gly Ile Pro Ala Gly Ala Val Phe Ile Leu Gly Thr
                165                 170                 175

Val Leu Leu Trp Leu Cys Gln Thr Lys Lys Lys Pro Cys Ala Pro Ala
            180                 185                 190

Ser Thr Leu Pro Val Pro Gly His Arg Pro Gly Thr Ser Arg Glu
            195                 200                 205

Arg Ser Gly Asp Lys Asp Leu Pro Ser Leu Ala Val Gly Ile Cys Glu
210                 215                 220
```

```
Glu His Gly Ser Ala Met Ala Pro Gln His Ile Leu Ala Ser Gly Ser
225                 230                 235                 240

Thr Ala Gly Pro Lys Leu Tyr Pro Lys Leu Tyr Thr Asp Val His Thr
                245                 250                 255

His Thr His Thr His Thr Cys Thr His Thr Leu Ser Cys Gly Gly Gln
            260                 265                 270

Gly Ser Ser Thr Pro Ala Cys Pro Leu Ser Val Leu Asn Thr Ala Asn
            275                 280                 285

Leu Gln Ala Leu Cys Pro Glu Val Gly Ile Trp Gly Pro Arg Gln Gln
        290                 295                 300

Val Gly Arg Ile Glu Asn Asn Gly Gly Arg Val Ser
305                 310                 315

<210> SEQ ID NO 110
<211> LENGTH: 597
<212> TYPE: DNA
<213> ORGANISM: Mouse

<400> SEQUENCE: 110
atgacgcgga gccccgcgct gctgctgctg ctattggggg ccctcccgtc ggctgaggcg      60
gcgcgagacc ccaaacctcc agggcctcct atggcttctt catcgtcatc cacaagcctg     120
ccatggcctg tggtgatcgg catcccagct ggtgctgtct tcatcctagg cactgtgctg     180
ctctggcttt gccagaccaa gaagaagcca tgtgccccag catctacact tcctgtgcct     240
gggcatcgtc ccccagggac atcccgagaa cgcagtggtg acaaggacct gccctcattg     300
gctgtgggca tatgtgagga gcatggatcc gccatggccc cccagcacat cctggcctct     360
ggctcaactg ctggccccaa gctgtacccc aagctataca cagatgtgca cacacacaca     420
catacacaca cctgcactca cacgctctca tgtggagggc aaggttcatc aacaccagca     480
tgtccactat cagtgctaaa tacagcgaat ctccaagcac tgtgtcctga ggtaggcatt     540
tgggggccaa ggcaacaggt tgggagaatt gagaacaatg gaggaagagt atcttag       597

<210> SEQ ID NO 111
<211> LENGTH: 198
<212> TYPE: PRT
<213> ORGANISM: Mouse

<400> SEQUENCE: 111

Met Thr Arg Ser Pro Ala Leu Leu Leu Leu Leu Gly Ala Leu Pro
 1               5                  10                  15

Ser Ala Glu Ala Ala Arg Asp Pro Lys Pro Pro Gly Pro Pro Met Ala
                20                  25                  30

Ser Ser Ser Ser Ser Thr Ser Leu Pro Trp Pro Val Val Ile Gly Ile
            35                  40                  45

Pro Ala Gly Ala Val Phe Ile Leu Gly Thr Val Leu Leu Trp Leu Cys
        50                  55                  60

Gln Thr Lys Lys Lys Pro Cys Ala Pro Ala Ser Thr Leu Pro Val Pro
65                  70                  75                  80

Gly His Arg Pro Pro Gly Thr Ser Arg Glu Arg Ser Gly Asp Lys Asp
                85                  90                  95

Leu Pro Ser Leu Ala Val Gly Ile Cys Glu Glu His Gly Ser Ala Met
                100                 105                 110

Ala Pro Gln His Ile Leu Ala Ser Gly Ser Thr Ala Gly Pro Lys Leu
            115                 120                 125
```

Tyr Pro Lys Leu Tyr Thr Asp Val His Thr His Thr His Thr
            130                 135                 140

Cys Thr His Thr Leu Ser Cys Gly Gly Gln Gly Ser Ser Thr Pro Ala
145                 150                 155                 160

Cys Pro Leu Ser Val Leu Asn Thr Ala Asn Leu Gln Ala Leu Cys Pro
                165                 170                 175

Glu Val Gly Ile Trp Gly Pro Arg Gln Gln Val Gly Arg Ile Glu Asn
            180                 185                 190

Asn Gly Gly Arg Val Ser
        195

<210> SEQ ID NO 112
<211> LENGTH: 1060
<212> TYPE: DNA
<213> ORGANISM: Mouse

<400> SEQUENCE: 112
atgacgcgga gccccgcgct gctgctgctg ctattggggg ccctcccgtc ggctgaggcg      60
gcgcgaggac ccccaagaat ggcagacaaa gtggtcccac ggcaggtggc ccgcctgggc     120
cgcactgtgc ggctacagtg cccagtggag ggggacccca caccgttgac catgtggacc     180
aaagatggcc gcacaatcca cagtggctgg agccgcttcc gtgtgctgcc ccagggtctg     240
aaggtgaagg aggtggaggc cgaggatgcc ggtgtttatg tgtgcaaggc caccaatggc     300
tttggcagcc tcagcgtcaa ctacactctc atcatcatgg atgatattag tccagggaag     360
gagagccctg ggccaggtgg ttcttcgggg gccaggagg acccagccag ccagcagtgg      420
gcacggcctc gcttcacaca gccctccaag atgaggcgcc gagtgattgc acggcctgtg     480
ggtagctctg tgcggctcaa gtgtgtggcc agtgggcacc cacggccaga catcatgtgg     540
atgaaggatg accagacctt gacgcatcta gaggctagtg aacacagaaa gaagaagtgg     600
acactgagct tgaagaacct gaagcctgaa gacagtggca agtacacgtg ccgtgtatct     660
aacaaggccg gtgccatcaa cgccacctac aaagtggatg taatccagcg gactcgttcc     720
aagcctgtgc tcacagggac acaccctgtg aacacaacgg tggacttcgg tgggacaacg     780
tccttccagt gcaaggtgcg cagtgacgtg aagcctgtga tccagtggct gaagcgggtg     840
gagtacggct ccgagggacg ccacaactcc accattgatg tgggtggcca gaagtttgtg     900
gtgttgccca cgggtgatgt gtggtcacgg cctgatggct cctacctcaa caagctgctc     960
atctctcggg cccgccagga tgatgctggc atgtacatct gcctaggtgc aaataccatg    1020
ggctacagtt tccgtagcgc cttcctcact gtattaccag                          1060

<210> SEQ ID NO 113
<211> LENGTH: 353
<212> TYPE: PRT
<213> ORGANISM: Mouse

<400> SEQUENCE: 113

Met Thr Arg Ser Pro Ala Leu Leu Leu Leu Leu Gly Ala Leu Pro
1               5                   10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Leu Thr Met Trp Thr Lys Asp Gly Arg
        50                  55                  60

-continued

```
Thr Ile His Ser Gly Trp Ser Arg Phe Arg Val Leu Pro Gln Gly Leu
 65                  70                  75                  80
Lys Val Lys Glu Val Glu Ala Glu Asp Ala Gly Val Tyr Val Cys Lys
                 85                  90                  95
Ala Thr Asn Gly Phe Gly Ser Leu Ser Val Asn Tyr Thr Leu Ile Ile
            100                 105                 110
Met Asp Asp Ile Ser Pro Gly Lys Glu Ser Pro Gly Pro Gly Gly Ser
        115                 120                 125
Ser Gly Gly Gln Glu Asp Pro Ala Ser Gln Gln Trp Ala Arg Pro Arg
130                 135                 140
Phe Thr Gln Pro Ser Lys Met Arg Arg Val Ile Ala Arg Pro Val
145                 150                 155                 160
Gly Ser Ser Val Arg Leu Lys Cys Val Ala Ser Gly His Pro Arg Pro
                165                 170                 175
Asp Ile Met Trp Met Lys Asp Asp Gln Thr Leu Thr His Leu Glu Ala
            180                 185                 190
Ser Glu His Arg Lys Lys Lys Trp Thr Leu Ser Leu Lys Asn Leu Lys
        195                 200                 205
Pro Glu Asp Ser Gly Lys Tyr Thr Cys Arg Val Ser Asn Lys Ala Gly
210                 215                 220
Ala Ile Asn Ala Thr Tyr Lys Val Asp Val Ile Gln Arg Thr Arg Ser
225                 230                 235                 240
Lys Pro Val Leu Thr Gly Thr His Pro Val Asn Thr Thr Val Asp Phe
                245                 250                 255
Gly Gly Thr Thr Ser Phe Gln Cys Lys Val Arg Ser Asp Val Lys Pro
            260                 265                 270
Val Ile Gln Trp Leu Lys Arg Val Glu Tyr Gly Ser Glu Gly Arg His
        275                 280                 285
Asn Ser Thr Ile Asp Val Gly Gly Gln Lys Phe Val Val Leu Pro Thr
290                 295                 300
Gly Asp Val Trp Ser Arg Pro Asp Gly Ser Tyr Leu Asn Lys Leu Leu
305                 310                 315                 320
Ile Ser Arg Ala Arg Gln Asp Asp Ala Gly Met Tyr Ile Cys Leu Gly
                325                 330                 335
Ala Asn Thr Met Gly Tyr Ser Phe Arg Ser Ala Phe Leu Thr Val Leu
            340                 345                 350
Pro
```

<210> SEQ ID NO 114
<211> LENGTH: 706
<212> TYPE: DNA
<213> ORGANISM: Mouse

<400> SEQUENCE: 114

```
atgacgcgga gccccgcgct gctgctgctg ctattggggg ccctcccgtc ggctgaggcg      60
gcgcgaggac ccccaagaat ggcagacaaa gtggtcccac ggcaggtggc ccgcctgggc     120
cgcactgtgc ggctacagtg cccagtggag ggggacccac accgttgac catgtggacc      180
aaagatggcc gcacaatcca cagtggctgg agccgcttcc gtgtgctgcc cagggtctg      240
aaggtgaagg aggtggaggc cgaggatgcc ggtgtttatg tgtgcaaggc caccaatggc     300
tttggcagcc tcagcgtcaa ctacactctc atcatcatgg atgatattag tccagggaag     360
gagagccctg ggccaggtgg ttcttcgggg ggcaggagg acccagccag ccagcagtgg      420
gcacggcctc gcttcacaca gccctccaag atgaggcgcc gagtgattgc acggcctgtg     480
```

```
ggtagctctg tgcggctcaa gtgtgtggcc agtgggcacc cacggccaga catcatgtgg      540
atgaaggatg accagacctt gacgcatcta gaggctagtg aacacagaaa gaagaagtgg      600
acactgagct tgaagaacct gaagcctgaa gacagtggca agtacacgtg ccgtgtatct      660
aacaaggccg gtgccatcaa cgccacctac aaagtggatg taatcc                    706
```

<210> SEQ ID NO 115
<211> LENGTH: 235
<212> TYPE: PRT
<213> ORGANISM: Mouse

<400> SEQUENCE: 115

```
Met Thr Arg Ser Pro Ala Leu Leu Leu Leu Gly Ala Leu Pro
1               5                   10                  15

Ser Ala Glu Ala Ala Arg Gly Pro Pro Arg Met Ala Asp Lys Val Val
            20                  25                  30

Pro Arg Gln Val Ala Arg Leu Gly Arg Thr Val Arg Leu Gln Cys Pro
        35                  40                  45

Val Glu Gly Asp Pro Pro Leu Thr Met Trp Thr Lys Asp Gly Arg
50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
            100                 105                 110

Met Asp Asp Ile Ser Pro Gly Lys Glu Ser Pro Gly Pro Gly Gly Ser
        115                 120                 125

Ser Gly Gly Gln Glu Asp Pro Ala Ser Gln Gln Trp Ala Arg Pro Arg
130                 135                 140

Phe Thr Gln Pro Ser Lys Met Arg Arg Arg Val Ile Ala Arg Pro Val
145                 150                 155                 160

Gly Ser Ser Val Arg Leu Lys Cys Val Ala Ser Gly His Pro Arg Pro
                165                 170                 175

Asp Ile Met Trp Met Lys Asp Asp Gln Thr Leu Thr His Leu Glu Ala
            180                 185                 190

Ser Glu His Arg Lys Lys Lys Trp Thr Leu Ser Leu Lys Asn Leu Lys
        195                 200                 205

Pro Glu Asp Ser Gly Lys Tyr Thr Cys Arg Val Ser Asn Lys Ala Gly
    210                 215                 220

Ala Ile Asn Ala Thr Tyr Lys Val Asp Val Ile
225                 230                 235
```

<210> SEQ ID NO 116
<211> LENGTH: 775
<212> TYPE: DNA
<213> ORGANISM: Mouse

<400> SEQUENCE: 116

```
atgacgcgga gccccgcgct gctgctgctg ctattggggg ccctcccgtc ggctgaggcg      60
gcgcgaggac cccaagaat ggcagacaaa gtgtcccac ggcaggtggc ccgcctgggc      120
cgcactgtgc ggctacagtg cccagtggag ggggacccac caccgttgac catgtggacc      180
aaagatggcc gcacaatcca cagtggctgg agccgcttcc gtgtgctgcc ccagggtctg      240
aaggtgaagg aggtggaggc cgaggatgcc ggtgtttatg tgtgcaaggc caccaatggc      300
```

```
tttggcagcc tcagcgtcaa ctacactctc atcatcatgg atgatattag tccagggaag    360
gagagccctg ggccaggtgg ttcttcgggg ggccaggagg acccagccag ccagcagtgg    420
gagcggactc gttccaagcc tgtgctcaca gggacacacc ctgtgaacac aacggtggac    480
ttcggtggga caacgtcctt ccagtgcaag gtgcgcagtg acgtgaagcc tgtgatccag    540
tggctgaagc gggtggagta cggctccgag ggacgccaca actccaccat tgatgtgggt    600
ggccagaagt ttgtggtgtt gcccacgggt gatgtgtggt cacggcctga tggctcctac    660
ctcaacaagc tgctcatctc tcgggcccgc aggatgatg ctggcatgta catctgccta    720
ggtgcaaata ccatgggcta cagtttccgt agcgccttcc tcactgtatt accag        775
```

```
<210> SEQ ID NO 117
<211> LENGTH: 258
<212> TYPE: PRT
<213> ORGANISM: Mouse

<400> SEQUENCE: 117
```

```
Met Thr Arg Ser Pro Ala Leu Leu Leu Leu Gly Ala Leu Pro
 1               5                  10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Leu Thr Met Trp Thr Lys Asp Gly Arg
 50                  55                  60

Thr Ile His Ser Gly Trp Ser Arg Phe Arg Val Leu Pro Gln Gly Leu
 65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
                100                 105                 110

Met Asp Asp Ile Ser Pro Gly Lys Glu Ser Pro Gly Pro Gly Gly Ser
            115                 120                 125

Ser Gly Gly Gln Glu Asp Pro Ala Ser Gln Gln Trp Glu Arg Thr Arg
        130                 135                 140

Ser Lys Pro Val Leu Thr Gly Thr His Pro Val Asn Thr Thr Val Asp
145                 150                 155                 160

Phe Gly Gly Thr Thr Ser Phe Gln Cys Lys Val Arg Ser Asp Val Lys
                165                 170                 175

Pro Val Ile Gln Trp Leu Lys Arg Val Glu Tyr Gly Ser Glu Gly Arg
            180                 185                 190

His Asn Ser Thr Ile Asp Val Gly Gly Gln Lys Phe Val Val Leu Pro
        195                 200                 205

Thr Gly Asp Val Trp Ser Arg Pro Asp Gly Ser Tyr Leu Asn Lys Leu
    210                 215                 220

Leu Ile Ser Arg Ala Arg Gln Asp Asp Ala Gly Met Tyr Ile Cys Leu
225                 230                 235                 240

Gly Ala Asn Thr Met Gly Tyr Ser Phe Arg Ser Ala Phe Leu Thr Val
                245                 250                 255

Leu Pro
```

```
<210> SEQ ID NO 118
<211> LENGTH: 979
<212> TYPE: DNA
```

<213> ORGANISM: Mouse

<400> SEQUENCE: 118

```
atgacgcgga gccccgcgct gctgctgctg ctattggggg ccctcccgtc ggctgaggcg      60
gcgcgaggac ccccaagaat ggcagacaaa gtggtcccac ggcaggtggc ccgcctgggc     120
cgcactgtgc ggctacagtg cccagtggag ggggacccac accgttgaca catgtggacc     180
aaagatggcc gcacaatcca cagtggctgg agccgcttcc gtgtgctgcc ccagggtctg     240
aaggtgaagg aggtggaggc cgaggatgcc ggtgtttatg tgtgcaaggc caccaatggc     300
tttggcagcc tcagcgtcaa ctacactctc atcatcatgg cacggcctcg cttcacacag     360
ccctccaaga tgaggcgccg agtgattgca cggcctgtgg gtagctctgt gcggctcaag     420
tgtgtggcca gtgggcaccc acggccagac atcatgtgga tgaaggatga ccagaccttg     480
acgcatctag aggctagtga acacagaaag aagaagtgga cactgagctt gaagaacctg     540
aagcctgaag acagtggcaa gtacacgtgc cgtgtatcta acaaggccgg tgccatcaac     600
gccacctaca aagtggatgt aatccagcgg actcgttcca agcctgtgct cacagggaca     660
cacccctgtga acacaacggt ggacttcggt gggacaacgt ccttccagtg caaggtgcgc     720
agtgacgtga agcctgtgat ccagtggctg aagcgggtgg agtacggctc cgagggacgc     780
cacaactcca ccattgatgt gggtggccag aagtttgtgg tgttgcccac gggtgatgtg     840
tggtcacggc ctgatggctc ctacctcaac aagctgctca tctctcgggc ccgccaggat     900
gatgctggca tgtacatctg cctaggtgca aataccatgg gctacagttt ccgtagcgcc     960
ttcctcactg tattaccag                                                 979
```

<210> SEQ ID NO 119
<211> LENGTH: 326
<212> TYPE: PRT
<213> ORGANISM: Mouse

<400> SEQUENCE: 119

```
Met Thr Arg Ser Pro Ala Leu Leu Leu Leu Leu Gly Ala Leu Pro
 1               5                  10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Leu Thr Met Trp Thr Lys Asp Gly Arg
    50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
               100                 105                 110

Met Ala Arg Pro Arg Phe Thr Gln Pro Ser Lys Met Arg Arg Arg Val
           115                 120                 125

Ile Ala Arg Pro Val Gly Ser Ser Val Arg Leu Lys Cys Val Ala Ser
       130                 135                 140

Gly His Pro Arg Pro Asp Ile Met Trp Met Lys Asp Asp Gln Thr Leu
145                 150                 155                 160

Thr His Leu Glu Ala Ser Glu His Arg Lys Lys Lys Trp Thr Leu Ser
                165                 170                 175
```

```
Leu Lys Asn Leu Lys Pro Glu Asp Ser Gly Lys Tyr Thr Cys Arg Val
            180                 185                 190

Ser Asn Lys Ala Gly Ala Ile Asn Ala Thr Tyr Lys Val Asp Val Ile
        195                 200                 205

Gln Arg Thr Arg Ser Lys Pro Val Leu Thr Gly Thr His Pro Val Asn
    210                 215                 220

Thr Thr Val Asp Phe Gly Gly Thr Thr Ser Phe Gln Cys Lys Val Arg
225                 230                 235                 240

Ser Asp Val Lys Pro Val Ile Gln Trp Leu Lys Arg Val Glu Tyr Gly
                245                 250                 255

Ser Glu Gly Arg His Asn Ser Thr Ile Asp Val Gly Gln Lys Phe
            260                 265                 270

Val Val Leu Pro Thr Gly Asp Val Trp Ser Arg Pro Asp Gly Ser Tyr
            275                 280                 285

Leu Asn Lys Leu Leu Ile Ser Arg Ala Arg Gln Asp Asp Ala Gly Met
        290                 295                 300

Tyr Ile Cys Leu Gly Ala Asn Thr Met Gly Tyr Ser Phe Arg Ser Ala
305                 310                 315                 320

Phe Leu Thr Val Leu Pro
                325

<210> SEQ ID NO 120
<211> LENGTH: 787
<212> TYPE: DNA
<213> ORGANISM: Mouse

<400> SEQUENCE: 120
atgacgcgga gccccgcgct gctgctgctg ctattggggg ccctcccgtc ggctgaggcg    60
gcgcgagatg atattagtcc agggaaggag agccctgggc caggtggttc ttcgggggc   120 caggaggacc cagccagcca gcagtgggca cggcctcgct tcacacagcc ctccaagatg   180
aggcgccgag tgattgcacg gcctgtgggt agctctgtgc ggctcaagtg tgtggccagt   240
gggcacccac ggccagacat catgtggatg aaggatgacc agaccttgac gcatctagag   300
gctagtgaac acagaaagaa gaagtggaca ctgagcttga agaacctgaa gcctgaagac   360
agtggcaagt acacgtgccg tgtatctaac aaggccggtg ccatcaacgc cacctacaaa   420
gtggatgtaa tccagcggac tcgttccaag cctgtgctca gggacacacc cctgtgaac   480 acaacggtgg acttcggtgg acaacgtcc ttccagtgca aggtgcgcag tgacgtgaag   540
cctgtgatcc agtggctgaa gcgggtggag tacggctccg agggacgcca caactccacc   600
attgatgtgg gtggccagaa gtttgtggtg ttgcccacgg gtgatgtgtg gtcacggcct   660
gatggctcct acctcaacaa gctgctcatc tctcgggccc gccaggatga tgctggcatg   720
tacatctgcc taggtgcaaa taccatgggc tacagtttcc gtagcgcctt cctcactgta   780
ttaccag                                                              787

<210> SEQ ID NO 121
<211> LENGTH: 262
<212> TYPE: PRT
<213> ORGANISM: Mouse

<400> SEQUENCE: 121

Met Thr Arg Ser Pro Ala Leu Leu Leu Leu Leu Gly Ala Leu Pro
1               5                   10                  15

Ser Ala Glu Ala Ala Arg Asp Asp Ile Ser Pro Gly Lys Glu Ser Pro
                20                  25                  30
```

```
Gly Pro Gly Gly Ser Ser Gly Gly Gln Glu Asp Pro Ala Ser Gln Gln
            35                  40                  45

Trp Ala Arg Pro Arg Phe Thr Gln Pro Ser Lys Met Arg Arg Arg Val
 50                  55                  60

Ile Ala Arg Pro Val Gly Ser Ser Val Arg Leu Lys Cys Val Ala Ser
 65                  70                  75                  80

Gly His Pro Arg Pro Asp Ile Met Trp Met Lys Asp Asp Gln Thr Leu
                 85                  90                  95

Thr His Leu Glu Ala Ser Glu His Arg Lys Lys Trp Thr Leu Ser
            100                 105                 110

Leu Lys Asn Leu Lys Pro Glu Asp Ser Gly Lys Tyr Thr Cys Arg Val
            115                 120                 125

Ser Asn Lys Ala Gly Ala Ile Asn Ala Thr Tyr Lys Val Asp Val Ile
            130                 135                 140

Gln Arg Thr Arg Ser Lys Pro Val Leu Thr Gly Thr His Pro Val Asn
145                 150                 155                 160

Thr Thr Val Asp Phe Gly Gly Thr Thr Ser Phe Gln Cys Lys Val Arg
                165                 170                 175

Ser Asp Val Lys Pro Val Ile Gln Trp Leu Lys Arg Val Glu Tyr Gly
                180                 185                 190

Ser Glu Gly Arg His Asn Ser Thr Ile Asp Val Gly Gly Gln Lys Phe
            195                 200                 205

Val Val Leu Pro Thr Gly Asp Val Trp Ser Arg Pro Asp Gly Ser Tyr
210                 215                 220

Leu Asn Lys Leu Leu Ile Ser Arg Ala Arg Gln Asp Asp Ala Gly Met
225                 230                 235                 240

Tyr Ile Cys Leu Gly Ala Asn Thr Met Gly Tyr Ser Phe Arg Ser Ala
                245                 250                 255

Phe Leu Thr Val Leu Pro
            260

<210> SEQ ID NO 122
<211> LENGTH: 421
<212> TYPE: DNA
<213> ORGANISM: Mouse

<400> SEQUENCE: 122
atgacgcgga gccccgcgct gctgctgctg ctattggggg ccctcccgtc ggctgaggcg      60
gcgcgaggac cccaagaat ggcagacaaa gtggtcccac ggcaggtggc ccgcctgggc     120
cgcactgtgc ggctacagtg cccagtggag ggggacccac caccgttgac catgtggacc     180
aaagatggcc gcacaatcca cagtggctgg agccgcttcc gtgtgctgcc ccagggtctg     240
aaggtgaagg aggtggaggc cgaggatgcc ggtgtttatg tgtgcaaggc caccaatggc     300
tttggcagcc tcagcgtcaa ctacactctc atcatcatgg atgatattag tccagggaag     360
gagagccctg ggccaggtgg ttcttcgggg ggccaggagg acccagccag ccagcagtgg     420
g                                                                     421

<210> SEQ ID NO 123
<211> LENGTH: 140
<212> TYPE: PRT
<213> ORGANISM: Mouse

<400> SEQUENCE: 123

Met Thr Arg Ser Pro Ala Leu Leu Leu Leu Leu Leu Gly Ala Leu Pro
```

-continued

```
                1               5                  10                 15
Ser Ala Glu Ala Ala Arg Gly Pro Pro Arg Met Ala Asp Lys Val Val
                    20                  25                  30

Pro Arg Gln Val Ala Arg Leu Gly Arg Thr Val Arg Leu Gln Cys Pro
            35                  40                  45

Val Glu Gly Asp Pro Pro Leu Thr Met Trp Thr Lys Asp Gly Arg
    50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
                100                 105                 110

Met Asp Asp Ile Ser Pro Gly Lys Glu Ser Pro Gly Pro Gly Gly Ser
                115                 120                 125

Ser Gly Gly Gln Glu Asp Pro Ala Ser Gln Gln Trp
            130                 135                 140
```

<210> SEQ ID NO 124
<211> LENGTH: 625
<212> TYPE: DNA
<213> ORGANISM: Mouse

<400> SEQUENCE: 124

```
atgacgcgga gccccgcgct gctgctgctg ctattggggg ccctcccgtc ggctgaggcg    60
gcgcgaggac ccccaagaat ggcagacaaa gtggtcccac ggcaggtggc ccgcctgggc   120
cgcactgtgc ggctacagtg cccagtggag ggggacccac accgttgac catgtggacc    180
aaagatggcc gcacaatcca cagtggctgg agccgcttcc gtgtgctgcc ccagggtctg   240
aaggtgaagg aggtggaggc cgaggatgcc ggtgtttatg tgtgcaaggc caccaatggc   300
tttggcagcc tcagcgtcaa ctacactctc atcatcatgg acgacctcg cttcacacag    360
ccctccaaga tgaggcgccg agtgattgca cggcctgtgg gtagctctgt gcggctcaag   420
tgtgtggcca gtgggcaccc acggccagac atcatgtgga tgaaggatga ccagaccttg   480
acgcatctag aggctagtga acacagaaag aagaagtgga cactgagctt gaagaacctg   540
aagcctgaag acagtggcaa gtacacgtgc cgtgtatcta caaggccgg tgccatcaac    600
gccacctaca agtggatgt aatcc                                          625
```

<210> SEQ ID NO 125
<211> LENGTH: 208
<212> TYPE: PRT
<213> ORGANISM: Mouse

<400> SEQUENCE: 125

```
Met Thr Arg Ser Pro Ala Leu Leu Leu Leu Leu Gly Ala Leu Pro
1               5                  10                  15

Ser Ala Glu Ala Ala Arg Gly Pro Pro Arg Met Ala Asp Lys Val Val
                20                  25                  30

Pro Arg Gln Val Ala Arg Leu Gly Arg Thr Val Arg Leu Gln Cys Pro
            35                  40                  45

Val Glu Gly Asp Pro Pro Leu Thr Met Trp Thr Lys Asp Gly Arg
    50                  55                  60

Thr Ile His Ser Gly Trp Ser Arg Phe Arg Val Leu Pro Gln Gly Leu
65                  70                  75                  80
```

```
Lys Val Lys Glu Val Glu Ala Glu Asp Ala Gly Val Tyr Val Cys Lys
                85                  90                  95
Ala Thr Asn Gly Phe Gly Ser Leu Ser Val Asn Tyr Thr Leu Ile Ile
            100                 105                 110
Met Ala Arg Pro Arg Phe Thr Gln Pro Ser Lys Met Arg Arg Val
        115                 120                 125
Ile Ala Arg Pro Val Gly Ser Ser Val Arg Leu Lys Cys Val Ala Ser
    130                 135                 140
Gly His Pro Arg Pro Asp Ile Met Trp Met Lys Asp Gln Thr Leu
145                 150                 155                 160
Thr His Leu Glu Ala Ser Glu His Arg Lys Lys Trp Thr Leu Ser
                165                 170                 175
Leu Lys Asn Leu Lys Pro Glu Asp Ser Gly Lys Tyr Thr Cys Arg Val
            180                 185                 190
Ser Asn Lys Ala Gly Ala Ile Asn Ala Thr Tyr Lys Val Asp Val Ile
            195                 200                 205
```

<210> SEQ ID NO 126
<211> LENGTH: 694
<212> TYPE: DNA
<213> ORGANISM: Mouse

<400> SEQUENCE: 126

```
atgacgcgga gccccgcgct gctgctgctg ctattggggg ccctcccgtc ggctgaggcg      60
gcgcgaggac ccccaagaat ggcagacaaa gtggtccac ggcaggtggc ccgcctgggc     120
cgcactgtgc ggctacagtg cccagtggag ggggacccca caccgttgac catgtggacc     180
aaagatggcc gcacaatcca cagtggctgg agccgcttcc gtgtgctgcc ccagggtctg     240
aaggtgaagg aggtggaggc cgaggatgcc ggtgtttatg tgtgcaaggc caccaatggc     300
tttggcagcc tcagcgtcaa ctacactctc atcatcatgg agcggactcg ttccaagcct     360
gtgctcacag gacacacccc tgtgaacaca acggtggact cggtgggac aacgtccttc     420
cagtgcaagg tgcgcagtga cgtgaagcct gtgatccagt ggctgaagcg ggtggagtac     480
ggctccgagg acgccacaa ctccaccatt gatgtgggtg ccagaagtt tgtggtgttg     540
cccacgggtg atgtgtggtc acggcctgat ggctcctacc tcaacaagct gctcatctct     600
cgggcccgcc aggatgatgc tggcatgtac atctgcctag gtgcaaatac catgggctac     660
agtttccgta gcgccttcct cactgtatta ccag                                694
```

<210> SEQ ID NO 127
<211> LENGTH: 231
<212> TYPE: PRT
<213> ORGANISM: Mouse

<400> SEQUENCE: 127

```
Met Thr Arg Ser Pro Ala Leu Leu Leu Leu Leu Gly Ala Leu Pro
1               5                   10                  15
Ser Ala Glu Ala Ala Arg Gly Pro Pro Arg Met Ala Asp Lys Val Val
            20                  25                  30
Pro Arg Gln Val Ala Arg Leu Gly Arg Thr Val Arg Leu Gln Cys Pro
        35                  40                  45
Val Glu Gly Asp Pro Pro Leu Thr Met Trp Thr Lys Asp Gly Arg
    50                  55                  60
Thr Ile His Ser Gly Trp Ser Arg Phe Arg Val Leu Pro Gln Gly Leu
65                  70                  75                  80
```

```
Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
            100                 105                 110

Met Glu Arg Thr Arg Ser Lys Pro Val Leu Thr Gly Thr His Pro Val
        115                 120                 125

Asn Thr Thr Val Asp Phe Gly Gly Thr Thr Ser Phe Gln Cys Lys Val
    130                 135                 140

Arg Ser Asp Val Lys Pro Val Ile Gln Trp Leu Lys Arg Val Glu Tyr
145                 150                 155                 160

Gly Ser Glu Gly Arg His Asn Ser Thr Ile Asp Val Gly Gly Gln Lys
                165                 170                 175

Phe Val Val Leu Pro Thr Gly Asp Val Trp Ser Arg Pro Asp Gly Ser
            180                 185                 190

Tyr Leu Asn Lys Leu Leu Ile Ser Arg Ala Arg Gln Asp Asp Ala Gly
        195                 200                 205

Met Tyr Ile Cys Leu Gly Ala Asn Thr Met Gly Tyr Ser Phe Arg Ser
    210                 215                 220

Ala Phe Leu Thr Val Leu Pro
225                 230

<210> SEQ ID NO 128
<211> LENGTH: 433
<212> TYPE: DNA
<213> ORGANISM: Mouse

<400> SEQUENCE: 128
atgacgcgga gccccgcgct gctgctgctg ctattggggg ccctcccgtc ggctgaggcg      60
gcgcgagatg atattagtcc agggaaggag agccctgggc aggtggttc ttcgggggc      120 caggaggacc cagccagcca gcagtgggca cggcctcgct tcacacagcc ctccaagatg    180
aggcgccgag tgattgcacg gcctgtgggt agctctgtgc ggctcaagtg tgtggccagt    240
gggcacccac ggccagacat catgtggatg aaggatgacc agaccttgac gcatctagag    300
gctagtgaac acagaaagaa gaagtggaca ctgagcttga agaacctgaa gcctgaagac    360
agtggcaagt acacgtgccg tgtatctaac aaggccggtg ccatcaacgc cacctacaaa    420
gtggatgtaa tcc                                                        433

<210> SEQ ID NO 129
<211> LENGTH: 144
<212> TYPE: PRT
<213> ORGANISM: Mouse

<400> SEQUENCE: 129

Met Thr Arg Ser Pro Ala Leu Leu Leu Leu Leu Gly Ala Leu Pro
 1               5                  10                  15

Ser Ala Glu Ala Ala Arg Asp Asp Ile Ser Pro Gly Lys Glu Ser Pro
                20                  25                  30

Gly Pro Gly Gly Ser Gly Gly Gln Glu Asp Pro Ala Ser Gln Gln
            35                  40                  45

Trp Ala Arg Pro Arg Phe Thr Gln Pro Ser Lys Met Arg Arg Arg Val
        50                  55                  60

Ile Ala Arg Pro Val Gly Ser Ser Val Arg Leu Lys Cys Val Ala Ser
65                  70                  75                  80

Gly His Pro Arg Pro Asp Ile Met Trp Met Lys Asp Asp Gln Thr Leu
                85                  90                  95
```

```
Thr His Leu Glu Ala Ser Glu His Arg Lys Lys Lys Trp Thr Leu Ser
            100                 105                 110

Leu Lys Asn Leu Lys Pro Glu Asp Ser Gly Lys Tyr Thr Cys Arg Val
            115                 120                 125

Ser Asn Lys Ala Gly Ala Ile Asn Ala Thr Tyr Lys Val Asp Val Ile
            130                 135                 140

<210> SEQ ID NO 130
<211> LENGTH: 502
<212> TYPE: DNA
<213> ORGANISM: Mouse

<400> SEQUENCE: 130
atgacgcgga gccccgcgct gctgctgctg ctattggggg ccctcccgtc ggctgaggcg      60
gcgcgagatg atattagtcc agggaaggag agccctgggc aggtggttc ttcgggggc      120 caggaggacc cagccagcca gcagtgggag cggactcgtt ccaagcctgt gctcacaggg     180
acacaccctg tgaacacaac ggtggacttc ggtgggacaa cgtccttcca gtgcaaggtg    240
cgcagtgacg tgaagcctgt gatccagtgg ctgaagcggg tggagtacgg ctccgaggga    300
cgccacaact ccaccattga tgtgggtggc cagaagtttg tggtgttgcc cacgggtgat    360
gtgtggtcac ggcctgatgg ctcctacctc aacaagctgc tcatctctcg ggcccgccag    420
gatgatgctg gcatgtacat ctgcctaggt gcaaatacca tgggctacag tttccgtagc    480
gccttcctca ctgtattacc ag                                              502

<210> SEQ ID NO 131
<211> LENGTH: 167
<212> TYPE: PRT
<213> ORGANISM: Mouse

<400> SEQUENCE: 131

Met Thr Arg Ser Pro Ala Leu Leu Leu Leu Leu Gly Ala Leu Pro
  1               5                  10                  15

Ser Ala Glu Ala Ala Arg Asp Asp Ile Ser Pro Gly Lys Glu Ser Pro
                 20                  25                  30

Gly Pro Gly Gly Ser Ser Gly Gly Gln Glu Asp Pro Ala Ser Gln Gln
            35                  40                  45

Trp Glu Arg Thr Arg Ser Lys Pro Val Leu Thr Gly Thr His Pro Val
    50                  55                  60

Asn Thr Thr Val Asp Phe Gly Gly Thr Thr Ser Phe Gln Cys Lys Val
 65                  70                  75                  80

Arg Ser Asp Val Lys Pro Val Ile Gln Trp Leu Lys Arg Val Glu Tyr
                85                  90                  95

Gly Ser Glu Gly Arg His Asn Ser Thr Ile Asp Val Gly Gly Gln Lys
            100                 105                 110

Phe Val Val Leu Pro Thr Gly Asp Val Trp Ser Arg Pro Asp Gly Ser
            115                 120                 125

Tyr Leu Asn Lys Leu Leu Ile Ser Arg Ala Arg Gln Asp Asp Ala Gly
            130                 135                 140

Met Tyr Ile Cys Leu Gly Ala Asn Thr Met Gly Tyr Ser Phe Arg Ser
145                 150                 155                 160

Ala Phe Leu Thr Val Leu Pro
                165

<210> SEQ ID NO 132
```

```
<211> LENGTH: 706
<212> TYPE: DNA
<213> ORGANISM: Mouse

<400> SEQUENCE: 132
atgacgcgga gccccgcgct gctgctgctg ctattggggg ccctcccgtc ggctgaggcg      60
gcgcgagcac ggcctcgctt cacacagccc tccaagatga ggcgccgagt gattgcacgg     120
cctgtgggta gctctgtgcg gctcaagtgt gtggccagtg ggcacccacg gccagacatc     180
atgtggatga aggatgacca gaccttgacg catctagagg ctagtgaaca cagaaagaag     240
aagtggacac tgagcttgaa gaacctgaag cctgaagaca gtggcaagta cacgtgccgt     300
gtatctaaca aggccggtgc catcaacgcc acctacaaag tggatgtaat ccagcggact     360
cgttccaagc ctgtgctcac agggacacac cctgtgaaca acggtggact tcggtgggg      420 acaacgtcct ccagtgcaa ggtgcgcagt gacgtgaagc ctgtgatcca gtggctgaag     480
cgggtggagt acggctccga gggacgccac aactccacca ttgatgtggg tggccagaag     540
tttgtggtgt tgcccacggg tgatgtgtgg tcacggcctg atggctccta cctcaacaag     600
ctgctcatct ctcgggcccg ccaggatgat gctggcatgt acatctgcct aggtgcaaat     660
accatgggct acagtttccg tagcgccttc ctcactgtat taccag                    706

<210> SEQ ID NO 133
<211> LENGTH: 235
<212> TYPE: PRT
<213> ORGANISM: Mouse

<400> SEQUENCE: 133

Met Thr Arg Ser Pro Ala Leu Leu Leu Leu Gly Ala Leu Pro
  1               5                  10                  15

Ser Ala Glu Ala Ala Arg Ala Arg Pro Arg Phe Thr Gln Pro Ser Lys
             20                  25                  30

Met Arg Arg Arg Val Ile Ala Arg Pro Val Gly Ser Ser Val Arg Leu
         35                  40                  45

Lys Cys Val Ala Ser Gly His Pro Arg Pro Asp Ile Met Trp Met Lys
     50                  55                  60

Asp Asp Gln Thr Leu Thr His Leu Glu Ala Ser Glu His Arg Lys Lys
 65                  70                  75                  80

Lys Trp Thr Leu Ser Leu Lys Asn Leu Lys Pro Glu Asp Ser Gly Lys
                 85                  90                  95

Tyr Thr Cys Arg Val Ser Asn Lys Ala Gly Ala Ile Asn Ala Thr Tyr
            100                 105                 110

Lys Val Asp Val Ile Gln Arg Thr Arg Ser Lys Pro Val Leu Thr Gly
        115                 120                 125

Thr His Pro Val Asn Thr Thr Val Asp Phe Gly Gly Thr Thr Ser Phe
    130                 135                 140

Gln Cys Lys Val Arg Ser Asp Val Lys Pro Val Ile Gln Trp Leu Lys
145                 150                 155                 160

Arg Val Glu Tyr Gly Ser Glu Gly Arg His Asn Ser Thr Ile Asp Val
                165                 170                 175

Gly Gly Gln Lys Phe Val Val Leu Pro Thr Gly Asp Val Trp Ser Arg
            180                 185                 190

Pro Asp Gly Ser Tyr Leu Asn Lys Leu Leu Ile Ser Arg Ala Arg Gln
        195                 200                 205

Asp Asp Ala Gly Met Tyr Ile Cys Leu Gly Ala Asn Thr Met Gly Tyr
    210                 215                 220
```

Ser Phe Arg Ser Ala Phe Leu Thr Val Leu Pro
225             230             235

<210> SEQ ID NO 134
<211> LENGTH: 340
<212> TYPE: DNA
<213> ORGANISM: Mouse

<400> SEQUENCE: 134
atgacgcgga gccccgcgct gctgctgctg ctattggggg ccctcccgtc ggctgaggcg    60
gcgcgaggac ccccaagaat ggcagacaaa gtggtcccac ggcaggtggc ccgcctgggc   120
cgcactgtgc ggctacagtg cccagtggag ggggacccac caccgttgac catgtggacc   180
aaagatggcc gcacaatcca cagtggctgg agccgcttcc gtgtgctgcc ccagggtctg   240
aaggtgaagg aggtggaggc cgaggatgcc ggtgtttatg tgtgcaaggc caccaatggc   300
tttggcagcc tcagcgtcaa ctacactctc atcatcatgg                         340

<210> SEQ ID NO 135
<211> LENGTH: 113
<212> TYPE: PRT
<213> ORGANISM: Mouse

<400> SEQUENCE: 135

Met Thr Arg Ser Pro Ala Leu Leu Leu Leu Leu Gly Ala Leu Pro
1               5                   10                  15

Ser Ala Glu Ala Ala Arg Gly Pro Pro Arg Met Ala Asp Lys Val Val
            20                  25                  30

Pro Arg Gln Val Ala Arg Leu Gly Arg Thr Val Arg Leu Gln Cys Pro
        35                  40                  45

Val Glu Gly Asp Pro Pro Leu Thr Met Trp Thr Lys Asp Gly Arg
    50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
            100                 105                 110

Met

<210> SEQ ID NO 136
<211> LENGTH: 148
<212> TYPE: DNA
<213> ORGANISM: Mouse

<400> SEQUENCE: 136
atgacgcgga gccccgcgct gctgctgctg ctattggggg ccctcccgtc ggctgaggcg    60
gcgcgagatg atattagtcc agggaaggag agccctgggc caggtggttc ttcgggggc   120 caggaggacc cagccagcca gcagtggg                                      148

<210> SEQ ID NO 137
<211> LENGTH: 49
<212> TYPE: PRT
<213> ORGANISM: Mouse

<400> SEQUENCE: 137

Met Thr Arg Ser Pro Ala Leu Leu Leu Leu Leu Gly Ala Leu Pro
1               5                   10                  15

Ser Ala Glu Ala Ala Arg Asp Asp Ile Ser Pro Gly Lys Glu Ser Pro
            20                  25                  30

Gly Pro Gly Gly Ser Ser Gly Gly Gln Glu Asp Pro Ala Ser Gln Gln
        35                  40                  45

Trp

<210> SEQ ID NO 138
<211> LENGTH: 352
<212> TYPE: DNA
<213> ORGANISM: Mouse

<400> SEQUENCE: 138
atgacgcgga gccccgcgct gctgctgctg ctattggggg ccctcccgtc ggctgaggcg      60
gcgcgagcac ggcctcgctt cacacagccc tccaagatga ggcgccgagt gattgcacgg     120
cctgtgggta gctctgtgcg gctcaagtgt gtggccagtg gcacccacg gccagacatc     180 atgtggatga aggatgacca gaccttgacg catctagagg ctagtgaaca cagaaagaag     240
aagtggacac tgagcttgaa gaacctgaag cctgaagaca gtggcaagta cacgtgccgt     300
gtatctaaca aggccggtgc catcaacgcc acctacaaag tggatgtaat cc             352

<210> SEQ ID NO 139
<211> LENGTH: 117
<212> TYPE: PRT
<213> ORGANISM: Mouse

<400> SEQUENCE: 139

Met Thr Arg Ser Pro Ala Leu Leu Leu Leu Leu Gly Ala Leu Pro
  1               5                  10                  15

Ser Ala Glu Ala Ala Arg Ala Arg Pro Arg Phe Thr Gln Pro Ser Lys
            20                  25                  30

Met Arg Arg Arg Val Ile Ala Arg Pro Val Gly Ser Ser Val Arg Leu
        35                  40                  45

Lys Cys Val Ala Ser Gly His Pro Arg Pro Asp Ile Met Trp Met Lys
    50                  55                  60

Asp Asp Gln Thr Leu Thr His Leu Glu Ala Ser Glu His Arg Lys Lys
65                  70                  75                  80

Lys Trp Thr Leu Ser Leu Lys Asn Leu Lys Pro Glu Asp Ser Gly Lys
                85                  90                  95

Tyr Thr Cys Arg Val Ser Asn Lys Ala Gly Ala Ile Asn Ala Thr Tyr
            100                 105                 110

Lys Val Asp Val Ile
        115

<210> SEQ ID NO 140
<211> LENGTH: 421
<212> TYPE: DNA
<213> ORGANISM: Mouse

<400> SEQUENCE: 140
atgacgcgga gccccgcgct gctgctgctg ctattggggg ccctcccgtc ggctgaggcg      60
gcgcgagagc ggactcgttc caagcctgtg ctcacaggga cacccctgt gaacacaacg     120 gtggacttcg gtgggacaac gtccttccag tgcaaggtgc gcagtgacgt gaagcctgtg     180
atccagtggc tgaagcgggt ggagtacggc tccgagggac gccacaactc caccattgat     240
gtgggtggcc agaagtttgt ggtgttgccc acgggtgatg tgtggtcacg gcctgatggc     300

```
tcctacctca acaagctgct catctctcgg gcccgccagg atgatgctgg catgtacatc    360
tgcctaggtg caaataccat gggctacagt ttccgtagcg ccttcctcac tgtattacca    420
g                                                                    421
```

<210> SEQ ID NO 141
<211> LENGTH: 140
<212> TYPE: PRT
<213> ORGANISM: Mouse

<400> SEQUENCE: 141

```
Met Thr Arg Ser Pro Ala Leu Leu Leu Leu Leu Gly Ala Leu Pro
  1               5                  10                  15

Ser Ala Glu Ala Ala Arg Glu Arg Thr Arg Ser Lys Pro Val Leu Thr
                 20                  25                  30

Gly Thr His Pro Val Asn Thr Thr Val Asp Phe Gly Gly Thr Thr Ser
             35                  40                  45

Phe Gln Cys Lys Val Arg Ser Asp Val Lys Pro Val Ile Gln Trp Leu
 50                  55                      60

Lys Arg Val Glu Tyr Gly Ser Glu Gly Arg His Asn Ser Thr Ile Asp
 65                  70                  75                  80

Val Gly Gly Gln Lys Phe Val Val Leu Pro Thr Gly Asp Val Trp Ser
                     85                  90                  95

Arg Pro Asp Gly Ser Tyr Leu Asn Lys Leu Leu Ile Ser Arg Ala Arg
                100                 105                 110

Gln Asp Asp Ala Gly Met Tyr Ile Cys Leu Gly Ala Asn Thr Met Gly
            115                 120                 125

Tyr Ser Phe Arg Ser Ala Phe Leu Thr Val Leu Pro
    130                 135                 140
```

<210> SEQ ID NO 142
<211> LENGTH: 67
<212> TYPE: DNA
<213> ORGANISM: Mouse

<400> SEQUENCE: 142

```
atgacgcgga gccccgcgct gctgctgctg ctattggggg ccctcccgtc ggctgaggcg    60
gcgcgag                                                              67
```

<210> SEQ ID NO 143
<211> LENGTH: 22
<212> TYPE: PRT
<213> ORGANISM: Mouse

<400> SEQUENCE: 143

```
Met Thr Arg Ser Pro Ala Leu Leu Leu Leu Leu Gly Ala Leu Pro
  1               5                  10                  15

Ser Ala Glu Ala Ala Arg
                 20
```

<210> SEQ ID NO 144
<211> LENGTH: 1389
<212> TYPE: DNA
<213> ORGANISM: Mouse

<400> SEQUENCE: 144

```
atgacgcgga gccccgcgct gctgctgctg ctattggggg ccctcccgtc ggctgaggcg    60
gcgcgaggac ccccaagaat ggcagacaaa gtggtcccac ggcaggtggc ccgcctgggc    120
```

```
cgcactgtgc ggctacagtg cccagtggag ggggacccac caccgttgac catgtggacc    180
aaagatggcc gcacaatcca cagtggctgg agccgcttcc gtgtgctgcc ccagggtctg    240
aaggtgaagg aggtggaggc cgaggatgcc ggtgtttatg tgtgcaaggc caccaatggc    300
tttggcagcc tcagcgtcaa ctacactctc atcatgtgga tgaaggatga ccagaccttg    360
acgcatctag aggctagtga acacagaaag aagaagtgga cactgagctt gaagaacctg    420
aagcctgaag acagtggcaa gtacacgtgc cgtgtatcta caaggccgg tgccatcaac     480
gccacctaca agtggatgt aatccagcgg actcgttcca agcctgtgct cacagggaca    540
cacccctgtga acacaacggc ggacttcggt gggacaacgt ccttccagtg caaggtgcgc    600
agtgacgtga agcctgtgat ccagtggctg aagcgggtgg agtacggctc cgagggacgc    660
cacaactcca ccattgatgt gggtggccag aagtttgtgg tgttgcccac gggtgatgtg    720
tggtcacggc ctgatggctc ctacctcaac aagctgctca tctctcgggc ccgccaggat    780
gatgctggca tgtacacctg cctaggtgca ataccatgg gctacagttt ccgtagcgcc     840
ttcctcactg tattaccaga ccccaaacct ccagggcctc ctatggcttc ttcatcgtca    900
tccacaagcc tgccatggcc tgtggtgatc ggcatcccag ctggtgctgt cttcatccta    960
ggcactgtgc tgctctggct tgccagacc aagaagaagc catgtgcccc agcatctaca    1020
cttcctgtgc ctgggcatcg tcccccaggg acatcccgag aacgcagtgg tgacaaggac   1080
ctgccctcat tggctgtggg catatgtgag gagcatggat ccgccatggc cccccagcac   1140
atcctggcct ctggctcaac tgctggcccc aagctgtacc ccaagctata cagagatgtg   1200
cacacacaca cacatacaca cacctgcact cacacgctct catgtggagg gcaaggttca   1260
tcaacaccag catgtccact atcagtgcta aatacagcga atctccaagc actgtgtcct   1320
gaggtaggca tatgggggcc aaggcaacag gttgggagaa ttgagaacaa tggaggaaga   1380
gtatcttag                                                           1389
```

<210> SEQ ID NO 145
<211> LENGTH: 462
<212> TYPE: PRT
<213> ORGANISM: Mouse

<400> SEQUENCE: 145

```
Met Thr Arg Ser Pro Ala Leu Leu Leu Leu Gly Ala Leu Pro
  1               5                  10                  15

Ser Ala Glu Ala Ala Arg Gly Pro Pro Arg Met Ala Asp Lys Val Val
             20                  25                  30

Pro Arg Gln Val Ala Arg Leu Gly Arg Thr Val Arg Leu Gln Cys Pro
         35                  40                  45

Val Glu Gly Asp Pro Pro Leu Thr Met Trp Thr Lys Asp Gly Arg
     50                  55                  60

Thr Ile His Ser Gly Trp Ser Arg Phe Arg Val Leu Pro Gln Gly Leu
 65                  70                  75                  80

Lys Val Lys Glu Val Glu Ala Glu Asp Ala Gly Val Tyr Val Cys Lys
                 85                  90                  95

Ala Thr Asn Gly Phe Gly Ser Leu Ser Val Asn Tyr Thr Leu Ile Met
            100                 105                 110

Trp Met Lys Asp Asp Gln Thr Leu Thr His Leu Glu Ala Ser Glu His
        115                 120                 125

Arg Lys Lys Lys Trp Thr Leu Ser Leu Lys Asn Leu Lys Pro Glu Asp
    130                 135                 140
```

```
                                    -continued
Ser Gly Lys Tyr Thr Cys Arg Val Ser Asn Lys Ala Gly Ala Ile Asn
145                 150                 155                 160

Ala Thr Tyr Lys Val Asp Val Ile Gln Arg Thr Arg Ser Lys Pro Val
                165                 170                 175

Leu Thr Gly Thr His Pro Val Asn Thr Val Asp Phe Gly Gly Thr
            180                 185                 190

Thr Ser Phe Gln Cys Lys Val Arg Ser Asp Val Lys Pro Val Ile Gln
            195                 200                 205

Trp Leu Lys Arg Val Glu Tyr Gly Ser Glu Gly Arg His Asn Ser Thr
        210                 215                 220

Ile Asp Val Gly Gly Gln Lys Phe Val Val Leu Pro Thr Gly Asp Val
225                 230                 235                 240

Trp Ser Arg Pro Asp Gly Ser Tyr Leu Asn Lys Leu Leu Ile Ser Arg
                245                 250                 255

Ala Arg Gln Asp Asp Ala Gly Met Tyr Ile Cys Leu Gly Ala Asn Thr
            260                 265                 270

Met Gly Tyr Ser Phe Arg Ser Ala Phe Leu Thr Val Leu Pro Asp Pro
        275                 280                 285

Lys Pro Pro Gly Pro Pro Met Ala Ser Ser Ser Ser Thr Ser Leu
290                 295                 300

Pro Trp Pro Val Val Ile Gly Ile Pro Ala Gly Ala Val Phe Ile Leu
305                 310                 315                 320

Gly Thr Val Leu Leu Trp Leu Cys Gln Thr Lys Lys Lys Pro Cys Ala
                325                 330                 335

Pro Ala Ser Thr Leu Pro Val Pro Gly His Arg Pro Pro Gly Thr Ser
            340                 345                 350

Arg Glu Arg Ser Gly Asp Lys Asp Leu Pro Ser Leu Ala Val Gly Ile
        355                 360                 365

Cys Glu Glu His Gly Ser Ala Met Ala Pro Gln His Ile Leu Ala Ser
        370                 375                 380

Gly Ser Thr Ala Gly Pro Lys Leu Tyr Pro Lys Leu Tyr Thr Asp Val
385                 390                 395                 400

His Thr His Thr His Thr His Thr Cys Thr His Thr Leu Ser Cys Gly
                405                 410                 415

Gly Gln Gly Ser Ser Thr Pro Ala Cys Pro Leu Ser Val Leu Asn Thr
            420                 425                 430

Ala Asn Leu Gln Ala Leu Cys Pro Glu Val Gly Ile Trp Gly Pro Arg
        435                 440                 445

Gln Gln Val Gly Arg Ile Glu Asn Asn Gly Gly Arg Val Ser
450                 455                 460
```